US012751983B2

(12) United States Patent
Kolar et al.

(10) Patent No.: US 12,751,983 B2
(45) Date of Patent: Oct. 6, 2026

(54) **BACTERIOPHAGE COMPOSITIONS FOR TREATING *STAPHYLOCOCCUS* INFECTION**

(71) Applicant: Armata Pharmaceuticals, Inc., Marina del Rey, CA (US)

(72) Inventors: Stacey Lynn Kolar, Los Angeles, CA (US); Brian C. Varnum, Santa Monica, CA (US)

(73) Assignee: ARMATA PHARMACEUTICALS, INC., Los Angeles, CA (US)

( * ) Notice: Subject to any disclaimer, the term of this patent is extended or adjusted under 35 U.S.C. 154(b) by 54 days.

(21) Appl. No.: 19/309,246

(22) Filed: Aug. 25, 2025

(65) Prior Publication Data

US 2026/0041723 A1 Feb. 12, 2026

Related U.S. Application Data

(62) Division of application No. 17/179,295, filed on Feb. 18, 2021.

(60) Provisional application No. 62/978,006, filed on Feb. 18, 2020.

(51) Int. Cl.

| | |
|---|---|
| ***A61K 35/76*** | (2015.01) |
| ***A61K 9/00*** | (2006.01) |
| ***A61K 45/06*** | (2006.01) |
| ***A61P 31/04*** | (2006.01) |
| ***C12N 7/00*** | (2006.01) |

(52) U.S. Cl.
CPC ............ *A61K 35/76* (2013.01); *A61K 9/0019* (2013.01); *A61K 9/0078* (2013.01); *A61K 45/06* (2013.01); *A61P 31/04* (2018.01); *C12N 7/00* (2013.01)

(58) Field of Classification Search
None
See application file for complete search history.

(56) References Cited

U.S. PATENT DOCUMENTS

| | | | |
|---|---|---|---|
| 7,825,084 | B2 | 11/2010 | Harris et al. |
| 8,197,807 | B2 | 6/2012 | Brenner |
| 10,517,908 | B2 | 12/2019 | Shaw et al. |
| 2004/0259170 | A1 | 12/2004 | Sokoloff et al. |
| 2018/0273910 | A1 | 9/2018 | Rohwer et al. |
| 2020/0030392 | A1 | 1/2020 | Fevre et al. |
| 2021/0252083 | A1 | 8/2021 | Kolar et al. |
| 2023/0092021 | A1 | 3/2023 | Kolar et al. |
| 2024/0189373 | A1 | 6/2024 | Kolar et al. |

FOREIGN PATENT DOCUMENTS

| | | | |
|---|---|---|---|
| CN | 110545670 | A | 12/2019 |
| CN | 110719784 | A | 1/2020 |
| WO | 2018146437 | A1 | 8/2018 |
| WO | 2018162566 | A1 | 9/2018 |
| WO | 2019136108 | A1 | 7/2019 |
| WO | 2019136109 | A1 | 7/2019 |
| WO | 2020128108 | A1 | 6/2020 |
| WO | 2021168147 | A1 | 8/2021 |

OTHER PUBLICATIONS

"European Search Report Issued in Patent Application No. 21757611.5", mailed on Apr. 16, 2024, 7 pages.
"International Search Report and Written Opinion Issued in PCT Application No. PCT/US2021/018623", Mailed on Jul. 27, 2021, 13 pages.
(2013) *Staphylococcus phage* vB_SauM_Romulus, complete genome, Accession No. JX846613.1, https://www.ncbi.nlm.nih.gov/nuccore/JX846613.1, 61 pages.
(2024) "Therapeutic", https://www.merriam-webster.com/dictionary/therapeutic, 6 pages.
Camarillo-Guerrero et al. (Feb. 18, 2021) "Massive Expansion of Human Gut Bacteriophage Diversity", Cell, 184(4):1098-1109.
Cochrane et al. (1970) "Depletion of Plasma Complement in Vivo by a Protein of Cobra Venom: Its Effect on Various Immunologic Reactions", Journal of Immunology, 105(1):55-69.
Database Genbank, (Sep. 17, 2013) "Cryptococcus neoformans 268 copper zinc superoxide dismutase (SOD1) gene, partial cds", Accession No. KC532239.1, 2 pages.
Database Genbank, (Mar. 14, 2019) "Staphylococcal phage MR003 DNA, complete genome", Accession No. AP019522.1, 57 pages.
Database Genbank, (May 20, 2017) "*Staphylococcus phage* qdsa001, complete genome", Accession No. KY779848.1, 59 pages.
Database Genbank, (Mar. 25, 2022) "*Staphylococcus Phage* SA11, Complete Genome", Accession No. NC_019511.1, 60 pages.
Database Genbank, (Dec. 21, 2020) "*Staphylococcus phage* Stau2, complete genome", Accession No. NC_030933.1, 68 pages.
Database Genbank, (Mar. 23, 2013) "*Staphylococcus phage* vB_SauM_Remus, complete genome", Accession No. JX846612.1, 54 pages.
Database Genbank, (Dec. 21, 2020) "*Staphylococcus phage* vB_SauM_Romulus, complete genome", Accession No. NC_020877.1, 61 pages.
Duplessis et al. (Mar. 1, 2023) "Skin Swabbing for *Staphylococcus aureus*-Targeting Phages", Military Medicine, 188(3-4):e463-e467.
Dutilh et al. (Jul. 24, 2014) "A Highly Abundant Bacteriophage Discovered in the Unknown Sequences of Human Faecal Metagenomes", Nature Communications, 5(1):4498.
Hsieh et al. (2016) "Genomic analysis of *Staphylococcus phage* Stau2 isolated from medical specimen", Virus Genes, 52(1):107-116.
Lai et al. (Aug. 14, 2024) "Long-Read Sequencing Reveals Extensive Gut Phageome Structural Variations Driven by Genetic Exchange with Bacterial Hosts", Microbiology, 10(33):eadn3316 (13 pages).
Malik et al. (2017) "Formulation, stabilisation and encapsulation of bacteriophage for phage therapy", Advances in Colloid and Interface Science, 249:100-133.
Manohar et al. (2019) "Improved Lyophilization Conditions for Long-Term Storage of Bacteriophages", Scientific Reports, 9(1):15242(10 pages).
Ping et al. (Dec. 31, 1994) "Identification and Phage Typing of Methicillin-resistant *Staphylococcus aureus*", Chinese Journal of Hospital Infection, 184-185.

(Continued)

*Primary Examiner* — Grant C Currens
(74) *Attorney, Agent, or Firm* — Mintz, Levin, Cohn, Ferris, Glovsky and Popeo, P.C.

(57) ABSTRACT

The present disclosure relates to bacteriophages and compositions capable of infecting and killing *Staphylococcus*, and use of the same for treating *Staphylococcus*, e.g. *Staphylococcus aureus*, bacterial infections.

44 Claims, 4 Drawing Sheets

Specification includes a Sequence Listing.

(56) References Cited

OTHER PUBLICATIONS

Sakamoto et al. (1998) "Physiologic Role of the Complement System in Host Defense, Disease, and Malnutrition", Nutrition, 14(4):391-398.

Thompson et al. (Nov. 11, 1994) "CLUSTAL W: Improving the Sensitivity of Progressive Multiple Sequence Alignment through Sequence Weighting, Position-Specific Gap Penalties and Weight Matrix Choice", Nucleic Acids Research, 22(22):4673-4680.

Vandersteegen et al. (Mar. 2013) "Romulus and Remus, Two Phage Isolates Representing a Distinct Clade within the Twortlikevirus Genus, Display Suitable Properties for Phage Therapy Applications", Journal of Virology, 87(6):3237-3247.

Vandersteegen et al. (2019) "*Staphylococcus phage* vB_SauM_Remus, complete genome", GenBank Database, Accession No. NC_022090.1, 52 Pages.

Walle et al. (Jun. 12, 2004) "Align-M—A New Algorithm for Multiple Alignment of Highly Divergent Sequences", Bioinformatics, 20(9):1428-1435.

BACTERIOPHAGE COMPOSITIONS FOR TREATING *STAPHYLOCOCCUS* INFECTION

CROSS-REFERENCES TO RELATED APPLICATIONS

This application is a divisional of U.S. patent application Ser. No. 17/179,295 filed Feb. 18, 2021, which claims the benefit of U.S. Provisional Application No. 62/978,006, filed Feb. 18, 2020, which is incorporated herein by reference in its entirety and for all purposes.

SEQUENCE LISTING

The instant application contains a Sequence Listing, which has been submitted electronically in ASCII format and is hereby incorporated by reference in its entirety. Said ASCII copy, created on Feb. 18, 2020 is named 054249-519P01US_SEQUENCE_LISTING_ST25.txt and is 377,606 bytes in size.

BACKGROUND

There is an increasing demand for alternative antibiotics as the number of bacterial strains resistant to traditional, small molecule antibiotic treatment regimens are becoming more numerous. Bacteriophage therapy uses bacterial viruses, or phages, to target and destroy bacteria at various sites of infection. Recent advances in biotechnology have allowed for the fast expansion of naturally existing phage libraries in order to generate potent and specific bacteriophages that can target and destroy a bacterium of interest. Antibiotic-resistant *Staphylococcus aureus* (SA) is typically found in hospitals and in areas where immune-compromised patients reside. Secondary SA infection is a potentially lethal infection (>20%) that is a common threat to these patients. Indeed, there are approximately 50/100,000 population SA bacteremia cases diagnosed each year in the US alone. Bacteriophage treatment approaches that can circumvent traditional mechanisms of antibiotic resistance, avoid the toxic side effects of traditional small molecule therapies, can be effective against biofilms, and avoid disruption of the native gut flora are especially attractive.

Thus, there is a large unmet need for a more efficient, potent, and specific anti-SA therapy to replace or augment the traditional small molecule antibiotics currently used to treat SA infections today.

SUMMARY

Described herein are bacteriophages, compositions of bacteriophages, and use of the same for medical and non-medical applications.

In an aspect, provided herein is an isolated, purified bacteriophage that includes a polynucleotide sequence of SEQ ID NO: 1.

In an aspect, provided herein is an isolated, purified bacteriophage that includes a polynucleotide sequence with at least 93% identity to SEQ ID NO: 1. In an aspect, provided herein is an isolated, purified bacteriophage that includes a polynucleotide sequence with at least 90% identity to SEQ ID NO: 1.

In an aspect, provided herein is an isolated, purified bacteriophage that includes a polynucleotide sequence of SEQ ID NO: 2.

In an aspect, provided herein is an isolated, purified bacteriophage that includes a polynucleotide sequence with at least 93% identity to SEQ ID NO: 2. In an aspect, provided herein is an isolated, purified bacteriophage that includes a polynucleotide sequence with at least 90% identity to SEQ ID NO: 2.

In an aspect, provided herein are bacteriophage compositions that include one or more bacteriophages selected from a bacteriophage including a polynucleotide sequence of SEQ ID NO: 1, SEQ ID NO: 2, a polynucleotide sequence with at least 93% identity to SEQ ID NO: 1, and a polynucleotide sequence with at least 93% identity to SEQ ID NO: 2. In an aspect, provided herein are bacteriophage compositions that include one or more bacteriophages selected from a bacteriophage including a polynucleotide sequence of SEQ ID NO: 1, SEQ ID NO: 2, a polynucleotide sequence with at least 90% identity to SEQ ID NO: 1, and a polynucleotide sequence with at least 90% identity to SEQ ID NO: 2.

In an aspect, provided herein are uses of a composition including one or more distinct bacteriophages that target *Staphylococcus aureus* in the treatment of subject with a *Staphylococcus aureus* bacterial infection. The uses include administering the composition to a subject; where at least one of the one or more bacteriophages is selected from a bacteriophage including a polynucleotide sequence of SEQ ID NO: 1, SEQ ID NO: 2, a polynucleotide sequence with at least 93% identity to SEQ ID NO: 1, and a polynucleotide sequence with at least 93% identity to SEQ ID NO: 2. In another aspect, at least one of the one or more bacteriophages is selected from a bacteriophage including a polynucleotide sequence of SEQ ID NO: 1, SEQ ID NO: 2, a polynucleotide sequence with at least 90% identity to SEQ ID NO: 1, and a polynucleotide sequence with at least 90% identity to SEQ ID NO: 2.

In an aspect, provided herein is a bacterial host manufacturing strain including a bacteriophage where the bacteriophage includes a polynucleotide sequence selected from SEQ ID NO: 1, SEQ ID NO: 2, a polynucleotide sequence with at least 93% identity to SEQ ID NO: 1, and a polynucleotide sequence with at least 93% identity to SEQ ID NO: 2. In another aspect, the bacteriophage includes a polynucleotide sequence selected from SEQ ID NO: 1, SEQ ID NO: 2, a polynucleotide sequence with at least 90% identity to SEQ ID NO: 1, and a polynucleotide sequence with at least 90% identity to SEQ ID NO: 2.

In an aspect, provided herein are methods of treating a subject with a bacterial infection including selecting a bacteriophage based upon resistance to blood complement inactivation and administering the bacteriophage to the subject.

In an aspect, provided herein are methods of treating a subject with a bacterial infection including administering to the subject one or more distinct bacteriophages selected from a bacteriophage including a polynucleotide sequence selected from SEQ ID NO: 1, SEQ ID NO: 2, a polynucleotide sequence with at least 93% identity to SEQ ID NO: 1, and a polynucleotide sequence with at least 93% identity to SEQ ID NO: 2. In another aspect, the methods of treatment include administering to the subject one or more distinct bacteriophages selected from a bacteriophage including a polynucleotide sequence selected from SEQ ID NO: 1, SEQ ID NO: 2, a polynucleotide sequence with at least 90% identity to SEQ ID NO: 1, and a polynucleotide sequence with at least 90% identity to SEQ ID NO: 2.

In an aspect, provided herein are methods of modifying the microbial flora in a subject including administering to the subject at least one bacteriophage that targets *Staphylococcus* bacteria, where the bacteriophage includes a polynucleotide sequence selected from SEQ ID NO: 1, SEQ ID NO: 2, a polynucleotide sequence with at least 93% identity to SEQ ID NO: 1, and a polynucleotide sequence with at least 93% identity to SEQ ID NO: 2. In another aspect, the bacteriophage includes a polynucleotide sequence selected from SEQ ID NO: 1, SEQ ID NO: 2, a polynucleotide sequence with at least 90% identity to SEQ ID NO: 1, and a polynucleotide sequence with at least 90% identity to SEQ ID NO: 2.

BRIEF DESCRIPTION OF THE DRAWINGS

Embodiments will now be described, by way of example only, with reference to the accompanying drawings, in which:

FIG. 5A shows bacterial growth measured by turbidity (absorbance at 600 nm) in the presence of AP-SA02 and vancomycin in a checkerboard assay. Grey boxes indicate lines on graph depicted in FIG. 5B. AP-SA02 is active against a VRSA strain. Vancomycin, 16 μg/mL; AP-SA02, 0.1 pg/mL.

FIG. 6A is data showing bacterial growth measured by turbidity (absorbance at 600 nm) in the presence of AP-SA02 and vancomycin in a checkerboard assay. Grey boxes show lines on graph depicted in FIG. 6B. AP-SA02 and vancomycin show synergistic activity against a VRSA strain. Vancomycin, 2 μg/mL.

DETAILED DESCRIPTION

Figure 1:
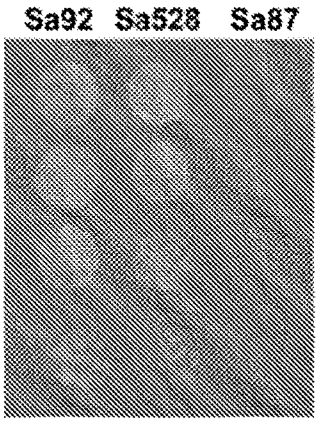
FIG. 1 shows efficiency of plating and plaque morphology. Equal titers of phage were serially diluted and 2 μL were plated on a lawn of *S. aureus*. Phage potency was assessed by plaques clarity and efficiency of plating.

It is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

The detailed description of the present disclosure is divided into various sections only for the reader's convenience and disclosure found in any section may be combined with that in another section. Unless defined otherwise, all technical and scientific terms used herein have the same meaning as commonly understood by one of ordinary skill in the art to which the present disclosure belongs.

Definitions

It must be noted that as used herein and in the appended claims, the singular forms "a," "an," and "the" include plural referents unless the context clearly dictates otherwise. Thus, for example, reference to "a bacteriophage composition" includes a plurality of such candidate agents and reference to "the bacteriophage" includes reference to one or more bacteriophages and equivalents thereof known to those skilled in the art, and so forth.

The term "consists essentially of" as used herein means that only the bacteriophage(s) explicitly indicated are present in the bacteriophage composition, but that said composition may also contain a further non-bacteriophage constituent, such as a pharmaceutically appropriate carrier, diluent, excipient, antibiotic (e.g., chemical antibiotic), etc., or combinations thereof.

As used herein, the term "about" when used before a numerical designation, e.g., temperature, time, amount, concentration, and such other, including a range, indicates approximations which may vary by (+) or (−) 10%, 5%, or 1%.

When a range (e.g., dosage range) is listed herein, it is to be understood that the value may include any individual value or range within the recited range(s), including endpoints.

As used herein, the term "mutant" refers to a bacteriophage differing genetically from ARSA0001 or ARSA0002 but still retaining the ability to infect and kill *Staphylococcus aureus* target bacteria. Mutants typically comprise bacteriophages with, e.g., silent mutations, conservative mutations, minor deletions, and/or minor replications of genetic material, and retain phenotypic characteristics of the reference bacteriophage. In an embodiment, the mutants retain any observable characteristic or property that is dependent upon the genome of the bacteriophage as described herein, i.e. phenotypic characteristics of said bacteriophage and/or lytic activity against *Staphylococcus* species. Preferred mutants retain the ability to infect and kill *Staphylococcus aureus* target bacteria and have less than 10% nucleic acid variation as compared to the genome of the reference bacteriophage, even more preferably less than 7%, more preferably less than 1%. Alternatively, or in combination, mutants have preferably less than 7% amino acid variation in a coded polypeptide sequence as compared to a polypeptide of the reference bacteriophage.

As used herein, the terms "% identity", "% sequence identity" and "percent identity" in relation to nucleic acid or amino acid sequences designates the level of identity or homology between said sequences and may be determined by techniques known in the art. Any of a variety of sequence alignment methods can be used to determine percent identity, including, without limitation, global methods, local methods and hybrid methods, such as segment approach methods. Protocols to determine percent identity are routine procedures within the scope of one skilled in the art. Global methods align sequences from the beginning to the end of the molecule and determine the best alignment by adding up scores of individual nucleotide pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22 (22) Nucleic Acids Research 4673-4680 (1994); and iterative refinement. Non-limiting methods include, e.g., BLAST, Match-box, see, e.g., Align-M, see, e.g., Ivo Van Walle et al., Align-M-A New Algorithm for Multiple Alignment of Highly Divergent Sequences, Bioinformatics 20 (9): 1428-1435 (2004). This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 100 nucleotides in length, or more preferably over a region that is 100-1000 or more nucleotides in length.

As used herein, the term "bacterial complementation" refers to the ability of a bacteriophage with a particular genome to compensate for a different, distinct bacteriophage with a different genome. More specifically, bacteriophage insensitive mutant colonies (of target bacteria) may arise to a particular bacteriophage but may still be sensitive to a different bacteriophage. In other words, bacteriophage resistant mutant bacteria arising to one phage are still sensitive to another phage.

As used herein, the term "generalized transduction" refers to a process by which any bacterial DNA may be transferred to another bacterium via a bacteriophage. It is a rare event; a very small percentage of phage particles happen to carry a donor bacterium's DNA, on the order of 1 phage in 10,000. In essence, this is the packaging of bacterial DNA into a viral envelope.

As used herein, the term "treat" or "treating" is intended to encompass prophylactic treatment as well as corrective treatment (treatment of a subject already suffering from a disease). This may include the medical management of a subject with the intent to cure, ameliorate, stabilize, or prevent a disease, pathological condition, or disorder. This term includes active treatment, that is, treatment directed specifically toward the improvement of a disease, pathological condition, or disorder; and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization, or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

As used herein, the term "lytic" or "lytic activity" designates the property of a bacteriophage to cause lysis of a bacterial cell. The lytic activity of a bacteriophage can be tested on a bacterium (e.g., *S. aureus* strains) according to techniques known in the art. The lytic cycle is named for the process that occurs when a phage has infected a cell, replicated new phage particles, and bursts through the host cell membrane. Some phage exhibit a lysogenic cycle during which the bacteriophage DNA remains practically dormant due to active repression of bacteriophage processes. Whenever the bacteria divides, the DNA of the phage is copied as well. In this way, the virus can continue replicating within its host without lysing the host. At a certain point, conditions may change and the phage enters a lytic cycle. "Obligately lytic" refers to phage that are unable to undergo a lysogenic cycle.

As used herein, the term "complement system" or "blood complement system" refers the part of the innate immune system that triggers phagocytosis, inflammation, and membrane disruption of foreign bodies, including bacteriophages. The complement systems consists of a classical pathway, an alternative pathway, and a lectin pathway. The classical pathway initiates when a multi-protein complex called C1 is formed upon antigen recognition by IgG or IgM. C1 multi-protein complex is composed of one molecule of C1q, two molecules of C1r, and two molecules of C1s. After undergoing several internal proteolysis steps, the subunits C4 and C2 are generated, and further processed to form C2a, C2b, C4a, and C4b. C2b and C4b combine to form classical-form C3-convertase. C3 is further processed to form C3a and C3b. C3b can then join C3 to form a C5-convertase. Low levels of C3 can be converted to C3b without the presence of an antigen, and can combine with other proteases to form alternative complexes in the alternative complement pathway. The lectin pathway replaces the C1q protein from C1 with lectin-binding proteins, including mannose binding lectin (MBL).

As used herein, the term "C3" or "complement component C3" refers to any of the proteins involved in the complement pathways: classical, alternative, or lectin. One form of activated C3 is a heterodimer of activated C2 and C4 proteins, C4b2a, also known as C3-convertase. One form activated C3 is a heterodimer of activated C3b and activated factor B, Bb, to form C3bBb.

As used herein, the term "bacteriophage target" refers to any bacteria species that can be infected by a particular bacteriophage. A bacteriophage recognizes the target bacterial cell surface, binds, and injects its genetic material inside the bacterial host. The genetic material from the infecting phage can be incorporated into the bacterial genome. The bacteriophage may become lysogenic, where the viral genome remains dormant in the bacterial host genome until a triggering event. The bacteriophage may also become lytic, wherein many copies of the infecting phage are produced by the machinery of the infected bacteria, and the copies are subsequently released by bacterial lysis, extrusion, or by budding.

As used herein, the term "bacterial host manufacturing strain" or "manufacturing strain" refers to the bacteria used to grow bacteriophage. A method for bacteriophage production may require a production process involving at least two operating units, growth of the host bacteria and bacteriophage propagation (or infection). It is important to consider basic parameters for bacterial growth and phage infection, such as the selected substrates for the bacterium and the optimal temperature, both for bacterial growth and phage infection, since these factors may influence the infectivity of phages.

As used herein, the term "bacteremia" refers to the presence of bacteria in the bloodstream. Bacteria may be introduced into the bloodstream by ordinary activities including brushing teeth, or may be introduced by surgical procedures, implantation of temporary medical devices, urinary tract infections, at the site of a severe injury, or at the site of long-term device implantation.

As used herein, the term "septicemia" refers to a bacterial infection elsewhere in the body which enters the bloodstream; also known as blood poisoning by bacteria.

As used herein, the term "*Silviavirus*" refers to a virus that belongs to Regum: virus, Group 1: dsDNA, Ordo: Caudovirales, Familia: Herelleviridae, Subfamilia: Twortvirinae, Genus: *Silviavirus*. Species of Genus *Silviavirus* include, without limitation, *Staphylococcus* virus Remus, *Staphylococcus* virus SA11, *Staphylococcus* virus Romulus, *Staphylococcus* virus Qdsa001, *Staphylococcus* virus MR003, *Staphylococcus* virus StAP1, and *Staphylococcus* virus Stsau2.

A use or method typically comprises administering a bacteriophage or bacteriophage composition described herein to a subject. As used herein, a "subject" is a mammal, such as a human or other animal. Preferably, the subject is a human.

The term "in need of treatment" as used herein refers to a judgment made by a caregiver (e.g., physician, nurse, nurse practitioner, or individual in the case of humans; veterinarian in the case of animals, including non-human mammals) that a subject requires or will benefit from treatment. This judgment is made based on a variety of factors that are in the realm of a caregiver's expertise, but that include the knowledge that the subject is ill, or will be ill, as the result of a condition that is treatable by the compositions of the invention.

As used herein, the term "isolated" indicates that the bacteriophage are removed from its original environment in which it naturally occurs. In particular, an isolated bacteriophage is, e.g., cultivated, cultured separately from the environment in which it is naturally located.

As used herein, the term "purified" indicates that the bacteriophage are removed from manufacturing host bacteria. In particular, a purified bacteriophage has production impurities, such as bacterial components, removed from its manufacturing or production environment. Bacterial components include but are not limited to bacterial host proteins, lipids, and/or bacterial endotoxin. The term "purified" may also refer to genetic purification in which the strain of bacteriophage is genetically homogenous.

As used herein, the term "substantially purified" refers to a composition containing less than 1%, less than 0.1%, less than 0.001%, or no detectable amount of contaminants such as host bacterial proteins or endotoxin. Also, as used herein, the term "substantially pure" when used to describe a bacteriophage strain refers to the genetic purity of the composition such that the strain is greater than 99%, greater than 99.9%, greater than 99.999%, or 100% of one particular genome sequence.

Typically, a composition is substantially pure when at least 80%, at least 85%, at least 90%, at least 95%, at least 98%, or at least 99% of the total material (by volume, by wet or dry weight, or by mole percent or mole fraction) in a sample is free of impurities or genetic variants.

As used herein, the term "subject" or "patient" refers to a human or non-human animal. Preferably, the subject or patient is in need of treatment with the composition as described herein, e.g., has a bacterial infection susceptible to treatment with the composition.

As used herein, the "synergistic amount" refers to the sum of a first amount (e.g., a bacteriophage) and a second amount (e.g., a different bacteriophage) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent.

As used herein, the term "substantially free" refers to something having less than 10% of the substance that it is to be free from. For example, 0.01% to 10% free of the substance, including any subvalue and subrange therein, including endpoints. For example, 0.01, 0.02, 0.03, 0.04, 0.05, 0.06, 0.07, 0.08, 0.09, 1, 2, 3, 4, 5, 6, 7, 8, 9, or 10%.

As used herein, the term "obtainable" as used herein also encompasses the term "obtained." In one embodiment, the term "obtainable" means obtained.

Additional terms and phrases are defined below.

Bacteriophage Compositions

In an aspect, provided herein is an isolated, purified bacteriophage that includes a polynucleotide sequence of SEQ ID NO: 1.

In an aspect, provided herein is an isolated, purified bacteriophage that includes a polynucleotide sequence with at least 90% identity to SEQ ID NO: 1.

In embodiments, provided herein is an isolated, purified bacteriophage that includes a polynucleotide sequence with at least 99.9%, 99.8%, 99.7%, 99.6%, 99.5%, 99.4%, 99.3%, 99.2%, 99.1%, 99.0%, or 99% identity to SEQ ID NO: 1. In embodiments, provided herein is an isolated, purified bacteriophage that includes a polynucleotide sequence with at least 98.9%, 98.8%, 98.7%, 98.6%, 98.5%, 98.4%, 98.3%, 98.2%, 98.1%, 98.0%, or 98% identity to SEQ ID NO: 1. In embodiments, provided herein is an isolated, purified bacteriophage that includes a polynucleotide sequence with at least 97.9%, 97.8%, 97.7%, 97.6%, 97.5%, 97.4%, 97.3%, 97.2%, 97.1%, 97.0% or 97% identity to SEQ ID NO: 1. In embodiments, provided herein is an isolated, purified bacteriophage that includes a polynucleotide sequence with at least 96.9%, 96.8%, 96.7%, 96.6%, 96.5%, 96.4%, 96.3%, 96.2%, 96.1%, 96.0%, or 96% identity to SEQ ID NO: 1. In embodiments, provided herein is an isolated, purified bacteriophage that includes a polynucleotide sequence with at least 95.9%, 95.8%, 95.7%, 95.6%, 95.5%, 95.4%, 95.3%, 95.2%, 95.1%, 95.0%, or 95% identity to SEQ ID NO: 1. In embodiments, provided herein is an isolated, purified bacteriophage that includes a polynucleotide sequence with at least 94.9%, 94.8%, 94.7%, 94.6%, 94.5%, 94.4%, 94.3%, 94.2%, 94.1%, 94.0%, or 94% identity to SEQ ID NO: 1. In embodiments, provided herein is an isolated, purified bacteriophage that includes a polynucleotide sequence with at least 93.9%, 93.8%, 93.7%, 93.6%, 93.5%, 93.4%, 93.3%, 93.2%, 93.1%, 93.0%, or 93% identity to SEQ ID NO: 1. In embodiments, provided herein is an isolated, purified bacteriophage that includes a polynucleotide sequence with at least 92.9%, 92.8%, 92.7%, 92.6%, 92.5%, 92.4%, 92.3%, 92.2%, 92.1%, 92.0%, or 92% identity to SEQ ID NO: 1. In embodiments, provided herein is an isolated, purified bacteriophage that includes a polynucleotide sequence with at least 91.9%, 91.8%, 91.7%, 91.6%, 91.5%, 91.4%, 91.3%, 91.2%, 91.1%, 91.0%, or 91% identity to SEQ ID NO: 1. In embodiments, provided herein is an isolated, purified bacteriophage that includes a polynucleotide sequence with at least 90.9%, 90.8%, 90.7%, 90.6%, 90.5%, 90.4%, 90.3%, 90.2%, 90.1%, 90.0%, or 90% identity to SEQ ID NO: 1. In embodiments, provided herein is an isolated, purified bacteriophage that includes a polynucleotide sequence with at least 89.9%, 89.8%, 89.7%, 89.6%, 89.5%, 89.4%, 89.3%, 89.2%, 89.1%, 89.0%, or 89% identity to SEQ ID NO: 1. In embodiments, provided herein is an isolated, purified bacteriophage that includes a polynucleotide sequence with at least 88.9%, 88.8%, 88.7%, 88.6%, 88.5%, 88.4%, 88.3%, 88.2%, 88.1%, 88.0%, or 88% identity to SEQ ID NO: 1. In embodiments, provided herein is an isolated, purified bacteriophage that includes a polynucleotide sequence with at least 87.9%, 87.8%, 87.7%, 87.6%, 87.5%, 87.4%, 87.3%, 87.2%, 87.1%, 87.0%, or 87% identity to SEQ ID NO: 1. In embodiments, provided herein is an isolated, purified bacteriophage that includes a polynucleotide sequence with at least 86.9%, 86.8%, 86.7%, 86.6%, 86.5%, 86.4%, 86.3%, 86.2%, 86.1%, 86.0%, or 86% identity to SEQ ID NO: 1. In embodiments, provided herein is an isolated, purified bacteriophage that includes a polynucleotide sequence with at least 85.9%, 85.8%, 85.7%, 85.6%, 85.5%, 85.4%, 85.3%, 85.2%, 85.1%, 85.0%, or 85% identity to SEQ ID NO: 1. In embodiments, provided herein is an isolated, purified bacteriophage that includes a polynucleotide sequence with at least 84.9%, 84.8%, 84.7%, 84.6%, 84.5%, 84.4%, 84.3%, 84.2%, 84.1%, 84.0%, or 84% identity to SEQ ID NO: 1. In embodiments, provided herein is an isolated, purified bacteriophage that includes a polynucleotide sequence with at least 83.9%, 83.8%, 83.7%, 83.6%, 83.5%, 83.4%, 83.3%, 83.2%, 83.1%, 83.0%, or 83% identity to SEQ ID NO: 1. In embodiments, provided herein is an isolated, purified bacteriophage that includes a polynucleotide sequence with at least 82.9%, 82.8%, 82.7%, 82.6%, 82.5%, 82.4%, 82.3%, 82.2%, 82.1%, 82.0%, or 82% identity to SEQ ID NO: 1. In embodiments, provided herein is an isolated, purified bacteriophage that includes a polynucleotide sequence with at least 81.9%, 81.8%, 81.7%, 81.6%, 81.5%, 81.4%, 81.3%, 81.2%, 81.1%, 81.0%, or 81% identity to SEQ ID NO: 1. In embodiments, provided herein is an isolated, purified bacteriophage that includes a polynucleotide sequence with at least 80.9%, 80.8%, 80.7%, 80.6%, 80.5%, 80.4%, 80.3%, 80.2%, 80.1%, 80.0%, or 80% identity to SEQ ID NO: 1. In embodiments, the bacteriophage genome comprises the polynucleotide.

In an aspect, provided herein is an isolated, purified bacteriophage that includes a polynucleotide sequence identified as SEQ ID NO: 2.

In an aspect, provided herein is an isolated, purified bacteriophage that includes a polynucleotide sequence with at least 93% identity to SEQ ID NO: 2. In another aspect, the purified bacteriophage includes a polynucleotide sequence with at least 90% identity to SEQ ID NO: 2.

In embodiments, provided herein is an isolated, purified bacteriophage that includes a polynucleotide sequence with at least 99.9%, 99.8%, 99.7%, 99.6%, 99.5%, 99.4%, 99.3%, 99.2%, 99.1%, 99.0% or 99% identity to SEQ ID NO: 2. In embodiments, provided herein is an isolated, purified bacteriophage that includes a bacteriophage that includes a polynucleotide sequence with at least 98.9%, 98.8%, 98.7%, 98.6%, 98.5%, 98.4%, 98.3%, 98.2%, 98.1%, 98.0%, or 98% identity to SEQ ID NO: 2. In embodiments, provided herein is an isolated, purified bacteriophage that includes a polynucleotide sequence with at least 97.9%, 97.8%, 97.7%, 97.6%, 97.5%, 97.4%, 97.3%, 97.2%, 97.1%, 97.0%, or 97% identity to SEQ ID NO: 2. In embodiments, provided herein is an isolated, purified bacteriophage that includes a bacteriophage that includes a polynucleotide sequence with at least 96.9%, 96.8%, 96.7%, 96.6%, 96.5%, 96.4%, 96.3%, 96.2%, 96.1%, 96.0%, or 96% identity to SEQ ID NO: 2. In embodiments, provided herein is an isolated, purified bacteriophage that includes a polynucleotide sequence with at least 95.9%, 95.8%, 95.7%, 95.6%, 95.5%, 95.4%, 95.3%, 95.2%, 95.1%, 95.0%, or 95% identity to SEQ ID NO: 2. In embodiments, provided herein is an isolated, purified bacteriophage that includes a bacteriophage that includes a polynucleotide sequence with at least 94.9%, 94.8%, 94.7%, 94.6%, 94.5%, 94.4%, 94.3%, 94.2%, 94.1%, 94.0%, or 94% identity to SEQ ID NO: 2. In embodiments, provided herein is an isolated, purified bacteriophage that includes a polynucleotide sequence with at least 93.9%, 93.8%, 93.7%, 93.6%, 93.5%, 93.4%, 93.3%, 93.2%, 93.1%, 93.0%, or 93% identity to SEQ ID NO: 2. In embodiments, provided herein is an isolated, purified bacteriophage that includes a polynucleotide sequence with at least 92.9%, 92.8%, 92.7%, 92.6%, 92.5%, 92.4%, 92.3%, 92.2%, 92.1%, 92.0%, or 92% identity to SEQ ID NO: 2. In embodiments, provided herein is an isolated, purified bacteriophage that includes a polynucleotide sequence with at least 91.9%, 91.8%, 91.7%, 91.6%, 91.5%, 91.4%, 91.3%, 91.2%, 91.1%, 91.0%, or 91% identity to SEQ ID NO: 2. In embodiments, provided herein is an isolated, purified bacteriophage that includes a polynucleotide sequence with at least 90.9%, 90.8%, 90.7%, 90.6%, 90.5%, 90.4%, 90.3%, 90.2%, 90.1%, 90.0%, or 90% identity to SEQ ID NO: 2. In embodiments, provided herein is an isolated, purified bacteriophage that includes a polynucleotide sequence with at least 89.9%, 89.8%, 89.7%, 89.6%, 89.5%, 89.4%, 89.3%, 89.2%, 89.1%, 89.0%, or 89% identity to SEQ ID NO: 2. In embodiments, provided herein is an isolated, purified bacteriophage that includes a polynucleotide sequence with at least 88.9%, 88.8%, 88.7%, 88.6%, 88.5%, 88.4%, 88.3%, 88.2%, 88.1%, 88.0%, or 88% identity to SEQ ID NO: 2. In embodiments, provided herein is an isolated, purified bacteriophage that includes a polynucleotide sequence with at least 87.9%, 87.8%, 87.7%, 87.6%, 87.5%, 87.4%, 87.3%, 87.2%, 87.1%, 87.0%, or 87% identity to SEQ ID NO: 2. In embodiments, provided herein is an isolated, purified bacteriophage that includes a polynucleotide sequence with at least 86.9%, 86.8%, 86.7%, 86.6%, 86.5%, 86.4%, 86.3%, 86.2%, 86.1%, 86.0%, or 86% identity to SEQ ID NO: 2. In embodiments, provided herein is an isolated, purified bacteriophage that includes a polynucleotide sequence with at least 85.9%, 85.8%, 85.7%, 85.6%, 85.5%, 85.4%, 85.3%, 85.2%, 85.1%, 85.0%, or 85% identity to SEQ ID NO: 2. In embodiments, provided herein is an isolated, purified bacteriophage that includes a polynucleotide sequence with at least 84.9%, 84.8%, 84.7%, 84.6%, 84.5%, 84.4%, 84.3%, 84.2%, 84.1%, 84.0%, or 84% identity to SEQ ID NO: 2. In embodiments, provided herein is an isolated, purified bacteriophage that includes a polynucleotide sequence with at least 83.9%, 83.8%, 83.7%, 83.6%, 83.5%, 83.4%, 83.3%, 83.2%, 83.1%, 83.0%, or 83% identity to SEQ ID NO: 2. In embodiments, provided herein is an isolated, purified bacteriophage that includes a polynucleotide sequence with at least 82.9%, 82.8%, 82.7%, 82.6%, 82.5%, 82.4%, 82.3%, 82.2%, 82.1%, 82.0%, or 82% identity to SEQ ID NO: 2. In embodiments, provided herein is an isolated, purified bacteriophage that includes a polynucleotide sequence with at least 81.9%, 81.8%, 81.7%, 81.6%, 81.5%, 81.4%, 81.3%, 81.2%, 81.1%, 81.0%, or 81% identity to SEQ ID NO:2. In embodiments, provided herein is an isolated, purified bacteriophage that includes a polynucleotide sequence with at least 80.9%, 80.8%, 80.7%, 80.6%, 80.5%, 80.4%, 80.3%, 80.2%, 80.1%, 80.0%, or 80% identity to SEQ ID NO: 2. In embodiments, the bacteriophage genome comprises the polynucleotide.

In an aspect, provided herein are bacteriophage compositions that include one or more bacteriophages.

In embodiments, provided herein are bacteriophage compositions that include two bacteriophages according to any embodiment described herein. In embodiments, provided herein are bacteriophage compositions that include two or more bacteriophages according to any embodiment described herein. In embodiments, provided herein are bacteriophage compositions that include three or more bacteriophages according to any embodiment described herein. In embodiments, provided herein are bacteriophage compositions include four or more bacteriophages according to any embodiment described herein. In embodiments, provided herein are bacteriophage compositions that include five or more bacteriophages according to any embodiment described herein.

In embodiments, the composition includes one or more bacteriophages that are resistant to inactivation in the blood. In embodiments, the composition includes two or more bacteriophages that are resistant to inactivation in the blood. In embodiments, the composition includes three or more bacteriophages that are resistant to blood complement inactivation in the blood. In embodiments, the composition includes one or more bacteriophages that are resistant to blood complement C3 protein-mediated inactivation in the blood. In embodiments, the composition includes two or more bacteriophages that are resistant to blood complement C3 protein-mediated inactivation in the blood. In embodiments, the composition includes three or more bacteriophages that are resistant to blood complement C3 protein-mediated inactivation in the blood.

In embodiments, the composition includes bacteriophages that target *Staphylococcus* bacteria. In embodiments, the composition includes bacteriophage that target *Staphylococcus aureus*. In embodiments, the composition includes bacteriophage that target one or more of vancomycin-intermediate *Staphylococcus aureus* (VISA), vancomycin-resistant *Staphylococcus aureus* (VRSA), and/or methicillin-resistant *Staphylococcus aureus* (MRSA). In embodiments, the composition includes bacteriophage that target vancomycin-intermediate *Staphylococcus aureus* (VISA). In embodiments, the composition includes bacteriophage that target vancomycin-resistant *Staphylococcus aureus* (VRSA). In embodiments, the composition includes bacteriophage that target methicillin-resistant *Staphylococcus aureus* (MRSA).

In embodiments, the composition includes bacteriophage that infect and kill *Staphylococcus* bacteria. In embodiments, the composition includes bacteriophage that infect and kill *Staphylococcus aureus*. In embodiments, the composition includes bacteriophage that infect and kill one or more of VISA, VRSA, and/or MRSA. In embodiments, the composition includes bacteriophage that infect and kill VISA. In embodiments, the composition includes bacteriophage that infect and kill VRSA. In embodiments, the composition includes bacteriophage that infect and kill MRSA.

In embodiments, provided herein are bacteriophage compositions that include one or more bacteriophages that belong to the genus *Silviavirus*. In embodiments, the bacteriophage composition includes a strain from bacteriophage genus *Silviavirus*. In embodiments, the bacteriophage composition includes a bacteriophage selected from MR003 (Accession No. AP019522.1), Qdsa001 (Accession No. KY779848.1), Remus (Accession No. NC_022090.1), Romulus (Accession No. NC_020877.1), SA11 (Accession No. NC_019511.12), StAP1 (Accession No. KC532239.1), and Stsau2 (Accession No. NC_030933.1). In some embodiments of the bacteriophage composition, the bacteriophage is *Silviavirus Staphylococcus* virus Remus. In some embodiments of the bacteriophage composition, the bacteriophage is *Silviavirus Staphylococcus* virus SA11. In some embodiments of the bacteriophage composition, the bacteriophage is *Silviavirus Staphylococcus* virus Romulus. In some embodiments of the bacteriophage composition, the bacteriophage is *Silviavirus Staphylococcus* virus Qdsa001. In some embodiments of the bacteriophage composition, the bacteriophage is *Silviavirus Staphylococcus* virus MR003. In some embodiments of the bacteriophage composition, the bacteriophage is *Silviavirus Staphylococcus* virus StAP1. In some embodiments of the bacteriophage composition, the bacteriophage is *Silviavirus Staphylococcus* virus Stsau2.

In an aspect, provided herein are bacteriophage compositions that include one or more bacteriophages selected from a bacteriophage including a polynucleotide sequence of SEQ ID NO: 1, SEQ ID NO: 2, a polynucleotide sequence with at least 93% identity to SEQ ID NO: 1, and a polynucleotide sequence with at least 93% identity to SEQ ID NO: 2. In another aspect, the compositions include one or more bacteriophages selected from a bacteriophage including a polynucleotide sequence of SEQ ID NO: 1, SEQ ID NO: 2, a polynucleotide sequence with at least 90% identity to SEQ ID NO: 1, and a polynucleotide sequence with at least 9% identity to SEQ ID NO: 2.

In embodiments, the bacteriophage composition includes a bacteriophage that includes a polynucleotide sequence of SEQ ID NO: 1. In embodiments, the bacteriophage composition includes a bacteriophage that includes a polynucleotide sequence of SEQ ID NO: 2. In embodiments, the bacteriophage composition includes a bacteriophage that includes a polynucleotide sequence with at least 99.9%, 99.8%, 99.7%, 99.6%, 99.5%, 99.4%, 99.3%, 99.2%, 99.1%, 99.0%, or 99% identity to SEQ ID NO: 1. In embodiments, the bacteriophage composition includes a bacteriophage that includes a polynucleotide sequence with at least 98.9%, 98.8%, 98.7%, 98.6%, 98.5%, 98.4%, 98.3%, 98.2%, 98.1%, 98.0%, or 98% identity to SEQ ID NO: 1. In embodiments, the bacteriophage composition includes a bacteriophage that includes a polynucleotide sequence with at least 97.9%, 97.8%, 97.7%, 97.6%, 97.5%, 97.4%, 97.3%, 97.2%, 97.1%, 97.0%, or 97% identity to SEQ ID NO: 1. In embodiments, the bacteriophage composition includes a bacteriophage that includes a polynucleotide sequence with at least 96.9%, 96.8%, 96.7%, 96.6%, 96.5%, 96.4%, 96.3%, 96.2%, 96.1%, 96.0%, or 96% identity to SEQ ID NO: 1. In embodiments, the bacteriophage composition includes a bacteriophage that includes a polynucleotide sequence with at least 95.9%, 95.8%, 95.7%, 95.6%, 95.5%, 95.4%, 95.3%, 95.2%, 95.1%, 95.0%, or 95% identity to SEQ ID NO: 1. In embodiments, the bacteriophage composition includes a bacteriophage that includes a polynucleotide sequence with at least 94.9%, 94.8%, 94.7%, 94.6%, 94.5%, 94.4%, 94.3%, 94.2%, 94.1%, 94.0%, or 94% identity to SEQ ID NO: 1. In embodiments, the bacteriophage composition includes a bacteriophage that includes a polynucleotide sequence with at least 93.9%, 93.8%, 93.7%, 93.6%, 93.5%, 93.4%, 93.3%, 93.2%, 93.1%, 93.0%, or 93% identity to SEQ ID NO: 1. In embodiments, the bacteriophage composition includes a bacteriophage that includes a polynucleotide sequence with at least 92.9%, 92.8%, 92.7%, 92.6%, 92.5%, 92.4%, 92.3%, 92.2%, 92.1%, 92.0%, or 92% identity to SEQ ID NO: 1. In embodiments, the bacteriophage composition includes a bacteriophage that includes a polynucleotide sequence with at least 91.9%, 91.8%, 91.7%, 91.6%, 91.5%, 91.4%, 91.3%, 91.2%, 91.1%, 91.0%, or 91% identity to SEQ ID NO: 1. In embodiments, the bacteriophage composition includes a bacteriophage that includes a polynucleotide sequence with at least 90.9%, 90.8%, 90.7%, 90.6%, 90.5%, 90.4%, 90.3%, 90.2%, 90.1%, 90.0%, or 90% identity to SEQ ID NO: 1. In embodiments, the bacteriophage composition includes a bacteriophage that includes a polynucleotide sequence with at least 89.9%, 89.8%, 89.7%, 89.6%, 89.5%, 89.4%, 89.3%, 89.2%, 89.1%, 89.0%, or 89% identity to SEQ ID NO: 1. In embodiments, the bacteriophage composition includes a bacteriophage that includes a polynucleotide sequence with at least 88.9%, 88.8%, 88.7%, 88.6%, 88.5%, 88.4%, 88.3%, 88.2%, 88.1%, 88.0%, or 88% identity to SEQ ID NO: 1. In embodiments, the bacteriophage composition includes a bacteriophage that includes a polynucleotide sequence with at least 87.9%, 87.8%, 87.7%, 87.6%, 87.5%, 87.4%, 87.3%, 87.2%, 87.1%, 87.0%, or 87% identity to SEQ ID NO: 1. In embodiments, the bacteriophage composition includes a bacteriophage that includes a polynucleotide sequence with at least 86.9%, 86.8%, 86.7%, 86.6%, 86.5%, 86.4%, 86.3%, 86.2%, 86.1%, 86.0%, or 86% identity to SEQ ID NO: 1. In embodiments, the bacteriophage composition includes a bacteriophage that includes a polynucleotide sequence with at least 85.9%, 85.8%, 85.7%, 85.6%, 85.5%, 85.4%, 85.3%, 85.2%, 85.1%, 85.0%, or 85% identity to SEQ ID NO: 1. In embodiments, the bacteriophage composition includes a bacteriophage that includes a polynucleotide sequence with at least 84.9%, 84.8%, 84.7%, 84.6%, 84.5%, 84.4%, 84.3%, 84.2%, 84.1%, 84.0%, or 84% identity to SEQ ID NO: 1. In embodiments, the bacteriophage composition includes a bacteriophage that includes a polynucleotide sequence with at least 83.9%, 83.8%, 83.7%, 83.6%, 83.5%, 83.4%, 83.3%, 83.2%, 83.1%, 83.0%, or 83% identity to SEQ ID NO: 1. In embodiments, the bacteriophage composition includes a bacteriophage that includes a polynucleotide sequence with at least 82.9%, 82.8%, 82.7%, 82.6%, 82.5%, 82.4%, 82.3%, 82.2%, 82.1%, 82.0%, or 82% identity to SEQ ID NO: 1. In embodiments, the bacteriophage composition includes a bacteriophage that includes a polynucleotide sequence with at least 81.9%, 81.8%, 81.7%, 81.6%, 81.5%, 81.4%, 81.3%, 81.2%, 81.1%, 81.0%, or 81% identity to SEQ ID NO: 1. In embodiments, the bacteriophage composition includes a bacteriophage that includes a polynucleotide sequence with at least 80.9%, 80.8%, 80.7%, 80.6%, 80.5%, 80.4%, 80.3%, 80.2%, 80.1%, 80.0%, or 80% identity to SEQ ID NO: 1. In embodiments, the bacteriophage genome comprises the polynucleotide.

In embodiments, the bacteriophage composition includes a bacteriophage that includes a polynucleotide sequence with at least 99.9%, 99.8%, 99.7%, 99.6%, 99.5%, 99.4%, 99.3%, 99.2%, 99.1%, 99.0%, or 99% identity to SEQ ID NO: 2. I In embodiments, the bacteriophage composition includes a bacteriophage that includes a polynucleotide sequence with at least 98.9%, 98.8%, 98.7%, 98.6%, 98.5%, 98.4%, 98.3%, 98.2%, 98.1%, 98.0%, or 98% identity to SEQ ID NO: 2. In embodiments, the bacteriophage composition includes a bacteriophage that includes a polynucleotide sequence with at least 97.9%, 97.8%, 97.7%, 97.6%, 97.5%, 97.4%, 97.3%, 97.2%, 97.1%, 97.0%, or 97% identity to SEQ ID NO: 2. In embodiments, the bacteriophage composition includes a bacteriophage that includes a polynucleotide sequence with at least 96.9%, 96.8%, 96.7%, 96.6%, 96.5%, 96.4%, 96.3%, 96.2%, 96.1%, 96.0%, or 96% identity to SEQ ID NO: 2. In embodiments, the bacteriophage composition includes a bacteriophage that includes a polynucleotide sequence with at least 95.9%, 95.8%, 95.7%, 95.6%, 95.5%, 95.4%, 95.3%, 95.2%, 95.1%, 95.0%, or 95% identity to SEQ ID NO: 2. In embodiments, the bacteriophage composition includes a bacteriophage that includes a polynucleotide sequence with at least 94.9%, 94.8%, 94.7%, 94.6%, 94.5%, 94.4%, 94.3%, 94.2%, 94.1%, 94.0%, or 94% identity to SEQ ID NO: 2. In embodiments, the bacteriophage composition includes a bacteriophage that includes a polynucleotide sequence with at least 93.9%, 93.8%, 93.7%, 93.6%, 93.5%, 93.4%, 93.3%, 93.2%, 93.1%, 93.0%, or 93% identity to SEQ ID NO: 2. In embodiments, the bacteriophage composition includes a bacteriophage that includes a polynucleotide sequence with at least 92.9%, 92.8%, 92.7%, 92.6%, 92.5%, 92.4%, 92.3%, 92.2%, 92.1%, 92.0%, or 92% identity to SEQ ID NO: 2. In embodiments, the bacteriophage composition includes a bacteriophage that includes a polynucleotide sequence with at least 91.9%, 91.8%, 91.7%, 91.6%, 91.5%, 91.4%, 91.3%, 91.2%, 91.1%, 91.0%, or 91% identity to SEQ ID NO: 2. In embodiments, the bacteriophage composition includes a bacteriophage that includes a polynucleotide sequence with at least 90.9%, 90.8%, 90.7%, 90.6%, 90.5%, 90.4%, 90.3%, 90.2%, 90.1%, 90.0%, or 90% identity to SEQ ID NO: 2. In embodiments, the bacteriophage composition includes a bacteriophage that includes a polynucleotide sequence with at least 89.9%, 89.8%, 89.7%, 89.6%, 89.5%, 89.4%, 89.3%, 89.2%, 89.1%, 89.0%, or 89% identity to SEQ ID NO: 2. In embodiments, the bacteriophage composition includes a bacteriophage that includes a polynucleotide sequence with at least 88.9%, 88.8%, 88.7%, 88.6%, 88.5%, 88.4%, 88.3%, 88.2%, 88.1%, 88.0%, or 88% identity to SEQ ID NO: 2. In embodiments, the bacteriophage composition includes a bacteriophage that includes a polynucleotide sequence with at least 87.9%, 87.8%, 87.7%, 87.6%, 87.5%, 87.4%, 87.3%, 87.2%, 87.1%, 87.0%, or 87% identity to SEQ ID NO: 2. In embodiments, the bacteriophage composition includes a bacteriophage that includes a polynucleotide sequence with at least 86.9%, 86.8%, 86.7%, 86.6%, 86.5%, 86.4%, 86.3%, 86.2%, 86.1%, 86.0%, or 86% identity to SEQ ID NO: 2. In embodiments, the bacteriophage composition includes a bacteriophage that includes a polynucleotide sequence with at least 85.9%, 85.8%, 85.7%, 85.6%, 85.5%, 85.4%, 85.3%, 85.2%, 85.1%, 85.0%, or 85% identity to SEQ ID NO: 2. In embodiments, the bacteriophage composition includes a bacteriophage that includes a polynucleotide sequence with at least 84.9%, 84.8%, 84.7%, 84.6%, 84.5%, 84.4%, 84.3%, 84.2%, 84.1%, 84.0%, or 84% identity to SEQ ID NO: 2. In embodiments, the bacteriophage composition includes a bacteriophage that includes a polynucleotide sequence with at least 83.9%, 83.8%, 83.7%, 83.6%, 83.5%, 83.4%, 83.3%, 83.2%, 83.1%, 83.0%, or 83% identity to SEQ ID NO: 2. In embodiments, the bacteriophage composition includes a bacteriophage that includes a polynucleotide sequence with at least 82.9%, 82.8%, 82.7%, 82.6%, 82.5%, 82.4%, 82.3%, 82.2%, 82.1%, 82.0%, or 82% identity to SEQ ID NO: 2. In embodiments, the bacteriophage composition includes a bacteriophage that includes a polynucleotide sequence with at least 81.9%, 81.8%, 81.7%, 81.6%, 81.5%, 81.4%, 81.3%, 81.2%, 81.1%, 81.0%, or 81% identity to SEQ ID NO: 2. In embodiments, the bacteriophage composition includes a bacteriophage that includes a polynucleotide sequence with at least 80.9%, 80.8%, 80.7%, 80.6%, 80.5%, 80.4%, 80.3%, 80.2%, 80.1%, 80.0%, or 80% identity to SEQ ID NO: 2. In embodiments, the bacteriophage genome comprises the polynucleotide.

In embodiments, provided herein are bacteriophage compositions that include two or more bacteriophages selected from bacteriophage including a polynucleotide sequence of SEQ ID NO: 1, SEQ ID NO: 2, a polynucleotide sequence with at least 93% identity to SEQ ID NO: 1, and a polynucleotide sequence with at least 93% identity to SEQ ID NO: 2; and where the composition's target bacteria range is broader than the cumulative range of the individual bacteriophage in the composition. In another aspect, the bacteriophages compositions may include two or more bacteriophages selected from bacteriophages including a polynucleotide sequence of SEQ ID NO: 1, SEQ ID NO: 2, a polynucleotide sequence with at least 90% identity to SEQ ID NO: 1, and a polynucleotide sequence with at least 90% identity to SEQ ID NO: 2; and where the composition's target bacteria range is broader than the cumulative range of the individual bacteriophage in the composition.

In embodiments, the bacteriophage composition includes one or more additional bacteriophages. In some embodiments, the one or more additional bacteriophages are suitable for treating a bacterial infection, in particular a *Staphylococcus* infection. In embodiments, the additional one or more phage can be natural or non-naturally occurring. In embodiments, the one or more additional phage can be a phage with at least 80% nucleic acid sequence identity to any of the phage described herein. In embodiments, the one or more additional phage can be a phage with at least 80% nucleic acid sequence identity to SEQ ID NO: 1. In embodiments, the one or more additional phage can be a phage with at least 80% nucleic acid sequence identity to SEQ ID NO: 2. In embodiments, the bacteriophage include a polynucleotide sequence with at least 80% but not 100% identity to any one of SEQ ID NO: 1 or SEQ ID NO: 2.

In embodiments, the range of target bacteria of the bacteriophage composition is broader than the range of target bacteria of any single bacteriophage included within the composition. Such activity can be considered synergistic as the effect of the composition (target killing range) is greater than the sum of individual effects (target killing range) of each component bacteriophage. In embodiments, provided herein are bacteriophage compositions where the composition's target bacteria range can have an effectiveness that is greater than the sum of effectiveness of the individual bacteriophage.

In embodiments, provided herein are bacteriophage compositions that include two or more bacteriophages, where the composition includes a bacteriophage with polynucleotide sequence of SEQ ID NO: 1 and the composition targets more *Staphylococcus aureus* strains than a bacteriophage with polynucleotide sequence of SEQ ID NO: 1. In embodiments, provided herein are bacteriophage compositions that include two or more bacteriophage, where the composition includes a bacteriophage with a polynucleotide sequence with at least 93% identity with SEQ ID NO: 1 and the composition targets more *Staphylococcus aureus* strains than a bacteriophage with a polynucleotide sequence with at least 93% identity with SEQ ID NO: 1. In embodiments, the composition includes a bacteriophage with a polynucleotide sequence with at least 90% identity with SEQ ID NO: 1 and the composition targets more *Staphylococcus aureus* strains than a bacteriophage with a polynucleotide sequence with at least 90% identity with SEQ ID NO: 1. In embodiments, provided herein are bacteriophage compositions that include two or more bacteriophages, where the composition includes a bacteriophage with polynucleotide sequence of SEQ ID NO: 2 and the composition targets more *Staphylococcus aureus* strains than a bacteriophage with polynucleotide sequence of SEQ ID NO: 2. In embodiments, provided herein are bacteriophage compositions that include two or more bacteriophage, where the composition includes a bacteriophage with a polynucleotide sequence with at least 93% identity with SEQ ID NO: 2 and the composition targets more *Staphylococcus aureus* strains than a bacteriophage with a polynucleotide sequence with at least 93% identity with SEQ ID NO: 2. In embodiments, provided herein are bacteriophage compositions that include two or more bacteriophage, where the composition includes a bacteriophage with a polynucleotide sequence with at least 90% identity with SEQ ID NO: 2 and the composition targets more *Staphylococcus aureus* strains than a bacteriophage with a polynucleotide sequence with at least 90% identity with SEQ ID NO: 2. In embodiments, the compositions can have any combination polynucleotide sequences of SEQ ID NO: 1 and SEQ ID NO: 2.

Provided herein are bacteriophage compositions that include two or more bacteriophage, where the composition includes at least one bacteriophage that is genetically modified. Provided herein are bacteriophage compositions that include two or more bacteriophage, where the composition includes at least one naturally occurring phage. Provided herein are bacteriophage compositions that include two or more bacteriophage, where the composition excludes naturally occurring phage. Provided herein are bacteriophage compositions that include two or more bacteriophage, where the composition includes one or more bacteriophage that is resistant to inactivation by the blood complement system.

In embodiments, the bacteriophage composition includes an additional component selected from a pharmaceutically acceptable carrier, diluent, excipient and combinations thereof. In embodiments, the bacteriophage composition includes a pharmaceutically acceptable carrier. In embodiments, the bacteriophage composition includes a diluent. In embodiments, the bacteriophage composition includes an excipient. In embodiments, the bacteriophage composition includes a combination of a pharmaceutically acceptable carrier, diluent, and an excipient. In embodiments, the bacteriophage composition includes a combination of a pharmaceutically acceptable carrier and diluent. In embodiments, the bacteriophage composition includes a combination of a pharmaceutically acceptable carrier and an excipient. In embodiments, the bacteriophage composition includes a combination of a diluent and an excipient.

In embodiments, the bacteriophage composition includes a storage media for storage at a temperature at or below 8° C. In embodiments, the bacteriophage composition includes a storage media for storage at a temperature at or below 7° C. In embodiments, the bacteriophage composition includes a storage media for storage at a temperature at or below 6° C. In embodiments, the bacteriophage composition includes a storage media for storage at a temperature at or below 5° C. In embodiments, the bacteriophage composition includes a storage media for storage at a temperature at or below 4° C. In embodiments, the bacteriophage composition includes a storage media for storage at a temperature at or below 3° C. In embodiments, the bacteriophage composition includes a storage media for storage at a temperature at or below 2° C. In embodiments, the bacteriophage composition includes a storage media for storage at a temperature at or below 1° C. In embodiments, the bacteriophage composition includes a storage media for storage at a temperature at or below 0° C.

In embodiments, the bacteriophage composition is in a liquid, semi-liquid, solid, frozen, or lyophilized formulation. In embodiments, the bacteriophage composition is in a liquid formulation. In embodiments, the bacteriophage composition is in a semi-liquid formulation. In embodiments, the bacteriophage composition is in a solid formulation. In embodiments, the bacteriophage composition is in a frozen formulation. In embodiments, the bacteriophage composition is in a lyophilized formulation.

In embodiments, the bacteriophage composition is stored in containers containing from about 1 ml to about 5 ml injectable solution. In some embodiments, this includes single dose containers for single use. In other embodiments, this may include multi-dose containers containing injection solutions that provide multiple doses of the bacteriophage composition described herein. The composition may also be stored in various suitable containers, including, but not necessarily limited to, vials, cuvettes, cartridges, prefilled syringes, plastic bags, ampoules, bottles, pouches, pumps, sprayers, stoppers, needles, plungers, caps, stents, catheters, implants, or blister packages. In some embodiments, the aforementioned containers may be made of glass or plastic, or they may be plastic-coated, or may be made of various other suitable materials. Containers may be clear, or may provide protection from light by being amber colored or of various other colors, or may be wrapped in aluminum foil.

In some embodiments (alternatively or additionally), a "mutant" bacteriophage is capable of lysing some or all the same target bacterial strains as one or more of ARSA0001 and/or ARSA0002, and/or further capable of lysing one or more additional bacterial strains. In one embodiment, a mutant may have at least 90, 91, 92, 93%, 94%, 95%, 96%, 97%, 98%, or 99% sequence identity to a nucleic acid sequence of one or more of ARSA0001 and ARSA0002. In some embodiments, a mutant or variant may have at least 90, 91, 92, 93%, 94%, 95%, 96%, 97%, 98%, or 99% sequence identity across its entire genome sequence when compared to one or more of the genome sequence of ARSA0001 and ARSA0002. In one embodiment, a mutant may have at least 90, 91, 92, 93%, 94%, 95%, 96%, 97%, 98%, or 99% sequence identity across its entire genome sequence when compared to SEQ ID NO.: 1. In one embodiment, a mutant may have at least 90, 91, 92, 93%, 94%, 95%, 96%, 97%, 98%, or 99% sequence identity across its entire genome sequence when compared to SEQ ID NO.: 2.

In embodiments, a "mutant" may be a bacteriophage progeny. A bacteriophage progeny may be a bacteriophage obtainable after lysing *Staphylococcus* (e.g., *S. aureus*) target bacteria using a bacteriophage as described herein (i.e., the "parent bacteriophage"). In other words, the bacteriophage progeny may be a second (or further) generation bacteriophage.

In embodiments, "genetically modified" may be a bacteriophage whose polynucleotide sequence has been altered by genetic engineering techniques. Genetic engineering of polynucleotide sequences can be achieved by any modern molecular biology technique well known in the art, including but not limited to homologous recombination, bacteriophage engineering, CRISPR-Cas based manipulation, transformation of full-length naked phage into a host bacteria, and any combinations of techniques thereof.

In embodiments, a bacteriophage progeny is obtainable by contacting one or more bacteriophage(s) described herein, including for example, one selected from ARSA0001 or ARSA0002, with a *Staphylococcus* target bacteria such that the one or more bacteriophage(s) infects and lyses the target bacteria; and obtaining a bacteriophage released following lysis of the target bacteria. The bacteriophage progeny will typically comprise one or more nucleotide(s) mutation(s) when compared to the relevant parent bacteriophage.

In embodiments, the bacteriophage may be provided in the form of a single therapeutic composition or as a number of separate compositions each comprising one or more bacteriophage components of the composition. In embodiments where the bacteriophages are provided in a number of separate compositions, the bacteriophages may be administered to a subject sequentially or simultaneously (suitably simultaneously).

In embodiments, the bacteriophage composition includes bacteriophage concentrations between $1\times10^5$ and $1\times10^{11}$ PFU per ml of each bacteriophage. In embodiments, the bacteriophage composition includes bacteriophage concentrations between $1\times10^6$ and $1\times10^{11}$ PFU per ml of each bacteriophage. In embodiments, the bacteriophage composition includes bacteriophage concentrations between $1\times10^7$ and $1\times10^{11}$ PFU per ml of each bacteriophage. In some embodiments, the bacteriophage composition includes bacteriophage concentrations between $1\times10^8$ and $1\times10^{11}$ PFU per ml of each bacteriophage. In some embodiments, the composition includes $1\times10^8$ to $1\times10^9$ PFU, $1\times10^8$ to $1\times10^{10}$ PFU, $1\times10^8$ to $1\times10^{11}$ PFU, $1\times10^9$ to $1\times10^{10}$ PFU, $1\times10^9$ to $1\times10^{11}$ PFU, or $1\times10^{10}$ to $1\times10^{11}$ PFU of each phage per ml of composition. In some embodiments, a bacteriophage composition is administered to a subject at a dosage of at least about $1\times10^8$ PFU of each phage, at least about $1\times10^9$ PFU of each phage, at least about $1\times10^{10}$ PFU of each phage, or at least about $1\times10^{11}$ PFU of each phage per ml of composition. In embodiments, one or more bacteriophage(s) may be combined to form a composition that includes $1\times10^8$, $1\times10^9$ or $1\times10^{10}$, or $1\times10^{11}$ PFU of each phage per ml of composition. Concentrations include any value or range within the recited ranges, including endpoints. In specific embodiments, the composition may be administered at a dosage of at least $1\times10^8$ PFU of total bacteriophages per milliliter. In specific embodiments, the composition may be administered at a dosage of at least $1\times10^9$ PFU of total bacteriophages per milliliter.

In some embodiments, the total dosage may vary depending on the formulation and storage container. In some embodiments, the total dosage may be lower or higher when administered to the patient, depending on whether it is delivered from a single-dose pre-filled syringe, or a multi-dose container. In some embodiments, the bacteriophage composition may be administered at a basal dose rate or a bolus rate. In some embodiments, the bacteriophage composition may be administered by an IV fluid drip.

In embodiments, the bacteriophage composition is stored at a range between 2-8° C. In some embodiments, the bacteriophage composition is stored between 2 and 3° C. In some embodiments, the bacteriophage composition is stored between 2 and 4° C. In some embodiments, the bacteriophage composition is stored between 2 and 5° C. In some embodiments, the bacteriophage composition is stored between 2 and 6° C. In some embodiments, the bacteriophage composition is stored between 2 and 7° C. In some embodiments, the bacteriophage composition is stored between 3 and 4° C. In some embodiments, the bacteriophage composition is stored between 3 and 5° C. In some embodiments, the bacteriophage composition is stored between 3 and 6° C. In some embodiments, the bacteriophage composition is stored between 3 and 7° C. In some embodiments, the bacteriophage composition is stored between 3 and 8° C. In some embodiments, the bacteriophage composition is stored between 4 and 5° C. In some embodiments, the bacteriophage composition is stored between 4 and 6° C. In some embodiments, the bacteriophage composition is stored between 4 and 7° C. In some embodiments, the bacteriophage composition is stored between 4 and 8° C. In some embodiments, the bacteriophage composition is stored between 5 and 8° C. In some embodiments, the bacteriophage composition is stored between 5 and 6° C. In some embodiments, the bacteriophage composition is stored between 5 and 7° C. In some embodiments, the bacteriophage composition is stored between 6 and 8° C. In some embodiments, the bacteriophage composition is stored between 6 and 7° C. In some embodiments, the bacteriophage composition is stored between 7 and 8° C. In some embodiments, the bacteriophage composition is stored at 2, 3, 4, 5, 6, 7, or 8° C. The temperature may be any value or subrange within the recited ranges, including endpoints.

In embodiments, the bacteriophage composition is stored at room temperature. In embodiments, the bacteriophage composition is stored at about 20-30° C. In embodiments, the bacteriophage composition is stored at about 20-25° C. In embodiments, the bacteriophage composition is stored at about 20-22° C. In embodiments, the bacteriophage composition is stored at about 20° C. In embodiments, the bacteriophage composition is stored at about 21° C. In embodiments, the bacteriophage composition is stored at about 22° C. In embodiments, the bacteriophage composition is stored at 23° C. In embodiments, the bacteriophage composition is stored at 24° C. In embodiments, the bacteriophage composition is stored at 25° C. The temperature may be any value or subrange within the recited ranges, including endpoints.

In embodiments, the bacteriophage composition is resistant to inactivation by the immune system of a subject. In some embodiments, the bacteriophage is resistant to inactivation by the mononuclear phagocytosis system of a subject. In some embodiments, the bacteriophage is resistant to inactivation by the complement system of a subject. In some embodiments, the bacteriophage is resistant to inactivation by the blood complement system of a subject. In some embodiments, the bacteriophage is resistant to inactivation by the blood complement C3-complex of proteins of a subject.

In embodiments, the bacteriophage composition includes at least one lytic bacteriophage. In some embodiments, the bacteriophage includes at least one lytic phage that can kill a bacterium and release phage progeny through cell lysis.

In an aspect, provided herein is a bacterial host manufacturing strain including a bacteriophage where the bacteriophage includes a polynucleotide sequence selected from SEQ ID NO: 1, SEQ ID NO: 2, a polynucleotide sequence with at least 93% identity to SEQ ID NO: 1, and a polynucleotide sequence with at least 93% identity to SEQ ID NO: 2. In another aspect, provided herein is a bacterial host manufacturing strain including a bacteriophage where the bacteriophage includes a polynucleotide sequence selected from SEQ ID NO: 1, SEQ ID NO: 2, a polynucleotide sequence with at least 90% identity to SEQ ID NO: 1, and a polynucleotide sequence with at least 90% identity to SEQ ID NO: 2.

In embodiments, provided herein is a bacterial host manufacturing strain including a bacteriophage that includes a polynucleotide sequence of SEQ ID NO: 1. In embodiments, provided herein is a bacterial host manufacturing strain including a bacteriophage that includes a polynucleotide sequence of SEQ ID NO: 2. In embodiments, provided herein is a bacterial host manufacturing strain including a bacteriophage that includes a polynucleotide sequence of with at least 93% identity to SEQ ID NO: 1. In embodiments, provided herein is a bacterial host manufacturing strain including a bacteriophage that includes a polynucleotide sequence of polynucleotide sequence with at least 93% identity to SEQ ID NO: 2. In other embodiments, provided herein is a bacterial host manufacturing strain including a bacteriophage that includes a polynucleotide sequence of with at least 90% identity to SEQ ID NO: 1. In embodiments, provided herein is a bacterial host manufacturing strain including a bacteriophage that includes a polynucleotide sequence of polynucleotide sequence with at least 90% identity to SEQ ID NO: 2. In embodiments, provided herein is a bacterial host manufacturing strain including a bacteriophage according to any of the various embodiments described herein.

In embodiments, provided herein are uses of a composition according to any of the various embodiments described herein in the treatment of a *Staphylococcus aureus* infection in a subject. In embodiments, the use includes administering a composition according to any of the embodiments described herein to a subject suffering from a *Staphylococcus aureus* infection.

In embodiments, provided herein are uses of a composition including one or more distinct bacteriophages that target *Staphylococcus aureus* in the treatment of subject with a *Staphylococcus aureus* bacterial infection. The uses include administering the composition to said subject; wherein at least one of the bacteriophage is selected from a bacteriophage comprising a polynucleotide sequence of SEQ ID NO: 1, SEQ ID NO: 2, a polynucleotide sequence with at least 93% identity to SEQ ID NO: 1, and a polynucleotide sequence with at least 93% identity to SEQ ID NO: 2. The uses may include administering the composition to said subject; wherein at least one of the bacteriophage is selected from a bacteriophage comprising a polynucleotide sequence of SEQ ID NO: 1, SEQ ID NO: 2, a polynucleotide sequence with at least 90% identity to SEQ ID NO: 1, and a polynucleotide sequence with at least 90% identity to SEQ ID NO: 2.

Methods of Use

In an aspect, provided herein are methods of treating a subject with a bacterial infection including selecting a bacteriophage based upon resistance to blood complement inactivation and administering the bacteriophage to the subject.

In embodiments, selecting a bacteriophage includes performing a blood/serum resistance assay and selecting bacteriophage based on survival in the blood/serum for a pre-determined amount of time.

In an aspect, provided herein are methods of treating a subject with a bacterial infection including administering to the subject one or more distinct bacteriophage selected from a bacteriophage including a polynucleotide sequence selected from SEQ ID NO: 1, SEQ ID NO: 2, a polynucleotide sequence with at least 93% identity to SEQ ID NO: 1, and a polynucleotide sequence with at least 93% identity to SEQ ID NO: 2. In another aspect, provided herein are methods of treating a subject with a bacterial infection including administering to the subject one or more distinct bacteriophage selected from a bacteriophage including a polynucleotide sequence selected from SEQ ID NO: 1, SEQ ID NO: 2, a polynucleotide sequence with at least 90% identity to SEQ ID NO: 1, and a polynucleotide sequence with at least 90% identity to SEQ ID NO: 2. In an aspect, provided herein are methods of treating a subject with a bacterial infection including administering to the subject one or more distinct bacteriophage as described in any embodiment herein.

In embodiments, provided herein are methods of treating a subject with a bacterial infection. In some embodiments, the bacterial infection at least partially includes *Staphylococcus*. In some embodiments, the bacterial infection at least partially includes *Staphylococcus aureus*. In some embodiments, the bacterial infection includes *Staphylococcus aureus* strains resistant to chemical antibiotics. In some embodiments, the bacterial strains include drug resistant and/or multi-drug resistant *Staphylococcus aureus* strains. In some embodiments, the bacterial strain is the drug-resistant strain vancomycin-intermediate *Staphylococcus aureus*

(VISA). In some embodiments, the bacterial strain is the drug-resistant strain vancomycin-resistant *Staphylococcus aureus* (VRSA). In some embodiments, the bacterial strain is the drug-resistant strain methicillin-resistant *Staphylococcus aureus* (MRSA).

In embodiments, provided herein are methods of treating a subject with a bacterial infection including administering to a subject a bacteriophage that is resistant to inactivation in the blood. In embodiments, provided herein are methods of treating a subject with a bacterial infection including administering to a subject a bacteriophage that is resistant to inactivation by a blood complement system. In embodiments, the bacteriophage can be any bacteriophage as described herein.

In embodiments, provided herein are methods of treating a subject with a bacterial infection including administering to a subject a bacteriophage that includes a polynucleotide sequence of SEQ ID NO: 1. In embodiments, provided herein are methods of treating a subject with a bacterial infection including administering to a subject a bacteriophage that includes a polynucleotide sequence of SEQ ID NO: 2. In embodiments, provided herein are methods of treating a subject with a bacterial infection including administering to a subject a bacteriophage that includes a polynucleotide sequence with at least 93% identity to a SEQ ID NO: 1. In embodiments, provided herein are methods of treating a subject with a bacterial infection including administering to a subject a bacteriophage that includes a polynucleotide sequence with at least 90% identity to a SEQ ID NO: 1. In embodiments, provided herein are methods of treating a subject with a bacterial infection including administering to a subject a bacteriophage that includes a polynucleotide sequence with at least 93% identity to SEQ ID NO: 2. In embodiments, provided herein are methods of treating a subject with a bacterial infection including administering to a subject a bacteriophage that includes a polynucleotide sequence with at least 90% identity to SEQ ID NO: 2.

In embodiments, provided herein are methods of treating a subject with a bacterial infection including administering to a subject a bacteriophage that infects and kills one or more of vancomycin-intermediate *Staphylococcus aureus* (VISA), vancomycin-resistant *Staphylococcus aureus* (VRSA), methicillin-resistant *Staphylococcus aureus* (MRSA). In embodiments, provided herein are methods of treating a subject with a bacterial infection including administering to a subject a bacteriophage that infects and kills vancomycin-intermediate *Staphylococcus aureus* (VISA). In embodiments, the bacteriophage composition includes bacteriophage that infects and kills vancomycin-resistant *Staphylococcus aureus* (VRSA). In embodiments, provided herein are methods of treating a subject with a bacterial infection including administering to a subject a bacteriophage that infects and kills methicillin-resistant *Staphylococcus aureus* (MRSA).

In embodiments, provided herein are methods of treating a subject with a bacterial infection including administering to a subject one or more bacteriophages. In embodiments, the one or more bacteriophages are suitable for treating a bacterial infection, in particular a *Staphylococcus* infection. In embodiments, the bacteriophage includes one or more additional phages and can be a phage with 93%-100% nucleic acid sequence identity to any of the phage described herein. The bacteriophage can have a polynucleotide sequence, that includes a polynucleotide sequence having at least 93% but not 100% identity to any one of SEQ ID NO: 1 or SEQ ID NO: 2. In embodiments, the bacteriophage includes one or more additional phages and can be a phage with 90%-100% nucleic acid sequence identity to any of the phage described herein. The bacteriophage can have a polynucleotide sequence, that includes a polynucleotide sequence having at least 90% but not 100% identity to any one of SEQ ID NO: 1 or SEQ ID NO: 2. Percent identity may be any value or subrange within the recited ranges, including endpoints.

In embodiments, provided herein are methods of treating a subject with a bacterial infection including administering to a subject a bacteriophage composition that includes one or more bacteriophage and the composition's target bacteria range can be broader than the range of any individual bacteriophage or the phage collectively in the composition, or have an effectiveness that is greater than the sum of effectiveness of the individual bacteriophage. In embodiments, provided herein are methods of treating a subject with a bacterial infection including administering to a subject a bacteriophage composition that includes a bacteriophage with polynucleotide sequence SEQ ID NO: 1. In embodiments, provided herein are methods of treating a subject with a bacterial infection including administering to a subject a bacteriophage composition that includes a bacteriophage with a polynucleotide sequence at least 90% identity with SEQ ID NO: 1. In embodiments, provided herein are methods of treating a subject with a bacterial infection including administering to a subject a bacteriophage composition that includes a bacteriophage with a polynucleotide sequence at least 91% identity with SEQ ID NO: 1. In embodiments, provided herein are methods of treating a subject with a bacterial infection including administering to a subject a bacteriophage composition that includes a bacteriophage with a polynucleotide sequence at least 92% identity with SEQ ID NO: 1. In embodiments, provided herein are methods of treating a subject with a bacterial infection including administering to a subject a bacteriophage composition that includes a bacteriophage with a polynucleotide sequence at least 93% identity with SEQ ID NO: 1. In embodiments, provided herein are methods of treating a subject with a bacterial infection including administering to a subject a bacteriophage composition that includes a bacteriophage with a polynucleotide sequence at least 94% identity with SEQ ID NO: 1. In embodiments, provided herein are methods of treating a subject with a bacterial infection including administering to a subject a bacteriophage composition that includes a bacteriophage with a polynucleotide sequence at least 95% identity with SEQ ID NO: 1. In embodiments, provided herein are methods of treating a subject with a bacterial infection including administering to a subject a bacteriophage composition that includes a bacteriophage with a polynucleotide sequence at least 96% identity with SEQ ID NO: 1. In embodiments, provided herein are methods of treating a subject with a bacterial infection including administering to a subject a bacteriophage composition that includes a bacteriophage with a polynucleotide sequence at least 97% identity with SEQ ID NO: 1. In embodiments, provided herein are methods of treating a subject with a bacterial infection including administering to a subject a bacteriophage composition that includes a bacteriophage with a polynucleotide sequence at least 98% identity with SEQ ID NO: 1. In embodiments, provided herein are methods of treating a subject with a bacterial infection including administering to a subject a bacteriophage composition that includes a bacteriophage with a polynucleotide sequence at least 99% identity with SEQ ID NO: 1.

In embodiments, provided herein are methods of treating a subject with a bacterial infection including administering to a subject a bacteriophage composition that includes a bacteriophage with polynucleotide sequence SEQ ID NO: 2. In embodiments, provided herein are methods of treating a subject with a bacterial infection including administering to a subject a bacteriophage composition that includes a bacteriophage with a polynucleotide sequence at least 90% identity with SEQ ID NO: 2. In embodiments, provided herein are methods of treating a subject with a bacterial infection including administering to a subject a bacteriophage composition that includes a bacteriophage with a polynucleotide sequence at least 91% identity with SEQ ID NO: 2. In embodiments, provided herein are methods of treating a subject with a bacterial infection including administering to a subject a bacteriophage composition that includes a bacteriophage with a polynucleotide sequence at least 92% identity with SEQ ID NO: 2. In embodiments, provided herein are methods of treating a subject with a bacterial infection including administering to a subject a bacteriophage composition that includes a bacteriophage with a polynucleotide sequence at least 93% identity with SEQ ID NO: 2. In embodiments, provided herein are methods of treating a subject with a bacterial infection including administering to a subject a bacteriophage composition that includes a bacteriophage with a polynucleotide sequence at least 94% identity with SEQ ID NO: 2. In embodiments, provided herein are methods of treating a subject with a bacterial infection including administering to a subject a bacteriophage composition that includes a bacteriophage with a polynucleotide sequence at least 95% identity with SEQ ID NO: 2. In embodiments, provided herein are methods of treating a subject with a bacterial infection including administering to a subject a bacteriophage composition that includes a bacteriophage with a polynucleotide sequence at least 96% identity with SEQ ID NO: 2. In embodiments, provided herein are methods of treating a subject with a bacterial infection including administering to a subject a bacteriophage composition that includes a bacteriophage with a polynucleotide sequence at least 97% identity with SEQ ID NO: 2. In embodiments, provided herein are methods of treating a subject with a bacterial infection including administering to a subject a bacteriophage composition that includes a bacteriophage with a polynucleotide sequence at least 98% identity with SEQ ID NO: 2. In embodiments, provided herein are methods of treating a subject with a bacterial infection including administering to a subject a bacteriophage composition that includes a bacteriophage with a polynucleotide sequence at least 99% identity with SEQ ID NO: 2. In embodiments, provided herein are methods of treating a subject with a bacterial infection including administering to a subject a bacteriophage composition that have any combination polynucleotide sequences of SEQ ID NO: 1 and SEQ ID NO: 2.

In embodiments, provided herein are methods of treating a subject with a bacterial infection including administering to a subject a bacteriophage composition that includes at least one bacteriophage that is genetically modified. In embodiments, provided herein are methods of treating a subject with a bacterial infection including administering to a subject a bacteriophage composition that includes at least one naturally occurring phage or can exclude naturally occurring phage. In embodiments, provided herein are methods of treating a subject with a bacterial infection including administering to a subject a bacteriophage composition that includes at least one lytic phage. In embodiments, provided herein are methods of treating a subject with a bacterial infection including administering to a subject a bacteriophage composition that includes at least one bacteriophage resistant to inactivation by the blood complement system.

In an aspect, provided herein are methods of modifying the microbial flora in a subject including administering to the subject at least one bacteriophage that targets *Staphylococcus* bacteria, where the bacteriophage includes a polynucleotide sequence selected from SEQ ID NO: 1, SEQ ID NO: 2, a polynucleotide sequence with at least 93% identity to SEQ ID NO: 1, and a polynucleotide sequence with at least 93% identity to SEQ ID NO: 2. In another aspect, the bacteriophage may include a polynucleotide sequence selected from SEQ ID NO: 1, SEQ ID NO: 2, a polynucleotide sequence with at least 90% identity to SEQ ID NO: 1, and a polynucleotide sequence with at least 90% identity to SEQ ID NO: 2.

In embodiments, modifying the microbial flora includes killing the majority of a particular bacterial strain in the microbial flora, limiting growth a particular bacterial strain in the microbial flora, and/or slowing the growth of a particular bacterial strain in the microbial flora. In embodiments, modifying the microbial flora includes killing the majority of a particular bacterial strain in the microbial flora. In embodiments, modifying the microbial flora includes limiting growth a particular bacterial strain in the microbial flora. In embodiments, modifying the microbial flora includes slowing the growth of a particular bacterial strain in the microbial flora.

In embodiments, provided herein are methods of modifying the microbial flora in a subject including administering to the subject a bacteriophage that targets *Staphylococcus aureus* bacteria, where the bacteriophage includes a polynucleotide sequence of SEQ ID NO: 1. In embodiments, provided herein are methods of modifying the microbial flora in a subject including administering to the subject at least one bacteriophage that targets *Staphylococcus aureus* bacteria, where the bacteriophage includes a polynucleotide sequence of SEQ ID NO: 2. In embodiments, provided herein are methods of modifying the microbial flora in a subject including administering to the subject at least one bacteriophage that targets *Staphylococcus aureus* bacteria, where the bacteriophage includes a polynucleotide sequence with at least 93% identity to SEQ ID NO: 1. In embodiments, provided herein are methods of modifying the microbial flora in a subject including administering to the subject at least one bacteriophage that targets *Staphylococcus aureus* bacteria, where the bacteriophage includes a polynucleotide sequence with at least 93% identity to SEQ ID NO: 2. In embodiments, provided herein are methods of modifying the microbial flora in a subject including administering to the subject at least one bacteriophage that targets *Staphylococcus aureus* bacteria, where the bacteriophage includes a polynucleotide sequence with at least 90% identity to SEQ ID NO: 1. In embodiments, provided herein are methods of modifying the microbial flora in a subject including administering to the subject at least one bacteriophage that targets *Staphylococcus aureus* bacteria, where the bacteriophage includes a polynucleotide sequence with at least 90% identity to SEQ ID NO: 2.

In embodiments, provided herein are methods of modifying the microbial flora in a subject including administering to the subject a bacteriophage that infects and kills *Staphylococcus aureus* bacteria, where the bacteriophage includes a polynucleotide sequence of SEQ ID NO: 1. In embodiments, provided herein are methods of modifying the microbial flora in a subject including administering to the subject at least one bacteriophage that infects and kills *Staphylo-*

*coccus aureus* bacteria, where the bacteriophage includes a polynucleotide sequence of SEQ ID NO: 2. In embodiments, provided herein are methods of modifying the microbial flora in a subject including administering to the subject at least one bacteriophage that infects and kills *Staphylococcus aureus* bacteria, where the bacteriophage includes a polynucleotide sequence with at least 93% identity to SEQ ID NO: 1. In embodiments, provided herein are methods of modifying the microbial flora in a subject including administering to the subject at least one bacteriophage that infects and kills *Staphylococcus aureus* bacteria, where the bacteriophage includes a polynucleotide sequence with at least 93% identity to SEQ ID NO: 2. In embodiments, provided herein are methods of modifying the microbial flora in a subject including administering to the subject at least one bacteriophage that infects and kills *Staphylococcus aureus* bacteria, where the bacteriophage includes a polynucleotide sequence with at least 90% identity to SEQ ID NO: 1. In embodiments, provided herein are methods of modifying the microbial flora in a subject including administering to the subject at least one bacteriophage that infects and kills *Staphylococcus aureus* bacteria, where the bacteriophage includes a polynucleotide sequence with at least 90% identity to SEQ ID NO: 2.

In embodiments, provided herein are methods of modifying the microbial flora in a subject including administering to the subject a bacteriophage that that is genetically modified. In embodiments, provided herein are methods of modifying the microbial flora in a subject including administering to the subject at least one naturally occurring bacteriophage or can exclude naturally occurring phage. In embodiments, provided herein are methods of modifying the microbial flora in a subject including administering to the subject at least one lytic phage. In embodiments, provided herein are methods of modifying the microbial flora in a subject including administering to the subject at least one bacteriophage resistant to inactivation by the blood complement system.

In embodiments, provided herein are methods for administering a bacteriophage to a subject, where the bacteriophage includes a bacteriophage concentration range between $1\times10^8$ and $1\times10^{11}$ PFU per ml of each bacteriophage. In some embodiments, the bacteriophage concentration is $1\times10^8$ to $1\times10^9$ PFU, $1\times10^8$ to $1\times10^{10}$ PFU, or $1\times10^8$ to $1\times10^{11}$ PFU of each phage per ml of composition. In some embodiments, the bacteriophage concentration is $1\times10^9$ to $1\times10^{10}$ PFU, or $1\times10^9$ to $1\times10^{11}$ PFU of each phage per ml of composition. In some embodiments, the bacteriophage concentration is $1\times10^{10}$ to $1\times10^{11}$ PFU of each phage per ml of composition. In some embodiments, the bacteriophage is administered to a subject at a dosage of at least about $1\times10^8$ PFU of each phage, at least about $1\times10^9$ PFU of each phage, at least about $1\times10^{10}$ PFU of each phage, or at least about $1\times10^{11}$ PFU of each phage per ml of composition. In embodiments, one or more bacteriophage(s) may be combined to form a total concentration of $1\times10^8$, $1\times10^9$, $1\times10^{10}$, or $1\times10^{11}$ PFU of each phage per ml of composition. Concentrations include any value or range within the recited ranges, including endpoints.

In embodiments, the methods provided herein include administering a bacteriophage, where at least about 80% of bacteriophage retain lytic activity after exposure to human plasma for a time period between about 10 minutes and about 120 minutes. In embodiments, the methods provided herein include administering a bacteriophage, where at least about 81% of bacteriophage retain lytic activity after exposure to human plasma for a time period between about 10 minutes and about 120 minutes. In embodiments, the methods provided herein include administering a bacteriophage, where at least about 82% of bacteriophage retain lytic activity after exposure to human plasma for a time period between about 10 minutes and about 120 minutes. In embodiments, the methods provided herein include administering a bacteriophage, where at least about 83% of bacteriophage retain lytic activity after exposure to human plasma for a time period between about 10 minutes and about 120 minutes. In embodiments, the methods provided herein include administering a bacteriophage, where at least about 84% of bacteriophage retain lytic activity after exposure to human plasma for a time period between about 10 minutes and about 120 minutes. In embodiments, the methods provided herein include administering a bacteriophage, where at least about 85% of bacteriophage retain lytic activity after exposure to human plasma for a time period between about 10 minutes and about 120 minutes. In embodiments, the methods provided herein include administering a bacteriophage, where at least about 86% of bacteriophage retain lytic activity after exposure to human plasma for a time period between about 10 minutes and about 120 minutes. In embodiments, the methods provided herein include administering a bacteriophage, where at least about 87% of bacteriophage retain lytic activity after exposure to human plasma for a time period between about 10 minutes and about 120 minutes. In embodiments, the methods provided herein include administering a bacteriophage, where at least about 88% of bacteriophage retain lytic activity after exposure to human plasma for a time period between about 10 minutes and about 120 minutes. In embodiments, the methods provided herein include administering a bacteriophage, where at least about 89% of bacteriophage retain lytic activity after exposure to human plasma for a time period between about 10 minutes and about 120 minutes. In embodiments, the methods provided herein include administering a bacteriophage, where at least about 90% of bacteriophage retain lytic activity after exposure to human plasma for a time period between about 10 minutes and about 120 minutes. In embodiments, the methods provided herein include administering a bacteriophage, where at least about 90% of bacteriophage retain lytic activity after exposure to human plasma for a time period between about 10 minutes and about 120 minutes. In embodiments, the methods provided herein include administering a bacteriophage, where at least about 92% of bacteriophage retain lytic activity after exposure to human plasma for a time period between about 10 minutes and about 120 minutes. In embodiments, the methods provided herein include administering a bacteriophage, where at least about 93% of bacteriophage retain lytic activity after exposure to human plasma for a time period between about 10 minutes and about 120 minutes. In embodiments, the methods provided herein include administering a bacteriophage, where at least about 94% of bacteriophage retain lytic activity after exposure to human plasma for a time period between about 10 minutes and about 120 minutes. In embodiments, the methods provided herein include administering a bacteriophage, where at least about 95% of bacteriophage retain lytic activity after exposure to human plasma for a time period between about 10 minutes and about 120 minutes. In embodiments, the methods provided herein include administering a bacteriophage, where at least about 96% of bacteriophage retain lytic activity after exposure to human plasma for a time period between about 10 minutes and about 120 minutes. In embodiments, the methods provided herein include administering a bacteriophage, where at least about 97% of bacteriophage retain lytic activity after exposure to human plasma for a time period between about 10 minutes and about 120 minutes. In embodiments, the methods provided herein include administering a bacteriophage, where at least about 98% of bacteriophage retain lytic activity after exposure to human plasma for a time period between about 10 minutes and about 120 minutes. In embodiments, the methods provided herein include administering a bacteriophage, where at least about 99% of bacteriophage retain lytic activity after exposure to human plasma for a time period between about 10 minutes and about 120 minutes. In specific embodiments, the time period is between about 10 minutes and about 90 minutes.

In embodiments, the methods provided herein include administering a bacteriophage, where at least about 80% of bacteriophage retain lytic activity after exposure to human plasma for a time period between 10 and 20 minutes. In some embodiments, at least about 80% of bacteriophage retain lytic activity after exposure to human plasma for a time period between 10 and 30 minutes. In some embodiments, at least about 80% of bacteriophage retain lytic activity after exposure to human plasma for a time period between 10 and 40 minutes. In some embodiments, at least about 80% of bacteriophage retain lytic activity after exposure to human plasma for a time period between 10 and 50 minutes. In some embodiments, at least about 80% of bacteriophage retain lytic activity after exposure to human plasma for a time period between 10 and 60 minutes. In some embodiments, at least about 80% of bacteriophage retain lytic activity after exposure to human plasma for a time period between 10 and 70 minutes. In some embodiments, at least about 80% of bacteriophage retain lytic activity after exposure to human plasma for a time period between 10 and 80 minutes. In some embodiments, at least about 80% of bacteriophage retain lytic activity after exposure to human plasma for a time period between 10 and 90 minutes. In some embodiments, at least about 80% of bacteriophage retain lytic activity after exposure to human plasma for a time period between 10 and 100 minutes. In some embodiments, at least about 80% of bacteriophage retain lytic activity after exposure to human plasma for a time period between 10 and 110 minutes. In some embodiments, at least about 80% of bacteriophage retain lytic activity after exposure to human plasma for a time period between 10 and 120 minutes. In some embodiments, at least about 80% of bacteriophage retain lytic activity after exposure to human plasma for a time period between 20 and 30 minutes. In some embodiments, at least about 80% of bacteriophage retain lytic activity after exposure to human plasma for a time period between 20 and 40 minutes. In some embodiments, at least about 80% of bacteriophage retain lytic activity after exposure to human plasma for a time period between 20 and 50 minutes. In some embodiments, at least about 80% of bacteriophage retain lytic activity after exposure to human plasma for a time period between 20 and 60 minutes. In some embodiments, at least about 80% of bacteriophage retain lytic activity after exposure to human plasma for a time period between 20 and 70 minutes. In some embodiments, at least about 80% of bacteriophage retain lytic activity after exposure to human plasma for a time period between 20 and 80 minutes. In some embodiments, at least about 80% of bacteriophage retain lytic activity after exposure to human plasma for a time period between 20 and 90 minutes. In some embodiments, at least about 80% of bacteriophage retain lytic activity after exposure to human plasma for a time period between 20 and 100 minutes. In some embodiments, at least about 80% of bacteriophage retain lytic activity after exposure to human plasma for a time period between 20 and 110 minutes. In some embodiments, at least about 80% of bacteriophage retain lytic activity after exposure to human plasma for a time period between 20 and 120 minutes. In some embodiments, at least about 80% of bacteriophage retain lytic activity after exposure to human plasma for a time period between 30 and 40 minutes. In some embodiments, at least about 80% of bacteriophage retain lytic activity after exposure to human plasma for a time period between 30 and 50 minutes. In some embodiments, at least about 80% of bacteriophage retain lytic activity after exposure to human plasma for a time period between 30 and 60 minutes. In some embodiments, at least about 80% of bacteriophage retain lytic activity after exposure to human plasma for a time period between 30 and 70 minutes. In some embodiments, at least about 80% of bacteriophage retain lytic activity after exposure to human plasma for a time period between 30 and 80 minutes. In some embodiments, at least about 80% of bacteriophage retain lytic activity after exposure to human plasma for a time period between 30 and 90 minutes. In some embodiments, at least about 80% of bacteriophage retain lytic activity after exposure to human plasma for a time period between 30 and 100 minutes. In some embodiments, at least about 80% of bacteriophage retain lytic activity after exposure to human plasma for a time period between 30 and 110 minutes. In some embodiments, at least about 80% of bacteriophage retain lytic activity after exposure to human plasma for a time period between 30 and 120 minutes. In some embodiments, at least about 80% of bacteriophage retain lytic activity after exposure to human plasma for a time period between 40 and 50 minutes. In some embodiments, at least about 80% of bacteriophage retain lytic activity after exposure to human plasma for a time period between 40 and 60 minutes. In some embodiments, at least about 80% of bacteriophage retain lytic activity after exposure to human plasma for a time period between 40 and 70 minutes. In some embodiments, at least about 80% of bacteriophage retain lytic activity after exposure to human plasma for a time period between 40 and 80 minutes. In some embodiments, at least about 80% of bacteriophage retain lytic activity after exposure to human plasma for a time period between 40 and 90 minutes. In some embodiments, the bacteriophage is administered to a subject for a time between 40 and 100 minutes. In some embodiments, at least about 80% of bacteriophage retain lytic activity after exposure to human plasma for a time period between 40 and 110 minutes. In some embodiments, at least about 80% of bacteriophage retain lytic activity after exposure to human plasma for a time period between 40 and 120 minutes. In some embodiments, at least about 80% of bacteriophage retain lytic activity after exposure to human plasma for a time period between 50 and 60 minutes. In some embodiments, at least about 80% of bacteriophage retain lytic activity after exposure to human plasma for a time period between 50 and 70 minutes. In some embodiments, at least about 80% of bacteriophage retain lytic activity after exposure to human plasma for a time period between 50 and 80 minutes. In some embodiments, at least about 80% of bacteriophage retain lytic activity after exposure to human plasma for a time period between 50 and 90 minutes. In some embodiments, at least about 80% of bacteriophage retain lytic activity after exposure to human plasma for a time period between 50 and 100 minutes. In some embodiments, at least about 80% of bacteriophage retain lytic activity after exposure to human plasma for a time period between 50 and 110 minutes. In some embodiments, at least about 80% of bacteriophage retain lytic activity after exposure to human plasma for a time period between 50 and 120 minutes. In some embodiments, at least about 80% of bacteriophage retain lytic activity after exposure to human plasma for a time period between 60 and 70 minutes. In some embodiments, at least about 80% of bacteriophage retain lytic activity after exposure to human plasma for a time period between 60 and 80 minutes. In some embodiments, at least about 80% of bacteriophage retain lytic activity after exposure to human plasma for a time period between 60 and 90 minutes. In some embodiments, at least about 80% of bacteriophage retain lytic activity after exposure to human plasma for a time period between 60 and 100 minutes. In some embodiments, at least about 80% of bacteriophage retain lytic activity after exposure to human plasma for a time period between 60 and 110 minutes. In some embodiments, at least about 80% of bacteriophage retain lytic activity after exposure to human plasma for a time period between 60 and 120 minutes. In some embodiments, at least about 80% of bacteriophage retain lytic activity after exposure to human plasma for a time period between 70 and 80 minutes. In some embodiments, at least about 80% of bacteriophage retain lytic activity after exposure to human plasma for a time period between 70 and 90 minutes. In some embodiments, at least about 80% of bacteriophage retain lytic activity after exposure to human plasma for a time period between 70 and 100 minutes. In some embodiments, at least about 80% of bacteriophage retain lytic activity after exposure to human plasma for a time period between 70 and 110 minutes. In some embodiments, at least about 80% of bacteriophage retain lytic activity after exposure to human plasma for a time period between 70 and 120 minutes. In some embodiments, at least about 80% of bacteriophage retain lytic activity after exposure to human plasma for a time period between 80 and 90 minutes. In some embodiments, at least about 80% of bacteriophage retain lytic activity after exposure to human plasma for a time period between 80 and 100 minutes. In some embodiments, at least about 80% of bacteriophage retain lytic activity after exposure to human plasma for a time period between 80 and 110 minutes. In some embodiments, at least about 80% of bacteriophage retain lytic activity after exposure to human plasma for a time period between 80 and 120 minutes. In some embodiments, at least about 80% of bacteriophage retain lytic activity after exposure to human plasma for a time period between 90 and 100 minutes. In some embodiments, at least about 80% of bacteriophage retain lytic activity after exposure to human plasma for a time period between 90 and 110 minutes. In some embodiments, at least about 80% of bacteriophage retain lytic activity after exposure to human plasma for a time period between 90 and 120 minutes. In some embodiments, at least about 80% of bacteriophage retain lytic activity after exposure to human plasma for a time period between 100 and 110 minutes. In some embodiments, at least about 80% of bacteriophage retain lytic activity after exposure to human plasma for a time period between 100 and 120 minutes. In some embodiments, at least about 80% of bacteriophage retain lytic activity after exposure to human plasma for a time period between 110 and 120 minutes. The amount of time may be any value or subrange within the recited ranges, including endpoints. The bacteriophage composition retains at least greater than 80% of its lytic activity in human plasma at the end of the time point.

In embodiments, provided herein are methods of treating a subject with a bacterial infection including administering to a subject a bacteriophage that is at least partially resistant to inactivation by immune system of the administered subject. In embodiments, provided herein are methods of treating a subject with a bacterial infection including administering to a subject a bacteriophage that is resistant to inactivation by the mononuclear phagocytosis system of the administered subject. In embodiments, provided herein are methods of treating a subject with a bacterial infection including administering to a subject a bacteriophage that is resistant to inactivation by the complement system of the administered subject. In embodiments, provided herein are methods of treating a subject with a bacterial infection including administering to a subject a bacteriophage that is resistant to inactivation by the blood complement system of the administered subject. In embodiments, provided herein are methods of treating a subject with a bacterial infection including administering to a subject a bacteriophage that is resistant to inactivation by the blood complement C3-complex of proteins of the administered subject.

In embodiments, provided herein are methods of treating a subject with a bacterial infection including administering to a subject one or more bacteriophages that belong to the genus *Silviavirus*. In embodiments, provided herein are methods of treating a subject with a bacterial infection including administering to a subject a bacteriophage strain from the bacteriophage genus *Silviavirus*. In embodiments, the bacteriophage includes a bacteriophage selected from MR003 (Accession No. AP019522.1), Qdsa001 (Accession No. KY779848.1), Remus (Accession No. NC_022090.1), Romulus (Accession No. NC_020877.1), SA11 (Accession No. NC_019511.12), StAP1 (Accession No. KC532239.1), and Stsau2 (Accession No. NC_030933.1). In embodiments, the bacteriophage is *Silviavirus Staphylococcus* virus Remus. In embodiments, the bacteriophage is *Silviavirus Staphylococcus* virus SA11. In embodiments, the bacteriophage is *Silviavirus Staphylococcus* virus Romulus. In embodiments, the bacteriophage is *Silviavirus Staphylococcus* virus Qdsa001. In embodiments, the bacteriophage is *Silviavirus Staphylococcus* virus MR003. In embodiments, the bacteriophage is *Silviavirus Staphylococcus* virus StAP1. In embodiments, the bacteriophage is *Silviavirus Staphylococcus* virus Stsau2.

In embodiments, provided herein are methods of treating a subject with a bacterial infection including administering to a subject one or more bacteriophage administered intravenously. In embodiments, provided herein are methods of treating a subject with a bacterial infection including administering to a subject one or more bacteriophage administered via an intra-articular injection. In embodiments, provided herein are methods of treating a subject with a bacterial infection including administering to a subject one or more bacteriophage administered via inhalation. In embodiments, provided herein are methods of treating a subject with a bacterial infection including administering to a subject one or more bacteriophages administered via nebulization. In embodiments, provided herein are methods of treating a subject with a bacterial infection including administering to a subject one or more bacteriophages administered intranasally, orally, by inhalation, vaginally, rectally, or parenterally, for example by intradermal, subcutaneous, intramuscular, intraperitoneal, intrarectal, intraarterial, intralymphatic, intravenous, intra-articular, intrathecal, and intratracheal routes. Parenteral administration, if used, is generally characterized by injection.

In embodiments, provided herein are methods of treating a subject with a bacterial infection including administering to the subject one or more distinct bacteriophage. In embodiments, the bacterial infection is selected from bacteremia, septicemia, pulmonary infection, rhinosinusitis, urinary tract infection, intra-abdominal infection, skin infection, skin structure infection, endocarditis, and an implant infection. In embodiments, provided herein are methods of treating a subject with a bacterial infection including administering to the subject one or more distinct bacteriophage, where the bacterial infection is bacteremia. In embodiments, provided herein are methods of treating a subject with a bacterial infection including administering to the subject one or more distinct bacteriophage, where the bacterial infection is septicemia. In embodiments, provided herein are methods of treating a subject with a bacterial infection including administering to the subject one or more distinct bacteriophage, where the bacterial infection is pulmonary infection. In embodiments, provided herein are methods of treating a subject with a bacterial infection including administering to the subject one or more distinct bacteriophage, where the bacterial infection is rhinosinusitis. In embodiments, provided herein are methods of treating a subject with a bacterial infection including administering to the subject one or more distinct bacteriophage, where the bacterial infection is urinary tract infection. In embodiments, provided herein are methods of treating a subject with a bacterial infection including administering to the subject one or more distinct bacteriophage, where the bacterial infection is intra-abdominal infection. In embodiments, provided herein are methods of treating a subject with a bacterial infection including administering to the subject one or more distinct bacteriophage, where the bacterial infection is skin infection. In embodiments, provided herein are methods of treating a subject with a bacterial infection including administering to the subject one or more distinct bacteriophage, where the bacterial infection is skin structure infection. In embodiments, provided herein are methods of treating a subject with a bacterial infection including administering to the subject one or more distinct bacteriophage, where the bacterial infection is endocarditis. In embodiments, provided herein are methods of treating a subject with a bacterial infection including administering to the subject one or more distinct bacteriophage, where the bacterial infection is an implant infection. In embodiments, provided herein are methods of treating a subject with a bacterial infection including administering to the subject one or more distinct bacteriophage, where the bacterial infection is a cardiac implant infection. In embodiments, provided herein are methods of treating a subject with a bacterial infection including administering to the subject one or more distinct bacteriophage, where the bacterial infection is a cardiac implant infection caused by a ventricular assist device. In embodiments, provided herein are methods of treating a subject with a bacterial infection including administering to the subject one or more distinct bacteriophage, where the bacterial infection is a cardiac implant infection caused by a pacemaker. In embodiments, provided herein are methods of treating a subject with a bacterial infection including administering to the subject one or more distinct bacteriophage, where the bacterial infection is a prosthetic joint infection. In embodiments, provided herein are methods of treating a subject with a bacterial infection including administering to the subject one or more distinct bacteriophage, where the bacterial infection is prosthetic valve endocarditis. In embodiments, the bacterial infection is resistant to one or more antibiotics.

In embodiments, provided herein are methods for treating bacterial infection by administering any bacteriophage composition described herein in combination with an antibiotic. In embodiments, the antibiotic is selected from the group consisting of a fluoroquinolone, carbapenem, aminoglycoside, ansamycin, cephalosporin, penicillin, beta lactam, beta lactamase inhibitor, folate pathway inhibitor, fucidane, glycopeptide, glycylcycline, lincosamide, lipopeptide, macrolide, oxazolidinone, phenicol phosphonic acid, streptogramin, and tetracycline.

In embodiments, provided herein are methods of administering to a subject any of the bacteriophage described herein, where administration is over a range of about 6 to about 24 hours. In embodiments, the bacteriophage is administered to a subject every 6 hours. In some embodiments, the bacteriophage is administered to a subject every 12 hours. In embodiments, the bacteriophage is administered to a subject every 18 hours. In embodiments, the bacteriophage is administered to a subject every 24 hours.

In embodiments, provided herein are methods of administering to a subject any of the bacteriophage described herein for up to 7 days. In some embodiments, the bacteriophage is administered to a subject every 6 hours for a maximum of one dose. In some embodiments, the bacteriophage is administered to a subject every 6 hours for a maximum of two doses. In some embodiments, the bacteriophage is administered to a subject every 6 hours for a maximum of three doses. In some embodiments, the bacteriophage is administered to a subject every 6 hours for a maximum of four doses (1 day). In some embodiments, the bacteriophage is administered to a subject every 6 hours for a maximum of five doses. In some embodiments, the bacteriophage is administered to a subject every 6 hours for a maximum of six doses. In some embodiments, the bacteriophage is administered to a subject every 6 hours for a maximum of seven doses. In some embodiments, the bacteriophage is administered to a subject every 6 hours for a maximum of eight doses (2 days). In some embodiments, the bacteriophage is administered to a subject every 6 hours for a maximum of nine doses. In some embodiments, the bacteriophage is administered to a subject every 6 hours for a maximum of ten doses. In some embodiments, the bacteriophage is administered to a subject every 6 hours for a maximum of eleven doses. In some embodiments, the bacteriophage is administered to a subject every 6 hours for a maximum of twelve doses (3 days). In some embodiments, the bacteriophage is administered to a subject every 6 hours for a maximum of thirteen doses. In some embodiments, the bacteriophage is administered to a subject every 6 hours for a maximum of fourteen doses. In some embodiments, the bacteriophage is administered to a subject every 6 hours for a maximum of fifteen doses. In some embodiments, the bacteriophage is administered to a subject every 6 hours for a maximum of sixteen doses (4 days). In some embodiments, the bacteriophage is administered to a subject every 6 hours for a maximum of seventeen doses. In some embodiments, the bacteriophage is administered to a subject every 6 hours for a maximum of eighteen doses. In some embodiments, the bacteriophage is administered to a subject every 6 hours for a maximum of nineteen doses. In some embodiments, the bacteriophage is administered to a subject every 6 hours for a maximum of twenty doses (5 days). In some embodiments, the bacteriophage is administered to a subject every 6 hours for a maximum of twenty-one doses. In some embodiments, the bacteriophage is administered to a subject every 6 hours for a maximum of twenty-two doses. In some embodiments, the bacteriophage is administered to a subject every 6 hours for a maximum of twenty-three doses. In some embodiments, the bacteriophage is administered to a subject every 6 hours for a maximum of twenty-four doses (6 days). In some embodiments, the bacteriophage is administered to a subject every 6 hours for a maximum of twenty-five doses. In some embodiments, the bacteriophage is administered to a subject every 6 hours for a maximum of twenty-six doses. In some embodiments, the bacteriophage is administered to a subject every 6 hours for a maximum of twenty-seven doses. In some embodiments, the bacteriophage is administered to a subject every 6 hours for a maximum of twenty-eight doses (7 days). In some embodiments, the bacteriophage is administered to a subject every 12 hours. In some embodiments, the bacteriophage is administered to a subject every 12 hours for a maximum of one dose. In some embodiments, the bacteriophage is administered to a subject every 12 hours for a maximum of two doses (1 day). In some embodiments, the bacteriophage is administered to a subject every 12 hours for a maximum of three doses. In some embodiments, the bacteriophage is administered to a subject every 12 hours for a maximum of four doses (2 days). In some embodiments, the bacteriophage is administered to a subject every 12 hours for a maximum of five doses. In some embodiments, the bacteriophage is administered to a subject every 12 hours for a maximum of six doses (3 days). In some embodiments, the bacteriophage is administered to a subject every 12 hours for a maximum of seven doses. In some embodiments, the bacteriophage is administered to a subject every 12 hours for a maximum of eight doses (4 days). In some embodiments, the bacteriophage is administered to a subject every 12 hours for a maximum of nine doses. In some embodiments, the bacteriophage is administered to a subject every 12 hours for a maximum of ten doses (5 days). In some embodiments, the bacteriophage is administered to a subject every 12 hours for a maximum of eleven doses. In some embodiments, the bacteriophage is administered to a subject every 12 hours for a maximum of twelve doses (6 days). In some embodiments, the bacteriophage is administered to a subject every 12 hours for a maximum of thirteen doses. In some embodiments, the bacteriophage is administered to a subject every 12 hours for a maximum of fourteen doses (7 days). In some embodiments, the bacteriophage is administered to a subject every 18 hours. In some embodiments, the bacteriophage is administered to a subject every 18 hours for a maximum of one dose. In some embodiments, the bacteriophage is administered to a subject every 18 hours for a maximum of two doses. In some embodiments, the bacteriophage is administered to a subject every 18 hours for a maximum of three doses. In some embodiments, the bacteriophage is administered to a subject every 18 hours for a maximum of four doses (3 days). In some embodiments, the bacteriophage is administered to a subject every 18 hours for a maximum of five doses. In some embodiments, the bacteriophage is administered to a subject every 18 hours for a maximum of six doses. In some embodiments, the bacteriophage is administered to a subject every 18 hours for a maximum of seven doses. In some embodiments, the bacteriophage is administered to a subject every 18 hours for a maximum of eight doses (6 days). In some embodiments, the bacteriophage is administered to a subject every 18 hours for a maximum of nine doses. In some embodiments, the bacteriophage is administered to a subject every 24 hours. In some embodiments, the bacteriophage is administered to a subject every 24 hours for a maximum dose of one (1 day). In some embodiments, the bacteriophage is administered to a subject every 24 hours for a maximum dose of two (2 days). In some embodiments, the bacteriophage is administered to a subject every 24 hours for a maximum dose of three (3 days). In some embodiments, the bacteriophage is administered to a subject every 24 hours for a maximum dose of four (4 days). In some embodiments, the bacteriophage is administered to a subject every 24 hours for a maximum dose of five (5 days). In some embodiments, the bacteriophage is administered to a subject every 24 hours for a maximum dose of six (6 days). In some embodiments, the bacteriophage is administered to a subject every 24 hours for a maximum duration of seven (7 days). In some embodiments, the bacteriophage is administered for at least 7 days. In some embodiments, the bacteriophage is administered for at least 14 days. In some embodiments, the bacteriophage is administered for at least 21 days. In some embodiments, the bacteriophage is administered for at least 28 days. In some embodiments, the bacteriophage is administered for at least one month. In some embodiments, the bacteriophage is administered for at least 2 months.

In embodiments, is a method of administration of a bacteriophage composition to a subject where the subject is human.

EXAMPLES

Example 1: AP-SA02 Product Optimization

Experiments were conducted to create a bacteriophage therapy that met the following criteria: 1) Obligately lytic, to avoid specialized transduction of bacterial genes; 2) Not known, by empirical testing and/or inference from genomics, to be prone to generalized transduction, and 3) Fully sequenced, to avoid phages with genes known to carry antibiotic resistance or bacterial virulence genes.

Collectively, the phages used together to treat a subject should: 1) Have broad activity against the target pathogen but not other species, to maximize potential utility and minimize off-target effects, and 2) Be capable of complementation, in which resistant mutants arising to one phage are sensitive to another phage.

In addition to characteristics of the phages themselves, material for clinical use should be produced in such a way as to give confidence that the final product retains these characteristics (i.e. are still the same phages) and does not contain potentially harmful (or harmful amounts) of impurities such as endotoxin or host cell proteins.

Each of the phages were identified by acquiring a diverse panel of MRSA isolates and several VRSA strains that were then screened against a variety of phages to identify phages that exhibited both broad host range coverage and robust potency. Similar to antibiotics, bacteria are considered susceptible to phage if the minimum inhibitory concentration is less or equal to the susceptibility breakpoint of 103 phage/mL which corresponds to 0.1 pg/mL of protein.

Each of the phage candidates was then advanced through a series of selection criteria and different methods, including sequencing, bioinformatics and comparative genomics, in order to identify potential receptors, phage identity and confirm lytic activity. This process yielded a smaller candidate phage pool with the desired attributes for a product candidate, namely, broad host range, complementarity, compatibility and targeting different bacterial receptors which are essential intrinsic attributes that contribute to the robustness and potency of the therapeutic cocktail. Complementarity aims to ensure that a clinical isolate is targeted by more than one phage which limits the emergence of resistance. Targeting different receptors on the surface of bacteria also contributes to resistance prevention and also has the potential to decrease bacterial virulence and fitness. Compatibility between different components of the multi-phage product ensures that the activity of one phage does not interfere with the infectivity of another phage.

Phage candidates were then validated for efficacy and potency. Specifically, this included performing killing kinetic assays to demonstrate cooperativity, activity in bodily fluids and in the presence of current anti-Staphylococcal therapies in vitro and biofilm inactivation.

Phages were also selected based on manufacturing feasibility and process optimization efforts with the goal of achieving high-quality phage product free host cell proteins and other contaminants whilst maintaining adequate phage titers. Equally important, the ability to formulate phage components in the same diluent suitable for inhalation and intravenous (IV) delivery that would allow long term stability is an important consideration in the selection process.

Example 2: Selection of Phage Components for Optimized Product AP-SA02

Host range and potency. The host range of SA phage is generally above 80% (Table 1), yet their potency is variable. While phages belonging to the family Kay virus, such as Sa87, have a broad host range, their potency is not ideal. By contrast, as exemplified by plaque turbidity, Silvia viruses such as ARSA0001 are extremely potent and completely eliminate bacteria, which results in the formation of clear plaques and very high efficiencies of plating (FIG. 1). ARSA0001 potency was further demonstrated by the failure of attempts to obtain phage-resistant bacteria.

TABLE 1

| Phage | Family | % *S. aureus* Isolates Sensitive |
|---|---|---|
| J-Sa36 | Kayvirus | 83 |
| Sa83 | Kayvirus | 86 |
| Sa87 | Kayvirus | 92 |
| ARSA0001 | Silviavirus | 83 |
| ARSA0002 | Silviavirus | 91 |

Figure 2:
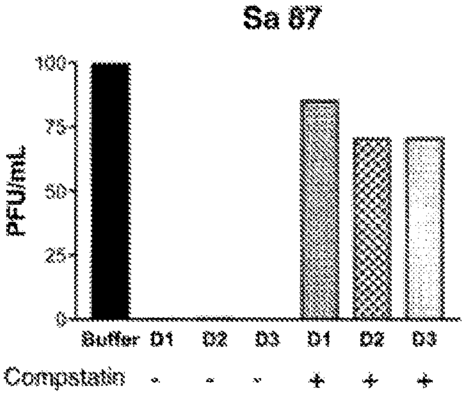
FIG. 2 shows compstatin effect on Sa87 activity after exposure to plasma. Sa87 was exposed to fresh plasma isolated from three donors, in the presence or absence of complement inhibitor compstatin, for 60 minutes; phage were titered using the double-layer agar method. D indicates donor.

Compatibility with relevant biological fluids. A criterion for lead candidate selection is phage activity in bodily fluids to ensure that infectivity is not locally or systemically inhibited. To ensure in vivo efficacy, the viability of individual phage after exposure to human blood and plasma was evaluated. Phages were diluted to a concentration of $10^7$ phage/mL into plasma obtained from three healthy volunteers or phage buffer and incubated at 37° C. The activity of each phage component was assessed by using a standard double-agar layer plaque assay. Ten (10) *S. aureus* phages were screened and most were partially inactivated within 60 minutes of exposure to blood or plasma compared to phage diluent (Table 2). The lack of recovery after exposure to blood was abolished by heat inactivation of serum and the complement inhibitor compstatin, suggesting that these phages are inhibited by complement (FIG. 2). No significant loss in phage titer was observed for 2 lead candidates, namely ARSA0001 and ARSA0002.

TABLE 2

| Phage | % Recovery |
|---|---|
| J-Sa36 | 0.06 |
| Sa83 | 0.95 |
| Sa87 | 6.33 |
| ARSA0003 | 1.07 |
| Sa474 | 0.03 |
| ARSA0001 | 93.94 |
| ARSA0004 | 1.76 |
| Sa101 | 0.05 |
| Sa68 | 0.71 |
| ARSA0002 | 94.44 |

Figure 3:
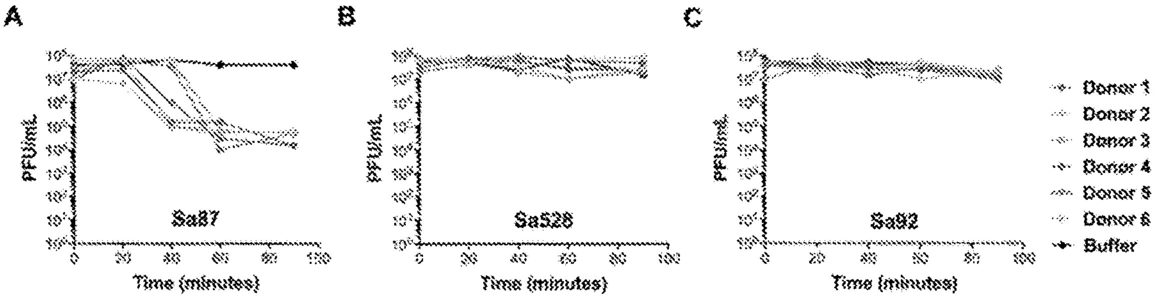
FIG. 3 shows lead phage activity after exposure to plasma. Lead phage candidates were diluted in fresh plasma from six donors and the infectivity was monitored for 90 minutes.

Next, the activity of Sa87, ARSA0001 and ARSA0002 was assessed at 90 minutes after exposure to plasma obtained from 6 subjects to ensure that the inhibition is not donor specific (FIG. 3). Since all phages from AP-SA01 are highly related, Sa87 was selected as an example of a Kay virus. A significant loss of activity was observed only in the case of Sa87. Recently published data also suggested that *S. aureus* phage may not retain full activity in human blood. The data herein demonstrate that antimicrobial activity of ARSA0001 and ARSA0002 is not inhibited by blood components and these viruses are suitable therapeutic candidates.

Example 3: AP-SA02 Characterization: Biofilm Activity

Figure 4:
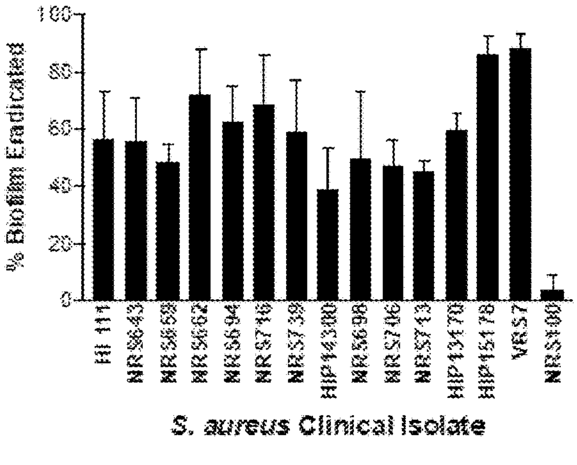
FIG. 4 shows AP-SA02 markedly reduces SA biofilm mass. Biofilms were treated with AP-SA02 ($10^7$ phage/well of a 96 well plate) for 5 hours and the percentage of biofilm that was eradicated calculated is reported as percent relative to the same strain treated with vehicle. NRS100 is the negative control.

AP-SA02 characterization: biofilm compatibility. Biofilms formed by several different *S. aureus* clinical isolates were treated for 5 hours with AP-SA02. The remaining biofilm biomass was stained with crystal violet and quantified (FIG. 4). NRS100 is not infected by any of the component phages of AP-SA02 and serves as a negative control. The extent of biofilm eradication achieved with one concentration of AP-SA02 ranged between 60%-90%. These data show that AP-SA02 can penetrate pre-existing biofilms and decrease attached biomass.

Figure 5A:
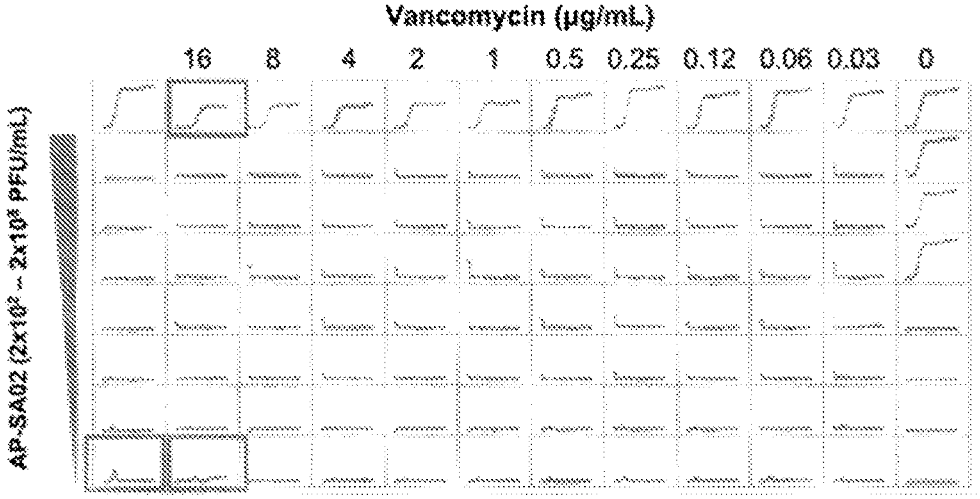
FIGS. 5A-5B show AP-SA02 activity in the presence of vancomycin.
Figure 5B:
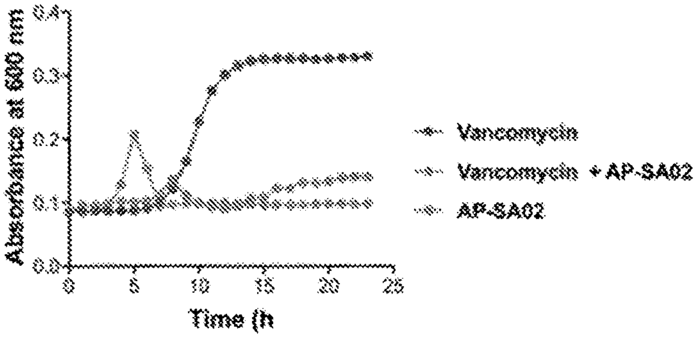
Figure 6A:
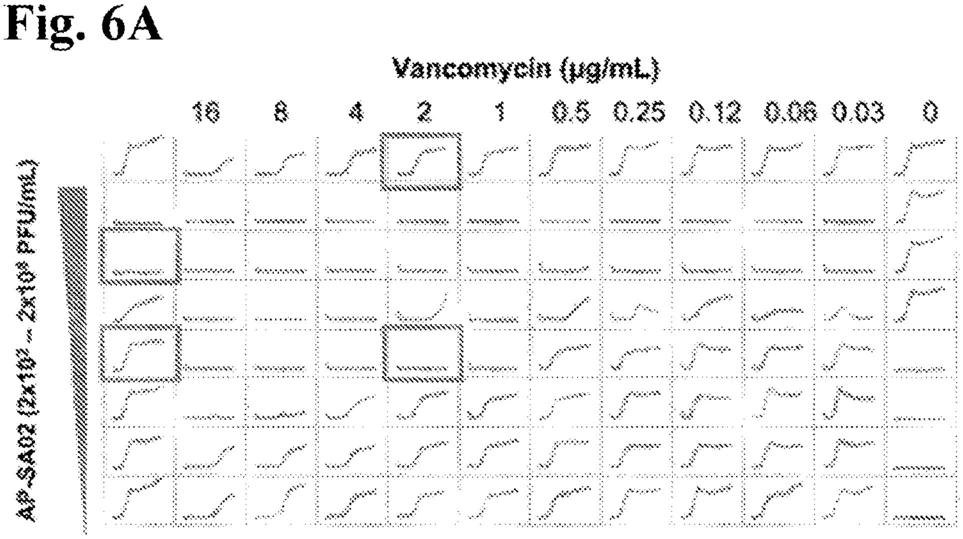
FIGS. 6A-6B show the synergistic activity of vancomycin and AP-SA02.
Figure 6B:
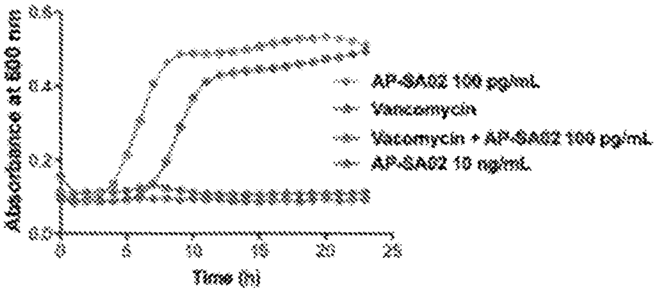

Example 4: AP-SA02 Characterization: Compatibility with Current Anti-Staphylococcal Therapies Standard therapy for subjects with a *S. aureus* infection includes vancomycin and daptomycin. Since subjects who receive AP-SA02 are likely to be on these therapies, the effect of AP-SA02 on these antibiotics and vice versa was assessed. Using the standard checkerboard assay, the minimum inhibitory concentration of each antimicrobial alone or in combination with each other, was used to calculate whether two antimicrobials are synergistic, antagonistic, or indifferent (Table 3). AP-SA02 showed additive, indifferent, or synergistic effects in combination with vancomycin in killing all *S. aureus* strains tested. No antagonistic effects of AP-SA02 in combination with vancomycin were noted. Several strains resistant to vancomycin were also tested (MIC of >16 μg/mL). While vancomycin does not have an antimicrobial effect on these strains, less than 1 μg/mL of phage was able to inhibit growth (FIGS. 5A and B). It was observed that in the presence of phage, the breakpoint for vancomycin changed from resistant or intermediate to the sensitive range (0.5-2 μg/mL) (FIGS. 6A and B). In addition, these data indicate that vancomycin and AP-SA02 act synergistically since addition of AP-SA02 at subinhibitory concentration (100 μg/mL) to a subinhibitory concentration of vancomycin (2 μg/mL) results in complete inhibitions of SA growth. Inhibition of VRSA can also be achieved with AP-SA02 alone at a higher concentration (10 ng/mL). AP-SA02 clinical candidate demonstrates robust activity against both MRSA and VRSA strains and maintains its activity in the presence of current standard anti-staphylococcal therapy.

TABLE 3

| Vancomycin | | Daptomycin | |
|---|---|---|---|
| *S. aureus* | FIC value | *S. aureus* | FIC value |
| HFH-29753 | 1.01 | HFH-29753 | 1.00 |
| F339777 | 1.01 | F336222 | 1.00 |
| NRS35 | 2.00 | NRS35 | 1.00 |
| NRS696 | 1.10 | NRS696 | 1.00 |
| HIP13170 | 0.07 | HIP13170 | 1.00 |
| NRS719 | 1.01 | NRS719 | 1.00 |
| NRS698 | 1.01 | NRS698 | 1.01 |
| NRS706 | 0.51 | NRS706 | 1.10 |
| NRS713 | 1.01 | NRS713 | 1.01 |
| HIP15178 | 1.00 | HFH 30364 | 1.00 |

Example 5: Manufacturing of AP-SA02

AP-SA02 manufacturing includes phage and host bacteria selection, and increased robustness in the purification process. Additional information and protocols for bacteriophage growth and manufacturing can be found in for example, PCT/US19/12113 (WO 2019/136108), PCT/US19/12114 (WO 2019/136109), PCT/GB17/50376 (WO 2019/136109), and U.S. Pat. No. 10,517,908, each of which is incorporated herein by reference in its entirety for everything disclosed therein.

All processes are conducted under cGMP conditions including manufacturing, product storage, Quality Control (QC) raw materials, analytical and stability testing, and product release by Quality Assurance (QA). Bacterial fermentation, filtration and chromatography are performed in ISO 8 certified cleanrooms. Aseptic filling is performed in an ISO 5 certified isolator located within an ISO 7 certified cleanroom. QC analytical and stability testing are performed in a controlled environment. Where possible, single-use disposable parts (filters, tubing, vessels, etc.) are used to reduce the risk of contamination during the manufacturing process.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the claims.

The invention claimed is:

1. A method of treating a *Staphylococcus aureus* infection comprising administering a therapeutic composition to a subject in need of treatment, wherein the therapeutic composition comprises two or more bacteriophage, and wherein at least one bacteriophage comprises a polynucleotide sequence with at least 97% identity to SEQ ID NO:2.

2. The method of claim 1, wherein the two or more bacteriophage comprise a bacteriophage comprising a polynucleotide sequence with at least 97% identity to SEQ ID NO:2, and a bacteriophage comprising a polynucleotide sequence with at least 90% identity to SEQ ID NO: 1.

3. The method of claim 2, wherein the *Staphylococcus aureus* infection is bacteremia.

4. The method of claim 1, wherein the two or more bacteriophage comprise a bacteriophage comprising a polynucleotide sequence with at least 98% identity to SEQ ID NO:2, and a bacteriophage comprising a polynucleotide sequence with at least 90% identity to SEQ ID NO: 1.

5. The method of claim 4, wherein the *Staphylococcus aureus* infection is bacteremia.

6. The method of claim 1, wherein the two or more bacteriophage comprise a bacteriophage comprising a polynucleotide sequence with at least 99% identity to SEQ ID NO:2, and a bacteriophage comprising a polynucleotide sequence with at least 90% identity to SEQ ID NO: 1.

7. The method of claim 6, wherein the *Staphylococcus aureus* infection is bacteremia.

8. The method of claim 1, wherein the two or more bacteriophage comprise a bacteriophage comprising a polynucleotide sequence with at least 97% identity to SEQ ID NO:2, and a polynucleotide sequence with at least 95% identity to SEQ ID NO:1.

9. The method of claim 8, wherein the *Staphylococcus aureus* infection is bacteremia.

10. The method of claim 1, wherein the two or more bacteriophage comprise a bacteriophage comprising the polynucleotide sequence of SEQ ID NO:2, and a bacteriophage comprising the polynucleotide sequence of SEQ ID NO:1.

11. The method of claim 10, wherein the *Staphylococcus aureus* infection is bacteremia.

12. The method of claim 1, wherein the two or more bacteriophage infect and kill *Staphylococcus aureus*.

13. The method of claim 1, wherein the two or more bacteriophage are resistant to blood complement inactivation.

14. The method of claim 13, wherein the bacteriophage are resistant to complement C3 protein-mediated inactivation.

15. The method of claim 1, wherein the two or more bacteriophage belong to the genus *Silviavirus*.

16. The method of claim 1, wherein the composition is substantially free of a bacterial component.

17. The method of claim 16, wherein the bacterial component comprises bacterial host protein.

18. The method of claim 1, wherein the composition further comprises a pharmaceutically acceptable carrier, diluent, excipient or combinations thereof.

19. The method of claim 1, wherein the composition is a liquid, semi-liquid, solid, frozen, or lyophilized formulation.

20. The method of claim 1, wherein the two or more bacteriophage of the composition target one or more of vancomycin-intermediate *Staphylococcus aureus* (VISA), vancomycin-resistant *Staphylococcus aureus* (VRSA), and methicillin-resistant *Staphylococcus aureus* (MRSA).

21. The method of claim 20, wherein the two or more bacteriophage of the composition target methicillin-resistant *Staphylococcus aureus* (MRSA).

22. The method of claim 20, wherein the two or more bacteriophage of the composition target vancomycin-intermediate *Staphylococcus aureus* (VISA).

23. The method of claim 20, wherein the two or more bacteriophage of the composition target vancomycin-resistant *Staphylococcus aureus* (VRSA).

24. The method of claim 1, wherein the composition comprises between $1\times1\times10^8$ and $1\times10^{11}$ PFU/mL of at least one of the bacteriophage in the composition.

25. The method of claim 1, wherein the composition is administered at a dosage of at least $1\times10^9$ PFU of total bacteriophages per milliliter.

26. The method of claim 1, wherein at least one bacteriophage is obligately lytic.

27. The method of claim 1, wherein the *Staphylococcus aureus* infection comprises a pulmonary infection, rhinosinusitis, urinary tract infection, intra-abdominal infection, skin infection, skin structure infection, bacteremia, septicemia, endocarditis, wound infection, or an implant infection.

28. The method of claim 27, wherein the implant infection comprises a cardiac implant infection, prosthetic joint infection, or prosthetic valve endocarditis.

29. The method of claim 28, wherein the cardiac implant infection comprises a ventricular assist device infection or pacemaker infection.

30. The method of claim 28, wherein the implant infection comprises a prosthetic joint infection.

31. The method of claim 1, wherein the *Staphylococcus aureus* infection is bacteremia.

32. The method of claim 31, wherein the two or more bacteriophage of the composition target methicillin-resistant *Staphylococcus aureus* (MRSA).

33. The method of claim 31, wherein the two or more bacteriophage of the composition target vancomycin-intermediate *Staphylococcus aureus* (VISA).

34. The method of claim 31, wherein the two or more bacteriophage of the composition target vancomycin-resistant *Staphylococcus aureus* (VRSA).

35. The method of claim 1, wherein the *Staphylococcus aureus* infection is resistant to an antibiotic.

36. The method of claim 1, wherein the composition is administered intravenously, via intra-articular injection, via inhalation, or via nebulization.

37. The method of claim 36, wherein the composition is administered intravenously.

38. The method of claim 1, wherein the bacteriophage is administered at least every 6 hours, at least every 12 hours, or at least every 24 hours.

39. The method of claim 1, wherein the bacteriophage is administered for at least 5 days.

40. The method of claim 1, wherein the subject in need of treatment is human.

41. A method of treating a *Staphylococcus aureus* infection comprising administering a therapeutic composition to a subject in need of treatment, wherein the therapeutic composition comprises one or more bacteriophage comprising a bacteriophage comprising a polynucleotide sequence with at least 97% identity to SEQ ID NO:2.

42. The method of claim 41, wherein the composition comprises between $1\times10^8$ and $1\times10^{11}$ PFU/mL of the bacteriophage.

43. The method of claim 41, wherein the composition comprises a bacteriophage comprising a polynucleotide sequence with at least 98% identity to SEQ ID NO:2.

44. The method of claim 41, wherein the composition comprises a bacteriophage comprising a polynucleotide sequence with at least 99% identity to SEQ ID NO:2.

* * * * *

SEQUENCE LISTING

```
Sequence total quantity: 2
SEQ ID NO: 1           moltype = DNA  length = 144299
FEATURE                Location/Qualifiers
source                 1..144299
                       mol_type = genomic DNA
                       organism = Bacteriophage ARSA0001
SEQUENCE: 1
ctwcatagtg tataaatagt taggtwtcta actgttagat acctaactat ttatttttat  60
atagttttaa ctactgtgaa ctatgcttat gtagtattaa actatgctga ttatatgcta  120
aactattcta atgtatagtt aaactaagct gaagtagtat ttactgtgta taaaggtata  180
tttagtatta gatattgtgt atatggtata ctataattct gaacattact tatttaatat  240
atatatatag tttgtttcta tggtagtatt gacttaattt tccctagagt aaaagtttaa  300
tatatttagt aatttccgaa caataaagaa attttaacta ttttacacat atgtgttgac  360
agtatattac ttatggttta tactaagtat ataaagttaa aggagatgat ttatcatgaa  420
gattaaaaga gaagtttcgt ttatagaatt aatgtatatg tattataaag gtgatgtagg  480
taaaggtcag tactattcta ctaatagtca gtttattgtt gttataactg ttgatgatat  540
atcgttttat aatgcattgt accctaataa atctattact attactatac ctaatgacac  600
taagtttatt gtagaagcgg ttatagatgc ttctactgag ttaagtagta tagtagttac  660
ttataagcaa ggtaacagtg tattaaactc agtatggtat aggattagta ttaatgaagt  720
tattgactac tatgtcgaag gtaaaaatac atggttacta tctgttagta ctgttgtaga  780
taatgagtta gttactatat ggaaagatgg taacgtattg tgatttggta tatagtaata  840
ttcagtatac ttatatatgt acatcacttg tattattatg tgtagtacta gtatatagag  900
gggttaaata accgcttcaa taaagactta gtaacgagga gttgtattat gagtttatca  960
gatatttatg tacatttaaa tcagttagga tataaaatag aagttttagg ggacatgagt  1020
acattaaaag ttaatgacta ctacatcgaa aatagatgta tagatagtgg ttttagggtt  1080
acaggggata atgtattttt atctgtatat tatggtgaag acgtagtaag attctttaaa  1140
caaaggttat taaaatagta ttttgttaag ttatacttga gaataattat aaaggaggga  1200
ttagtttatg agtatattta taagtatagt ttctatattt ttagctacta ttagtattgt  1260
actaagtata aggtttggta agaagtatta taagcatgta cttgataatt atgatagtgt  1320
tagtgattta gaatcagcta gtgtatttgg tttattattt atgagtattt gtattggtac  1380
tatttctatt gttttgagtt taggttacat agtaagtaga gtattttatt atataggagg  1440
gttgtagatg atgagttcaa ctttaatgta tattgcggtt agtattttag gtattagtat  1500
tatagttggt atgcttagtg ctttaattac tgatatagtt aaatctatta agcagaaaga  1560
agtgtttttt agtatatatc ttattgtttc ttttgtttta actgttttag tttttgcttc  1620
tataatacta catatgttag gtatgtaata gaaagagggt attagtatag gttactttgt  1680
agtaagttta tcattaatgt atttagttat agatatagat atatgttata gaatatatag  1740
taaagaaggt aatagtaata gatttaagtt agcagtgttt ttaactatac ttatattgat  1800
tatgtttata tatggagtag gtgttttatt aacacaatag aaagaggctt attatggaag  1860
aattagatat actagataga gtgttacata ataaatcagg tataggtgag tttacgtata  1920
caaattgtat aagaacaagt gatgataagt atatttatag gttctttctg gaagatactt  1980
attttggttg tgctattatg gtatatgatg atatgagtga gtatgaagta gtagtacaag  2040
gtacaggtaa ggtgtatgtt tccttattga aagatgtagt tagtaatatg tataagatac  2100
```

-continued

```
tagtagatga gtatgataag tatttaaaag atagtgcata tcaaaaatat atgtataata  2160
tatttgaaga acaagtagaa cagtataact aaagtttttc tctagggaaa agcagtcaaa  2220
ggtaaaaata gggcttgaac ccgcattcta tggttgacat ttaggtaaaa ttagataggt  2280
tttccctaga agaaaagttt aaaaggtaaa aaaggagttg gttactatgt caaaattagc  2340
taagttttgt aggaagtatg gagaagttac tggcataatg gagagtatta cagattatga  2400
ggtgtactta ggtaggggtt ataaagtaag gtgtagagta ggtaatagcc ttatttatat  2460
tcttgtatat aaagacaatc atatcattgc taggtttgag gaagcggata atatagtatt  2520
tcctttgagt gatacgcttg aggtgggaac aattaaagac ttagaggagc tagaaggttt  2580
gtatactaat atctatatat tactaggta tttatataca gaatatgaaa ataaagttat  2640
gtatgaatat gggaggttag aataatggat attatggtaa gtgaattatt tgagtatata  2700
ttaggtcata acactcacat tcttgggaat tggcatactt attacttaga taaaggttac  2760
tgtattaaag ttaatgatga taaacattat aataacatga agtttatcaa aaatggtaga  2820
gtagtaaaag aggttattaa cagtgacacc ttactaccta aaggattcag tagtatctat  2880
agtcttattg attactatga ggaagcttta gatgaaaagt gcagaaaaga aaaagagcgt  2940
ctgaaagaaa ttcgtacgtt cctaggtaag taagtattat atataaccgc ttctatatga  3000
aactttatac ctatagctat tataactata ggtatttttt tatatttctt acataaatgt  3060
gttgatttta tgtgtgttaa ggtttatact taatatataa ttaaaggagt gaatataata  3120
tggatatgaa caaggaagta ttagaatgat tagatagttt aggtggtaag ttagaacaag  3180
caggtacaca tagttatgaa tctttaatta aatacacaat tactcaaggt attatagatt  3240
tatgttcaat aagtatatta ttatctataa cagctatctt atgggtggct tgtataagt  3300
cagataaaaa gtctaatgaa ggtcatagta ccctattatt tgagtttgtt tataagaatg  3360
aaaaagagct ttctgctgca ggatgcacag taattatatt tgctgttact ctgtctatta  3420
tttctttttt agtgctatta ataggcttgc ctattgctat tcaagagatt tttaatccag  3480
aaggatattt gattaagagt acgatagata atttaaaata attgtaaaaa taaggaggaa  3540
aatataatgt tagaacaagc taaaggcata actacagatt atattatgga atttattgat  3600
gaacatgagc attatttcta tgaagactta cacaagttag caggggagtt agtgttgaaa  3660
gatacacatg acacaaaccc tattgttatt aatgatggtg atggttactc aggtactatt  3720
atatctaaat ttaaatcaaa ggtagagggt gttccagata tcactgttag tgatttttac  3780
ggttcatgtt ctttctgtga tactttagct aatatctatg aaggtagtga tgaacttgag  3840
ataattagag atttagctac tatggtacta catacaattc aatctatgga agagaaagta  3900
gaataatgta taagggagtg atatagtgtt tagtaagaga aaagaaatta aagagtataa  3960
gaaacaaggt tactctgttg attatatggg tggtttttta ggattatttg gtcttggcga  4020
tgttttatac tatgtagaaa ctaataagaa atacttaaag tcaattagcg taggtaaaga  4080
tgacaaccaa tatgtatatg actttaatgg ttatgaatac ttatcaagac ataagttaaa  4140
tatcaaagaa gaagaactaa tgtctaaagc tattgctcag ttaagtatca aaggtttaaa  4200
gaattttaat ggagttaagc atatttggga tgtaggtttc ttagagcaat cttttaatat  4260
acatcgtaaa gatattgata cggttaaact taaactaagt tttgatgaag agggtaacct  4320
atattatgaa ttagaattag gttggattaa tatttataaa gagtatacag gtgtaaaaga  4380
ctttcttaat acagtagata actatctcaa cttcttctat aaagatatag tcactagtgg  4440
tcttgagtta aaacaagtac tatataatac ttttatggga ggagattatg agtttgtagt  4500
atctccatat aatgttgtag tatataggga agttgagtta attgatataa agaaatttta  4560
ctctgatact tatggaattt attcctatgg ttatggcact aatgtacata aacctttaca  4620
aacaattaag tattatctgg aataccctat gaatgaagta taaccacttc aaatattata  4680
taaaaggagt gcttaatatg agtaacggaa aagtagcgtt aattggtagt aaggtattag  4740
aagattataa tatttataca atcatgagtg agaaacatat atacttaaga gatagtgttg  4800
atgtgacttt taatgatggg aaggtattac ctatatacat tgatagtgta ttaaaacaat  4860
taagtaaaga tgataaaaat ctatattttt ctgaagaaga tatagatatt agtaaactta  4920
ctaatgacga gtattataca gttactaaaa aataaaagga gaatagataa tgagtagtaa  4980
taaaaaaata gcagaaagag ttattgagaa atttttagat gagactaata aaggtgtaga  5040
ttttactaat caagatgaat ttaaccgctt cttagataat acagaagact tgtatgaagt  5100
atctggtact caaagagata agattattaa gtgtttacaa aacattgtag ttactgtatt  5160
tatggataag gggaaataac aatgaaaaca ataaaaagaa aaatagtaca agaaggtatg  5220
aacaaagaag aaactatgat ggaagacgat tctgttgtaa taaaaaaaat tcaaaaaata  5280
acaggcggag ctattcttcc tttagccaat ggcaaggaat atgtagtagt gtttagtaaa  5340
gtagacccta ctaaattaat tgtatttaat gtggaacgta atcaaatcta tttaagtggt  5400
tctggtttcg atagtgaact gtcttatgta gacagtaaaa gcaaccctat taccttagaa  5460
acagttaggt taatcactaa tttattataa aggttattag gcttttaaag attaagttat  5520
tttatagaat aaatactact agaaaatgat tactgtttaa tacagaattt taacgtacct  5580
agcttaaggg tattaaatat aaaggagggt attagaatga ctaaagttgt aagtagagga  5640
tatagttttg aagaacaaga agtaagtatg aactataatc aaggacaatg ggtgatttat  5700
gcaagtagaa aaccttatat tactgatatt atgaaaaagt accctgataa ggtggaagta  5760
ttagaacaat tagaaaatga aacaccagta ttggttaaag ttgtattgga tgaagattta  5820
attacattga gaaagccaat aagtaacgag cgtaaagaac aaatgaaaaa gattgctaaa  5880
gaaagatttg gtaaataata gagaggctga ctttaatgaa catcagtatg tacactaaca  5940
cctgtaggga ctagattaat attacaagat atcttatagg gttatagtgt cattgagaat  6000
gagtatgctt tattaaggtt agttaaagaa gataaacagt atttataata tcatattgaa  6060
gaagtagaag cggtattaaa ccgcttcttt tttatattat atttatattc tgagtaatta  6120
tgttgtattt aatcttggct aataattgta tatcaatttg agcatagtat gcccgtttca  6180
acatagttaa tctaataatt tgtatattta tctgttagtt atgtataaat atttgttatt  6240
acttatttat atatttgtat ttcgtactaa ccgtacgact tatctttttta aaaagataag  6300
aacaaaacag cgtatacctt gttgttttac gctacgctac aacaaggtaa cgcctgtaat  6360
aagttattcg tattaaaata ctaacaacta attacttgtt gtttagatta taacatatgt  6420
ttatgagaat tagatgagaa tttagttaca acagcattat aataatatta cagttatgtt  6480
acaagttgct aagtatgttt tgttactaca atatattgaa tatgaaagct ttagaccttt  6540
tctgcagaca agtaattatt acaggtatgt atgataaaag ataagtatca gggattaaat  6600
taaggttgga ttaatgaagc ggataagtta gatactggtt aaaataaaat actttacatt  6660
acctaaaact tatgatacac ttaggatagg ataaaggagg aatatcaatg aatattcaag  6720
aagcaaagga taaattatac gatgaattac tttatacagt aagtctttgt gagggaacag  6780
aagaagattt actagaactt attgagaatt tattttatat ttacaatgac gagcctgcat  6840
```

-continued

```
ttttaagtaa agacggtatg caatatacta ttaaagattt tatggagaga agaaaaacat  6900
tagaacctat cttaactgaa ttaggtatag ggtacgcaat gatagaatat cacacacata  6960
cagaatacga gttagttact tattcagtac ttaaagttat acagtatgat gtagataact  7020
atactgtaat tattgatact aatagtgata agaatattaa gttatcagat ttaacattag  7080
aagctgttaa ggatatttg  aatcaaatta agtagctagg gttgttttac tctagctttt  7140
tcatatgctt gtgttgccta tttaactacc ttatataagc aagtaagtat tataggataa  7200
atactaccta aaaagtatta ccgttgaata tagacctata agcttaatgc tctcttactg  7260
ttataaacat cataagtata aatctatgat tttcctaagt agcaggcgct gttttccctt  7320
tatattaacc gcttcaaaca acataaaaaa agattaggtt aatagcctaa tctataactc  7380
ttttatataa ttcttgtaat tctttttcta actttttat  tgtttctata tcattatttc  7440
ttttaataga ctgacatata aatgcaatac ctttaatcaa attaaatggt tagttttaca  7500
ctgcattgta tacaattaaa tcgatcgatt ataataatta atttaatctg tactttctag  7560
tttcttctat ataatagtaa gaaatcattt cttttgaaaa actttcgtat aacctattga  7620
cattaaatct aggatagtgt aatgtaataa gcgtagtaaa caaaccgaaa ggaattgata  7680
agatatgaac gtaaatcaaa ttggagatat actaatggaa ttattagata tagatggtta  7740
caaaagcaat aactactata gaaatgactt aaaatactca acacattatc aagttaaata  7800
tttagcttac attgatggta gttatgaaac attagaacta tttaaagaaa cgaaagtctt  7860
tagcgtatca cattcaaata gattaccaat taacattaat gttaaggtag tgaacaaaca  7920
cttatttata gagctagata atacgttata cctagtgaat gagaatgcag aaattattaa  7980
agaaaaaaag ttaaaataat agttgacact atcattaaga tagtgtaata taatagatgt  8040
agtaaacaaa cagaaaagga attgattaat tatgaaaaca ctaattacta acagtaaacc  8100
atataagaac tacggctatg aaatggaaca attcgagaga gaaaacaacg taattatcac  8160
acgagcatac cacgaaccaa caaagcaagg ttatagtctt gtaatacact atacggaggt  8220
taaataatat gaaatattta tattacatta aaggaactta taacagaatt aaagcacaag  8280
gtacaatatc aaatgactat agattatggt caggtattga tgaatgtgat gacttatact  8340
accatattaa taaagcttgt catagtcttt ataataatgg tgtaaaggaa attacagtta  8400
cagacaaatg cgttaaacta acacttaata ataataaaac aaaacttatt aaaaaagttt  8460
aagaaaagtg ttgacactta ctaaaataca tggtaatata taaatataaa gaaaacacaa  8520
taaacgaaaa ggattgatta attatgaaaa acacagtaaa agaaatggca aacggaaaca  8580
ctaaacttga aagattatta gttttagcaa ttgaggaagc ggttatgaca gagcttgttg  8640
aatatgatgc attagataaa tacaaccact tagaacaaca gttattaaac aatgaagcat  8700
taacacaagc agaacgtaaa ccatctaaca ttgattatag cacttacgag ggagctatat  8760
tagcacaaga caaagcagaa cactttacta acgttatctt aaaccacatg aacaaagaac  8820
aatttgaaca aatgattatg gatattgaaa cactagaatt taatgcagaa caaatgctat  8880
tctaaggaga cattacacat gaacttatct gataaagaac ttatagatat aatggacaac  8940
gttaatagct tcactgatat cagtgaagct attaacgaaa cagtaagcaa acaaacaatt  9000
aaaggcagtg acaaagacag cggaacgatt aaacagtaca atagtttaga tgagttaaga  9060
caagactatg acataacaac actagcacca gacgtaataa aagaattact gaataatcat  9120
tagtgtaaaa cttcccaaaa taattaacta aaactattgc aattaactgt atatttgata  9180
taatgtaatt aaggaaatac aaataaaaga aaagggattg ataaactatg aaattactta  9240
accaaatgga acaaacagca gaacttgaag gaattgaatt tgacttatta ctaacagcta  9300
tctatgaaac aatagaggta gatgttgctg aacacgattt actatgcaaa tacattcata  9360
ttgtaaacca attaaaagag aataaagaca taacaccatt agaatatata ccgtctaacc  9420
tagactttac agacgataca acaataagac tagttgataa taaagtgttt gagttagcag  9480
attatatatt ggaacatatg cgtgttgaag agtttaataa acacattaaa gactatgaac  9540
aaattaaagc agaagctata gaaatgatgt aaaacaaatt gaaagggaat aaactcccct  9600
tcttttttt  tattatttat taggattgta tacaataggt taatataaat atattatacg  9660
ggggcagggg taaaatgcca ctaaagtggg tgggtctgac agggctatgg ggctacctaa  9720
ggaacctaat tagtgagtaa tattatataa cttattatta aaagtcaaca ttaaccatta  9780
ctttattaaa ctaggtcaac attactaata actaattgta ttcattttac aataaagtta  9840
gtaatatatc cccctcttcc cttacactta attagagtat tagtatatta cagcatataa  9900
gtagtttagt atataggagc ctttccttat atatagtttt ctatggtatt ctttagtata  9960
ccatttttaat aactagttat actatgtact attagtagtg agtaatatta tataacttat  10020
tattaaaagt caacattata aagtatataa taataaaaag tcaacatagt tttattattg  10080
ttattaaagt aaacatggta agatttcttt tactgttatt attgtcctgt ctatctctac  10140
tgcctttact attatagtag tagtgttact ctatttctta caatataaaa aacacctaaa  10200
ttaataggta tttaatgtga catatcatat ctatattcaa ataattctct atctacttgt  10260
tcgaaacctt tctttttatc ttttataata tagttaccat gtaaaacttt ttcaatacct  10320
gaaggtgcat taataaacag gctattgttt ccttgtttgt ctactgctct aaatgtctga  10380
ccttctgtcc actgattgat gtcattctta ttatagcctg tatattgaat atattctact  10440
acgtattcca tgtcaattaa gactttttagc atatactctc ttactttagc ataatcatct  10500
gtaagggtat ctaagtctag aggttttact tttgctatat tgcttatact acgttctttt  10560
acaggtgttt ttgcatattc taccattaaa tcaaataact cactatctgt gcctaagctt  10620
cgaaaagaat atggttcatt tagaaatacc caagcaatag gttgttggtt ttctttttta  10680
ataagtattt tttcttttct cttggtagta tttttatttg cgaggctggt ttcatatcct  10740
aactgattta ccttcttaat aaattcattt gtatacattt tttaatacct ccttatttat  10800
tgtccacgat ttctatttca tgtattgtaa tcatgtcatc tctaaaatca tctatatgtt  10860
taaggtaaac aataccatca tgatttctag acatgccttg taattctttg tatccttcag  10920
atttaatgtc tttaataagc tgttcttgac tagtatatat tttatcttct ctataagagt  10980
agctgtcttc gtatagctca caattatcat gctctacttg gtaatatttc attctttttt  11040
actccttttt tcatagatat ttcctacaac ttcagtatta ccaatctctg aaatgcacat  11100
catagagaat ggtatgtaat ctccccccttc aacccatcca aaagaagctt ctttaaatat  11160
tacaggtcta caatcccccc aatatctaag tatatcacct tcaaatattt cagtaccatt  11220
cttatcttca agtcctgtag attgcataat tacaaggttt tctcctaagt aaccatcaca  11280
agcaaatagg tgtgaatata ctgtatggtc tgcaaagtca aatctagcaa tattaaacat  11340
tctttgtgat tcttttatccc atgctctaaa tttcggtatc attctattac ctccaataaa  11400
tgagatgatt caaatacgtt gcctttaacc tcacagtcgt acataaggaa agatttttttg  11460
tctgtatact caaagtaatc attttcagag attgcgctct caaacataaa gtcttttaag  11520
tgaatgccac ttacaacatc aatagatatc actgctctgt taattgtttc tactgcagat  11580
```

-continued

```
tcaaaatcac ctggtattgc taacacttca tcttcgaact caataatatc accctcatat  11640
attttagtac cgtttttgtc tttaagtcct gtgtattgta gtaactgtat atccttagaa  11700
aaaataaaat taccaccttc taacattatt ttctcatctt ttttccatgc tctaaaccta  11760
agtgtcatac tgctaccttc acttttttcga ccccatgct tgcagttttg aatgggagtt  11820
ttttacgagt cagttttaat gtcctatttt tggcttcttc ctcattcgta ctttgcacaa  11880
aataatgctt ttttatttta taatcacatt taaacgctaa gaacttaata caaagactca  11940
ctttataggt ttgcatcatt ctaccaactc cccatctttc cagattaacg tcatagttag  12000
gtcatcgttt aagatgtaga atgctttggt aggcacacat ctgccatata aacattcttt  12060
tatactagtg ttctcatata gtgtagagtt atagtctcct tcttgaatct cgaataattc  12120
aatcaaccta tcaaccttag cctcttctgt gatttcctct tcagcttcga cttcaaaagt  12180
gtcgtcagct gatataaatt cactaacaag acattttctt ccgtcttccg aagaaaaata  12240
aacaaagttc tcattatctt gattttctgt gtaaattctc tttccttttg ttaaatcagg  12300
atattcccaa gcccattcca tgagttcggc tagcgtcatt acttttttag tttttatttt  12360
catttctata tctcctaatt atttaatttt tctatcattt tcacaatctc ttttgatttt  12420
ctaatgtcag cattttcaca gtttttaat atgaagttaa ttttgttttt tacatcatta  12480
acgatactgt ctacttcttt ttctgttggc ttagtaggga aaagcaaccc tacaactacc  12540
tgaatttgat ttttatttag tgagtaaaca ctaatgttac atttctcatt aaagtcaata  12600
tgtggtttac ttgaattaaa tacctcatct acaattgtat ttaattcttg tataggttta  12660
aaataatgtt gttttctttg tattattacc tgtgacatta gtttatatag tttctgttct  12720
ttatcaagaa cttcttttgt aagcctttta acttctccta tccttatagt attaccccat  12780
gcatcataat tatttttaac atactcagct tcttctatgt tagtagtata tcctattact  12840
tttgaggtgg gttcctcatc ataataacag tcctcttcta catatatagc atatatctta  12900
ttcatatcta tcaaaccttt ctttaagtta aattaactat aacatataaa cattaggatg  12960
tcaactacta atatacactt ttttcagtaa gcaaaaaaaa agaacctttt tacaggttct  13020
ttactgggtt attaattttt taaatcttgg tttcctttta ttaatttttt atcatcaata  13080
ggatgaccat tgtataaata ttttacttcc atatatacat gattatccgt agccgtaagg  13140
gcatctagga tatccggatt tgtgttaatt gcatttgtat caggaaacga aaattttctt  13200
ttatccgact ggattatatc tacatgaaat ttttcttgtt ttggtaaagc gtaattaagg  13260
tcttctaaat tttgtaagaa tttagtaaga gaaaagggtt taaactttcc ttgtaaatta  13320
ttatctatat agtcatttaa tagtcttgtc atttcctctt tatttaaagt cattgtttca  13380
taatcgttaa catcataaaa aacaacaaca ttaggttgct caatacttgt gtctccatct  13440
ttgtacttag caatgtaata gcctatttca cctttgtgag ctaaataatc ttctttcatg  13500
atattaaata cttctctagc aataggtttt gtatatagtt cttcccattt atttgtttct  13560
gtgttgtaaa aatgtggtaa taagtttgcc attctgagtt atcctttctt attctgattt  13620
aagccatatc ttattagtat ttttaggcgg ttcattactt attgtgtatc catcagtacc  13680
catatctagt gtgtttacaa tgacaggctg agctacagct tcttttcac tctctaatgt  13740
tttgaaacta ggcacgtctg ttttattaga ttcttgtcca tcgactaacc aagagacttt  13800
aaagtcacct ttattataag tagtattagg ttttaaatct gttaatgtta cttttacaga  13860
actacctgta acttcatcag aagttaaaat aagctgttcc tctttgttgt agacctttaa  13920
ttttttagac ataatgttat ccctttctgt tgtgtaatac actaataata taacatataa  13980
aaaacaggta aggtctttca aaacctttac ctgcttattc tttactgata atcataccaa  14040
tcaagaaaat catctgaaca gcttaactct atagttatat catttataag tttagtagct  14100
tcatctttac ttaatgactc tatatcaaaa gtaaactcat catataaaca atctatatgc  14160
ttataaataa aatcttttg tttttccgta gctttgttta attcattgct ttttttactt  14220
ataaattgac taaagttatc actcatttaa atcttcctct ttaataaagg taccattaac  14280
tgttcttcct ttacgacctt taatttcatt ataagcaaac tctaaacact cttgtaatga  14340
catgtcgtgt tgctgagcta aaataattaa agtaactaca gtgtccccaa taccatcttt  14400
aagagcttct aggttaccac gtgataatgc cgatgctact tcacctgctt cttcgtagaa  14460
tttaagagct tgtctatcag ggttgttatt gttcaatcct ttatctttac tccattcctc  14520
tacttgacta actaaacctt ctagcgtgcg gtcttctgtt tcaccttcat taaagttagg  14580
tttttcatcg tttggtatat ggtcttcttg ttctctatcc tctattgtaa taaataaagt  14640
gtctatttct ttttcgtact tatttctctg catataatta tactgctcat actcaggata  14700
aggtacatat acagtatcgt ctgtaccatc ctcataattc aaacaaacac aaacaatatc  14760
tttgccactt agtctatcat ataatgtcat gttgtagggc tcatctaaga aaccatgaaa  14820
ctcttcaaag tattcatcct tcataccact tacctcaata gaaacttttt ttgctgattt  14880
acttgtatct acttcactat ttccatatat catagttttt tcttcactaa tgccttctag  14940
tatcaactct acattttctg gttctaacat tgcgctatct aagttttcaa aaacaatttc  15000
aatattttta attttttag tcattaataa tcattccttt tttttagtat atagtaaata  15060
taacacataa gtaaatagaa gtcaataaaa agacacctac tttaaaaata agtaggtgta  15120
agatattttg acaggtagct tgtggaaaaa aatcctgaga gaggactcga accccaacga  15180
ctaggtagct acaactagcc aataccatta ctcaggattg atagtaacgc taaatagagt  15240
cataacgtta ccatagacct tttctacgct tggtatatag gtagaatata atgattttac  15300
agtacccata tagttagact gttactctca ttataaggtt aaaaaatgct aactttgttt  15360
cgcattgtca agaggcgtta gttaactact ataataatat agcatatatt ttattgtttg  15420
tcaagttctt tattccattt actttttttct tttagtaatc ctttttttaat tagttcttca  15480
ctaatatttt tatactcttt attttctttg tagaaaactt tagctaaata tctaccaaaa  15540
gaatcatctt tgtatgtttg aattaaaaca tcttttcctt ctagcatagt tgttgtaaat  15600
tccttagctt cttggtaatt attttgtttc ttttctggtg tgtcgacacc tagtaatctt  15660
attctttgct cagaatatgt tctcattccg tggtcaatag ttacatgtat agtatctcca  15720
tccactactt tgtccacatg tgctttaaat aaatataaat tgtcttctat catcattaaa  15780
tcccctttttt actaatttaa aattatccaa tcagtattgc ttgatgtacc cttaactaca  15840
tatacagatg aacctattat agcaatttga cctttattta cagatatcat ttagatgaat  15900
atggtcttgt actgaaaagt ctacaatgac atgtttatgc tttttctttt ttgttaatac  15960
tttatatgtg ataaagaatg atataatagt taaacatata tttaattttt tcataaaatt  16020
tctcctttaa agaaggtatt taccatctca gtagttaatt ctttgctttt aaagatacaa  16080
tattctgtat ttttattcaa tatttctaac atattttgca tactacttgc tttttgtaaa  16140
tccgttaagt ctataacaac tgttatttct gcgttatcta ttagaatatt acctatgtaa  16200
taatttttaa ctccattctc cgtagcatga gaggtaacat tatgatttaa aacaactata  16260
ccttttgatg gtaagtactc tgaaaagtat aagtaacaaa agtatttgtg tatctttttt  16320
```

```
ttattctctt ccattactat taccatattc tatgaagttt aatagccttt cggtataggt  16380
tttaattttc tctacttctt ttctttcatc gtcttttctt cctaatcttg ttgtatattt  16440
aacaatatta aatagcatgc agtctataaa gccaataatg tagaaatatt cttctaaaaa  16500
tgatataaca tcttttttac ctttataatg gttcggtgta ttagtggtag aattgacatt  16560
atagtataac tccagttgtt ctacattttt cataagcttt ttagcataat ataatgtgtc  16620
atctaaagaa tgtgtcacat ctaaagatgc ttcaacaatg tttatcttta attcttttaa  16680
ttctgttgcc tctttgttac ttccaatttg tgaatcaata aattctctag tatccatatt  16740
ggtgtccttt cgtatctaaa ataaaaaccc tatctagaat atagataggg aaaaggaaag  16800
atattatgga agtgtactat aaagtacaca tataatataa cagttccttt gccttttaat  16860
ctatatcatt tattttaact tcttgtactt taacataatc tgataaacta ttaacgacga  16920
tattatcttc tactaattcg tttctattat ttgtaacatc atatgagtct ctataaggtg  16980
tttgtactaa tgctctaact gtaatgtcta tatctacata ttctttacta tacctttcca  17040
ttactcaacg tagtttcctt tagcaagctg atactttttg tgtaattctt catataattt  17100
ctccatatct ttatattttc gtacatcttc ttcaaaatga cttaaatact ctattaatgt  17160
cttaacttct ttaggttcta aagttataac tggttttacc attacgcaac atcctcacta  17220
aattgtttat ttatattttt aatatctttt attaattcgt cttttaattc tttaggtaac  17280
tcatgacttt ttaaagattg ttgttgacct aacgtatatc catattttgt tatccttact  17340
tctacagtat accatgattt ttctaaatcg tcaacttttc tagctagtaa tattaaacat  17400
ctgtcattta taatattcga agcataactg ccgacacaat gagatagctg ttcaccttct  17460
ctttttaatt tttcagtagt atccgcaggt aaaaatttaa ctttagagcc atcgtttaac  17520
ttatattctt tatttgtgat attatttaat ttattatcat atttttgttg taactttaag  17580
tcatcgactt catctttaac tgttaaatac tcatcagtaa caatatcatg ctctagtttt  17640
aaagaatatg gtgttaagtt aatactttct ttagttctat atccaagaag tactaggtct  17700
gaagcaaagt ctatataatc tctatataaa ttattaacag cgtatgaatg tatacgttgt  17760
ctgtttctga catcatagtt tatataattc accatttttc taaagtcaga aaatgaaaag  17820
ttaagaactt ctttcgtagt acctttaaaa gataaagcat ttcctattga atatgaatta  17880
gtcaccatta taaagtcgtc atcgaatagt ttgtgtaagt tagactcatt atataaacta  17940
ggaaatttat ttatgataac tcgaagtata ttaaggtaat tttcttgctc ttctttacta  18000
agagtaataa acttattata tgtttgttta cttaaattta aagcttcatg taatttccat  18060
ttatttttgt ttggtattac tagaaactct ttgtgttctt taaatatatc acaatcttcg  18120
ttgttataaa ctttatcaat attagacaca actaatttta acatattgtt taaattatca  18180
gtagcatttt cacctttact aactgtgcga taaccatcag gtctatctat catagagtat  18240
acatcaaagt tttttacatt aagtctactt agatttaagt aataatcatt attctttagt  18300
gtttggatta ttatgttaaa agctaaattt tcctttccat atttacttaa aataatattt  18360
aaaaggacag gtaaagtaat gttatttttt agtttatcct tattaaaatc atcttcatac  18420
atattaaatt taaattcttt atgttgtagt gtatttgata ggtgtaggta tacatttcca  18480
tttttattat taaagtcacc gtttactata ctccaatctg ttgttactat acttatgtct  18540
tttaaataac aagtcttaat taaaaacgga gtattattat cttttatagg tgttaatttg  18600
ttaagcccta tttttatgtt ttttaaaact tcattgtagt attcgtagtt attatcataa  18660
gatttaccaa atgcataagg gtcaatatta ataccaaata tactatagtc acccattaat  18720
aatacatcaa gtatatcatt agttgtagta tttatttgtc tttttaagtc tcttattttt  18780
tttgtaaggt aattattact attcttattt tgcgtattgt caaactgttt tagttcattt  18840
tcatagtttg cacggcagta tatattatta cgatagtgtc ttttgttata taaaggaaat  18900
tcagacctat cgtcactttc tatatactca ctatatacag tatttacatc tgtaactgtt  18960
ttacttaact cttgtacttt tttatatggg tctcccttaa acgtagtaag tttttttattt  19020
ccacataatg ctataaataa aagtaaattt aaagcgctag aataacaaaa ggtattatta  19080
atatctctta ataattcttt agagccaata tctacaatat ttttattatt tatttttaaa  19140
tatactcttt cttcacctat aaatatacta tttctattta ctttagacaa tttaagaatt  19200
tcttcttccg ttaatcctgt ttcttttatat tctactgaca tgtgtcatca cctcatttat  19260
tattatataa gtatgataac atagttaaat ttaatagtca acaaaaaaga agaacttttt  19320
tacagttctt ctagataagt ttcatattta attttttttag ttcttcttac gggtacaata  19380
tcgggattac tcattaagtc tttgtacttc ttagaatttt taaagttaat agtattaggc  19440
attgctaaaa cttcctctaa ctcatctgtg tacatagtaa ctttagatat tatatctatg  19500
tcactaatat ataaattttt agatttactt ttaaaaataa tctcatcggt actagttact  19560
tctttattat ctattaaatc catatagaag tcctttctag tctacataaa caagtataca  19620
atctttgtct gataaagaca ccgaggtcat atcattaagt tcttgtagtt gtttaataga  19680
cacatcatat ttcttactta tagtccataa ggtatcacca tttctaacct tataataaaa  19740
tttattacct ttttgtatta agtctttcat tgttatctac gcctttatat tcataataag  19800
atgcctgtag gtaacatatc gtaataagaa taaagttagc tacttctgta tatattacat  19860
gtggtgtcgt atttgttatt aacatactaa taattaaaca agctaatgca atacctataa  19920
taagaaataa atatttgcta gttccatttg tacttttagt tttataaaat ttatttattt  19980
gggataaata agctacgata atactaatag tagccattat ctgtccatat tcaacactat  20040
agttagctac tgaatagcca atataaataa caattataaa cataaccatt tctaaaatac  20100
taacttctgt tgttctaaat aagtatataa taaaacaaat aatacctagt aataaattaa  20160
tacttactga tataatttga aataggggtg catgtgttac aaataagctt gttaagctaa  20220
tacttactgt aacaacaata taaaaccaaa aatagctatc tacaccttta acattcttat  20280
ctcttatcaa acctactaaa gcaggtatat atcctacagt aactaatata gcatatagga  20340
tgcttaatat atgagctaaa ttattcatat gaccctccga aattctctat ctcatttaaa  20400
acttcttccc atgaaataaa acctttaccg ttggttaatg ataaaatgtg cttggtaaga  20460
ttattccatg ttttattatt tttaatattt gtaattgtag tataagtaac tttaaatttt  20520
ttagataaag tagatgcctt ctctttgctt gtgtaaatca agtagacatc atagtctgtt  20580
aattttgaat ttataccaaa aatattgtcg ttccttagac tggtttttat tgcatgtaaa  20640
gtgttctctc taggagtaac ccattctaag ttttcaactc tattatcatc ttttatccca  20700
tttttatgat tcacttggtt tctatcaata tttttattta agtctagcaa aaagcattct  20760
gctataatcc tgtgtacttt gcattgaata cgtttgttat tttctccaaa taacgttact  20820
attatatacc catctttatc ttttcttgtc tttaatacat ttttacgctt acctttgatg  20880
atacctgcta tacttataga atattctttt gcaaatggaa tagtagacca taaaagacca  20940
tcttcaaaat aaatatttct aggagtgtat ttcaaagggt aatacttcat agaatctttg  21000
tagcttctag gagaatagtt atattttttta aatatagttc tcagttccgt ataactaact  21060
```

```
ccatactttg tagcaacttt cctcatactg agaccactct cataatctct tattgcatta  21120
tcaatcttgc tgtcccaatc tttcaagttc taataatacc tcctcccacg aaatgaaacc  21180
tttgccatcg gttaatgaca gaatcatacc aaaaataaac tggttcgttg aaaactccgc  21240
tctgtctggg tcagtgtatg gttttccgtg cccttgacga atatcagagc aataaattaa  21300
aacaggttta ttgacgacat gatacgcttc taatatatca tcttgtgtgt ttttatctaa  21360
ctctctaaaa tctacatctt catatttgtt gataatttgt tgagcttggt gtttcattcc  21420
taataaaata ctaagttctg ctattgtacc taatccctca ttcaatacat caaatacaaa  21480
tatatctgac tcttgcatag ccttaaagtc attatttaga atacgctcag ccaaaccctc  21540
ctgtctagca tttgctttgt cgttaattga gccatcttga tgaggagagt atggagatac  21600
acctacaatt ccttctactt gattgtgttg tttttctcta tattctatca ttgcttgatt  21660
aagtagatga cctcccatat agcaaatctt atctttgatt ttatttacca ttgtttttat  21720
ctccttttta tttatttaaa agttacttta cccatttcca atacttgtat tctcttattt  21780
ctctgattgt agttctattt acaccatact tttttgctaa ttctgtatga cttaaatcac  21840
tcactcttac ttcttttatt ttttcttcat ttaacttaga aacagggttt tttcttttac  21900
cacttatata agaattaagt ttatgctctg tattatactc attagtacac cactctagat  21960
tagaagcata gttgttactt ttatcaaaat ccttatgatt gacttggggt aggttgtaag  22020
ggtttaaaat aaaaacacta gcaactaatc tatgcactat ttgagtgtta ctcttatctg  22080
agtagtttct taaagacaca atatgatacc cttttttgtt tatcgtatgt tttagtatct  22140
ttttggtttt atcactgtat acatttcctt tttcgtttat ataataaccg tagaagttaa  22200
ataaagggta aaataccttt ccatcaacat ttttaatatt taaaggctct tgatttctat  22260
taacaaaacc atatttattt ttcttcttgt atgctgagta acaaccacaa cttctaatag  22320
ttctattttt atactggtct tttcttacct ctactatatt accacactta cataagcatt  22380
taacatattt acgctttcta tttttacatt gtttaaatag tgtttttatt gggattaacc  22440
atgtttcttg taattccatc atacaactcc cttatatctt ataatttctc cttttctttt  22500
tcaaactcat ctcttagtgt gatgatatct ttattaagtt catctgaatc tttcatttta  22560
gcccaatagt aaaagtctct aagttcagga tttcttgcta aaatatattg cttaggtctt  22620
acatctcttc cttgtgataa gaagtaagct atatctctca tatatttcca gtctttgtaa  22680
tagtcagact tatatttaaa cataaatcct ttcaaatctt caaatacata cccttcatgc  22740
aatatattat aagagccatt attatcctta taccatttat aaaattcttc ccaactagca  22800
aactccaact ctttttcttt tagttgtaat cctacttcat cagcaacata tttcaaataa  22860
tcataatctt tctttttcat atttaacgta tttgaaataa tatcgagtaa gaatatatcg  22920
ctttttcgat attttatgat atgagggtct tcttcgatat caactacttc aaacactaaa  22980
gtaaaactat cgtcagcaat ataatgattt tcaaggaatg ttgttaatgt ctgtatctgt  23040
cttttagtta aagtttttc taccagctct ttaaataata atgcgtattt attcccatgt  23100
ccacttaaat gtgtttttga tttacttgca tatacaattc cttctaacgg gtcatagaac  23160
attaatccta aaaatccatt ttctttctta tatccagtta aagggaattg gatagtgtct  23220
ggcatattct ctaatttggt ttcttctact tcattgatat taaagaactt attatatcct  23280
cttcctaata ctgtatttct accttcatca atataaagac ctctagagct cactgttaat  23340
tgattccatt tctttttaga aaaagctctt tttgtaaagt taactgagaa cacatctcta  23400
tattgtttat tggttttgat gattttattt tcttttctag ctatatctaa gtattgatta  23460
ggagtgaggt ctttgtcaat actatcattt cgtctgtttg ataaaaggaa tttagggtcg  23520
tagacagtgt tttttatttc atgtttctca atgttgttgt ttttgtctat tgttactgct  23580
cttaaacaac cacctttttc tacgcgccct tctaaattaa ttgatttttt attattattt  23640
aaaggttctc tatataaatt tctataccca tgtatttgga ttacgtcaga atgttcccat  23700
tggtcatcaa cattaaaatc atatcccccg attccattaa taagctgact tgttgaaatc  23760
ttgtttaaat taccaagaac ttcaggaagg actccgccat gactaacaat atagtcctga  23820
cctttaaaac taaagtaagc cacctgttgt aattttctaa gaatagactt tactctattt  23880
tgagttattc cgttctctat gaaggatttc aaggtaggca taaatcctct tgcatgaaac  23940
agatttagag catgtttata aaaataactt ttcccaaaat ccaccttttt gaaacttctt  24000
tgataatttt ttcatcataa tatttctcct tatattccaa ttgctttttt tgctaatgca  24060
tctacatatt cattccattt gttattatca tgagacttta cttttataaa atttatatct  24120
ataaactttg agtattccct tagcatatta atatatgttt tacttaaatt gtttttagtt  24180
ttccacgaac cttcatacca ttgaataagt cctatataat ctacatgaat aatagcctgc  24240
ttataaccta gttttatagc ctcttcaata ccataacaac aagctagtat ttcacctgca  24300
acattattat acttaattaa attactattt tcaataggtt tactgatttc ttttacaatg  24360
ttctcatttt tatctaagat aatagctcct gctccaacaa gacctttatt ataagatgag  24420
ctaccatctg tatatattaa tgcagtctta tgcatattta tgcctttcta caaagcaagg  24480
gaacatctca cttgtataaa tctctttgta gtcttgtaat tttatagtag agaaatcaaa  24540
aaacttataa caatgttctt ctgcttcgat atagtcatct gcaataacat taacttcaaa  24600
accatcaact aaaataacga acaatttctt aaacatttaa aaaaccccctt tataatttaa  24660
taaggtactt aattaaatca atttcagtgt actttctga gtgttctagc tcttctaatt  24720
tttcttttac ttcttcaagt ctgtatgact cttctaaaag ttcaaactgc tctaataatg  24780
tgatactatc aaattcacta ctattaataa tgttgtgtat atattctaga tgtgtgtctt  24840
taataacgtt tgttaagtca tcaccagtat aataatcctc gatatacgat aggtctccta  24900
ataactcagc cgtacttcta ataatactat atttagatat attagggtaa gattgatata  24960
aacaattatc taatttatta cttaaatgct ctactacttt ttgcattgta ttaccttttt  25020
cttcagtact atatgaaatt ctaatattag ggtttttaga atcataatca actaaagaac  25080
tcctattagt gtttaataac ttatctaaag aagttaaaat aatagctcta tcttctatat  25140
tatctaaggt taagatagta tctataatag tataaaatgc tttgtctcct attgctttat  25200
taacatcttg aagttcaaaa atattaatca tatcctcaat ctcatgacgc tcaacaaagt  25260
taataataga ttttgtaaat ttattcatca acgtcaacat ctttaaataa ttctacacta  25320
ttagtattta aagcttttc taatttcata agattagcac tcttaggttt tcttttacca  25380
ctctcccaat aagaaataag tgagtagtga actccaatct cttgtgctag acttctaact  25440
gtatgacctt tttcttctct tactttttttt aaatttaata ctttattctc ttccataata  25500
aaccactacc tatctttctt caatttttaa aatactatag ttatttttat tataagcata  25560
cttatttaaa acgtcaagcg tttttcttt agcctctact ttacctttag ctttcatatt  25620
aacatagaaa acattacttt tatttgaacg tgtatgctta atatatactt tgtactgcgt  25680
aacctcactt tttaatacat tacgtttaaa ccatttcttt aatttttcca tttattataa  25740
ccacctttaa aacttatata tgtattgtag catatgataa atacattgtc aacttaaaaa  25800
```

-continued

```
taaaaaaata ctagggaatt ttccctagta aattatttcc aattaatacg accccaatac  25860
ttctctttta gcatacgttc ccacttgtca gtgattttac atactgccat atagaagttc  25920
ccagctgacg ggtttgtagg atatttaaat ctaatccacc aatagccatc tgctttaata  25980
acttggtcaa agtttacata ttgaccacta taaataaatg attcagctcc tacgattgaa  26040
ccacttaaac ctggtgttcg tcttacctta atcgttctat cagcagtaaa tttacctctc  26100
caattccaag ttgtttgtac ctcgtctttg aaattaggtt ctataaacca cataggaaag  26160
tcgtaaccat gggctctaat agtagctttt tcccagccac cgcctccttg agcatctccc  26220
caagtccaac ctccacctaa ccaattattt tcaattacta taatttggtt ttggtttgca  26280
cttagtaccc atgcgacatg accatgacca cacccgtatg aattattaaa gataaccata  26340
gtgcctggtt taggaatgta ggatagtgta ttttctacta ctctagcttt atcttttaac  26400
atagctttat tatcccatgg aatattacat gcacttgctc cacctaaaga ataacctggg  26460
aagagcttgt taaatccata gttagctaag tcgtaacatt gctgaccata ccaaccatca  26520
aagtctattg ctttgccttc tagacttttt aaaaatcgaa caaattcact tctagtcatc  26580
gatgctttca aaagtttca ctccttattt ccaatctatt tttccaaaat atttttcttt  26640
cttaatacgc tcttgtttat ctgttatctc acatacagca caatagaaat aatttttact  26700
agagcctggt tttggatatt taaatcgaat ccaccaatag ccatctgctt taataacttg  26760
gtcaaactca acccaatcat ccttatcgta tagccatgaa tctctattta ctatagtgcc  26820
tttaagtcct ggagatttc taactttaat agctctatct ggataaaaag tacctttcca  26880
gctccacata gttttagtag attgtgtttt tactctaggc tcagcattac ctgatttctt  26940
tacatctact gacttaataa ctttcttgta atacttagct acttccttat ctaagttact  27000
agtgtttcta cctaatccac atgcttctaa taagttacct gggtcttgtt tgtcgttttg  27060
gatgtcttgg tgacctggca tatttgtttt gtaatcaaca ccccagtatt cagctaaata  27120
agctaagaca cgagctccat tgtctaatga ttttttagaa cgttctttat cactaaagta  27180
acaaatttct acaccaatag caccatcatt agcgttaatt ccgtaccata ggtcatccat  27240
aggagcgtta tacaacacat gccaagcttt ttctgtagta ggaacacata tgatagcttc  27300
tttatcatct acaaagatat gtgcggatgc agtggaagcc caatcaatgt tatatgtatt  27360
tttgtaataa tctacattat tttgagctgt agtattaata ttccctgtat catgagctac  27420
aataaaaacg ggttttttaa ccgccatagc ttgacctgtg cgtcttgttc caataggcag  27480
taaatcatat ctaacattta cacctttcca aatttctatc attactgttc acctacttct  27540
tttgggttat cttctttatc taattcagac actaagtctt tttctacttt accatgttct  27600
aatggttctg catgacttgt atctatgtct tcattattaa ctccttcagg agccatcggc  27660
atctttgtag gaggtaactc tgaggtacta ttcattgctt cactcttgta tgttaaagct  27720
ttatctgggt cattataatc tctaggtttg ttaaagtcct gtacaatagg gctatccgct  27780
atacctttag tgtcatgact tacaagaaca cctaaaccag tcaagaaact aataactaca  27840
cctgcaattg cagtgccttg gtttacaata tcttctgcac ctttgattcc tagtaaacta  27900
catacactaa caataaacgt agctaaaaca ggtacaaaac ctgtccaaaa tgtagcactt  27960
tttgcttttg cagtaatatt gttacctgct attaataatg gtttttttatc tttttttgac  28020
ataaaaaaat accatccttt ctgttattgt aaagctaata ataatataac aaaaagaatg  28080
gttttagtta ttaaatttta agttattgtt cgttaatttg agaaagtgtt ttgattactt  28140
ctgacatttg tttattatct aagtcttcta acttagtgtg tggaagtaaa tctaatttat  28200
cccaaatatc ttttttagtt gtgaattttt cattaataat tgctctaccg attaaacttt  28260
cggtataata aatttgtttt gcagatgcca tattagtatc taccgttgtc aaaaatttat  28320
aaaactttat aaatcctatt ccttttttcaa cgtatcccct tttgagtacc ctcatcatta  28380
ctgattactc ttatatactc tactcggatt tgtatgatac tccaaaggct taaattccca  28440
tacaacgaat ggtacacata tttagtatct tatttgtgat aacttaaata ttatagttag  28500
ctaaattaat actagcatta aggtctctat caatactaaa accacattta catttaaata  28560
ctctgtctga tagttttagg tttttatgga tactaccaca tgtagaacat gttttactag  28620
aagggaaaaa tctatctaca ataacaagtt caattccttg tctttcacat ttgtattcta  28680
attgccttct aaactcataa aatccttgtt tttgtattgc tttagctaaa tgtctattct  28740
tcatcatccc ttttacattc aaatcttcaa taacaattct tctaggtttg gttttcacga  28800
tagaagatgt tacttgatgt aaatagtttt tacgaatatt agacaatctt cgttgtagga  28860
gtttaatttg tttttctagt tttatgatat tgcaagtttt gacaaacgta ctcccttctt  28920
tattttttttg gtatttgaaa gataccttac gttgcaacct acgtaatcgt ttttctaatt  28980
ttttaacctt tattgtttta ttaatattac cataaatagt accatctgaa catacagcta  29040
actcttttat ccctaaatca atacctaagg actcgttggt caaatcttca tatttatttt  29100
cttcttctat agagatactt atataccagt atttaccatc aaaagtaatt ctaggattgt  29160
agtacttagt gtctataggt agttgttcag aagttctaac ccaacctacc ttttctatta  29220
gtacttttttt ctcttttact actagtgcat acgtgtcatt atagaaacta ggtcttgttt  29280
tctttttaga tttgaactta gggaaaccag atttcttttt aaaaaatttt ttatatgcat  29340
tgcatgcgtc tttaactgct tgtttaggaa cattgttact tacttcatgt aaccaactaa  29400
actctttagt tttctttagt tgtgtaattt cttttcttaa tactgtgtct tgtataaatt  29460
ttttaccttg ttcgtaattt tcttgctgtt ttgctatagt ccaattatat ataaatcgtg  29520
ctataccagc tgatttacat aattttaatt tttgttgctt ggtaggttta agtctgactt  29580
ttttcgttat cactattcaa ttcacctact attttttttag cgttgttctt gtgtcttatt  29640
tgatttactt ctaagaactt atttggtttt atttctgttt tttacggagc atataggatt  29700
tgaacctatg agtgaaataa atcacctatt gagttagcaa cccaacctct taagccactt  29760
gagtaatact ccttagtata attaaacata catacataaa ccgtctcact ggtaagtaac  29820
atattagacc tattgttaag ttaatcacta cgcttgactc tattaggtag ctaacctaag  29880
tccatctcac gtaacctact aaagcagtac aaccataggg ttgagtccgt ttaatagtgt  29940
aatgtgatac taacatatta attagtaact ttcacatggt atgaagaatt ttaacggcat  30000
ctttatattt ttaccaatta ttattttgca ggtttatgct actcgtacta gtatcgtatg  30060
ttatcaaaca tttttcaatg ctccaactgc atgtacttgt taaggtgtat ttgtaaagga  30120
taccaccaaa acccccctaca aaaattaagc ccatcggata ctatacttta taaacctaat  30180
acattactgc taagcattcc gattgtaata aacattacta ttgacgaatt accttaccga  30240
cgtataccga taagttttaa ttcgttcgac aatcttacgc cttacaggta ccaccctgtt  30300
taaatcagcc attatgtatg tatgtttaat tatactacat ttaaagtata acatattatc  30360
attcatttgt caattaaaaa atgtgttacg ttttatagtt tttttatact agggtaaaaa  30420
cgtaataaaa gacctagttt cgacaaataa aaataaggag aagaatgttt attatgcaaa  30480
atgaaattat agctctttat gagcttatat ataatataac atactatttt gagtttgtca  30540
```

```
agttattttt tactttttta tcttgataat tcttcttgta ctctatccca atatttttct  30600
gattctgttc tattatcctc aatgtgagca gtagtacatt tacatttgat acagtataaa  30660
tgctttatat gtccctcttc tcttttctga gctctttttc ttggtactgt aaaagtatta  30720
ccacattttg aacaaactaa attactgtgg aacatttttct gtctttttttt catgattatc  30780
aatccttttc ttttaatttg ttttatattt agattatatc aggtgttgag tattaggtca  30840
acacctttat ttaatgtttc tagttaattt ttaatactca agctttaaga aacaagatgg  30900
gtattcttct gatactggag tagtatattt atcttctaag ttatctaggg ctttgaataa  30960
tttatcaacg tactcaatat cagttcctat agtgtcaata atttttgtat tatctattgt  31020
actttgagga acgttattac ttttcatttt ctttaatctt cgagtatgtt ttgatttaat  31080
attgagattt tgagaatata gcatttcttt ataaacctca ttccatgttt taccaaagtt  31140
ggggttgata atactactaa ttttaggtgt taattttcta accctttttat ttgcttcttg  31200
tttccaatca ttattttcag gtctttttttg taaaaactct agtttatttt ctaattccat  31260
aacttcgttc tctactgaag ataacctatc attttctttt tgtaaatcag tcaccaattt  31320
atttaatctt tctgactcct caaagtactt aagcatttct tttttagctt cttgaggatt  31380
atctataata gctttagcaa aatcatcatt catgtacatt ccatactttc taatatcagg  31440
tagaacttct gaagttaccc aacgcttgaa tcgtttagct tattctagtt ttgatgaaaa  31500
gattaaactg tataaacctg attcgttgat taatgtcaca ttccttaatt gacctgcgta  31560
cctaatttgg gtacgtagct tatcttcatc ctctgcatgg ttatttatag cgtttcgata  31620
atttgaatat cctaatatct tagctacttc gttacctaca aagtaagttt gattgtcttt  31680
aactactgtt cttactgatt ctccttcaaa attaaacatt aattggtttt ccatgttaca  31740
tcagtccttt tcttttaatt gatactctta ttctaacgta agacttaata aatgtcaatg  31800
ctttttgtta aattttatgt aattattttg agaaatcctt ttatatcaag gtttttaaag  31860
attttttttac ctatttggaa aataaggagg attccttata tatataataa ataattataa  31920
atactaaaat aataatacta gttataataa ttaataaatat atataggaaa gtcaacaaag  31980
agtaataaaa aagtgactta cttaaaagtc actaattttc aaatactaat ttaaatgatt  32040
ctatgaataa agggttaatg aatactgtat cagaattaat atcctcagag actctaactc  32100
taactgatgc ttgtccatgt cctctaattg ttccatttat ctctctttgt gtatactcaa  32160
tactatcgtc agagattaaa taatattttt ttccactaat cattgttacc tcagcatgtt  32220
ttaccatatc aaaactccta actaaattta ttgaaaatga aagttataat agaacctaac  32280
actagtaata gtactttctc ggtagtatcc ttctttcttg tgtccttaac aactgtattg  32340
ttagtgagtt cttttatctt ttcgtctaat ctatctagct gtatgtagat agacgattgt  32400
ttctcactat taacagctac ttctttgtct aaactaacta ccatttttct tagttcatca  32460
acttcatttt ctaattcctt atacgtattt ttatcaatat agctaccatc ttgtatttta  32520
tcttttatct tatctacttg tcctacaagg ttttttagtt cttcattcaa ctaaagtcac  32580
ctcttaatgt ctaacttttc agattctgaa tggacgtcat agttttcgaa aaagttatta  32640
ataatttgca tataatcctc agtaactatc tcaccgtatg acgttttagt atttatttca  32700
aacctaagct taccaaactc atggaggtct atttctttaa taacggtatt aggattatca  32760
gatggtatgt aataataatc aaaatatata atagagccgt tgataagcaa cctatcaatc  32820
ctatagacgt ggaagaattt tctatctcgt ctaaagtgag ctaaggcatc tttaaactct  32880
aattttaata tatctttata cttagtcaaa tcaacttacc cccttataat taattttgag  32940
ctacactagt tttgtgttat aatagttatt gcagtagcag atataagtat tatgtttaat  33000
aaaattagca accaccaacc acctgtactt attaaccata atgaaaaaca agatagtata  33060
taaacaacca ccaagtagcc tatatatttc ataatgtttt tacactcttt taatactact  33120
acgtatgcta gtgatttaga taagctaaac agaaaaataaa aataaaaaat aaaaagaggt  33180
atagctataa tgcctgctag tataaccact aattacacct aatttctttt agctagataa  33240
taaaatctta tataatacaa ctttaatata acattgaaac ctgtttataa atcaacaatg  33300
ttacattaat agtgtacggt atattttaaa ttaggaggac tgaactaata gggtgaataa  33360
taacatagct gtatttatat ttaaaactct aataattatt atttttattt tgtttatttt  33420
gtctattatt aactcactgt cattaatata ctctattcga cctagtacag ttatgactta  33480
ctttatattc ggtgggatag tttctaatgt ggcattaaca ataactgata aattattatt  33540
acacaaagaa gaccccttac ccgattatat tctaaaagaa gtagagctaa ataacaatga  33600
attacaagta ctaaagaaaa ttgtggagtc acaaactaat gtttctgctg aggaagtaag  33660
agtaagagca aaagcacaac gtcgaatact aaaagataaa aagagagatg ctgtcgatga  33720
aaacgaagaa ggacattaag gaacaacgta aagagctaaa agataatgca accgctgttt  33780
ccttaacaaa aaaaggagat aaacgtattg caagtcctag tagggtgtgt tgtttatgtg  33840
gtcaatctct ttcagggatg aactatacta aaggtaaatc tatagctaaa gttaatcatt  33900
ttcatttaca gtattctaag tacttatatt ttgacatatg cgcagatatt aataactgtt  33960
acaagaattt aaagaaagta ggtgaattga tagagtgagc gctgaaagtt taagggatat  34020
gttatctaag aagaaaattg aagacgaaga taaacgtaaa tatatagctg atggatttat  34080
gtcaggtatt actaaactta tgtatgactt taataaaaag attgatagag gggaaataga  34140
agtaagagac cctaatgatt tgtacaaagt atttgttatc ttccaacaaa tgcaaaactt  34200
aattacagat ggttctgatg gtggtggtgc tataccgcaa ttatcaagac cacaacaaga  34260
gctctttgat gaaataacaa atgagaatag taaaggtgag aaagaagtag atttagagaa  34320
gttatctcaa ctatctgctg atgacattac tgctatgatt attgataaag aaaaggttat  34380
gaacgaagag aactcaaata cattctaaag aaaggtgtat atgaatggac ggtaaagaat  34440
tattaaaaat aacacaagaa acattcggta cacaaaatgt tacgcaagaa caagttgacc  34500
atattatcaa catgttaaac cctagtactt atatgctaaa atatcatacg ttacgaggtc  34560
acccgataac ttttagtatt ccaaacaggg acagaagtaa agcacaagct catagacctt  34620
ggcaagtccg taaacatact gtgcggacta taaacctttt ctaaacttgg aaactctaag  34680
tgcttaaaca agcatatgac aatcaagtgc taaatttagt agtgatacta ataaatgcct  34740
aacgactaaa cttactggta aacttataaa tggataagtg tagaacagta taaaagggaa  34800
accgtaacga aagagggcgt atacacctaa atgtatacgt atgatatagt ctaatcccct  34860
aataaatatc gggaaaccga gggtaataaa tgatagtaaa tgacaaccat cctaataaag  34920
ttgtgattaa atcacgacag cttggataaa gctttgttca agtaaaactt tcactaaaag  34980
gaaaaactct aagggataat atcctatgac aattccttgc taaaaaaatg cctaacgact  35040
aaatttctag gtagataaac gaataggttt attgagaact agataaaagg gttaatgacc  35100
cgtaacgtga aagagttaat gtcttttcat tagctaagat atagtctaaa ccgattctta  35160
aatgaatgtt aaagtattac gaaagtaacg gtagtaattg taagtgagat gggtgtaatg  35220
gaaatggtac attttgctga tatgcatagt tatgcaagtg taaagtgtct atacacattc  35280
```

-continued

```
cctagattat aagttgggga attaaaactc tgttaaacgg tcataggaaa ataaagaata  35340
tcctggtaag agagactaag tcctaatgga tagagttaat accgtgctaa atcaacctaa  35400
taagttgtaa atgccgaacg actaaatttc tagatagctt attaaaagga ataagtgaaa  35460
actagataag aaagtcttga caaaaatacc aaagtaagtt aatatattaa ataggaggtg  35520
gaaaaacaaa tgcctagaaa aaaacacatg aagaatttgt aaaacaagta gaagacatag  35580
caggaaatga atacgctgta atagggcatt atgaatacgc aaatcaaaat ataaaaatgt  35640
ttcataacga atgtaaggaa gaatttgaaa taagaccaaa taatttccta caaggtaaaa  35700
gatgttctgc ttgtagaagt aaaagaataa gtaggataca agataaacca cttagtgaag  35760
ttaaaagaca actaaaagag aaacataagg gtactataga gattataggt gagtatacaa  35820
atactcacac taaaacagat tttaaatgtt taacatgcaa ccatactttc tcttcagaac  35880
ctaattctgt tttaagactg agtggatgtc ctaaatgtaa agtttctaaa agggaaaaat  35940
taatagctga attccttaaa gaaaataata tacgttttaa agaacagaaa agatttaaag  36000
attgtgttca taaaagacct ctaatatttg atttctacct attagattta aatactttaa  36060
tagaatatga tggattacag cacagtaagc caatagatta ttttggcggt gttaaagctt  36120
ttgaagaatt gaagtataga gatagcttaa aagatgatta cgcaaaaaga aataatatta  36180
ggatggtaag agtgtcctat aaacaaaaag agaaagagat aatagaagaa ttagaaagtg  36240
ttttgggtgt ggtaacccgt caagaaagta aagcagagag ctcaacacca aaaagttgag  36300
ttaagatata gtctagtccg tatgtaaata tcacgaaagt gacggtagta acgactaatg  36360
aacagatgaa gaaattcgta caatcaagac ttaatccagt attagaaaaa ccttatttta  36420
gagatattgt taattgggat aaggactcat taggttataa acaaataaga aattctagtt  36480
tatttttcag aactagtagt aaagctagta ctgtcgaagg tgtggatagg taacaagtcc  36540
acattaaact ctgttaaacg gggaaacccc taacgtaaag acgagggcaa tcccgtgcta  36600
aatgttgact ttataaaaag aatatgatat aatgtattta taaggttagc taaatgccta  36660
acgactaaat ttctaggtat ctatacaaaa gggtatagtg agaactagat aagaaaaccg  36720
ccaagattat ttttaataag taaataattt tatgaaaaaa agcgtgtaaa gcatattact  36780
aatgataaga ataaagtaca agccttaatt aaagattatc aatatatgga cttacatgga  36840
tgagttattt gaaggggaat ataaattttt agaaccttat ataaatagtg acacagctat  36900
caaaggaact aatattagaa cttcttggcg gaagtaaagc agagaacctt tcacctaata  36960
gaaaggttat gatatagtct aaacccactc ttaagtaagt gttaaagtac taggaaacta  37020
ggggtacaaa ttgattgact atctttcact tgacgagtac gaccgtgtaa ataatttagc  37080
tgagagctca gctttagaat ctatgtcaag ttcacctttt aaaatagtaa gaaggtggtc  37140
tacaccaact gtaagagatt atggtataga taaactgtat aaacaatcag accaatggtt  37200
ttatggttat gattgtgaac actgtggtca ttttaatgaa atgaagtatg ctgattataa  37260
acctgatgac ttagaaaata gtggtaatgt attactagta aatccagatg gaatagatga  37320
gatagctaaa actgtccaag atggtactta ccaatatgtt tgtcaaaaat gtggaaagcc  37380
tttagatagg tggtactctg gacgttgggc ttgtaaatat gccgagagaa cagaaaataa  37440
taaaggtatt cgtggatact atataagtca attaaacgca acgtggataa gctgtgatga  37500
gattaaagaa aaagaaatga atacagaatc taaacaaagc ttttataact acatcatcgg  37560
agccccttt gacgatgtaa aaatgaaagt aacagaagat gatgtattca ataataaatc  37620
tgaaattgca aaaacacaat tatttaatag agataaatac aaatttattt cttgcagtgt  37680
tgactggggt aattttcact ggtgtgctgt acacggtatg acagaagatg gtcatgtaga  37740
tttaatacgt ttattttctg ttaagaagaa tagtagacct gatatggtag aagcagacct  37800
agaaagaatt atattggagt tctctaagta cgaccctgat attattgttg ctgataatgg  37860
tgattctggt aataatatcc ttaaattgat taattttttt ggtaaagata aagtatttgg  37920
ttgcacttat aagtccagcc cacgttcatc aggtcaattg tacgcacagt ttaatgagaa  37980
tagtaataca gtaactgtag ataaattaat gcataataaa cgttatatac aggatttaaa  38040
agctaaacgt attagtgtat accaacaagt agatgaagag ttaaaaactt atcttaaaca  38100
ttggcaaaac gttattataa tggatgaaga agatgataag acaggagaaa tgtaccaaat  38160
tattaaacgc agaggagacg attttgtaat atggtcgtct ataaacagtg ttaaacgggc  38220
atagtaaaat aatgtataga aaaacaatat actggtaaga aaccctaaat ctgactatac  38280
acagacagtg ggaaccaacc gtgctaaatt cttaatttaa atattaacat tatattttt  38340
aatgttatta ttaaattaag ataaaagcct aacgactaaa ttcgttacta ttaacgtaag  38400
agattaaaat aatttattga gtatactaaa aaggagggta gttaagtggt ttatgataac  38460
gagtggttta ttaatagaat taaagatgtt agaccagagg actatgaaga atatgaattt  38520
ttagatgact atgttaatca gtacacaaaa ctaagagcta ttcataaaaa atgtggtaac  38580
aaaatactta taacaccatc aacatttatg agtaaacgta agacaggttg taatacatgt  38640
tctcaaaaaa gagtccatag taagcaaaga aaaacacatg aagaatacca aaaggaatta  38700
cctgaaggta taatggctat aacaaaatat gaaggtgcat ttaagaagat aactttacac  38760
tgtttctttt gtgatagtac ttatactatt actgcaagag atattttaaa gtataaacaa  38820
tgttcgagat gtaacaggag atttaatagg acattggaag atattaaatt tgaagtacgt  38880
aaagaaacga aaggaaacta tgaagtagtt tcaaatcatt ataaaaatgc acacacccc  38940
atagaaataa agcataatga gtgcggaaaa acatatcggg gaactatggc aaattttaga  39000
aaaggtagaa gatgctcaca ctgtagaaat tccataggtg agaaattagt agaaagttat  39060
ctagagcaaa aaggtataac atatgaaaaa caaaaaactt ttgaaggctt aaagttaata  39120
aataacttat catatgattt ttattttcct gaatataact tacttatcga atatcaaggt  39180
gaacaacacg ttaaacctgt caagcatttt ggaggagaag aacaatttaa gctacaaaaa  39240
aagatagata gtataaaaag ttcttatgca aaagataacg gttatgagct ttttgagata  39300
ttctatacaa ctaaggatta caaaagtata gagaaattgt taaacaataa attattttat  39360
tcgtaaagca ctgagttatc aatctagata actaagatat agtctaatcc cctaataaat  39420
atcgggaaac cgagggtatg aaatgcatta cgcacagtct tcagtaattg gttacattgg  39480
tcttactcgt ttaaaagaat tgtatgataa aggcaacggt acagcattca catccacttt  39540
tataccaacg gattataata atacacaaaa caactcgtct aatgagttct attttgatga  39600
ataagaaagg actgacgact tgacaaatat attaaattat gatacaatac aagaagatga  39660
tataagcaag gagacattta atttattaat tgaagagcct ttaacattat catatgtttc  39720
tatacatagt gattttttag ataataaata cgattacata tataaatcct taggctttga  39780
taatttcatg gactgttatt tatacgtaac aagagaacca gaacgtatat ataaaggcgg  39840
agctaaagat ataggctcat tgaataaagt aaaaagaact gtagtacgta atgggaaaga  39900
aattgaaatg acaatctatg aagataataa aaacgatgat aaacctaaag agagtaatag  39960
tgaagaacca aaagaaccta aaactgctaa aggttctagg gttattactc acggtgatga  40020
```

```
tgagaaacct aatcctaaaa agattgccag ttctctatct accttaaaga ataaaggtgt  40080
gaacactgac cacatagatg gcaacgcatc attatataaa gaatttgtag atgataataa  40140
taatacaata ggactagctt cctttaaaga gacagattct gatattatat tacatggata  40200
tgtatcagac tttgaaacta ctggcgtagg tgctaggtct ataatagagt taatttattt  40260
agcaataaag aagaacaaga acgctgttgt ctatgctata gaattacctc aagctataga  40320
gttcttaaaa ttgttagggt ttattaaaaa taaagattac tatgtattaa aaaaacaaga  40380
tataaagtta tttttaggtg agtacagtga gcttatttag cactgtactc atttatacaa  40440
ttatatatat aagtattatt atattagtag ttgtaaatgt aatagtaaaa gaaaaaagat  40500
tgaataatgc taagcagtta cttatacaag taaaaaagga tattataaac aacttaaaaa  40560
agggagatat gaatgattaa agataataat acaaaaacat tggaagagtt aattacacct  40620
atttctacag aagaaaaaga aaataaagtt aaagaattta gtaaaacatt atgtgagatg  40680
attaataagc tatatagttc ttacaatgta ttaaggcaag accctattga tgaaacacaa  40740
agattagacg gttctctaat ggtgtttcaa agtagattag atgatacatt aacaggtgaa  40800
gaacaccaaa aactttttaa attagctttt gattataata ttgatatttt tgaagctaac  40860
aagcagttta aagaagatgt acaaaatgga gaagctatta agttaggtga tgttgttgta  40920
accgacacag ctttaagtaa tgttttatct agtaatgagc ttaatgttag tattacattt  40980
atgttaagca aagactatga agaaaagaaa cgtattgaag aagaagaaaa ggaaaaacta  41040
gataagttat aatagatatt atgagacctt tatggatagg taggaataaa taatatgaaa  41100
cgtaagttta gtagtaatga gattactata acacttataa ctattgtagt tgctctattt  41160
atagtattaa ttacagtagc atttaacaag taccaaattg ctaaagaaga taaggacaga  41220
tatcaaaagc tagtagaaat ttatcaaaaa gcagatgatg atgacggtaa aactaaaaaa  41280
aggtatgttg agaagttaaa tagggctgag gaagaactta aaaaggttaa agaagaaact  41340
aattataaag gttataatga taaaacagaa aaagaaagag ataaagagga taagagtgta  41400
agagaacgta tttatggtaa tgataaggat aaagatttag tattagtaaa taataaggtt  41460
gttgtaagta atgaagttac tagacctaag ataatagaag ataatggtgt cagtacagtt  41520
gtagtacctc ctgttgtaag tcctgttgag ccaccaagtg aacctagttt atcttctcct  41580
actataccta aacctattat tcctaatcct attaacccta aacctattat tcctaatcct  41640
attaacccta atcctattct acctaaacct aacatcccta cccctaaccc actacccct   41700
atagaacctg aaaaacctat agaacctgaa aaacctatag aacctgaaaa acctatagaa  41760
cctgaaaaac ctatagaacc tgaaaaacct agctcagata ctacaatacc tttagttcca  41820
ttggaaccta gcacacctgc agatgaaagt aatgatacta atggagaggg ataacctctc  41880
cttttttttg ctatattaaa agagtaataa aataaacatt atagttggtg attttttgat  41940
aggattaaac gtacttacag ctatatccgt agtttttgct tgtgtaagtc tactagcact  42000
aatggtattt gcgtatatta aaactgaaaa aagtagtaag ttggttctat atttgatata  42060
tgctataatt gctataggtt cttatgtagt attaacaatg tttcaagcca cgtcaatcat  42120
tataaaaaat gatgtcatag actctattga gaatacggag cagtatgtag ggtttaataa  42180
ccctttaatt gtttttggta taagtttctt tggagctgta ataggcagtt tttggttttt  42240
agttatgaag attgtaaata ctaggaattt aaaaaaataa aaattaaagg attgaagcat  42300
ttgctatttt caaaagacga taaatgggat gaagcaaaag actttataaa aggtcaagga  42360
ttagcagata attggataga agtagtggat tattatagac agataggtgg taaacatgta  42420
gctatgttta ttgctattga taaagttaaa tatatggtac tagaagctac aaaggataat  42480
aaagtaatat tggtagataa ggataataat attgtgttag aggattatga tattgttatg  42540
gaaagtaaga aaatgtttta ctatatagaa gaaccattcg aagtaaagat aaatattcct  42600
aaacatatcc aagacattac ctataataac actgttatac taactactat tcgaggaggt  42660
aaataaaaag ttgcctgatt tatttaaaag tctaaggtta ggtagtatgt ataaagaaga  42720
cactgaagac cttatggttc ctatagatga cggaatacaa gctaacatta gacaaataga  42780
acaagataca aaagagatgc aagaaattac taaatctcta tatggtaaac agcaagctta  42840
cgcagaacca tttttagaaa tgatggatac aaatcctgat tatagagata agaagagcta  42900
catgaggaat gctcataact tacatgaagt gttaaagaaa tttggtaata actctatact  42960
aaatgctata attattacaa gagctaacca agtatctaca tactgtaaac ctgccagata  43020
ttcagaaaaa ggcgtaggtt ttgaagttaa attaaaagac ttagacgcta cacctggtat  43080
taaagaaaaa gaacagatga aacgtattga agaatttatt cttaatacag gtacagataa  43140
agatatagac agggattcat tccaagagtt ttgtaaaaaa atagtaagag atacttacac  43200
gtacgaccaa gttaacttcg aaaaagtttt tagtcctaaa aacaaaacta agatggagaa  43260
gtttattgca gtagacccta gcaccatttt ttatgctact gataaaaacg gtaagataat  43320
taaaggtggc aatcgctttg tacaggtcat agataagcaa gtagtagcta gttttacaag  43380
cagagaactt gtcatgggta ttaggaaccc taggtcagac ttaaattcta gtgggtatgg  43440
attgtcagaa gtagagattg caatgaaaga atttatagct tacaataata ccgaaagttt  43500
taacgatagg ttctttagcc atggcggtaa caataagtta caattaaatt aaaataaaaa  43560
aatatttaat ataaactttg ccgtgcatgt ttagtaataa gcatgtatca agggttaaat  43620
gctatgaaat cctaaagctc aattaactaa aacagaaaga gaaatcttag acggaaaagt  43680
tacgaaagta gaaaaaataa ttgagatacg ttaaggttaa atcctaagac gaagaacaat  43740
ggaagtatag cagggaaagt cctaagttca aatgaataag gaagaccctc aacgactatc  43800
tcctgacggg agagtaaagc cacaagctat tggtggaaga aaaatcctta tcctacgaaa  43860
agtaggaatg acaaatagtc tccactcgta tcgaaagata gagctataga ttaactatag  43920
gagttataag tagcgttata actcaaagaa agttaaaatt tatagataat tacaatttta  43980
ttccaaataa ctgttgacat tatttccttt atgtagtata ttatatacta taaggaggtg  44040
aatataatgt cggaagagaa atataaacgt attaatatta gattactacc aacaaaagaa  44100
caagaagaat taatgtggaa gtccgtaaat aatgttagat ttattaagaa ttattttatt  44160
gctcgatgtt acgaggaaaa agataaaggt acttttataa atttgtcttt ggaaaaagac  44220
tttaaaaaag aattaacata tattactaaa ctaaacgaat ataaatggtt aaccgaatcc  44280
gatagacatt ctaaagtagt agcaataaaa gatgttttga atggttttgt tagatactat  44340
aagggcatag caggaaaacc taaatttaga aagagagggc taacacctaa tacctttttct  44400
gttagaaatg atgtaatgcc tagtggatta tgtaggttta gaagagatgg taatacattt  44460
aaagtatctg taataggata tattaagtat tctaaaagaa gctttaataa tttcaaacat  44520
atatttgata ttatagagga taaagataaa ttttattctc ctgtaataag acatgatggt  44580
aagtactggt atatttcatt gttatataaa gataacttag ttacaaatca aaaaccaaga  44640
gagttaactg atgaaattat aggtatagat ttaggattaa gaacattaat gacttgttca  44700
aatggtatta aagtcagaaa tattaattta gatagaaaag ttttaatact agaaaaaaga  44760
```

```
gaacgacgat tacaaaaaca ggtttttaga aaatatgaca tgaataaaca aggtaataaa  44820
tatgttaaaa ctaaaaatat tattaagtta gaacgtaaaa taagacacat aagaagaaaa  44880
cttaaaagta taagaaataa tcatatacac acagaaacta aaaaaatagt tgaaatgtta  44940
ccgaaagaaa tagttataga agatttacat gttaaagaaa tgttaaaaga taaatggaga  45000
agacatgaaa tacaatatgc taagttcttt gctataagac aaatactttc atataagtgt  45060
aaagatagag gtattctact aactgttgct aatagatggt acccttctag tcagttatgt  45120
agtaattgtg aaactagagt aactggtaaa caaaaaacaa ctattaagtc gggttatcat  45180
acttttaaat gtaaaaactg taatcataat ctagatagag atttaaacgc tagtattaac  45240
ttaaagaact atagatactc caattggtat cgaaataata ttattgagaa acaacaatag  45300
taatattata tgtaccgttc catgaacggg agtttaagcc tttggagtat ctagttagta  45360
gaatattaaa agtaactaac ttagttagtg aatgaatgaa tggattattc aaaaacagtt  45420
acagaataag gaataaaata tataattatt tataaatttt aactcatggt actactcggg  45480
gcatattaca gattagagct gaccaacagc aatctcaaca tgcgttagaa aattttaaaa  45540
gagaatggaa atctagtttt tcaggtataa atggtagctg gcaggtgcct gttatgatgg  45600
ctgatgatgt taagtttgtt aatatgacac caacagcaaa tgatatgcaa tttgagaaat  45660
ggttaaactt tttaatcaat attatttctg ctttgtatgg tatagaccct tctgaaatag  45720
gattccctaa tagaggagga ggagccacag ggtcaaaagg cggttctaca ttgaatgagt  45780
cagaccctgc taagaaacaa caacagtcta tgaataaagg tttacagcct ctattaagat  45840
ttatagaaga attaattaat agacacatta tatctgaatt tggtgataag tatactttcc  45900
aatttgttgg aggagatact aagtctgaat tagataagct tagtatctta caaaaagaag  45960
tacaagtata taaaactgta aatgaagcaa gggaagaaca aggattgaaa ccaatagatg  46020
gtggagatgt aattcttgat tcagcatttt tacaaagtac agcacaagaa atacaaaaag  46080
accaatattt agatactaaa caaaaagaaa gacttcaatt acttatgagc tatacacaac  46140
cacaaactga tgagcctact gatgatagta aacaagaaac aactaatcaa gaggtaggaa  46200
cagataatca gttaaaaggt gatgataacg tatatagaac acaaacatca aataaaggac  46260
aaggaagaaa aggtgagaaa tcttccgact ttatgtaaat aatactaaca acctaattaa  46320
tacttaggtt gttatttttt aatttggagc tataaatatt ttatgctata ctatgtgtgt  46380
agtaatgaat aatgttgatg atatactttt tgttatatta tgtatgtaca tataaaataa  46440
caattaagtg aggtgtataa tcactttgga agaaatgaaa tttaatgctt ttgttcctat  46500
ggacttaaag aaatccatag atacggaaga tgatacaaat aaatattcta tcgtatctgg  46560
ttgggcttcc acaccagctg ttgatttgca gaatgacatt ataaatccaa aaggtattga  46620
tatagaatac tttaaaaaaa atggatatat taactacgaa catcaacaag ataatgtagt  46680
aggtatacct acagataact gttatgttga tttagaaaaa ggtttattta tagaagctaa  46740
gctatggaaa gatgatgaaa atgttataaa aatgttagac ctagctgaga aactagaaaa  46800
gtcaggtagt ggtagacgtt tagggttttc tatagaaggc gctgttaaga aacgtaacat  46860
aaatgacaat agaattgttg atgaacttat gattacaggg gtagcactag taaaaaaccc  46920
agctaatcct gaagctacat gggagagttt tgttaaatca ttccttactg gaacggaaac  46980
aacaccagac acacaagtag atgcaggagc cttacgtaaa gagtcattag caagctctat  47040
tactaattta acctatgtaa caaaaattaa agatgttaaa gagtataatg atatttggaa  47100
taatgtagta gaggacttaa ctaaatctaa taatatgggt tatgaagaat cagttattac  47160
attacaatta gccaaaggac tatcaagaaa agatgctgag atagcagtta tgagtattaa  47220
taaaaaaaat ttagaatagg ggattatatt atatgcctac ggaattacaa aatattctac  47280
aagaatatga taacttagac aaagaagaag tatcaaaatc tgtagaagag tctaaagaag  47340
aagtaaaaga agataaaaca gaagacacta aaacagaaga cactaaaaca gaagaaaaag  47400
aagaaattaa aaatgaagta gaagctacag aagagcaagt agcagaagct aaagaagaac  47460
cacaagaacc tgcaaaggtt actgaagaag atgctaaaga agcacatgaa caagaagaaa  47520
atctagaaga agaagtatct aagtcagcta aggagtcgaa agaccctgta gataaaaaag  47580
atactaaaac agaagacaaa gacaacgaga aacgaaaaaa taaaaaagac aaaaaagaag  47640
aaaaagatga agaagaggaa gaaaaaacat ctaaatctat ttctgataaa gatattgtag  47700
atggtttccg tactatcttg aaatcattcc aagacattaa aaaagaaaat gaacaatatg  47760
tgactaaatc agatttagaa gaagtaacta aatctattca agctttaact gataaaatta  47820
attctaatga agaagtttct aaatcagttg agagcaacca agaagataaa gaagaagcag  47880
tagaaaaatc cgtaacgact aataacactt cgaatgaaca agatgtagtt ggttatgtag  47940
ctaaatcagt acaaacagaa gaacaagcag aaactacaga agataaagaa gaacaagaag  48000
tagaagttaa agaagaaagt agagacttat ctgtagaaga ccgtgaaaaa ttcatgagta  48060
cctataaaga aaaatctcaa aacccacata cgaatcgttc agaagtattg aatgcttatc  48120
aagcttactt aaatatccgc aacaatccag agcaagcaag tgaaaaagac tttaatattg  48180
taaaagaatt tgctaatctt taattaagaa acaaagttgt gttatattat agtgtgtaaa  48240
ataaaacaat aaaaaaaaag agcatatatg aaaggtgata tatataaatg aaccaaaatg  48300
aactttcaaa aaagcaacat gcagttgctg atgaattaca agaaaaatta tcgaaatcct  48360
tccaaactgg atatggtatc actcctgaaa cacaagtgga tgcaggtgct ttacgtcgtg  48420
aaattttaga cgaccaaatc actatgctta catggggaaa taatgattta gtattttacc  48480
gtgatgttgc acgtagacca gctgaatcaa cagtaattaa atatgatgtt ttcttacgtc  48540
acggtaaagt aggtcattct cgttttgtac gtgaaatcgg agtagcgtca gtttcagacc  48600
ctaatatccg tcaaaagacc gttacaatga aatacatttc tgatactaaa aatatgtcat  48660
tggcatctag tttagtaaat aacattgctg accctggtca aatcttgact gaagatgcta  48720
tctcagttgt tgctaaaaca attgaatggg cttcattcta tggtgatgct tcattaactt  48780
ctgaagttgg tggagaagga ctagaatttg atggactagc taaattaatt gatgctgata  48840
acgttatcga cgctaaaggc gctcacttag atgagaaatt attaaaccta gcttcagtta  48900
aaatcggtaa aggttttggt acagctacag atgcttacat gcctatcggt gtacattctg  48960
actttgttac taatatttta ggtcgacaaa tgcaattaat gcaagacaat agtggtaatg  49020
taaatactgg tttcagtgtt aacggattct attcatctcg tggattcatt agattacatg  49080
gttctactgt aatggaaaat gaattaatcc tagatgaaac tttaatccca caaccaaatg  49140
caccacaacc agctacagta aaagctgaag taaaaacaaa ccaaaaaggt aaatttacta  49200
aagaagaaga ccgtgcaggt ttatcttata aagtagttgt tcactctgat gaagctgaat  49260
cagcaccatc agaagcacaa gttgctacag taacaaatgc tacagatgga gtagaattaa  49320
agattactgt taactctatg taccaacaaa gcccacaatt cgtatctatt taccgtcaag  49380
gtaaagaaac aggtatgtac tacttaatta aacgtgtagc acttaaagat gcacaagaag  49440
atggttcttt agtattcgtt gataaaaacg aaacattacc tgaaacagca gacgtattcg  49500
```

```
ttggtgaaat gtcaccacaa gtattacact tgttcgagtt attaccaatg atgaaattac  49560
cattagctca aattaatgct agtattacat ttgcagtatt atggtatggt gctttagcgt  49620
tacgtgctcc taaaaaatgg gctcgtatta aaaacgtaag ttaccttgca ttaaaatagt  49680
aaatacaatt aaaaattgaa tacaatagaa taaggagtat acctaagggt tgctcctttt  49740
ttattactac ttatagtata caagaaagga atttaaaaat caatgttaac ttataaatta  49800
aaaaatatta aaatggctac tgtacatggt caagtagaag tagacgataa aggcgtagtt  49860
aaaggactaa ctgctaaaca agaaaaagat tttgctaatt taccaggttt tacacatatg  49920
gaagacaaga aaacaacaaa gaaagaagta aagcctaagg aagaaaaaga agagaagaaa  49980
ccaactaaaa aaacaactaa aaaagaagat aagtaggttg ataaaatggt aaacagtatg  50040
tttggtggta gtttagaccc ttacgaaagc tctttatcat atgagtatcc ttatcaccca  50100
tctggaaacc caaaacatat agataaaaga gaattagata gtattactct agctgattat  50160
ggttggtcag cagatgctgt gaaagcctat atgtttggta taacagtaca aaaccccgat  50220
acaggacaac ctatgggtga tgattttttat aatcatatat tagaaaagagc tataggtaaa  50280
gcggaaagag ctttagatat atctatttta cctgacttac aacatgaaat gagagattac  50340
tacgaaacag aatttaatag ttatatgttt gtacacgcat ataaaaaacc tatattacag  50400
gtagaaaatt tacaactaca atttaatggt agacctatgt atgattatcc agctaactgg  50460
tggaaagtgg agcatttagc aggtcacgta cagttattcc ctacagcttt aatgcagacg  50520
ggtcaatcta tgtcttacga tgctgtattc agtggatacc ctcaattagc aggaatgtac  50580
ccaccaagtg gagcaacttt tgcacctcaa atgattacat tagattatat tagtggtatg  50640
ttacctagac aaagagcagg tagaactaaa ccatgggaag taccaccaga attagagcaa  50700
ttagttatta aatatgcact aaaagaaatt taccaaatat ggggttacga tgatattacc  50760
ctgtgtgtag cgtaagttgc acattttcaa aggttaactg ctaagaaatc ctaaagctaa  50820
ctaaactaca aagtaagtcg aaagactaag cttgaatgtt gagaaatcag aaaaaattag  50880
ttagatactc taaggttaaa tcctaaagag aagagcaatg gaagtttagc atcgaaagtc  50940
ctaagtcaat agataaggaa tacgttcaac gactattctg tatagacgac agaagtaaag  51000
ctccaagtga ttgggagaag aaaaatcttt accctagtct tagggataac aaatagtctg  51060
cacacgtctt gaaaaggagt gctaggaatt gacctagact tatttagtag cgtaagtaag  51120
gaaacaatgt taattaaatg aaaacttcct aggaagttaa tttaattaac atatggtaat  51180
ctcattatcg gtgcaggaat agcaaacaaa actctagatg tagatggtat tacagaaaca  51240
ataggtacta cacaatctgc tatgtatggt ggagcaagtg ctcaaatact acaaatcaat  51300
gaagatataa aagagctatt agctgggtta aaatcttact ttggctccaa tatgataggc  51360
atatagtagg aaggagatat taaatgcaaa aacctttttat gataggtact aataataata  51420
cttctaatat aattaataag tctactatgt atacatctac aacacaagca gatgaacaag  51480
aacaaaagtt atctacagct agactagagt ttgacactaa ggatatgaga agatttgtca  51540
atgatagagg tataaaggta ctgtgggaaa gagcttactt ttgtccttgc cttaaccctg  51600
acacaggaca tcctagagta gattgtccta ggtgtcacgg taaaggtatt gcctatttac  51660
ctcctaaaga gacaataatg gctattcaat ctcaagaaaa aggaactaac aatttagata  51720
taggaatttt agatactggt acagctatag gaactacaca actagaaaaa cgagtatctt  51780
atagagacag gtttactgtt cctgaagtat tgatgccaca acaacttata taccatgtta  51840
ctaaagagcg tatacaaaaa ggtattcctt tgtattatga tgtcaaagaa gtaactttta  51900
ttacatctaa cgatggtaat gtttatgaag atgactataa tatagagaat aatagattat  51960
tcatggacgc taagtttgaa aacaaaacta tatccttaaa tattttaatg gtacttagat  52020
atgtagtatc agatatatta aaagaaagtc gataccaata tactaaattt aatcaaccta  52080
atacaaagtt tgaaaattta cctcagaagc tattattaaa aagggaagac gttattgtac  52140
tacctgagcc atttaaagtt aatgatggta tagaagagga cttagagata caggtagaag  52200
accctaaaaa agaatctaaa gataatcatt caggtggttt ctttggagga atgctataat  52260
gcctataaaa gcaactagac ctaagttatt tagagacaag aactataaaa atataggtaa  52320
gagaacagta gatgctatgc gttctgatat tttagataga ttacaagcta cagcattaca  52380
agtagataat gtaagtgtca aacgcatgcc tacttatcta caaataactg agaaaaagct  52440
agagaagcaa ggtgtaatag accttaagaa agcttttgct cattcatcta aaaagaaaag  52500
gactaaagat ggtggttggt atctaacggt gcctataaga ataaaaacaa gtaagatgaa  52560
taataaaaca taccaagact taaggtcttt aaaaatagac agttcaagta attcagtatc  52620
tactcttact gattatctag aaggtagacg aagtaatatt agtcacccat cactaaagcc  52680
tgctagtaaa tcaagtagaa ttactaaagt aagaaatggt aaaaaatcta gttactttat  52740
gtttagaaca gtatctagta aatcccctgc aagttcatgg atattaaata gagataaggt  52800
taatgaaaac aacttctcta aaacaacatt aaagtatgtt agaaatctga tgaactggaa  52860
gattaagaat ttaatgtaga aaggttatgg aagtaggatg gcaataacat cagtagactc  52920
atatttatta gagcaaataa agcccagatt acatacagta ctaagtaatt gttatattat  52980
agatgaagtt ttaaaagact ttgattatca aactagggaa atgttcaaag aggcttttg  53040
tggtaagaac gcaaagcacg aagtaacagt agggttcaat ttccctagct ttaaaaacaa  53100
ctacgaagct cattacctaa tacaactagg gcaaggtcaa gaggttaaaa actctttagg  53160
tagtatacaa gggtcttatc tagaagcttc gggtaacaca tatagtgaac aatcagtagc  53220
taaaagagaa ggtaatcgtt tagtatttca tgtatctaaa cctatttcta atgtaataag  53280
agtagaagac atagcgtttg attcttacga tgatgttaaa gtatcagata acactgtatc  53340
ttttaattat actaacaatg agacttatga aggctacaac gcaaatattg tatatgtaga  53400
aaaaacaaat gatagtaaag ggttagtaaa aggtattacc atagaagaac aagtaacaat  53460
tgtgggtatg tcgtataatg tagatgttgc tagatgttta gatgccgtat taaaaatgat  53520
attgatatct atgagagaca gtatagaaga acaacaaaca ttccagctac aaaatcttgc  53580
atttggagat atcgcaccta tattccaaga cggtgagtca tctatctttg gtagacctac  53640
tataattaaa tacacaagtt cattagattt agattataca ataacacaag atattaataa  53700
gattactttc aagaataaag gagcaaaaag ataatggtta agaaaacacc taaaggtaaa  53760
acctttacag gttatgtaca tatagataca tttttaaaaa cagcacagac cttgtttaat  53820
atgaaagagt cacaggtagc aggttttaaa gcctacatgg aaggtaaaca ctacctgttc  53880
aatgaaaaag actttattcc atttttagaa aagtatttag gtagagaatt agaaatttaa  53940
tatatagata ggagaattat acatggcagt tgaaccgttt ccacgaagac ctgtcactcg  54000
tccacatgca gtcattaatg tagacagtac aggtatcggt aaatcagcta gctccagtga  54060
aaagatttta tgtttaattg gacaagctga aggtggtaaa cctgataccg tatatgaatt  54120
aagaaactac gcacaagcta aaagactatt ccgctcaggt gaattacttg atgcaattga  54180
attagcttgg ggttctaatc cacaatacac agcaggtaag atttttgcta tgcgtgtaga  54240
```

-continued

```
ggatgctaaa ccagctacag ctgaagtagg cggattgaaa gttacttcac agatttatgg  54300
taacgtagct aacaacattc aagtaggatt agaaaaaaat acaatcagta attcattacg  54360
tttacattta atcttccaag atgatagatt taatgaaaca tatgataata ttggtaatat  54420
cttcactatc aaatataaag gtagtgaaag tacagctact ttttctgtag agcacgataa  54480
agaaacacaa aaagcaaaaa gattagtatt aaaagctaat agcacagaag ttaagtctta  54540
tgacttaaca ggaggagctt acgctactac taatgccatc attaacgata ttaaccaatt  54600
acctgatttt gaagctaagt tatcaccttt tggagataag aacttagagt cttacttatt  54660
agaccctatg acagatgtta acattaagga taaagctgag tatgtaaaag cagtatttgg  54720
tgatttagag aaacaaacag cctataacgg acttgtgtca tttgaacgat tagtatctga  54780
acaagcacct aaaaacgtag aagtagacgc acatgaagaa tctgctactg taacagctgt  54840
gtccccaatt caagaaatca caccttttga attaacaaaa ctttcaggtg gtacaaatgg  54900
tgaacctcct gctacatggg cggataaaat cgaaaaattt gcacatgaag gtggatacta  54960
catggtacca ctatcttcta aacaatctgt tcatgcagaa gtagcttctt ttgttaaaga  55020
acgttctgat gcaggtgaac ctatgcgtgc tattctaggt ggaggattta atgaaacgaa  55080
agaacagttg tttggtcgtc aatcatcatt atctagccca cgagttgctt tagtagctaa  55140
ctcaggtata ttcacaatgg acaatggtcg taagttacat gtaccagctt atatggtagc  55200
ttctgctatc ggaggtttgg taagtggttt agctataggt gagtctatta cctttaagca  55260
actacgtatt aataatgtag accaattata tgaatcatta gacttagatg agttaaatga  55320
aaacggtatt atcaccgtac aatatgttcg taatagagct aatacattct ttagattaac  55380
agacgatgtt acgacattta atgataaaaa tgaccctgtt aagtcagaaa tggctgttgg  55440
ggaagcaaat gacttcttat gttctgagtt aaaacttgag cttgaaaata actttattgg  55500
tactcgtact atcaatacaa gtgcttcaat tatcaaagac tttgtacagt cattcttagg  55560
acgcaagaaa cgagataacg aaattcaaga cttcccacct gaagacgtac aagttattgt  55620
agaaggtaat gaggctagaa tttcaatggt tgtataccct atcagaagct tcaagaaaat  55680
ttctgttagc ttggtatacc aacaacaaac attaagagcc taaactaggg caaggagtac  55740
ctagtttagg tactcctatt taatttaata ggagagtgaa ttaatatggc atcggaggct  55800
aagcaaagtg tccatactgg taataccgtt atgttaatgg taaaaggtaa accagttgga  55860
agagcacaat ctgctaaagg tcaacgtgaa tacggaacta ctggtgtata cgaaattggt  55920
agtattatgc cacaagagca tgtttactta aaatatgctg gtacaattac actagaacgt  55980
ttacgtatga aaaaagaaaa cttcgcagat ttaggatatg cttcacttgg tgaagagatt  56040
cttaagaaag atattattga tatcttagta gtagataact taacgaaaca agttattatt  56100
agttaccatg gtttaactaa atagacccct tgtacagtga tgtgcattga ataatacctt  56160
aaattgctag aacaccgtaa agctaactaa actacaaagt aagtcgaaag actaggcttg  56220
aatgttgaga aatcagaaaa aattagttag atggtataag gttaaatcct aagtactaca  56280
taattggtaa ttagcatcca agctcctgta aaatggagaa ggttcaacga ctataatagg  56340
taagtcttag ttacatatta agattatggt atagtctagt ccctttaaaa tatatcgaaa  56400
gatagggtat aaacggttca gcaaacaact acaacgagac ttggcagaca aatgaaattg  56460
taacagaaga aattgagttt agctaccttt aactaataga ggctatgttt ggtgacaagc  56520
atagaaaaca ctttaaattg cgtgaaagtc ttaaagacta gataactaca aagtaacctg  56580
aaagggtaag cttgaatgtt gagaaatcag aaaaaatatc tagtatagta taaggttaaa  56640
ccctaagtac agtaaaatag atgatacgca ggcaagccta cgagagtggg aagcttcaac  56700
gactataata agtgagtctt agttacacat taagattatg gtatagtcta ctccctttaa  56760
aatatatcga aagatagggt atagaggaca gcatcagata aggctagaac ttaaatttcg  56820
tattaagacc taacaataaa agttaggtct ttttttatac ttgttttatt agaagtactg  56880
tattataatt aaaaataaaa ggaggtgtac taaatgacaa acaggaaaac aataggtaaa  56940
gtaagtaatt caagggcaac atggaaaatt aaaccaacaa caagaattaa aaaagataaa  57000
acaaaatatt ctagaaaaaa taagcataaa ggtattgaca attataaata actgtaatac  57060
tatagttata taaggagatg atgaactgtg aaaacttttt attcaggcag aagaacaaca  57120
agtaaaaaca ggcaagtaaa gaagcattat aaacaaatga ctaatcaaga aataattata  57180
tgtaggaact tactaaaaga ggcttataat aaaaataatt actttaagtt aacaaatcac  57240
ttcaaaggta aatgtaagaa accagtaaat tttaaagcgt ttgttcatta tatacataat  57300
aagaacttag atattataga atataatgaa acattataca ataacaaaat acaacgtagg  57360
gtagttgtta gacaccctta tgtagtaaaa gtaaataata aattatctta ccaatattta  57420
gttatagaag ttgaaacagg tgaagttgta actatgtact ataacagagt cacagataac  57480
cacaaaacat taaatttaaa tgattattat gataaaaatt taaaaataaa gtattgacat  57540
aagtaaatac ataatatata ctaaggttac attaataaag aggagaataa aaaatgacaa  57600
ataaattaag agctatccat gaagaaatga aaattgagtt acataaattc ccacagaatg  57660
tagatttaac aagtaagaca actgctattg caatcaatca aattcttgac aagtttaaaa  57720
ccttaacgga acaagcaggt aaaatcacta aaaagtattt tgagggtcaa gagattttga  57780
cgattgattt tgaatattat gactcacttc aagattacta catttactta cttaaaaata  57840
gtgaaacaat tgaacaaagg ttacaagaaa ttgaaaaaag agtagctgaa tatgttaagt  57900
aatttggagt tataaccaca ttatgttata ctgtatgtgt ataaaaaaca taagttagct  57960
gttatattaa ttatgagaaa ataataaagg atggataaag aattggaaaa agaacaaaaa  58020
gatattaaag atatgacacc tgaagaaatt gatgagttaa aatatcagca acgaaaagat  58080
aaagagcgtg ttattaacaa agtaattaaa ggtgttaatg atgtatggga gaaagaatac  58140
aactttgaag aattagattt aaaattcaaa gtaaaaatta gattacctaa tgctagagaa  58200
caaggtaata tcatggcttt acgttctgca tacttaggtg gaatggatgc ttatcaatct  58260
gaccaagtta ttaatgctta tcagatgtta gctactctac aagaagtagg ggtagaagta  58320
cctaaagaat ttagagaccc tgaagagatt tataacctaa ctccacttgc tattatgtgg  58380
gatgattggt tagactttat gacgtccttt cgttactagt aacgtaaaga agttaaatga  58440
agatatagaa cggttaggtg gactttcaca tatagctaga gagcctttat caagaaactt  58500
atgggctatc atgcgtgagt ttaatgtgct acctaccgaa caacgtttta aagatttaga  58560
tgactatcaa atagagttta ttatagctaa catgaattta gatacaaaag aaatgatgga  58620
agctagagac ggtaaaaact atgatatgaa agcggaagac gtagacacat catggttcga  58680
agcgccgaca gatgaatttg atgttgttcc tgatttctta gacttagatg atttaaatac  58740
acaagtagat aaaagtttaa gtgagaaaga aaagatagaa agagatagac gagttgaagc  58800
tgagttagaa gatgaaaccg agggattaac aactcaacat ttagctatga tggaacacat  58860
aagacaaaaa caaaaagagc ttgatgaaag tttaggtatt gataacaaag aaacaacaca  58920
agaagatata aacaaagcaa tagaagatgt agatgattgg tacatgtagg gtaatggtat  58980
```

```
aacaccaata cccttatttt ttgattaggt ggtgaatact gtttggcaat gaatgacgat  59040
tataggttgg tcttgactgg tgatagttct agcttagaac aaagtttaaa agctatagag  59100
atgtacatgg atgcgttaga gtctaaaaac atagatgcac cattaacaaa cttcttagag  59160
aaattaaaag taatagcaaa agaagtaaaa tctgtacaaa acattatgga taaacaaagt  59220
gataagtctt taatatcacc aaaagctatg gatgaggcta ttagttctac acagaatgta  59280
actaagaata taaacgacct aaagaaagct ttaaatgaca tacaaacaga taatattaca  59340
aagggtatag ctcctgaccc tgaagtagag aaagtatata gtaaacttaa taagacacta  59400
aataatacac aaacagaact agagaaagta gcatctcaaa agattggttc agactcagat  59460
ataacaaaca gaataaaaga aatgaaaaca ctgaaccaag ttacagaaga gtataataaa  59520
ttagtaaaag atgccagttc agctaaggag tacacaaagc aactaagagc taatcgtaat  59580
atggttagag gtcatatatc taggtctgaa ggctctaata gaatgtccta tgaccaaggt  59640
gctagagtac gttctgaatt aggtaaagta gacacttttg aaaagcaacg agaagctaac  59700
aatagaagaa taaaagaaaa ccaagataga tatagaggtt atagacaaca acaacaagat  59760
ttagtaggca aaagagctcg tggtgaaata agttctgagg attataaaaa acaatcagct  59820
tctattaaaa tgatgattga tgaaagtgaa aagctttctg aagtttatag aaaaacaggt  59880
gctgaattag acaagtcaat caactactat aaaaatagtg ctaaaaaaca gtttgctcag  59940
cgtgagatag aacagcaacg aggaacaatg ggtaaattgt tccaagatag attaccatct  60000
attggtgcac atgctactat ggcagtaact gctcttgcag gtggtatgta tatgaaaggt  60060
gcctccttat ccgaggcaaa tagacctatg gtaacatcat taggacaaaa ttcagataat  60120
atggatatag acgcagtaag aaatacatat ggagatttgt caatagataa taagcttggt  60180
tataattcaa ctgacatgct aaaaatggct acgtcatatg aaagttctat aggacataaa  60240
agcgatgcag atacgtataa aggagctaaa cagttagctg taggtggtcg ttcattaggt  60300
atacaagacc aagaagctta tcagcaatcc atgtcacaac ttatgcatac aggtggcgta  60360
aactcagata atatgaaagc tatgcaagat gctttcttag gtggtatacg tgaatctgat  60420
atggttggta gacaagacga gcaattaaga gctttaagta ctattgccga gcagtcagga  60480
caaggtagaa cattatctaa aggggaaatg tctaatctta cttctttaca agctcaagta  60540
gcgggtacag gtagtaaagg tctacaaggt gcacaaggag ctcaagcctt aagtagtatt  60600
gaccaaggta ttaaaaatgg tatgggtaat tcttatacta gattagcaat gggatggggt  60660
actaagtacc aaggattaga aggtatgcat gacttacaag cacaaatgga taaaggtata  60720
tcagacccta ataacttagt taatatattt gaccaagcta ataatatagg aagtacaaca  60780
aaagaaaaac aagccatagc taaaaaaggc tttgaaagca tgggagctaa cttaacacaa  60840
gagcaaacag atgagttgta caatctttat gcctcaggta aactatctaa agaagagtta  60900
gctagtaaag ctaagagcat ggaacaagaa ggctctaaag caggagataa aaataaggat  60960
aagtattccg agtctaaagc aggtagaaat gaccagaaca aagctaagac agatgataaa  61020
gctgaggata tttatgactt agctcaacct attagagatg ttcatagtgc tatggcaagc  61080
ttgccagctc ctttatacct agcttcagga gcagtacttg cctttgtagc atctttagct  61140
aaatctactg ccatgatggc tggtggttct ttattaggta aaggtcaaaa aggactaaaa  61200
gattggttta ataaccgtaa aggaggttca acaggtaaga ctggtggtgg taatcctaac  61260
ggtggtggac gctttggagg acttaaaaac ttagctgaca ctatactagg tgataaccct  61320
agaggtggag accgaccatt taaagaccaa gcaaaaggag caggacaaac tgctaaaggc  61380
atgggtaaaa ccttatttga tacctttgga aaaagagatt ttacttttgg tgaatatatg  61440
ggaagaacca aagacctagg taaaggtgta tggaacaaag gtaaaggagc ttttggtaaa  61500
gctaaaggta aatttagtgg taaagactct aacttaggtt ttatgtcaca agcacctact  61560
gctaatgcag gcggtcttgg taaactaaaa ggtcttacaa gtaagctagg ttggattggc  61620
gcaggtctat cagcctttga cataggtagt tctctaatac aaggagatac taaagaagct  61680
tcttctaaat ttggtaatac tataggaagt gtcatagacc cattaaacct aggttatgga  61740
gacggcttaa gagattatgc tacgaaaaca gcggaaggtt ctatgacaag tgatggttgg  61800
aaattatggt ctaatggaga taaagatggt aagaataaat tccaagactc tcctgtaggt  61860
aaactatggg gtggcataac agatttcttc acaccagata acccttctaa attagacgag  61920
acagtgaaaa ataaaaaagg taacataatt agttatatac taattgcctt gcttatagag  61980
caatctgtaa gtaccgagtg ttaactgcta tgaaactact aaagctaact aaactacaaa  62040
gtaagtcgaa agactaagct tgaatgttga gaaatcagaa aaaattagtt agatactcta  62100
aggttaaatc ctaaggagaa gtacaatggg tgtatagcat cgaaagtcct aaagacctga  62160
aaggtctatg gaacacgttc aacgactatt ccgtataggt gacggaagta aagctccaag  62220
ctattgggag aagaaaaata ctcaccctat actaataggg ataacaaata gtctgcgcac  62280
gtaccgaaag gtagtgtcta gaaataacta gagaatatac agtagcgtgt atatttaaac  62340
attgttaaaa tatataaata attaaaattt gtattctact tctgcatata aacctttctt  62400
attttgtaag gtaaacttgt tattaaataa atatacataa ctaatacgat aggttatata  62460
tgaaagtata ctattgttta tatgttttaa cttatggtat taatgataaa tcacaaagta  62520
aagacaggca aaaagcagaa gaaaaaagag aaaagaataa tgattctaga gaaggaaatg  62580
taacagtata ctcacatttc ttagaccatt tagcagataa cctaacaaat aaaggtagta  62640
gttctaacga cagttcatca ggaggaacac ttgactacct tgatggtaaa aactttacgg  62700
ataaagacgt aactaagcat gacctaggta aaactgctaa aggtgtaaac gccgaaatgt  62760
taaataaatg gattgagtct caagcaccta gtaattctaa aatgcgtggt ttaggtgagc  62820
tttatatgaa agcaggtaaa gagtcaggac ttgacccaag gtatttagta gcacatagtg  62880
ctgttgagac aggctgggga acatcaaatc tttccaaagg cggagaccct aacaaaggta  62940
actggttcgg tataggtgct tttgataaca atcctaataa tggttttaac tatggtttgg  63000
gtattgttgg tggtgctaaa tggattagag acaacttcta caacaaagga caaaagaact  63060
tacacgatat gagacacaac aatggtgttc atgaatatgc aacagcaggt aattgggata  63120
ctatgattgc cagtattatg aaaggttcag acaagttcat aggtggcgga ggtggaggca  63180
gtgatgttat gcctagacat gctctaaaaa acgaccatca accaaagaat cttaaatata  63240
acatagaagt acctaaaagt aaaaacccta atgaaacagg gaaagcaata ggtagaaaat  63300
taaaacaatt attagaatct aatttttaga atacaattat aatacttata tactttaaca  63360
aatggtacaa ataataaaaa acagaaaatg tctacagaac aactaagaga aaagaataat  63420
aaatcagaaa ctaaaaactt aaaaacttac agtaacctat tagatagagc acaacaaatt  63480
atagaagatg ctaaagcgct agactcagga ggttcagaca gtagttctga ctcagggggt  63540
tcagcttccg atgtagatgg agaaggtgcg ggtaagattt acaaattcct taaaggtaaa  63600
ggtttatccg ataaccaagt aggtgccgtt atgggtaacc ttaagcaaga atcagggctt  63660
gaccctaatg caaagaacgc ctctagtggt gcttttggca ttgcacaatg gttaggtagt  63720
```

```
aggaaatcag accttgatag ctttgctaaa tctaaaggta agaagtctaa tgacttagac  63780
gcacagttag atttcttatg gaaagaaatg agttctggtc aaaatagtga tatgcttaaa  63840
aatgcaggat ggagtaaaag tggtagttta gaaaaaaata caaaagcttt tgcacaaggt  63900
tttgagcgta tgggtgctgg agaggctatg atgagtactc gagtaaataa cgctaaaagt  63960
tatgtaagca aatatggtaa gtcaggtggc ggtggcggtg gcggtggagc tataccatca  64020
tcatatacgt ccgtattaag aaacccgata cttagtagtg cttcaggaag tactgcatct  64080
caaaataatg tatctgtgaa tgttagcatt acaggaacaa atgacaaaag ggatgctgaa  64140
gaaataggta aaggcattaa gtctactttt ggtgacgatt tagacatctt ctcaaacacg  64200
tataaacgta attattaggg tagtattatt aagtactacc ctttatataa aaataaagga  64260
agtacatata tgtatagaat tagacgacct aagataagaa tagagatagt aacagatgac  64320
aatacattta cattaaggtt tgaagatact aaagattaca caggaaatca gtttgcttca  64380
aaattaataa acttccaaac taaaaatgca atggaagatg acagtgcagt attccaaata  64440
acaatggcag gggatacata ctgggataag ttagtaatgg caaatgatat tgttaagata  64500
tatattacac ctaacaatga ccctaaagat aaggaaggaa ataaagagaa acttatacaa  64560
gtaggtatgg tatctcaagt ttctaaagta ggaagctata gtaatgacca ggttcagttt  64620
agaataacag gtcaatcttt tgtaaaacct tttatgaaat ttggtttagg tgttatacaa  64680
gaagtacaag ctgtattacc aactgttggt tggttagttg atggtgatgg agagaaccaa  64740
gttaagttta caggtagttc agctaaagat gtaatgcaag gtattataca acgatttatc  64800
ccatacatga aatataatta tacagataaa acgtataaca cactagagag ttatttagat  64860
tatgatgatt tatctagttg ggatgagtac gaaaagttaa ctgaagtttc cgcttttact  64920
aacttcgatg gtacattaaa acagctaatg gacttagtaa ctgctagacc ttttaatgag  64980
ttattttta gaaattcaga taaacataaa ggtaaagcac agctagtatt aagaaaaact  65040
ccttttaatc caactgaatg gaaagcatta gaatatatag ttgtacctac ggaagatttt  65100
atagaagaag atgttggtaa gagtgacgta gaaacatact ctatatttac agtaaaacca  65160
gcaggtatgt taaaagaatt aacaggggat gtattctcta aacctcaatt ccatcaagaa  65220
ttagtagata gatatgggta ttctaaatat gaaacagaaa acctatacat aggaactaag  65280
agtggtagtg ctacagaaga tagtgaaact acaggtggag ataacggtca tgaacgagta  65340
acttatgaca gactacttaa agatttaaat aactatggta gagagtctat atctaaagga  65400
ttagataaat actctagtaa gatatcatca aaatacaaca atattactaa acctgaagta  65460
aagagtattt tagaatctta tataaaaaaa ggtaatctaa gtaaggaaga atatgaaaaa  65520
ataacaaaga acaatacttc aagagagtca gtatctgata ctagaccaaa actaacaaaa  65580
gaaaaattaa agtctatatt agcggaaaag tttaataaga aagaaacttt tgatgataaa  65640
gatttaaata agaaaacaac aaaagctgta atagatgata ttacaaagaa ttataagtat  65700
ggtaatccta cacatgctaa gaaactacta gaggattaca ctagatttaa aggtaaccca  65760
cctacaagta ccacaggtga tatttatgat aagtatctta aagccgtaga aggagtagct  65820
aatgttgcta tagatacagg ttctgacgca agtgatgacc ctttaattat atttactaaa  65880
atgctattta attggtatca ctcaaaccct aatttttatg caggtaatat tgttgtatta  65940
ggtgacccta agtatgacct aggtaaacgg ttatttataa aagataaaca acgaggggat  66000
atatgggagt tttacataga gtccgtagaa cataagtttg attataaaca aggatacttt  66060
actacaatag gagtaacaag aggactaaaa gatgctatta taaaagatgg tgaaggaagc  66120
aaacataggt ttaaaggact atggaatcag tcatctgact ttatgggtgg tcttatgggt  66180
gaagagacat ctaaagaatt aaaagaaaaa ggtgtagccg agaagaaaac aaaaggaaat  66240
aaagatggag attctgacgg aggcgcacaa gatggaggta ccttagcttc actagaaaaa  66300
tataatggta agttgcctaa acatgacccc aactttgttc aaccaggcaa taggcattat  66360
aagtaccaat gtacatggta tgcctataat agacgtggtg agctaggtat tcctgtgcct  66420
ttatggggag atgccgccga ctggattggc agtgctaaaa gtgcaggtta tggtgttgga  66480
agaactccta aacaaggggc ttgtgccata tggcaaagag gtgctcctgg gggaagctta  66540
caatatggac atgtcgcttt tgtagaaaaa gtattagacg gtggagctag tatatttata  66600
tcagaacata attatgcaac tcctaacggt tacggcacaa gaacaataga catgagttca  66660
gcaataggta aaggtgctca atttatatat gataaaggat aattgatatg gcaacggata  66720
aacaagttaa agatgttata gataaattta tagataatct tttcaatttt gaagtattaa  66780
ccaaagaaaa ggttgaagaa aaagataagg aagttaaaaa gataactaca gaagacgtat  66840
acaataaagt tgtttatatt agaccatatg taggtgttat acaaagtata acacctagac  66900
aggtaacata tgatagtttt actaataatg gtacagatat agaagctaaa ctcacactta  66960
gaaaaataag ttatactact gataatctca cagtacctac tgatgcatta tcaacttgta  67020
tggtacatat ggtagaaaga aatggtgtac ttgttataga ttactttgat gagttacaga  67080
acatactgta tggtagttac atggataatg agcatatatt tgatgaagat gttccagtta  67140
gtacattagt aacattagac ttgaaagaga atttaaataa ttataaacat atacagtata  67200
tgtttaaagg gaatacggat aaaaaccctt ttgaaagtaa ggatatagta cctttagata  67260
catacaactt attatattgg atgtataaaa agagaaatgt agagctaaaa aatccattaa  67320
cagttaacta cttcttcaca ggtaaaagct tttatactat atttggtaaa ggacacaaat  67380
ataaagttga tattgacaaa ttcaaaatag gtgatatact attctttgga cgtagtgatg  67440
ataatatagg gatatacata ggagataaga agtttatttc tcttatgggt acatttccta  67500
aagataacac ctctattagt acctataagt tagacgatta ttgggatgac tttaatggta  67560
gggttatgag gtttgatgag gatgatatag catggtggta agattacaat cttctttagg  67620
tagaagttta aaaaagatag actcagaaga acttaatgtt aaaggtctat tattaggtac  67680
agtaagcaaa ataaattata agtaccaaac tgtagaagtt aaaataaata gcttaacatt  67740
aggacataac cctagtgatg atggcaagtt agctgttcct tatcctaaag attatgtagg  67800
aagaacacct gaaggtagcg tgtatggcag taatacttta ataacggaag gaactactgt  67860
actgttagga tttattaatg atgacattaa ttaccctatt atactagcta tctatggtaa  67920
tacagaagca aaccaactca taaatacgaa tcctttagag ggtggtaaaa tgagtaatga  67980
tgatgtttat aaatatagta gtgctttgta ttctatatta cctgacctaa cttatacata  68040
taaagatggt gaaggtacat ctataaaaac attcaatggt aaatctttct tatccattac  68100
ttcaggtgat aaagaaaaac ctttatcttc agacttttat acaggtactg aataccaaga  68160
cttatttcca tcatactata gtaacaaaaa tttaatagaa cctagaatac aaaaggcacc  68220
taacatgtta tttaaacacc aaggtctata ctttgatgat ggttctgaag ataatcatgt  68280
tacaacttta tttatttccg aaaaaggtga tgtaagagct tcagtattag acaaaagcac  68340
acaaaaaaga acaacacaag agatgtctca cgatggttct tatagagtta taaagcaaga  68400
tgatgaccta ttattagact cagcgcaagt atgggtagag tttggtataa atgataataa  68460
```

```
tgtgttttac ataaaaaacc ctaagcatat gtttgaattt aatgataaag gtatatattt  68520
agatgataag ccaattttag atacgttaga tgctagcatt acagagtcta tagatagact  68580
taaggaagta cagaaagaat tagatgacat taactactta cttgagggtg taggtaaaga  68640
aaacttagag gagttaatcc aagagactaa aaaatctata gaagtttcta gtaaggcaag  68700
tagcgatgtt acgactatga aatctcaaat atctaatgta agtagtagag ctgagggtat  68760
tattacacag tttcaagagt ttagagacaa aacatttaaa ggcttatatg aagatgcttc  68820
tactatgata aataaataca accaagaaat acctgagtta aaaagtagat tgaatactct  68880
agatacaatt acattaccta acattaataa taccttatta gagaaatcaa gtaagaccta  68940
tgttaataat agttctcaaa gtgttagtag taattatcta ggttcattac tgcaattaga  69000
tagtaacctt actatttatc catacacacc tacacgtatt acatggaata agatagtttt  69060
taataattct gagtttgtaa ataagactaa ggatgctttt gttattccgt taggtgtatc  69120
taaagttaaa gtttctatta atcttaaatg ggatatatta caagataaag taaaaactat  69180
tatagtcaag aagaatagta atacatacaa aactataact aatggtaata cacacgataa  69240
tataattaca aatgttatac ctgttaaaca aggagataca ttcacagtag aagtacaaca  69300
agataatgat attaacctta cattactaca agataataca atgtttagta tagaagtatt  69360
agaaactact ttagcaccta ctaacactga gttattaggt acagcatccg aacaaacaga  69420
taagcaacta caaacacttg taaattctaa tgttgattta ttgagtttga caacacaagt  69480
tactaaagac aatcagttag tctgtcttaa tgattctaaa ttagatacta taacaacagg  69540
taaaggtaat gtgtctgatt acactctaca acaaataaag tcattttcat ctaagaatgg  69600
tgagagtatt ttatctttag aagatgtatt agctaaatat aaaaattcta ttagatatag  69660
tattaattta ccaactactg caaacatagt agaactactg aaaaaatata atttaattgg  69720
tataagagca cctaggaatc aagtgtattt gaaagttaaa gatttaacaa tcacacaaga  69780
agtattaaat aatttttcta acttaccagt attatataat acttcctatc taacaagtac  69840
agatattaac aaaggtatat atacaaatat atatggagta ctactaccat atactagtat  69900
cactcaagat acagtaaata cagcacataa taataaccta tctatatatg ctagtggtga  69960
tatgacaagt gacattataa ataagcttat tttatatggt atagatggtg tagaaacaaa  70020
taaaatatta gagtttaaaa aagtttaaaa gtcctattaa tagggctttt ttatatatgt  70080
catgttatat taaacttgag aaagtagttg tatttaaata ctatatatga tataatacga  70140
tatagaaagg tggtaagtta tgcctcaatc agatggaaag aatacaataa gacgtattgc  70200
attacgtttt ccaacagcaa gcggtaaata taatatgtac cgtttcaaag taaaccctga  70260
aagttatgaa atagatgcac cacaaagaac atctataact aaaactaaat cagacattat  70320
tgttgaagac tatggtaaag atatagagac aataactttt tctggtacta ctggatttag  70380
acctgtaaaa gaagtagatg gtactaaaac aggaaaacaa aaaatagagg aactacaaga  70440
acaagtagaa gcatacgcta agcagggtgg agatggtagc gtagcaggag cttatataga  70500
gttctataac tttactgatg ataaatatta caaagtacat ctagcaccgc aaggtttaaa  70560
aataacaagg tctaaagatg aatccttgtt atatagatat gaaataactt tagttgtgat  70620
aggtaacctt gctgaagcag atagaggttc cgtaacatct gctgagtttg gtaatgtaaa  70680
acctaatgct aaacaaagag ttgatgaggg tgttaatgat ttagatagta acgcacgaaa  70740
aacaagaaac aagaataatc aaatagtatc acaatttgaa aataaaagta gtcaaagctc  70800
ttctaattct agtagtagcg gttcacgata tggaacggca ggaacattaa gaggaggtag  70860
tggcataaga acaggtggtt ctgaaggtaa tagagacggt atgagtaata taggtatata  70920
taaccctaga cagaatacta atggtcttag tagtactgtt gatgatatgg cacttaaaat  70980
aggatacggt gatggaggtg tatctaggta atgaataatt atatacctca accacaagga  71040
ttattaaggt ttttaaatgg attagagtta gacatgtctt acacacatat gaacttatta  71100
gatgaggaag taccttttgt ttctaaattc tatacaccac aaatacaact aagtgaactt  71160
gcaagaataa aattaaaaga gattaagtct actgatatcc ctactttaga aagaacattt  71220
aacaacaata caatagttaa taaagtagaa caaacaagtt taaagttaca atcacctaga  71280
atgtatttaa ttatgcaatc tatcgtaatg gaagcttacg ctattgtaaa ctgctttgta  71340
gaaagtcctg aatacttaaa atatttaaca gaaaaagatg tatctatagt aagaagtaat  71400
gttaactacg tagctgacta tttaagtgat tatgaagaat acaatagtat tgttctcgat  71460
ttaagagact tagacttatg ttttggctct ttggaattac aactaccact aattaagagt  71520
gaggtggtat aatgagattt agaaagcatg aagtacaatc agaagaaacc ttacaagcta  71580
tatcacaaag gtattatggt gatgttagtt actggttaga tttaatagaa cataacaatc  71640
tacaatatcc ttatattgta gatacagatg aagaaaagaa acagaacccc gagcacttaa  71700
taactaaagg tgatattatt atcatacctt tagattctga gttaacagac tcggtttcta  71760
aagaaataac atcaagagac aaagatgtat tagtagaatt agctttaggt agagacctaa  71820
atatgacgga taataacgag tatatagacg ctcatggaac agatgatgaa atattagccc  71880
tatcttcaga tggtagagga gaccttgata tagttaaagg catagataac attaagcaat  71940
ctttaagagc tagactattg acacctaaag gttctttatt attacatcct gaatatggtt  72000
ctaacattca taatttattt ggtttaaata tacctgaaca agctacgtta attgaagtag  72060
atgtattaaa aaccctaaca tcagatagta gagttaaatc agctaactta aaaggttggg  72120
agataaaagg taatgaatac tatgggtcat ttaatgtaga aatcaagtcc gtagaagaat  72180
ctatagactt tgtattaggt caagatgatt caggtgtctt tgctttattt gactaagaaa  72240
ggaaatttat atgagaacaa gaaagttaac acagatatta tctaggttaa tggataagac  72300
gatacaaggt acaagcaaaa taacagactt tacacccggt tcagctgtac gctctctttt  72360
agaagcagta gctttagaaa tagaacagta ttatatatta acaagagaaa acattaattg  72420
gggcattcaa gaagggatta ttgaagcttt tgattttcaa aaaagaaaag ctaagcgttc  72480
ttatggtaat gtagatattc aattttacca acctttagac atgagaatgt atatacctgc  72540
aggtactaca ttctcatcta ctaggcaaga ataccctcaa caatttgaaa cattagttga  72600
ttactatgct gaagaaggaa ccactgaaat tacagtagaa gtttactgta aagaagttgg  72660
tattgtaggt aatatacctg aagatatcat taatacaata gcctcaggct ctagtttaat  72720
tcgtacaatt acaaacccga cttcctttaa tacaggaaca aaagaagaat ctcaagagga  72780
ttttaaacgt aggttccata tgtttgtaga atcgagagga agagctacta ataaatctat  72840
tagatatggt acattacaag tacctgatgt tgatggtgtt tatgtttatg aagaagtagg  72900
tcatgttact gtatatgcgc atgataaaaa cggaaattta tctgctactc taaaaaatga  72960
cataataacg gcattagaag attacagacc tagtggtata aagttagatg ttgtaggcgt  73020
agagaaagag gaaatagatg tgtctgcagt agtaacaata tctaataaag ctaggatagg  73080
tgatacatta caaagacata ttgaaagtgt tattagagga tacctaaata gtctgactac  73140
ttctgatgac ttaattatta acgatttaat tcaagctatt atgaatatag atgataattt  73200
```

```
aatttatgat gtagcattta agaatttatc tacaaatata gaagtatctt cgaaaggtat  73260
tattagagca ggggatatta aggtagaatt aatataaggg ggtaaacaat ggctaatttt  73320
ttaagaaact tacacccttt attaagaaga aataagaata ataaagataa ccaagaccct  73380
aactatgctt taataacagc acttaatgat gagatgaaca acatagagtc agacaccatt  73440
aaaagcaaac ttcaatcatc attaaaaact accacaggag attacttaga taagtttggg  73500
gattggtttg gtgtatacag aagaataaat gagaatgatg acagctatag aaaaagaatt  73560
ataaaatact tattattaaa aagaggaact aacaacgcta ttattagtgc tattaaagat  73620
tacttagata atgagaatat aaatgttagt gtatatgaac cttttaaaaa tatattctat  73680
accaataaat caaaattaaa tggtgaagat tatttaatgg gttattatta tagatttgct  73740
gtgataaatg tttctgttga tggttacttt cctttagaga ttatagatgt aataaatgaa  73800
tttaaacccg cgggtgttaa gttatattta acttatgatg gtgctactac cataaagggt  73860
gatggtgttg ttaaatggct taaaaatcta cctaaaattg aaacatatac ggatttagat  73920
agattattag gttatgatga aactttctat gggcatttaa acatgagtga agcaacagct  73980
gaacaatctg ataaaacaag gttcagaaca aataagagta cattaaatag tgaagatatt  74040
ctatcaggct cttctaatat tggacgtaga tttataaatt atgcttatgt tacgacatat  74100
gcatatgaac ctactagtac atcagccgtc acacatatag cttctttaaa tgataaagga  74160
aaagaagcac ctttagatta ttacttatat acatccttaa agaatactaa tgatataaat  74220
atatcaatgg aaactgctta tggtgtgtct tatttataca ataactttaa tgtaggtgag  74280
tttatcagta gatacaaacc taatatagat ataactagag ataatgctaa aaaacaaata  74340
tccgattttg taggggaact aacaattgat ttctttgcaa aagctttagt ttcacctgat  74400
gaatcattac ctattaagtt acaaatattt gattttcgta ctaatgaatg gttaactgta  74460
tcagaaacag aactatcttt ttacgagaaa aacataggtg taaacatagg ttatataaga  74520
gattacttaa atgatgacct taatttattt acaagattag aggttaatat aggtaaagat  74580
gagcaaaaag atataagtat taactacatg gatttacatt tttataatta taaaaaagat  74640
gtgtatacta tcaaaccttt taaggcacta gttgaaaact acatagattt gactaaagat  74700
acttatattg aaggctttaa agtagcctca ttattaaatg gagacataat taataaaaat  74760
ggatatcaac ccataaaata tttaaggtta catgctactt atgattcaac taaacctatt  74820
gtaagtatta caggtaaaaa cagcaataat gaggtacaaa ataatacacc tatagattta  74880
tataaaaata caactaatag aaacttattg caatcatata aaggtgatag tagtatattc  74940
aagggtgttg taagcacaaa agagttttat atctcatcat ggtctgacac cttatataac  75000
tcaacgtatt tatctaaagt actagaaccg caaaaagtat atactttgtc attcgagatg  75060
gaaatcacag atgctaatat ggacttaaaa acatattctg acaatcatgg tatatattta  75120
tatagtagta ctaaaggtat tgttgctaat ggtgttaaaa gcatgcaaag aaagataggt  75180
aataagattg atgtatctac cacatttaca gcacctacaa ttacagacca tagacttgtt  75240
gtttacacag gtagatatac agcagatggt actgcctcta aaacacctat tgcttctaat  75300
acggtaaaag taacaaacct tcaactaaaa gaaggagcta ctaagaagga ctacacggta  75360
gcacctgaag atgtaactaa tgttatagac aaagctattg tgtttgataa catattaaca  75420
gatatacaaa caataggaat aaatacaaca acacctctta aaaatattga gctaagttat  75480
tcttattatg gggataattg gacaaaccta aaaacaataa gtaatttaag tcaaggtgaa  75540
acaataacac ctaataacct agtagattta tatggcttag aaacaataga ttactcaagt  75600
attacacctt tctctagggt tatacttaaa actatatgga atgctaacct gaataattta  75660
acaaataaaa aaggtagtat ttctaacatg agtaataact atttcaatgc tgtatggcaa  75720
gaggtagata tgatatataa cactacatta agtagcatga gcatacttac tgatagtgaa  75780
ggtaatgtat ttgatagttc aacaggacag gtaataaaat tagcacctaa gatataccaa  75840
ggatatactg atgtagatag attgctaacg tctacgactc tatataacga gaatattaca  75900
ttaggttcaa atagatttat ttatgactta cgggatatgt tactatcaag tgatacattc  75960
acagtagata ataaaattaa agtaatagat acatacacag aagtacagta aagatattga  76020
caataaagta ttaatatgat atagtaaggt atgcgtatta tagtatacct tgttatatta  76080
atacagaata ctagacatga aaggaataaa aaatatggct atagcaacaa atgcttcaca  76140
tgtagaatta gctaaataca ttgtaagtaa ggctgattct atttatttaa caattggtaa  76200
aagtacagcg tggtctaatg aaacaagtcc acctcaacct gaagaaacag caacatcatt  76260
acaagaagtt atcggatata aaaaagcaac taaggtagca ttagttagac ctgcaaaaac  76320
aacgggtgat gaaagtaaaa aagaaattac atatggtaat aaacgatggg tagaaattga  76380
ctcagctaat gcagttgctg aaggtgctaa gtgggtgtac ttagaaagta gtattgttgg  76440
agatgagtta cccttaggta cgtatagaca agtaggattt gttatggatt tgttagctaa  76500
agatagtatt tctaaattta acttattacc tagtgaagtg caatctacag gaactttatt  76560
attttatgat aataaacaat tccaaaatag aagtgaacaa acaactgtaa aagagcgctt  76620
tatcattgaa gtttaaaaag gagaattgaa tatatatggc aattaatttt aaaagttctc  76680
catacttaga tagatttgac cctacaaaag atagaacaag agtactattt aatccagata  76740
gaccactaca acaatcagaa ctaaatgaaa tgcagtctat tgaacaatat tacttaaaaa  76800
atttagggga ttctattttt aaagatgggg ataaacaatc aggattaggt tttacattaa  76860
ctaaagataa tgtactacaa gttaacccag gttatgtgta tataaatggt aagatacgtt  76920
actatagtag tgaagacact gttaaaatta cgggtgtagg taaagaaaca gtaggtatta  76980
aactaacaga aagaattatt acacctgatg aagataatag cttattagac caaacaagcg  77040
gagttcctag ttatttttct aagggtgcag accgtctaga agagaagtta tctttaacag  77100
tcaatgaccc tacttctgct actatttata cttttatgga tggagacctc tatatccaat  77160
ctactaatgc tgagatggat aaaatcaaca aagtattagc agagcgtact tatgatgagt  77220
cgggttcata taaagttagt ggatttgagc tattttcaga aggaaacgcc gaagatgata  77280
atcatgtatc tgttgttgta gatgctggta aggcatatgt aaaaggttat aaagtagata  77340
aaccagtttc tactagaatt agtgtagaga agtcaaggga actaggtaaa gcagaaaatg  77400
aaagtactgt atttaataaa tcatcaaata atattacttt agctaatacc cctgtaaaag  77460
atgttcaacg tgtaacagcg caagtattag tagataaaga gcgtgttaca agaagttcaa  77520
caggagattc tcaagactat ttatctaata aaacagcttt tgaagtagtt agagtatgga  77580
cagaaacaag tccaggtcag acaacaaaag aatacaaaca aggagaagac tatagactta  77640
ctgatggtca aacaatagac tggtctcctt caggtcaaga acctaatgga ggtacatctt  77700
attatgtttc gtataagtac aacagaaaga tggaagtagg taaagattat gaagtatcta  77760
cagtaggtga gggagtaggt aaacgttggt ctattaattt cacacctgtt aatggtacta  77820
agcctattga ccaaagtgtt gtacttgtag actatactta ctacttagct cgtaaagatg  77880
ctgtttttat taataagttt ggtgatattg ctattcttaa aggtgaacct aatattatga  77940
```

-continued

```
gattagtaac accaccttta aatacagacc ctgagaacct acaattaggt actgtaacag  78000
tattaccaga ctctaatgaa gcagtatgta tttcatatgc tattactaga ttatctatgg  78060
aagacttaca aaaagtaaaa actagagtag ataatttaga gtataatcaa gctgttaatg  78120
ctttggatga tggtgcaatg gaaaaacaaa acccattaac attacgttct gtatttagtg  78180
aaggttttat atctttagat aaagccgaca ttacacatcc tgactttggt attgtattta  78240
gttttgatga tgcagaggct actctagcgt ataaagaagc tgtgaaccaa cctaagatta  78300
ttcaaggaga cactacagct catatatggg gtcgactaat ttccgcacca tttacagaag  78360
agcgtacaat ttatcaagga caagcatccg aaactttaaa tgtaaaccct tataatatac  78420
caaataaaca aggtgtgtta aaattaactc ctagtgaaga taactggata gacactcaga  78480
atgtaacaat cacagaacag aaaactaaaa aagtaacaat gaaaagattc tggagacata  78540
atgaaagtta ttatggagaa acagaacatt acttatattc taacttacag ttagataaag  78600
gacaagagtg gaaaggtaag tcatacgcat atgatagaga acatggtaga acaggtactc  78660
tattagaggc tggaggacag cgtacacttg aagaaatgat tgaatttatt cgtgttcgtg  78720
acgtatcttt cgaagttaat ggtttaaatc ctaatgataa taatttgtat attttatttg  78780
atggtgttcg ttgtgctatt acaccagcaa caggttatag aaaaggttct gaagatggta  78840
caattatgtc tgatgctaaa ggcacagcta aaggtacatt tacaattcca gcaggtattc  78900
gttgcggtaa tagagaagta acattgaaaa atgctaactc tacaagtgct acaacatata  78960
cagctcaagg acgtaagaag actgtacaag atgttattat caaaacacgt gttacagtaa  79020
acttagtaga cccattagca caatcattcc aatatgatga aagtagaact attagttctt  79080
taggtttata ctttgctagt aaaggagata agtctagtaa tgtaactgta caaattcgtg  79140
gtatgggaga tacaggttac cctaacaaga cggtatatgc tgaaacagta atcaactcag  79200
atgatattaa agtatctaat aatgctagtg ctgaaactag agtatacttt gatgacccta  79260
tgatggctga agcaggtaaa gagtatgcta ttgtcattat tacagaaaat agtgattata  79320
ctatgtgggt cggaacaaga acaaaaccta agattgataa acctaatgaa gttattagcg  79380
gtaatccata tgtacaaggc gttctattta gttcatctaa cgctagtact tggactccac  79440
accaaaattc agatttaaaa tttggtgtat atacctctaa gtttaatgaa acagctacaa  79500
ttgaatttga acctattaag aatgtatcag cagatagatt agttttaatg tctacgtact  79560
taactcctga aagaacaggt tgtacttggg aaattaaaat gattttagat gacatggcta  79620
catctactac atttgaccaa ttaaaatggg aacctattgg taactaccaa gatttagagg  79680
tattaggttt agctaaacaa gttaaattaa aagctacatt tgagtctaat aagtatattt  79740
cacctttatt aagttctaat gacttaacgt ttactacatt cttaactgag ttaaaaggtt  79800
catatatcgg tagagctatt gatatgacag aagctccata caacacaata agatttagtt  79860
atgaagcatt cttacctaag ggcactaatg ttattcctaa gtattcagac gatgatggta  79920
aaacttggaa aacatttact aagtctgctc aggtagttaa ggctaataga gactttaata  79980
gatatgttat tgatgagaaa gtaaatcaat ctactaagaa taacaaatta caagtaagat  80040
tagacttatc aactgaaaat agtttcttaa gacctcgtgt acgtagactt atggttacaa  80100
caagagatga gtaagtttaa agagggtttc ataccctctt tttatttaac taaggaagtg  80160
atattatgcc tacagaatat agagaccctt actcacaagc taaactcttt attcctactg  80220
tagaagaaaa agctataaaa gaaatggaac aaacatataa agataaacta caagaagtta  80280
atgagcttat tgatgagctt aaaaaattga aaggtgatta cacacatgac gtttaactac  80340
acacctctaa cagaatcaca aagattaaag gatatgtacc ctaaagtaaa tgaaatgggt  80400
aaatacttaa aagaagaagt taacttatct gatttaaaaa cgattagtta tcctgattta  80460
aataatgttt taaatttcat acaagactca ggtgactact ttgtaacaca agcaagaaac  80520
accccgcaag gtgtaagtaa tatagggttt ttacacttag ataaaaaggg tagtacttat  80580
tataagttat attatgcccc gtctaacaca aataaattgt ttgtgaaaac ttattataat  80640
ggtactgtct atgattgggt tagttttaaa ctagatgaag gtacattata cgattcagga  80700
aatacaatta atgtaaaaaa tttaacagag tccacaactc aatttgcaac actcataaat  80760
ccccctaaaa gtaatttaaa cacaggatgg ataaattata aggaaagtaa aaatggtacc  80820
tcagctttag ctgaatttaa tcctattaat tctacttcaa catttaaaat gattagaaag  80880
ttaccacgcc aagaccaaca acctaactta ttaagagata gtttattcac attaccaatg  80940
acggatgtag ctaatataag aacggattat atagataata catctttttg gggttttact  81000
aataatgcat ctacctcaac agttagatat atgggtgaaa atactattca attagatgat  81060
ggaggggaat catatcctac agttatgtca aaacgattta gaataggaga cgaactatat  81120
gtaggggata ctgttacaat gtctgtttat attaaagtaa atgaccctaa tttgttaaat  81180
ggtaatttcc cctactttga gattgctggg tataattatg tttatcaaga caataaccca  81240
tacacaggag gtaggagaga ggttaactat tatgacttat ctacggagtg gaaaaagttc  81300
tcctttactt ttactttaca atcatataac caagagtcta gtaatgatag ggttaattat  81360
atatcagccc tactaagatt taactgctct aattctacta ataatggagc tattgtgtat  81420
tatgcactac caaaattaga aaaatcatac tcggtaactc cttttattac tcatacttat  81480
gataaaagaa aatatgatga aatatggagt aattggactg agacaacaag taaagatgag  81540
cttcaatcac acagtagcgt agatacatat agtaatgact actataaata cgtatgggat  81600
taccaaagct cgaatggtag aagtctgcaa caattagcaa tgtctgtacc tcaaggtttt  81660
tataccttct actgtgatgg ttctataagt ggaactccta gtaataaaac aatacaaggc  81720
acaatacaag tagcgtataa aaataataat ataaacacta caaataaagt aatacaaatg  81780
gattttagtg atactaaagg caagaaatat tctttaacat ataataaaga taataatggt  81840
tggcaagcca tgaaagttca aatggctagt aatagccttt gggaaggaac gcttgacctt  81900
gcttcaggaa acacagtaaa tctatcagat tcgttatata actatgattt tattgacgta  81960
gtatattgga ctagaagttc tggacataat gcaactagaa gattccctgc tactacatct  82020
agtattgtaa ttagagactt taacttagta aatgatggct ctaattctag cgtagatttc  82080
tttgaaggat attgtgacat tactgataag ataaacgtca ctgctaaaat gtcaaaaaca  82140
attaacctag atggaaatag aaataccaca acagtcgcac aattcaatca aacaggtcac  82200
attgaagtac taagagtaat agggttaaca tatatttaag agaagaggtt ttatagatga  82260
taaagtatga cattggtaaa gacgaaattg tgttacactt aaaagataat aaatatatta  82320
tgggatatac tattgtaggt ggatatgaag agaacaatgg tgatgtaaaa gtatcaaggt  82380
ctattctacc tgatggattc tttgttgatt ttgttagtaa taagtatgcg tattataaga  82440
acactaacga agtaatatat aataaaagct ttgaagataa ctcgaagagt gtagaggata  82500
tagaatacca accaccagaa gagtttgtac ctaaagaaga ctacaaaaaa ttagagagtg  82560
aagtagagga actaaaaaga atgttacaag aattgttatc taagaaagga taaatagtat  82620
ggcactaaat tttacaccta ttacggaaaa cagtacaata gcagacctaa caaaacaagt  82680
```

-continued

```
taataacata ggtagtgtat taactgagga tagaaatatc tttgaagtaa ctacagactt  82740
acaattagac gtaagtaaag cacagaaagt taagttaaca acggatagag gattagctaa  82800
agatatagat tataccaatt acttaagaga cattaaaaaa gtaggtttat attacatagg  82860
agcacgtaca ttggctacta tgtatgataa accagatatg gaaaatatag atgtattact  82920
gcaagtatta acattagata ctgaggatag agtaatacaa atattgtata cattgtcaac  82980
ggaggacagt aaatcaaaag tgatgcaccg attcgttact aactaccaaa catcacaatg  83040
gcaagtagta caaagtttac ctaataataa atatacatca catataggtg gaagtccttt  83100
tgatattaat acacaaggta catattacgt gtctaatatg tcggatatgc ctagtggtgt  83160
ttatgaagga ttcttacaag tttccataga cagtaatgat aatagaatgt taagattaac  83220
ggatagtaac acgggaaaag aatatcttaa tgttaagaaa tcgtatgaca attggggtga  83280
ttggagaact gatttagacg tacaaaagat aagcaagtat cttgtatcta atgtaaatgg  83340
agatgcggaa aacaataatt actcattatc cgtatataca tcagacaata taacattcca  83400
acaagctata gctaaacata ttgaagaaac aagtaaaact gtttttactt tctatataca  83460
aggtggtgtt tcaggctctc cgtctacggt tagttgcaga ggtatattta tatcagactc  83520
aaacaactat actaatttat atggtgtata taccgcaata ggtactgacg gtagaactat  83580
taatggttcc gtaaatggta atacatggaa cacaacaaaa acattacctg gttttaaaga  83640
actatggaat ggagcacata actttaaaga tacaaataaa aaagaaacta tgtctgattc  83700
tatatctaac taccaatacg tagagatata cacaagatac agagccttac aaaacacaaa  83760
aggtacggat aaaacaggta ctttatgtca taagttttat atagatggag atggtattta  83820
cacatgttca ggagcttatg tatcaggaga ctctaatatt ggagtagagt actatcgagt  83880
aactttatct attactggtg atacatggac aattaaagat agtgcagtaa ataataataa  83940
agaccaatat gttacacgtg ttgtaggtat ctctttacca tagactagga taattcctag  84000
tctttttttt ttcttgacta actttaataa atatggtaag ataataaagg actaaaaaga  84060
aaggagaata tatgcagtta agacaacaga atatatatac atatgtagat tttgatgaaa  84120
gtgacgggta tattaaagat atcatactta agcgtgttca taaaacgtta ggagctaaga  84180
aagagggcta tcaacatagc ttagctttta aacgaggtgt gtgggatggt tatgtggatt  84240
tctacgatta tgctgagaac aaattcccta gcgggttgtt acctaagatg ataacattac  84300
taggtgagtt acaatcaaga cataactttc aatacgaaat tattgatgaa aaatctgaaa  84360
gctttttagc tgaagaagat attgatgatg aaatacaact actagataat aacgtaggta  84420
agattacatt acgtgactat cagtatgaag ctgtgtttaa tagtcttgtc aattataatg  84480
gtatatgcaa gcaagctacc aatgcaggta aattttgccc cttatagtag aaatattata  84540
agtgtaactc ctttaattca tgggaactct ctcatttgag acaatcatga gccaagctta  84600
ataaattact aggaaggtgc aacgactatt atgtacaatc aagtgattgg aaacagggag  84660
aacctaagtc tcattagata tggttaagat atagtctgaa ctttgtagga gactacaaga  84720
aggttaggag taacgaacct aatcgtaaca taattgaaaa cagaggttgc tagcggtatc  84780
atagaccaac tattaccaca actagaaaaa ggagagcgtg tagctttttt tacaagttct  84840
actgagattt ttaatcaatc tgctgaccgt ttaagtgaac gattgaatat accagtaggt  84900
aaagtaggtt ctggtaagtt tgatgttaaa caagtaactg tagttatgat tcctactgtt  84960
aactctaact taaaagaccc tacagaagga gtaaaagtat ctgctaaagt aaacttaagt  85020
aaaaagatag ctaaagagat acttcctaaa tttgaaggtg gtaaaaatca aaaaaggtta  85080
cttaagttat tattagaaag tacaacacct aaaactaaag tagagcagaa tgtgcttgat  85140
atacttcaag atatttatca taattcaaag acggatgctg aagtattaat ggcattaaac  85200
aatcataatg ttattttcca aaaagaagta agaaagaaaa atcaaaagag ctatgataaa  85260
tatcataaaa tgcgtgagtt cctagactct atagctgtaa tgatagttga tgaagcacat  85320
cacagtaaat cagattcatg gtatacaagt ttaatgtcct gtgagaatgc actatacagg  85380
atagcactaa caggctccat agacatgaaa gatgagctac tatggatgcg tatgcaagca  85440
ttattcggag atattattgt aagaacatct aatgagtttt taatcgagaa tggctattca  85500
gctagaccta caataaatat tatccctatt gctaaccctg atgatataga taatattaag  85560
gattacaggg atgcatataa taaaggtatt gtacataacg agtttagaaa taaacttatt  85620
gcaaaactaa cagctaagtg gtataatcaa gataaagcta cgcttattat tattaatttt  85680
gttgagcatg gtgaaatact atccactatg ttgaatgaaa tgggtgtaga gaatttcttt  85740
ttacatggtg aaatagagtc ggatatgcgt aaacaaaagt tagatgaaat gcgtaatggt  85800
aaacttaaag ttatgattgc tacaagcctt attgatgagg gtgttgatat cagtggtatt  85860
cgttcattaa tcctaggtgc aggtggtaaa tctttacgac aaacactaca acgtgtaggt  85920
cgtgcgttac gtaaaaagaa agaagataat acaacacaga tatttgattt taatgacatg  85980
acacataagt ttttatataa acattctaat gaacgtagaa aaatatatga agaagaaaaa  86040
tttgaaatta aagaattagg aaagtaggta tgagtagtga ctaagacaga aagaagatta  86100
tatgattaca ttgaaaaaaa atcaaaaaat aatacttatc aaatagctac taaaaaagag  86160
ttagcagaag aactagatgt ctcagtctct actttatcta aaaaccttaa aagattagag  86220
caggataaca aaattaatgt tgtctctaaa agaggaaata aaggtggtat tgttatatca  86280
ctagtaagag attatgatac agatagtctc ttacatttta atgacacaaa tgataatgtt  86340
attacttcta atctagaata cgctactgaa ttacgaaata gatttttttcc tagctacgta  86400
tatgaaagaa aagaaaataa acgtagaaca aaattagaaa tggttcaata taatgctagt  86460
aaagataaaa acaggaaaat aatatcagat atgaattttt ataatagtag cttaccttac  86520
cctactaaag atatttttaa tatgtcttat gaccctgagg gtttttataa agcttatatc  86580
ttatgtaagt tatatgacca atatgctata gcacacatga atgctaaata tatacaacat  86640
ttaacattat caaatggtaa tgaagacgta gatagacata agcatttatc tgagtactac  86700
agaaagaaaa tgttacagaa tttatcacga gatagtattt gtaaagactt ctttggtagt  86760
aagacattta atacattcta caacttttac ttaaagataa aagataagaa cattaatgtt  86820
tttaaataca tgcaaaatgt ttttaagaat accacatttg ggtttgagaa taaaacacaa  86880
ccttacccta tacctgcacc aaattttttt agttccgata aatacttaac taattatgaa  86940
aattatgtaa aaggtattaa acgaggtgta aataaaacaa atagacaaat tggggaagta  87000
gagtctttaa ttaagtcatc tgattactta ttaaatcctg ctgtagcaca attacatcaa  87060
ctatatacaa cacctttaaa tgaagagata catgatattg atacaatgtt taaaacagct  87120
ttagatatag aagatactat ttatggtata tttaatggca tgaaacatat tatactttta  87180
tcatataata aatatataga acatctaata gaaaaattac ctagtaaaca taaaaactta  87240
ttaaataaat ttattaaaca atgtattgta aatgagtatt cacctactac aatacctaac  87300
aatgctagac tatctatgtt tttaatgcaa aaagagtata aagcaaatat cgcagaatta  87360
aatggtggta tagatagaag agacttaata gatataagtt tagtaaacac tacagactta  87420
```

```
agtaaacaag atattgtaaa tatagaacaa acaacaatga attatctaca tatgagaaga  87480
tttacttcaa catcatatat tctacaaatg tatagtaatt atttaggata tgaggttaat  87540
ttaacagaag ttaagactat tattgaaaag tataatttat ttaatgaaat accattgaca  87600
aaagaaggta tgatagaata caataaggtt attgatatag taaaggatga cacatatgag  87660
taaacgaatt aaggagatta tcctacataa gtctatgaag gatatacatt ttgcaagaga  87720
agtactagat aagttaccta aaagtctatt tgctacagaa tcagaagaca tgggttactt  87780
attcacagct ataaaaagaa cagcacacat tgctgataaa atgtcaaacg aatctttagc  87840
tattaaagta gagcaattaa tgggtagtga taaacaagat gatgaaaaag taacacaaac  87900
attaaaatat ttagatagtt tatatacagt agacatgaat aataaagacg attctgtaaa  87960
ctatgaagta gaaaaatata ttaaaacaga aatgtctaaa gaagtattag ttaagttcat  88020
agctgagaat aagcaagagg actcagataa cttacctgaa ctagtagaga aactaaaaca  88080
aatagaagtt agtgacatta atggtactga tggtgaattt attgatttct ttgaagatat  88140
agacaagaag agagaactat taagtaactt aagtattaat aaatattcta caggtttcca  88200
ttctatagac caacaaattg aaggtggtat tggtagaggg gaagtaggac tagttattgc  88260
acctacaggt agaggtaagt ctcttatggc aagtaattta ggtaagaact atgttaaaca  88320
aggtttaaat gttttatata ttgccctaga ggaaaagatg gatagaatgg tattaagagc  88380
ggaacaacaa atggtaggtg tacaaaagaa tcaattactt aatggtgact tatctttaaa  88440
cacagatgct tataataaga tacaagaaca ctataaaaag aatagacaac tgctaggtaa  88500
cttttatatc gttaaacata tgcctggtga ggtaacacca aaccaattag aacaaattat  88560
aattaataca acaattaaga aagataagca tatagatgtt gttattattg attatcctaa  88620
acttatgcgt aacccttacc ttaagtatca aagtgaatca gatgctggtg gtcgtatctt  88680
tgaagatatt cgaaaattat cacaagaata caattttgtt tgttggacat tagcacaaac  88740
aaacagaaca gcttatggtt cagaaattat tacaagtgaa catgttgagg gaagtagaaa  88800
gattgtcaat gctgtagagg ttgcttttgc cgttaaccaa aaagatgaag aatttaaaaa  88860
tggtttttta agattgtact tagacaaagt aagaaacagt tcaaacacag gtgagagatt  88920
tgttaatctt aaagtagagc ctactaaaat ggttgttaga gatgaaacac cagaagaggc  88980
agaagaacat aagcaaatac tagcggaact taatggtgaa gataaaagta gatttaaaga  89040
aaaacctaat aaagctgaag ctattaataa ttcttttgga gggctgagtt tttaatggat  89100
gactttacta agctttataa aaaagtacgt agaacattta cacgtaataa agcagaatgg  89160
gattatacaa atacaggatt aagaaccttc caattaaaag gaactaatgt atgtgttaca  89220
ttactagact ctatagcaag gaataataca acaggatata agtacaacgt tatgtctaat  89280
aaagtacctg ctataccttg caatacacat caagaagtaa ttaaagcaat tgaatataag  89340
ttaaaaaatt gagaaaaagc cttgacaatg tatttgttaa ggattatact tttattataa  89400
acaataaaga ggtggtaaga tttgaactta aatgaagcaa aagtaaaatt aaaaaacttt  89460
aaagtcattg tagtgaggga gatatagtat ttgatggttt catgggtagt ggtaccactg  89520
ctattgcctg tatgaatact aatagaaatt atataggttt tgaattagat gaagaatact  89580
ataatttagc cagtgaaaga atagaaaaac ataaggagat actaaacaat gaaaatgaca  89640
atacaggaac tacaagataa cactgaattt ttaagacatg taaaggtaga tacggaagaa  89700
gcaatggata tccttgaaga tatattaaga ggagagcctt acacagatga ggtatgtgaa  89760
ttgatacatt tttattcaag taagctacta aatgagatta atgacaatca tatgtttaaa  89820
ttacaggagt ttgctaatca tgatgttata ggaattagtg aagagggagt aaaataatga  89880
taaaattatt acagggggat tgcctagagt cactagatac agttgaagat aatagtatcg  89940
atgctattgt aacagaccct ccatataaca ttgcaaaaga gaacaggttc acaactatgg  90000
gtagagctgg tattgatttt ggggaatggg ataaaaattt tgaagctact ttatggatta  90060
ataaagatat accaaaagtt aaaaaaggtg gtaatatcgt tgtgttttgt gacatgagac  90120
aatttacacc tattattgat actatggaag cattaggctg tgaatttaaa gatgttatac  90180
gtatggaaaa atctaatcct atgcctcgta atagagatag acgatttatt tttgatactg  90240
aatttgctct ttattttgtt aaaaaaggag ctaaatggac ttttaaccgt ttagatgaaa  90300
aatatgaaag accttgtatt aaaacaagtg taacacctag aagtgaaaaa ttaggtaaag  90360
gacacccaac acagaaacct ttatatgcta tggaatggtt gttagagcgc ttaactaatg  90420
aaggagacat tgttctagac tgcttcatgg gaagcggaac aacaggtgtc gcatgtaaaa  90480
agttaaatag gaattttatt ggttgtgaat tatcagaaga atacttcagt atggcacaag  90540
atagattact aaataataca aattaaaaca aaaccccttga caacatgttt gttaagggtt  90600
atactttat cataacgtac taaaggagga cactaatgaa atttatattt tttacagata  90660
gccattttca tatgtttacg aattatagta aacctgatga agaatatggt aatgatagat  90720
ttaaagaaca aattgagaca ttacaaaaag tatttgattt agctagagaa aataaagcta  90780
aagttatatt tgggggtgat ttgtaccaca aacgtaatgc agttgatact agggtatata  90840
acaaagtgtt tgaaacattt gctaataatc aagatattca agtttacatg gtacgtggaa  90900
atcatgatgc tatttcaaat agtttgtata ctcaatctag tattgacatt tttgaaacgt  90960
tacctaatgt tgaagttact aagtctttgc gtagtgaatc attaagttca aaagtacagt  91020
taactatgtg tgcatatggt gatgaggtac aggaaattaa agactttatt agtaagtcat  91080
atgttaaaga taaggtaaat attttagtag cacacttagg cgtagagaat agtttaacag  91140
gtaaaggctc ccatagatta gaaggtgcat ttggttacca agacttatta ccagaacaat  91200
atgattttat tcttcttgga cattatcata gacgccaata tctaaacaat aatcctaacc  91260
atatgtatgg tggttcttta atgcaacaat ccttttcaga tgaacaagaa gctaacggcg  91320
tacacttaat agacacagac aagctaacat caacgttcat ttcattagat actagaaagt  91380
ttattacagt acaaggtgac aatgtaccag ataacatgaa tgatttagta aaccaaggtc  91440
actttattag gtttattggt actccagaac aagctaaagt aattgaatta gataaaacag  91500
aagatgaatc taatgtacaa gtacaaatga agaaagaata cacagtagaa aagagagtcg  91560
acgctgacgt gtctgacagc cctataacga ttacttctag ttatgcagac aaatactatc  91620
cagaagcaaa agatgagctt ctagagtgtt taaaggcggt gttgtagtat gatagatatt  91680
attataaaga atattaaacc aagtatagat aaatctaaac ctattttaca gttcttacat  91740
aataaaagaa catatgatgt atgtaatgtt aaaaatattg atgatgcgat gtaccttatt  91800
aacaaagtat tagaggaagc taactacgct cattattata cgagggttat tgaacaagaa  91860
gattgttata ttctagatta tggttcacat caatgtttct ttaaattgtt aaaagaaggt  91920
ggtacaaatg gttaagttta attatgtaga gatgaataac tttttagcta ttgagcatat  91980
caagctaaat ctggataagc aaggtcttgt acttattgaa ggtattaata aaacaaatga  92040
tagttttgaa agtaatggaa caagtaaaac aagcatgata tcctctatca catatgcact  92100
gttcggaaag actgagaaag gtttaaaggc agatgatgtt gttaataagt ataagaagaa  92160
```

```
agacacctac gttaagcttt ctttcaacat aggtaaagac gagtatttaa tcgaaagata  92220
tcgtaaacac aaggaacaca agaacaaggt taagctgttt tgtaataaca aagagataac  92280
aggctctaca aatgatgtta cggatactca aatacaagag ttatttggta ttccttttaa  92340
tacatatgta aatgctatta tatatgggca aggtgacatc cctatgtttt cacaagctac  92400
cgacaaaggt aaaaaagaaa tattagaatc tattactaag actgatattt ataaacaagc  92460
ccaagaagta gctaaagaaa aagttaaaga agtagaggag aaacaaagta aagaacaaca  92520
agaaatagaa aaactagaat ataaaagaaa cctaaaacaa gaacaatata ataatgaagt  92580
aaataaatat aataacttat tagagcgtaa gaagcaagaa gaggaacagt ttaatcaaaa  92640
gaaacaagag tacgagaata aattaaaaga tttagacaat cagattggtg tatgtaaagg  92700
tagtattcct aaagttgaag actttgaatt tgtatttagt gaaaattata caaaagctaa  92760
ccaaggtatt gaaaagatta acacaaatat taatgataaa ttattgccat tattgagtca  92820
agaaacaaca aataagaata caactctaaa tataattaat caattaaaac aatctattaa  92880
taaactagat acaaatgacc attgtcctgt ttgtggttct cctatagata atacacacaa  92940
aataaaagaa aaagaaaact tagaattaca aattaaagaa aaacaagcta aaatatctca  93000
gtacgaacat aatgagcagg ctataattaa taagaaagaa gagctactag ctaaatctaa  93060
agaattacaa caatttatac agcaagaaga tatagaaaag aaaaaacatg atgatgatat  93120
tcaacggcaa tacagagaac agcaagaagt atatgatgaa attagccaat tagaaaacac  93180
taaagctaat ttaaaagaac caatattaaa tgattactct tatatagaag aacctaatga  93240
agaattacac aataaagaac taaaagatat tgacaatact attgacaaac ataaggaaaa  93300
tatagtacaa ttagagagta agaaaacaaa atataaacaa gctgtagatg catttagtaa  93360
taaaggatta cgttctgtaa tattagactt tattacaccg ttcttaaatg agaaagctaa  93420
tgagtattta caaatattag cgggttcgga tatcgaaatt gaatttcaaa cacaagtaga  93480
aaatgctaag ggagaactta aagataagtt cgatgttatt gttaagaata acaatggagg  93540
agagtcttac aaatctaatt cagcaggaga gcaaaaacgt attgacctag ctattagttt  93600
tgctatccaa gacttaatta tgagtaaaga agatatatct acaaatatag ccctttacga  93660
tgaatgcttt gatggtctag acactattgg ttgtgagaac gtagttaaac tactaaaaga  93720
tagactaaaa acagtaggta ctatttttgt tattactcat aataagagtc tagcaccttt  93780
atttgagaat acaattacgg tagtaaaaga aaacggtgta gctacactaa gaaaggaatt  93840
aaataatgaa actaaagatt aaagataacc agtttgcatc tttaacagta aattatacaa  93900
acaatgcaaa gttacatata gataatattc ctgtttctac tttagtagac tggtaccctt  93960
taagtaatgc atacgagtat aaagctagta atgactttgg atatattgaa ctaaagagat  94020
tacgctctag cttacctgtg tcttatgggt taactcacca aaccttatat aaatgtgaaa  94080
ctgttaaatg taaattagga ttatggtata acgaaaaaat aaaagaagat aatgagaaaa  94140
ttattgagaa agctaagttg tacggtttac ctactataga tgaacccttc acaagtaaag  94200
atgtaaagca aggatttagt gacttaggtg ttattttcca aacactaaaa acaatcagta  94260
caaacgagta cttgaaagat aaaacaattg aagagattaa caccttttagt aagaaatcag  94320
aggattatca attaaatgaa gtactcaagt acagtacaac actggtagat gatacttata  94380
gtgatttaag tcaaatctat aatatgttac tattaatgaa gaaaattgtt tctatatagg  94440
aagtgactga aaatgaggtt tgaagacttt ttaagtcaag agattggaac acccaaagag  94500
aatactgtag gagaattacg atattgttgt ccttttttgtg gagaacagaa atacaagttt  94560
tatgttaagc agtctttaga ctctactaat ggtatgtatc attgtaagaa gtgtggagaa  94620
catggtaatc ctattacttt tatgaaatct tattatagta ttacaggtag acaagctttt  94680
gagttattag aaacaaagaa tattgatata caattctcac caacattaga aatatataac  94740
acagatttaa ctgacagtga gaaactatta ctaaggctta atggatatac aaaagataat  94800
agtagtataa aatcaaaagc acctgaacta cctatagggt ttaaattgat taaagataac  94860
ttaaataata aagaagtagt accgtattta agatatctca agaatagagg tattacacta  94920
cagcaaatcc tagactatag tatagggtat attataaatg gttattgcta ttcttatggt  94980
attaataatg agaaaaagaa aatagtactt agaaatagtg ttatattttt tacttatgat  95040
aatgaaggta agtatatata ctggaataca agaagtattg aaacaaatcc atatattaaa  95100
tctataaatg caccttctaa acctaatgag tatggtaaaa gcgatgttat atttaattta  95160
aatatagcta gtaaacaaaa gtttgttgtt ataactgagg gtgtttttga cgcccttaca  95220
tttgataagt acggtatagc tacgtttggt aaacaagttt caaagataca agttaataac  95280
ctcatttcaa gtattcctaa agaaacacct atatatatta tgttagacac agacgctaca  95340
gactttagta ttaatttagc taataagctt atctcacatt tcaatgtagt gtatttagta  95400
ccacatggta atgaagatgc taatgatatg ggtatggaaa aagcttttag tactttgaaa  95460
cacaatagat ttttagttac acctgaaagt attcaaagtt acaagttaca acaaaagtta  95520
aaactttaat cttgcattat aatgtatagt atgttacaat acatatataa aaataaagga  95580
agtgttattt tggaagagaa agatattcta cattttgtag atgagtatgt tacagcatta  95640
cgtgtaggta atgaacagcg tatgcaccaa ttagaagagt taggtaaaga acaaacagca  95700
actttaacag atgtaatgaa ggctattact aacttattgt taggtgttaa taaacaaatg  95760
gttgacctag agcaaaatac agagttaaac ttaaacattc taattgatgc tttatacaaa  95820
gctgagttag ttaacgatga cgtattaaaa tatattgagg aagcaattga agaatcaaaa  95880
gaaaaggatg aagaataatg gaaaaaaata ttagtacaca tacaaaaggt atttcacaaa  95940
aagatatgga catgtggtta gaagctatta cacaaggaac agtagaaggc aaggaattaa  96000
ctgaggacac tgctaaacaa ttacatcgta ttggagcacg tagtgtatca ttagatgagg  96060
ctactagaat tgcacgagca attaatgccg ttacagttca agagtatgca tctgccttta  96120
atgatgcttt taatgctatt gatttgttaa tgattgttat ggaagataac ctagatgtaa  96180
ctactgagca agtagagaag gcgcaactta aattaaaaga aaaacgtgaa aagtatttag  96240
aagaaaaaca agaagaagta agaaaaaaac aagaagagca taaagcaaaa gaagataatg  96300
aaaaagtagt gcagttgaag aaacatgaca aatagtaaaa aaaaaggtga tgtattcgaa  96360
agaaagattg ccaaagaact ttctgattgg tggggttatc cttttagtag gtctccacaa  96420
tcaggaggtg catcatgggg agctaacaat aatgctgtcg gtgacattgt agcaccttta  96480
gagtctaatt ttccattagt tgtagagtgt aaacatagag aaaattggat tatggataat  96540
gttctactta ataataaaga acctcataca tggtgggaac aagttatagg agatagtttg  96600
caagttaata aaactccttg tttaatattt acaagaaata gagcacagtc atatgtagca  96660
ttaccttata tagaagatgt atatgttaag ttaagagatg aagaataccc tattatgaga  96720
acggatttta ttgtagaaaa tgttagaaaa gataaacatt tttatgatgt tcttataact  96780
acgataggtg ggttgactaa cttaacacct tcttatatta tatcttgcta caacaaaaaa  96840
gagattaaac catatagagt tgtcaagtct aaaatatcta aagttagtaa aaaagaagat  96900
```

-continued aagttgattg atgatttact tgatggtata taaggaaggg atactagttg attacacaaa 96960
taaaaaaacg tgatggttcc gttgtagatt atgatttaag taaagttact aatgctattt 97020
taagagccaa ctcagaaaca gaagaatata ttgaagatgt tattgattct cttgtagatg 97080
acgtagactc tttactagaa gaacaagaca ctatcattac tgtagaatta atacaagata 97140
tagtagaaga agttttattt agtagtatgt ataaagatac tgctaaagct tttattttat 97200
atagggataa aaagaaaaga gagcgtaaaa gagacttatt caaaccaaga aaagaattaa 97260
aaccctatga ataccctgaa ttattagaat ataaagatgc tatacgccaa agttactggg 97320
tacacaccga gtttaactat acatcagata ttcaagacta taagaataac gttaaataca 97380
atgagcaaat gaccattaaa aaagctatgc tagcaattgc ccaagtagaa gtagcagtaa 97440
agactttctg ggtgacccta tatcatagaa tgcctaaatg ggaaactgga gctgtgggtg 97500
caacttttag tgagagtgaa gcacgtcatg ccgacgctta ttcacattta ttagagattt 97560
taggtttgaa tgaggagttt aaaacaattg acgatattcc tgctcttaaa gaacgtgttg 97620
atgagttagc gatgcatgta aaactaagta agagtgagga tgatagagat tacgtactat 97680
ctgttttatt attttctata tttattgaac atgtatcttt atttagtcaa tttttaatta 97740
tgatgagttt taataaatat aaaaacttat ttagaggttt atcaaatgct attgaagcta 97800
catctaaaga agagcaaatc catggattat ttggaacaga aatcattaat attcttagag 97860
aagaaagacc tgagtggttc aacaaagaaa tggaagatgc agtttacaca gcctgtaaaa 97920
aatcttatga atcagaaaca cggttacttg attggatgta tgaagatggg gaactagagt 97980
tcttacctaa gaaagtagta caagaattta ttaaaaatag gcttaataac tctctagtag 98040
ctgttgggta tactaaactt tttgatgttg atgaagagtt actaagtgaa gtgtcatggt 98100
ttgatgatga agttattagt actaagttaa cggacttttt atctaaacgt tctgtaaact 98160
atacaaaatt tagtaattct gtaacggaag atactatttt ttcaacggaa tctgattttg 98220
aaaatactgg taaacgagtt actaaagata aagtaaacgc tattttaaga ctaaaaatga 98280
tataaaggca gtgtatatag atgagtaatt ttgaatggtt aaataatgat tctagagttt 98340
ttctagaacg tggttattta agtgatggtg aaacaccaga acaaagaatt aaagatattg 98400
cagattatgc tgaagatatt ttagatattg atgggttttc tgacaagttt tatgattata 98460
tgagtaaagg ttattattcc ttatccagtc ctatatggtc taatttcggg aaagatagag 98520
gatttagtat tagttgtttt ggtagttggg tagatgatac tataccatcg atacttaata 98580
ctgctagtga agtaggtatg atgagtaaat acggtggtgg tacaagtggt tacttcggta 98640
acatcagacc tagaggctca gaaatcactg ataatggtgt aacaagcggt tccgttcact 98700
ttatgaagtt atttgagcaa atgacggaca caataagcca aggatgttat gatgataaaa 98760
ctgaaatact cacagagaat gggtatgaat tattatctaa tgtagttagt agaaaagatg 98820
gaacaaaaat tgcacaggta acagataatg atgaaataga gtttgtagag cctacagatt 98880
atatggaatt tgtacctgaa gataatgaat tagttcattt taaagatagt aaaaatattg 98940
acttattagt gactaagaac cataatatgg tttttaaata cagaactaaa aggactaata 99000
aagaaacagg aaaaagagaa agtgttttag tacctgagta tagaaataga ttagcagaag 99060
atatgccatt acatagagac gtttatttag cacattcttc atttgctaaa gaaggcagag 99120
gactcacatt taaagaacgt cttttggtag ccttgcaagc agatggtagt attattaaaa 99180
aataccctaa atctttgaag tttagattta gtaaagaacg taaaaaagat agactattat 99240
ggatattaga tggtctagga gttgaataca catataatgt agacaaagac aataatcata 99300
atatttatgt taatatgggt gaagaattac ctaaagaatt tagtaaatgg gtaaatttac 99360
aaaatgtcac acaacaatgg gcttatgatt ttattgatga gttgtctcat tgggatgcta 99420
gtagaagaac ggataaatca tttatctaca tgagtgtggt tgaacataat gtagacattg 99480
ttcaagccat agcttctatg gtaggttata aatctcgtaa atcagttgat ttaagggaaa 99540
gagaacctaa taaagccact atgtataaaa tatatctatc tgaaggtcaa ttatttggag 99600
gctcaaatat tactgtggaa acggtacaat ataaaggtaa agtatattgt gttgaagtac 99660
ctactcataa acttgttgta agaaggaaag ggcatacatt agtttgtggt aattctacac 99720
gcagagggcg ttttagccct tatctaccta tagaacacaa agatattgac gagtttttag 99780
agattggtac cgaaggtaat ccaattcaaa acttaacaca tgcagtaaca gttactgatg 99840
attggttatt agacatgatt aatgggaaca aagaaaagag aaaaatatgg gctaaagtat 99900
taacaagaag aacacaaata ggataccctt atatcttctt tcatgataat gcaaatagta 99960
atacagtaga tgtatataaa gacaaagggt taactattaa taactcaaat ttgtgtaaaa 100020
atttgcacct ttagtaagta attactatcg aaaaatccat ctaaacggtg aatatctaag 100080
ttaaaatata cgacaacacc gtgctaaatc agattataaa tctgtaaatg cctaacgact 100140
atccgtaacc tattcacata agtgaaggga taaggttaga gccaagtggt ataagtattg 100200
agtaataatc aagtaaatct tatttaaatc gaaatggtgg acttccttat taaggaagat 100260
gatatagtct gctctatatg gaaacatata gaagttcata ttaacaataa taattaagag 100320
ggtcgaaaat ggagtaccat atttataaaa ttacaaacaa aaacaataat aaaatataca 100380
tcggaattac atcaaaaaca gttcaacata gatttaaaaa tcatattaga aaagctaaga 100440
taggctcaac aactaattta caccaatcaa tgatgaaaca tggtgaagag aatttttatg 100500
tagaagaatt atacactttt agtacagagg ataaaaagtt tgcttacatg gtagagcaaa 100560
tttttataga catgtacgaa tctgtaaaaa aaggttataa tatggagata ggttttgggt 100620
ggaatataat ggatagacga ggaaaaaaca atccgatgta tggtaaagaa agcgctaatg 100680
ctaaaaaagt tattgttgat ggcgtagttt ataaaaatat gggtatatgc tctgaagagc 100740
taggaataaa cagaaataca ttaaccagaa gatgtaattc tgaaaaattc cctaactata 100800
aatattgtta attagagaac tggtagtgat taacgaccac tattgaacat gtaggagtga 100860
aattatgtta cctaataaag aagattggtc atttgtatgt gacctatcta gtatgaacct 100920
tgttaagtat gatgaatgga aacacacgga tgctgtagag acacttgttt actttttaga 100980
tgctgttatg tctgagttta ttagagactt agaatatcta agagactcag ctgaaaaaga 101040
taaacaagaa gcatttaaat ttatggagag agcttataac ttttctgttg agaacagagc 101100
cttaggaata ggcgttcttg gatatcattc atacttacaa tcaaaactca taccttttga 101160
aagtattaaa gctagtcaaa ttaatgaaga gatatttaaa ttattaaaag aaaaaactta 101220
taaagctagt gagcagttag ctaaacttta tggagagcct tctattttaa aaggttatgg 101280
tagaagaaat tcatgtttga tggcggtagc accttaattt atagggcgta tatggattaa 101340
catatatgat aacactcttg aatttctgaa aagcctaagt gtgtaaacat aaggtaatca 101400
gaagctaaga tttatttata gctaacttga caaaaacaaa tatatacatt atactagtta 101460
ctaagaggtg ataataaatg tggaaaaata gtattagttt tcctaggctc gaagtaacta 101520
aggatggaag agtaagaatg tggaataaat catggaaaag atatgtagaa aaaagacata 101580
ggtatgataa agatggttac tcaataattt ctacaagaaa agaagatggt acatccacat 101640

```
cagcaagagt tcatagatta gtagcagaag cgtatatacc aaacccatac aataaacctg  101700
ttgtaaatca taagaatggg attaaagatg ataatagggt tgaaaattta gaatgggcta  101760
ctatatcaga aaatactaaa catggttatg atgttttagg tgttaaacac gctaacgctc  101820
aactaatttt agtctactta gatggcaaac ctttttctag ttatgactcc ttaactttaa  101880
tgggtaaaac attaggtata aatagaaatc ttatacgtag agtagaaaaa gaaactgatg  101940
ggtacatctc atttaaatgg atagaaaaac catataaagt acacaataaa gatttttgga  102000
aaacatcaag aaaattaaat acgagaggct cttgttatgt tgtaaataat gtatactata  102060
atagtgcaaa gaaagctatg gaggctctta aagtaagaca agatgttttc tataatagac  102120
ttaaaaaaga taaaaatgta tatagtgtaa gtattaaaga gtacttaaaa aactgtcaag  102180
atataaatag ataaagttca acgactatcc tgttgcgggg agtacactca agtgagtgga  102240
agtgggagtg gtcttacatt tagtaagatg tgatatagtc tgctctctat ggaaacatag  102300
agctgttatt aaattaacgc atgtaaagta acgaactaca tggaacataa aggacaacaa  102360
gttcgtcatt tatcctaggt caagtttcta aatcaattga acctttttatg agtaattatt  102420
acgttgtaga cactgctaaa gtaaagaaaa ctatgattaa tccttacctt aaaagactat  102480
taaaagaaaa aggaaaggac aataaaaaag ttattgagag tattagggac aatgatggtt  102540
ccgtacaaca cctaactttc ttaagtgatt atgaaaaaga agtatttaaa acatatggtg  102600
aaattaatca atataatata ttagaccaag cttctacaag acaaaaatat attgaccaag  102660
gacaatctat aaacattatg attaacccta aacatgttac agcagaggag ttaaatgaac  102720
tttatctctt tgcatggtct aatggtatta agtcattgta ttatcaacat ggtacaaatg  102780
catcacaaca attcaattta tctaaaattt gtattaattg tgaagcctaa agaggtgact  102840
aaatgaataa aaaagaagcg tttggattac taagtagaac tgaagatata ttcaaatcaa  102900
atgatatttt ctcacaagta agtaatgtac aagaccctat taagatgttt aatagggaag  102960
atgatactaa agcagatagt aaatcaagta aatttcagct agagtttatt tataatacat  103020
atgtgtacat tcttatatat gaaggtacat taaagctatt taaagctgat ggtacggagc  103080
agttaacaca tgtagctgat attgaaacat ttaaagatat tattgacaca ctagaaaagg  103140
atgatacaga aaatggaaaa agtgaatagt ttactagaat taaatacaac aattagacaa  103200
aagaaagatg ttattgtcat ggttacacaa gatgagtgtg ctaaatgtga aattttaaaa  103260
agtgtgattc ctcttttcga agcagaagga gatattacta aacctgttta tgttattaac  103320
ttagatgata aagatgtaga tagagaaaaa gcggtcaagt tatttgacat tatgagtaca  103380
cctgtactta ttggttataa agatggggaa cttgctaaga agttcgaaga ccaagtaaca  103440
cctaaaaact taatggaatt agatttactt taatttgtaa ttacctacta cttatgctat  103500
acttatatta gtaaaaggta gtaggttttt tcatgaaagg atgaatagtt atcgcaaaaa  103560
ataagacatt aactatatat aatagtgata gatattttaa tatacatgta aaaaacaaag  103620
atgaattatc taaagctatt aaagttacaa ctttaaatga agatgatata gaaaaagata  103680
tggatatctt agctaataaa tcaactaggt atatactaag agacaataaa cattacatgc  103740
tatttaatga gaagtataac aatgataagt tgattgaaaa aatatgtaag catggtggac  103800
aagtaacata ctataccgat tcagtagttc cttactatgt gcttaaagac ttatcagccc  103860
accctaaatc ctcagttgta tacagaatgc gtagtaaatt caatagcaaa gagatggata  103920
atatagcctt gagtttcatg ggaacaaaag tcattattga tatttcagtt gtatttcctt  103980
acgtcaatcc ttacgatatt attagaagtt tatatgatgt taaaacaaat gtagacgagg  104040
ttcatctatc attccctcgt attagttcta tagacgctaa acaaggtaag tactatacgt  104100
atgataaaga agcttataaa ctaaatcctg agtatacact tgattttgca gataaattaa  104160
gagtttcttt gtccgtgtgg aaaatgtata tctatattct tgctagtaaa gaaaataaag  104220
attatgaaat aatagaagac ctacttactg aattaaaaag acaaagaaag attaagattt  104280
aggtgatttt gtgagtacag caaatagaag agatatagca agaaagatat ctgagagtac  104340
agggtactat atccaagacg tagaagagat actagaagca gaaacaaaag ctatttctga  104400
attgttactt gaagattatg ataaggtaaa gaatcataag tactttcaaa tagaagtagt  104460
agagcgtaaa ggtaaaaaag catgggatgg actaaataaa acatacttca ctttacctaa  104520
tagaaaggca ctaaagttta aacctttgtc tgaattagat aaagttatag atgtattaaa  104580
caaagaggat taagttcctc ttttttttat tgactactat gattagatat gctatactgt  104640
atttaagtta aagaagggat tggtaataac atgaaagttt taattttata cgactatatc  104700
agagaggaac acttttcagt tagtaatgat ggtagtgtta agaatgtact actaaataca  104760
cctaatggta gagtattaaa acaactatta tctaatattt ctggtattaa tcgagataga  104820
agtacaaaag attatgatat tgagtttta tatcctatgg tgcctacacc tattaagaat  104880
aattatggta aaacaattaa gtaccaagac gttaagttat ctgaagttaa accttactat  104940
gaaagaatga atcaaataat cataaacaat aagtacgata ttattattcc tttaggtaag  105000
ctaggggtta aatatttatt aaatgtatca gctattggta aagttagagg tgtacctaat  105060
aaagtaacta ttactagtga agataaaaaa catgatgttt gggtattacc tacttatagc  105120
atagagtaca caaacgttaa taagaatagt gagcgtcatg tagtagcaga ccttaagtta  105180
ttaggtaagt ttgtagaaca aggtgaagac gtatttaaac ctaaagaagt taagtatgaa  105240
cttgttacaa gtattgagcg tgtaagagaa atatttaata aagaagtaaa gaatgataat  105300
catgacggtg tagacattac cgcatgggat ttagaaacta actcacttag tcctgataga  105360
gaaggaagta aaccccttagt attatcaatg agttgggaaa atggtcaagg tgttacaata  105420
cctttatata aatcagactt tacttgggag aatggacaac aagatattga tgaaattctt  105480
tccttactaa aagaatgggt agctagcaaa gaagacatta aggtactaca taatgctact  105540
tatgatataa attttctaat gacaacacaa ggtttcacag actttgaaaa taatcaagac  105600
actaaggtag gttggtattt agctgtaaca caagaacaag cagagtctct aagattatca  105660
gaccttgctt acgaagtaac agatgtagga ggatatgaca aaccccttga agattttaaa  105720
gagtggtatg tattgaagct actaagattc ttatcagata aactaaaaga gattaaaaaa  105780
gaaaataaaa aagttgttaa gaaagaatat aacataaaag caaatgagta tgatacttgg  105840
ttgaaaaata aactcgataa cattgatata gaactaacag atgaagataa gtattatggt  105900
atcacagaag agcaaaaaag atatttagag ttaaaactaa cacctgaggt tattacaaag  105960
aatatgctta tggattctga atttaaagaa gtagccgaat catcacctga gtatatgagt  106020
ttatctaaca aagctaaaga ttatgtatta ggtacatcta ttaatttaat taacacgtat  106080
aaagacaata ctaaagttat taatgaggta gatggaggtg actttaatta tgattggatt  106140
ccattagagc ttatgcatcc ttatgccagt ggtgacaccg atgtctgtag aagaatatac  106200
tgtgatgtta ttgaaaagtt aaaagaacaa aatagaccta aagcattgga cttaatgtca  106260
ataagttacc ctagattaat tagaacatta gctagaatac aatcaaatgg tttacattgt  106320
gacctagaat acatgcataa aaatgatgaa ttttatatta atgagatgga aaaaacccac  106380
```

```
caagaaatta gagaacattg ggctatccaa gaatttgagg agactaggta taatttatac  106440
caattagcct tagcagaaca tgagaagaaa ccatctgata gaaataaaga aatacatgag  106500
tatagagcta aatttaaaga tgaaggttgg aagtttaaac caagctcagg tgaccataaa  106560
ggtgaagtat tgtatagcat tttaggtata cagttacctt atagtaaaga gacagttaag  106620
gataaacctt tcagtaatgg tactaaagaa gatgagttat catggaaaga ttacaaaaca  106680
gatactaagt ctataaagat ggcattatct ttggttgaga atgaagataa taaaaagcta  106740
ctagacttac ttatttatta tgcctctttg caaactaaaa gaaattcttt tactaagaaa  106800
ttacctaaaa gagtaaataa gaatacacat aatttacatg gtaactataa tagtacagga  106860
actgcatgta ttacaggtga ttctttagtt attactgata aaggtataaa aaaaataaaa  106920
gacttatcaa ataatagaaa agaaaaagta tttagtagta ttgatgtagg tattgttaat  106980
agacagggaa atttagaaaa agcttcacac ttttattata gtggtgtaag aaatggatta  107040
aagattactt tagaagatgg tactacatta actactactt taaaccaccc cttattacga  107100
aataattatt atagtaatac tggtagggtt ctaaataaaa caaaacaaac aactaagcat  107160
ttactagata atgattgggt tgtagctgaa gatttaaaaa taggtgatta tataaaaatg  107220
tcttataatt ctaatcttta taataatagt tatattgatt tagatactaa agattttata  107280
tatagtaaag aaaaaagtat tacaaacaca aaaagctata cactacctaa ttatgtatct  107340
gaagattttg ctgaatggta cggtatgtat acagctgatg ggtctttttc tacaaataac  107400
ggttcattca gtataagatt aactaatagt aatcttgaag ttaggaatag attctttaac  107460
ctaactaaag atttatttga tattacacca tactacatta gtaataaaga tagaagtgat  107520
tctattgaat tttcttcaat tggtttaggt agatggttag aacatatttt taatatgcaa  107580
agtaaagcat taaataaaga aatcccacaa caaatattag atagccctaa aagtgtacaa  107640
caagcatttc ttaagggttt aagtttagat actgcaacag aaaagaaaaa gtatcctagt  107700
ttgtactata atactgtatc taataaaatg gctttacaaa taagaacaat gctaatgaat  107760
atgggtatct attgtaggta ttctatagt aaagtttata aaaatattaa tagaaaagta  107820
caaaatgaat gctattctat acaaataact tatgatgcat tagataaatt ttacgatgaa  107880
atagggttta ttgagagtat taagcgtgat agagtaaagt ataaatcaga aaatctaaag  107940
gcattaggca gaagaaacgg tattctttta tatgataatg ttttattagg taaaataaag  108000
aaaattgaaa aaataaaaga tatggaattt tttgatttac atgttcctag tagccattca  108060
tttgtagcta ataatattgt aaatcataat actagcaggc tttctagtaa caaccctaac  108120
cttcagaatc ttcctgctca tacatctgat gtaaataagt ttgattatca ccaccctatt  108180
aaacgttctt ttatctctag atttaaagat ggtgtaattt tacaagccga ttacagtgcc  108240
ttagagatgc gtattacggc actatataca gatgataaag aaatgttaga gatgttttta  108300
acaggacaag atattcataa aaatacggca agtattatgt atggtaaaag tatgaaggac  108360
gtaacagcag aagaaagaca agccagtaaa gctgtagcct ttggtttaat ttacggttaa  108420
caaaatatag ccgtagtaaa actaggtaaa cctattgagt atagggtgta tagttcacgt  108480
taggagctac aggaaatggt agttaagaac tatgctaaca gggaaggctt taaaatgcta  108540
atcctgtgta gaataattta agtgtaattt aataagtaag gatgatttaa atagaattta  108600
aaataggaga aagatataat cacaataagc tatattctaa attagctcat gtatggtctc  108660
atatgataga tagatgttat aatcctaaat gtaaggaata taaatattat ggattactag  108720
gaataacagt agacgataga tggcataatt ttaataactt tcttaaggat gtagagttaa  108780
ttgatggttg gagtttagag aagtataaaa atggtgagtt agtgttagat aaggatatta  108840
aagaactagg taataaagta tatagcttag ataaatgtaa atgggctact agagaagaga  108900
acttaggatt tgtaccttca agaagtaaaa agatattagg tatagaccct acaggtaaag  108960
aatatacatt cttcaatcag tctaaatttg ctaaggaaca taacttaatt caaagccata  109020
tttctgcagt tcttagaggg gaaagaaaac atcataagaa ctgggttttt aaaacactac  109080
aagaatataa ttatcaacct gtagaaaacc cttctaaact ttatgcacct cactatgttg  109140
cttataagaa tcatgtggaa attgattatg atagagtaaa aactaagcta ctaaagagac  109200
taaatatacc tacgtcaggc actaacttta gaaaaatgga aaccggtgaa gattgttatg  109260
ggattacatt caaaatagag aaaagagaac gatttgatta cacttaaaca cttaaattat  109320
tttatcgaac gactatcaaa aggtgagctt tacgccgaga gggcttattg caatataacc  109380
gagtagagta catgtagctc atacctacat ggaatagcct agaagtagat agtaacgtat  109440
ttacttaaga tatagtctag tcccctaata aatatcggga aaccgagggt ataaacggag  109500
tcagagtttt cgtttgcagg taaaaataat atgacagttg atgaagctac tgaaatattt  109560
aataagtttt attctaataa acctgctatt aagaagtcta tagatgaaac tcatgagttt  109620
gttcaaaaac atggatatgt agaaacaatg aatggacaca gaagatatat acactcagca  109680
caatctagag ataaaaagat taaaaatgag ggtcttagac agtcctttaa cacgattatt  109740
caaggtacag gtggttacct tactaacatg gctattactt atattgacga ctttattcaa  109800
aataagaata tgaaatcgaa gttagtagct actgttcatg atagtattgt agtagactca  109860
cctcctgaag aagttaatat tatggctaaa gttattgtcc atgtaatgga gaaccttcct  109920
tatgatttcc taaaaataaa aattaatggt gagttaaggc agtatcctat agatgctgat  109980
atagaaatag ggctaacata taatgatatg gtagaataca acgaagagtt aataaataaa  110040
tttaattcat ataaaggata tattaaatat aaactagcct tacagcaaat taaggactac  110100
tatgaatcag gtaaactaac tgaagagcag tacaaacaaa aaacggaata tattaaaaat  110160
aatattgaca gtttcaaagt tatatagtat agtaacctat atcataataa aatagaggat  110220
ggtattatgg agatacattt agatacatta gatttcaatg agttaacctt aaaagataac  110280
aatggaaaca cacagacttt taatatccat gatgaactaa aacttagtga gtatacaatt  110340
caagacgaaa tgtaccaaca gtcgtctaaa tttgcatggt gggcttcctt aaaagaacgt  110400
gtgagtaatt atgccgaagc agagcaacgt aagttagaaa aaataggagc tcaacttaat  110460
ctacaaatta gagctcagta cgaacaacag ggaaagaaac ctacaaaaga ccaagtagag  110520
tctgctgtat ttctttctga tgaatatcaa cagcaagcaa aggttgtaga agcatggaat  110580
tatagagaaa aacaattaca ttatatcgta aaagcttttg aaacacgtac aactatgtta  110640
gtacagatta gtgcggaact aagacaaaca aataaaaatg gtggtgttac taacccattt  110700
acacattagg tattgacaaa caaaagaaaa catgttatac taattaagta atttttaaaa  110760
taaaaggaga aaagatatta tggattttaa tcaatttatt aatcagcaat cagaaaagct  110820
acaatcaagt ggttttgaca atgaggtaga gacgtacaaa ccaaagaatc cggttttgcg  110880
attaggaaag attaaggacg ttaacaataa tcaaattaat aaagagtctg cacttgtacg  110940
tgtactaccg cctgtagcag gttctaatga gttctttaag gaatttagaa cattaggtat  111000
taactatgtt aaaaaagacg gggcacaaaa gttctctatg cttactttac ccgagaaagt  111060
taactcatct gttgtagacc cttatgtaaa tacatggtta aagcaaggtg tacaatttag  111120
```

```
taacttccct aataaacctg cacgacgagc atatattcat gttattgaat actttaatca  111180
aaatggtcaa ttagttccta acacagatga acaaggtaat gttgttattc aacctatgga  111240
gctatctaac acgggtctgt ctcaattgat tgaccgatta aaagataaaa tgttatcacc  111300
atcacctact gctacacaca gctttatttc agccgatgat gcattcccta ttaatattgc  111360
taaagctaaa aaaggtgaaa aatcatggaa tgtaactgtt tatcctacag taaaattagg  111420
tgccttacct caaggttggg aacagcagtt atcggattta gataagttag ctacaccaac  111480
agaagaaaat aaccctaact ttgtaaactg gttgattaac aatgttaata acacagaagt  111540
ttctcatgat aattttaaat tcagtagaga aacaaacaca ttaggtgaag aatcatcaac  111600
acaagagcaa acacaagctc ctacgcaaca aagtgtagag caacaattac ctagtaattt  111660
aggtggacaa aataacacac aaccaaactt taataatgta caacaaccaa caccacaagt  111720
tcccccacaa caaaatacac agtttggtca aggaacacct gtgcaacaag caccacagca  111780
accaacacaa caagaacaaa gtaatccatt tgagaacttt gatgctaata acattgacga  111840
ttctcaaatc ccattcaaca caaatgaatc aacaccagaa ccacctaaac aaaatcaacc  111900
taagagtgta gatgatgtat tagcaggttt agatttataa taactttata gagtgctatc  111960
ttagcactct tttatttaaa tttcatataa aaggatgata taatggctag agcaaaaaaa  112020
ggtaaagaag tagatactac aaatttaaat actattgact taggtaaaga attaggttta  112080
actttactat cagatagtaa tagagcagat attaagaata tcattcctac tatgattcca  112140
caatatgata gaattttagg tggaggtatt cctctaggaa gacttacaga agtttacgga  112200
ttaacaggta gtggttacct taaatagcca caatggctta taatgagtta ttacaaatcc  112260
acgtgaattg ctgggaagcc ttaaagactt gttaactaca acgtaactgg aaacggtaag  112320
cgtgaatgtt aaaaataaca agtatatgag ttatatggta taacgagtta ttaaactgtt  112380
atattatata gtgtaggtaa tcagcatcca agctcctgta aaatggagaa ggttcaacga  112440
ctatcgaaaa ggtagctaat attgagaagt attagtgagt aactgagtag agtagggaaa  112500
ccgaagtacg tgggaattgc ctacgaaatc tatttaaaat ggagagtagt ataatatggt  112560
aaaacgagta tggtctaatg aagaaaaaca agatatagtg aaatcctttc aagaaggtaa  112620
gaaatttagt gagatacaaa aaaagtataa tgcacattac tttacaatta aaaaagtatt  112680
agatgagttt aatattgaca caaatagcaa gagaagatgg actagtaaac aaaaacaaga  112740
tattttaaga atgtacactg aagagtctat gtctattgca gagataaaag cagtctatac  112800
aacacatgca agagagataa gtaaaatatt aagagacttt ggtattgata catcttacta  112860
tcaacctagg agagttaata gaaatattaa taaagatttc tttgaagtaa ttgatactga  112920
agagaaagca tatattttag gtttattgat ggctgacggt tgtgttagat atagaagaga  112980
aggtcaatgt tacttaacac tagagttaat tgataaagaa atagtagaaa gagttcaaaa  113040
agaattgaat tcagacagta aaatttatga atctcataga aaaagagatt atataaaaaa  113100
tgaaaattct acgtatactt ttagtgttac cgatgaaaaa ctatgtaatg atttagctaa  113160
atatggtata atacctatga aaactaaaaa aacagattgg ttaacacaag acatacctta  113220
tgatttaagg aaacattact taagaggatt gtttgatggt gatggttcta ttggatgtta  113280
taataataat aataataata gatggtcaat aactttagtt aacaatcatc ctgaattttt  113340
aaaagaagta ggtagttgga ttgaagactt attaggtttt aaatgtccta caatatctaa  113400
aacttctacc tcttatagaa taggttatac aggtaaaaaa gctaaaaaat taatgaaaac  113460
attatatcga gataataata ttcatataga ccgaaaacaa aaacttgcag accaagcaat  113520
taaagatata gtctaagccc actattaagt tagtgttaaa gtactaggaa actaggggta  113580
gtaactgaaa tcgacctttg cagtacactt atctagagta gcaacacaat taggagttat  113640
tacagtttgg attgacattg aaggaacagc ggataaccaa cgtatggaac agttaggtgt  113700
agacgtatct aaattgttct caatacagtc aggtgaaggt agacttaaaa atgttactga  113760
actatcagta gaaaccgtag gtaaagagtt agaatactgg attgatacat ttaatgagaa  113820
agcaccaggc gtacctattt tgttcatttg ggattcccta ggagctacac gcacacaaga  113880
tgaaattgat gcaggagtag accataaaaa acttggaacg aaagcgacaa gtacacaaaa  113940
agtagtaaat gctatttcac ctaagcttaa tgatacaaat acaggattaa ttgttattaa  114000
ccaagcacgt gataatttaa atatgagtaa tccttatgat gaccctatta agtctacagg  114060
aggaagagct tttgaacatg gtgctagttt acgtattaaa gtatctaaag gtaaagaatc  114120
agaattaaaa cagaatgatg ctatgacagg taaacctacg tataaaggtc atgttatgcg  114180
tattgaaact aagaagtcta agctatctag acctggtcaa aaagcggaag ttgatttatt  114240
atcaggttat gaagtaggtt ctgatgaaga tactattcaa ttaaacggtg ttgaccctta  114300
tcatactatc tataaagaag ccgttgagcg tggtttaatt actaaaggaa catggcgtaa  114360
ttatgttacg ttaaatggtg aagaaattaa aaaatatgat aaagattggg taccgacatt  114420
aatggacaac catgaattat acttagaatt atttagtaga gtttaccacg agaatttccc  114480
tcataagtat gcacctttaa acaatacaaa agtagacact actcaattag aagagtttaa  114540
agcattacaa gattactacg aagagcttag ctctactaat aaagagacta aggaagatgt  114600
aaatgaataa tctaatagat agaaatatta atagtgttaa agaagcatta ggtagggcta  114660
atacaaatga tgtattgccc ttaccttata ttgaaatagc agaacgtttt aaaaaagcta  114720
gagataataa ggagcctatc attgtagaag agtcgggatt tccttacact gattctacag  114780
ttatgtatat tgagcatgta gagtcaagat gggcaggagg ttactcttta gtacgttata  114840
atagttctga agtcaaagta cctaaaacaa tacattattc cgatatctat gtatcaaatg  114900
atgtacacag gattaagatt gtatttgagg gagcacatcc ttatgaagaa agttaataat  114960
gggaatagat atattataga cttagatggt attcctattg actttggtag agacttagac  115020
atgcttttaa agagatataa aaaccttaga tggtcattat ttcataggta ctctagaggt  115080
atgagtcatg actttgagaa acaagagcta cgggaataca tagatgagca gtttattaag  115140
ttagttaagg agtatgatat acaaagtaaa gtagattttc cagggtatat taaaactaaa  115200
ctaacactac gagtacagaa cagttatgtt aagaagaaca ataaatataa acgtactgaa  115260
cttgtaggta aaacagatta tacagtagag tccttaacac aggagttaaa tgtgggatta  115320
gaagaaaatg aattacttaa ttatgtcttt gatgatacac aatttactga agtacaaagt  115380
gaactgctaa aagagctcct tattaatacg gataaagaag acaacgcatt tattgtgtct  115440
actgtagcta ataggttaga tgtagaacgt tcagaagtat ctagagagct tacagaactt  115500
aaagattatg ttaaatttaa aataaatgct tatcacgaac aaaacagtag aagatacatt  115560
agagacaaca aaatagatac acaaaatcat gtatgggaat aacacaaaca agccttcctt  115620
ttgttatatt attaatgaaa ataataacat agggaggttt tttctatgtt ataatgtaaa  115680
aaataatgat tggagattaa ttattatggc taagaaaaat attaatgaag tattaaaaca  115740
agataccgct actgtagcag ataagtattt acaagttcaa gtagagcaag atggttatac  115800
acgtacacac cgtggtcagt ataactacaa agtagtagat aataagggag aattattctt  115860
```

```
atacccgatt gaaacagatg gtagaggaaa tattaaaatt atgaaaaagg ctcctgttgc  115920
ttatacagat ggagaccaaa ttcattttgt agttaatact gttaaagacc cttacaacca  115980
tgcttttatt agaactgaaa atattaaagg taaagataaa ggtaaacaat taattcaagc  116040
gtttttagca ttcgttgaag accgtttcag ctttggagta tacaatgtat tccttgctaa  116100
taacaagagg gatgttttg ctttagttga tgctgaaagt aaagatgcta aaaaagtagt  116160
agatagtaat gagaaacctc atgaagacgt gagcgctgag tttcctgcta gtccactacg  116220
taaagacgtt aaaggagtag actcaggaga aggtcaagga gatacttcag aaccgtcagt  116280
acctaaaaat gtaacagtaa cagctaaaga aacaacagct gatattacag ctgaataatt  116340
atataaagga tgacttagtt tggataaatt aaatttatat aaaggtgacc agctattaaa  116400
aagtgaagag aaacaagcag gtaaaacatc aattacaatt gataacttaa ctgctaacac  116460
agactaccca caaggtacat ataaagtatc tttctctaat gaatcaggag aatcagaaaa  116520
agtagatgtt cctgcgttta agactaagga cattaaagta gtatccgtta ctttagatgt  116580
agaaacacta gatttaaaag taggagaaac acataattta gtagctacga ttgaacctag  116640
taacgcaaca aaagctactt atacatttac ttcagaacat gatgatattg ctagtgtatc  116700
aagtaaaggt ttagtagaag ctaaagcaaa aggtcagact acaatcactg ttacaactga  116760
tgatggtaat catacagata ctgtaactgt agttgttaaa gataaagtac ctgaagctcc  116820
tacaaatgta actgtagacc ctaaagaaac aacagctgat attacagcat aatcggaggt  116880
aaaaataaat ggaaaaaaca ttaaaagtat ataaagatgg tgaagtagta ggtactaaga  116940
ctgctgaaca aacaggtaaa acaactattt ctattagtgg tttaacagca gatactacgt  117000
atcctaaagg aacttataaa gtagcatact ctaatgagtc tggtgaatca gaaaaggtag  117060
atgtacctga atttaagaca gcaccacata gtgagctata ataaattaaa gtccaactta  117120
attgttgggc tttttttat tgacttatat ttatttatat gctatagtta aacaagaatt  117180
aataaaggag gtactatatg gatattaaaa cagtacactt aacttcagat aacgaccatt  117240
tgaaagttaa aaaattaatg gaagataagg aaaagtatat tgcagttgcg tatgataata  117300
aatcagtaag taaggtcaat atcattatgg ttattaatgt tattaaagac ctagtgcata  117360
tgtataggta taaaattgtt gagtatggat tatctaataa tgataaggaa aatgaaaagg  117420
tagggtattt aatagaaagg attgaggatt gatgttattt attttaaatg aagtagcttc  117480
acacacagaa catttatccg aaggtataga tatgttcgac gttgaaagtg tagtatcttt  117540
tgactcggca ttacatttag ctagtgataa tacgtatgat tctgttattt ttttaggttt  117600
tatatacaat aatgaggatt acttaaagta taaagaatta ttaaaggata caaaattata  117660
ctttgtttct aatattaact tacccgataa caaagatttt attaccgtag gtgatgattt  117720
aaaataccta tccttattag agcaacttgt ggttctagat gacaaaggtt taaatattaa  117780
tttcagtagt tatacaaaag acattgctca caagtacact gagttgttta gctttaaatc  117840
tacttatgag gaggcaaaag aaaagggtct agtaggttac cctgtagata tagtattacc  117900
tattatgact gacaagtttt acaacgtaaa tgatttgtat gtactatatg aagtagcacc  117960
tgagtataaa ttacctttag catatgaatg ccttaaggat aaagaaaaag gtattgttgt  118020
tataggttca caaacaagag gtactagtga tatccttact ttctatgtaa aagggtatga  118080
tgtcagtagt gttgctaaaa cgtttggagc atcctataat gaaaattcta atatatttag  118140
tatctttatt gatagtcata ttagtgtatt aggtgagaat atgaacaagt atttaataac  118200
ggaaggatgt atttatgagt aattataaaa caatagaaga gttacaagca attattgtag  118260
gtattttatt taaagatgaa ggtaaggtag ttacatctaa atttaataag attctaacaa  118320
gttttggtat tgatagagta aaccgtaatg agttaaaaga cattgtagaa aatattagaa  118380
gtgatgagta ccttaaccaa ctaaagaata aagctgttaa aggtgaagtg ttattagaag  118440
acttaagaga tgtagaagat aaacaagtat ttgagggtaa tgactatcat caagaagtgt  118500
catcttatgt agtagcacat gaaaaagaac tatctagact aagggaatta cgaaagatta  118560
atagacaaac tgcataccct actattttgt ttgatgaatt aaagcgtact atggttaatg  118620
agctaaaagg gaataagtta ctagaccata aagtaagtaa gtatacttct actgaggaag  118680
aagaagagct ggttatctta ctgtcggact tccatgtagg ttgtgctttt caagatttaa  118740
ctaatgagta taactttgag gtactaaaaa gaagattaaa tcagctacta caggaaacta  118800
ttaaggatat tagtaaacgt ggtattagta atgttacagt atactttgta ggtgatttaa  118860
tagagcatat taatatgaga gatgttaacc aagcttttga tactgagttc actatggcag  118920
agcaggtagc aaaaggaact agactattaa tcgacttctt aacagaatta tctccatatg  118980
tatggggtaa tttacgtttc ggtatgatag caggtaacca cgaccgtgta cagggtaata  119040
agaaccaaaa agtatacaat gatagtgtag cttatattgt attggattct ttactgctgt  119100
taaaagaaaa cggtgtatta gaaggtattg agattatcga caatagaaaa gatgtatata  119160
ctattaaaga cacagtatgt aacttaaata ttattataaa ccatggagat ggacttaaag  119220
gtaaaggtaa gcatattcct aaatttattg agaacactca cattgatttg ttaattacag  119280
gtcatgtaca ccacttctca gtaacacaag aagattacaa tagaatgcat attgtagcaa  119340
gtagtcctat gggatataat aattatgcta aagaactaca tctatctaga acaaaaccat  119400
cacaacaact actattttta aataaaaaaa ataaagacat tgacattaaa actgtattct  119460
tagattaggg agagataata tggacattct atcaattata gccttaacat tgcttatcat  119520
tattattgtt aataccacaa tgaactttgt aggtatgtta cgtggtgagc gtgaattagt  119580
aaaaaaagga ggtaaccctc tacccaattg gcagtactat aatgtgttat tacctaattt  119640
atgtggtatt atcctcttag gtattgttgt ttattttgga gattcgattt ataaaattac  119700
aacaaggtta gaagttcttt ttgctattat tgcgcttatt gtaatagatg tattgttaac  119760
agcgttagta ttattagtat tgagtttcgt aacaaaaaat aaagaatagt aaagaaggga  119820
gtctggttta tacttgactc tctttgttat ttatggtata ttagatatga ggtgattttt  119880
gttgcaatta aattttggta aatttgataa tgaaattatt aagacaaaag taagtgaagg  119940
tgtttactct tttagaggtg ttccttatta ctacatagaa catgtccaag atgaaacttc  120000
tgagtatgta ttagtatata acatacatag tgttgatgat gaggtaccac aaaagaaata  120060
taaaatagaa acagtaagta aaactattag aggtggtacg atattaagta atacaattaa  120120
gtcaatgcta cctaataata agaagtataa aaaagtatat gaacctccta tctttttagc  120180
taatattata cctttaggta cagatacaac tacaggttct gtaggtaaag ggtttttcga  120240
aagagaaaaa gatagagtaa ctattacaca aaaagaaggc actaaagtta tacatggtga  120300
gtatacagga gtatttatat gtttatctaa tgttaaatgg attaagtctt atacaccttt  120360
agatagtata ttacaatatt atcaacgtat taaaggggat agaataaatg tctgagataa  120420
ctaaattcta tgagcaggat attaaagatt taattagaac gaagagacac atgtttaaag  120480
atgatgagat aacaagtaat atacaagata ttagaatatt taatgaaaaa gctatttgtc  120540
aaggtaaatg tagaactgac tgtttaattc ttgatagaaa tggtactgtt atgggtatag  120600
```

```
agataaagac agaacgagac tctacacaaa gacttaataa acagttatac tattatagtc  120660
tagtatgtaa gtatgtttat gtgatgtgtc atgataagca tgtacctaaa gtagagcaaa  120720
tactaaaaag gtataaacac catcatgtag gtattatgag ctatattaac tttaaaggca  120780
gtccagtagt aggtaagtat aaggaagcta cgccttcacc actaagaagt ccttatcata  120840
cactaaatat tttatggaag caacatttaa tgactatact taaacagtta agagattata  120900
atacatacct aactggatat aactataggg agcacggtaa aaatactaac aatgagggta  120960
gttatacaga gggaacccaa cgtatgagaa tgaaaaagtc agctattatt aaccaagtta  121020
ttcattactt aggtgtagag aactcttata agatatttac tagaggtgtt atctatggtt  121080
acagtaatag atggcagata ttagaagatg atttctttaa agttatacag aacggagtga  121140
gggtattata tggcaaagag gaaacctgat acatttaaac ctaaatctaa cggatataaa  121200
catcaacctg ttaactttgc tcctacgggt aacttatcag gtagaagtac ttcttttttt  121260
aataaaaaaa gaaaagatat atcagatgaa agtattgttg ttaaatacaa acctttgttt  121320
gttaaaaggt ttgataatat tactgctaca gacattaaaa tacaaaagaa gtatgcgtta  121380
gacttaatta gtgaagctgt gaatataaag aagaaatatc ttgtaatgaa gcaaaaaggt  121440
aaattaacac aaactatttt acatacggat agagtttatt atgtttatag aggtaagaaa  121500
ttaataggta aatgtagtat tcgtgaacaa cgtacattta gaggtacaca tttaatctac  121560
atttttagta ctagacatag aatatctata cgcaaaaata gtagattaga taagaaaaga  121620
acaccaaaga aaatgatata taaaggtggt aaataatggt taaatattta agaacaaaag  121680
ctaaaaaaac aaatataagt actttattta agaaactaca aagtaaagat attacactat  121740
taggagtgtc ctatgatagt gattatttcc ctagcggtgt aacaataata ccttatttag  121800
aggacatatc acaagtagaa gatggtatag aatttacgaa taaagtaata gttactgaga  121860
acttaaaacc tgctattgta ggtatgaata atatgataag tgattcagga ctaggttatg  121920
ttaaaacaga gcagttaaat aaaagattag aaaatactgg attaatgaca gatttattat  121980
ctaaaggaac agaattaact tcaacaaaga aagtagacat tgtatcaact tttattgaac  122040
ctactattat gtaccaagat actactatta ataaagaatt aaaacttaga ttatacacta  122100
tcgaagatgt atccccttta aatgattaca cacatgttgt atacttacta gtaactgata  122160
agcaatatga cggtcaatca ttcataggta cattatgtaa ccaaggtaca ttaaacaaat  122220
tagatactct aaaagttctt acattcttca agggtaataa tttaatcaat agaagtgtgt  122280
tttctgttaa gttagatacg aataaatatc attatagttt atataataca catgagaccg  122340
gtattttctt tttagatgat gataaagact taattattgc ttgtggtcaa tcctatgtaa  122400
aagttagata taaagatatt gttagtagta aagtagagaa agttagtgat aataactata  122460
aaatgattgt taatcttgtt ggtaatgatg agctaacaat tctcttatag tataatactc  122520
ccttaaatat gtatactaag gtataaatat acgtatataa gggatttttt atacatattt  122580
ttttcaagta gttagttaat ttctaaaagg tattattctt attttaaaat tatatttata  122640
aaacattaaa ataccttta ggtataggt tttagaaaaa agatttatat tgcttaaaat  122700
agttacacta tagtgtaaaa aattagaata tcctttatga aaataaaata gatgcagaaa  122760
ttgtgatata ttatatagtg taaagtataa aacagttgat ttgataaggt tatgtgaata  122820
cacatactcc ttattttagt tcacacatat gtaaagacac ttgagacaag aagggaatat  122880
ataatggcta gaaaaaagaa tttaagaaat aaaaaatctg atataaaggt agttccagat  122940
aaggaaagta ttctatctaa actatataat aataaactat taaggtctaa agtggataat  123000
gctatagatg aagatgttag ttatgatgat attatagacc tatgtaaaga gtatgactta  123060
gagttatcca aatctgccat tacaagatat aagagtaaac gtaaagaagc tattgaaaat  123120
ggatgggatt taggggaact tattgataaa agaaagaaag ttagcgctac tcaaatacag  123180
aaaaaagaaa atcctatgaa agaattagat agtgagaatt atacaccttt tgaactggct  123240
acacagaatg tacaaacaat atatgatgat attcaaatac tagatatgat tattcaaaaa  123300
ggtgctaaag gtttaaactt tgtagaaaca ttagaccctg ctttaatgat taaagctatg  123360
gaaacaaaag atagaattac gggtaaccaa ctaaaaggta tgtcattcat aggactaaga  123420
gaactaatga ttaaacaaca agcacaagat actgctatga cagaagttat gcttgagttt  123480
attcctgaag ataaacatga agaagttctt caaagaatgg agcaactaca agaagagttc  123540
tataaaaact tagatttaga tgaagaagga agaaagttaa aagatacatt agatagagta  123600
ggctatacaa tatagataat gaggtaatac atatgacaga agaaattagt ttaattccaa  123660
taaaagatgt taaaccactt acagatatag tagatattat aacacaccta tataaaggtg  123720
atgtacttag agttaaacaa gagaaccaag gagatatatt acttagacta agtactggaa  123780
aacataagtt tactgaagtg tcaagagact tagataaaga aaccatgttc tataaaaggt  123840
attgggtact atacaatgta tctattaatt ctttactaac ttttgatgtt tatttagaag  123900
acgattatgt agaatctaca aaagttaagt tccctaagaa cacaattgta gaatatgtaa  123960
gagataatca agaatcagat gtagctaagg ttaaagatat tttagtagat agtaacggta  124020
attatttcta tgcactttca ggagaaacat ctttatataa tgaagataaa cttaataaaa  124080
ttaaaagtta atgattgaca cactcatatg ggtgtgttat tcttttatta caaacaataa  124140
aaggagcaat tgattatgat tattacatta aatgaagaag agaaagcatt attagaaaat  124200
aaaagcaact atacgccatt aagtaagaat aaagagttca atacaccaaa agaagaatat  124260
attgttacaa gttataataa aggtgtacct gtaactgata ttgccaaaga agctaaagta  124320
agtatgggtt tgatttatac agtgttaaac ttctataaag tacctaagaa acataagaaa  124380
tctagagtag caaaacgtgt aaagcatatt actaatgata agaataaagt acaagcctta  124440
attaaagatt atcaatatat ggacttacaa agtatctata aaaagtataa cattcacaag  124500
aatggtttat actatatttt agatttatat aatattgaaa gaaaatcaga tttaaaagag  124560
aaagccttag aagatactat cgaggtagaa taagaggtgt catatgcgca aagaacgaat  124620
tgtagattac ttgtataatg taaagaacat tgataataat ttaactatac aaggaataga  124680
aaatagttta tttaataaag aatctctaca agacttagta cctgattttg atacttctag  124740
taaagagatt aatgaaagta atttatacct atgtacaata ccagaagatt ataactccga  124800
ccatgtagaa agtggtcagt atataggtat agatgttggg tatgtatctg aagaccctgc  124860
ttttgaccat ttaataggtc aagttcctag aagtgtatat gagaaagcgc atgttatgca  124920
accactaatt aagatagaaa atactgatat agattatacc caggctgata tgattaatga  124980
tattaaagta ggtacaagta ttagtgatgt aaagattaaa gataaattaa gtttaatgtc  125040
aaataatctt attacacatt tagaaattgt tgataagtat tactttgata gtagtataga  125100
agaagcacta ctaaagtatt atgagttaaa aaatcctgac tattatttaa aacattttct  125160
taaactaaaa gaacttgtca gagacaatag aatgatatat tgtcctttac tgttaaaatg  125220
tattaaagtt atagactaag ttattatatt ataagtagta aaggatggtg cgctatgagt  125280
aaaaaagcaa taattgctta tgtaattatc ttagttatgt tagctttatc tatatctact  125340
```

```
tattacgtat cctcatactt atatcatgaa aaaaccaaat cacaagttac agaccaatta  125400
acacaccacg gtaaactaaa aaaagataag aatgtagagt atgtagggga ctatacactt  125460
aagaaagtaa tagacaacaa agcatacttt atggaaaaac tacctaccta tttaccagga  125520
agaacaagtg ataaaagtat tgatatgaga tattatagga ctagtaaatt tagagaaggt  125580
gtaaacttta aacttattcg tgtatacaca gaggataatg acaataatcc agtacacaaa  125640
tataggtttg aggcagtatt aaataaaaag taaaggtatg atagtctatg accgtagtaa  125700
ttatactagt atgtattgct attatatact atttatttaa caaggattga gtcaagttta  125760
tacttgactc ttttttatg ctatgttata gtttaaatat aaggagatga taaatgatga  125820
aaaaaagtga tttagataat ttgtatattg tggtcgtaag tattaagaat ggtgttttac  125880
ctgatgagcg tgtaattcca attggtttag atgtactaag taaagtatta gagggtaaaa  125940
ctacatggac agttaagaaa gaaattaaac atacatttgg taaagatgaa ttaaaaagat  126000
ttaaagataa ttacaagttc ttgcaacata aaattgtaga ccttgctaca caaggatata  126060
ggtaggtggt ataaatggat atagtagata aactcatgtt aggttttatt ttattgtttt  126120
atgtaggtgt atttatttgg tacttatggg aagtctggaa attaacttct ttaatatctg  126180
atatagttat taagtattat gttcgtaagg gatgggttaa aggtttatta ccttatttga  126240
ttcatcaagt tattattacg ttagtttggg ctactctagt attagtacct tttatactta  126300
gttatataat gataaaatat ttgataggag gttactaaat ggaagtagta tatgagaatg  126360
aatgtagagg atattatatt tgtgtcatag ataatgaagg taagtatgaa gtatcatctt  126420
ttaaaaaatc agtaaacaaa tataccccctg aaattatagg gtatactaca gaaaagttac  126480
tcttggaatt aaaaatacca tgtacatatg taaatgctag tgaagtagaa agttttatgc  126540
aagaattaaa agtagcacgt attgcgcttg acaagtttac taaagattta tataataaag  126600
gcataacaaa tattatattc taaagggtgg ttagtatgta tacagaaaaa tatagaaatt  126660
taatccatat tacacatagt atcttggtta gtattcaaga attagcaagt aatttattaa  126720
ataaggaagt aaaactagtt acaaaagaaa ataagtactt atgtgttgta gatggtatta  126780
ttatgttaat tgttgaagaa gggttagtat acacctattt tgataaggta ggtttaaaag  126840
tgcctgaacg tattgcactt ggtcatttag caaaaagttt acagtttaca atatcagaat  126900
caaataaaga tttagaaaat caaaaataag tgttgacacc tttaacatgt tgctttatac  126960
taagagtaac aaaacgttag aggtgatttt ttatgtgtaa agaaaaagtt catagacagc  127020
tatctaatgc tatagaaata ttagcaactt acaaagagtg gtggtctttt ccaaaagaat  127080
taagtaccac agaaacattt aagattatta actggaaaga agatacatta gtatttgaag  127140
ttagagataa cggtaattat ataggtaggt ttagtgtagc aactcctatt attgactttc  127200
attatgatag aattaaaaaa acgacagcac aatacatgat aaattatttt gctaaactag  127260
tatgtaaaga tatgtatacg tattataaat tacagagagg acagtaaaaa tgaaaaattt  127320
aaataaacag aaacgcttga cgttggaatt gattagtgat aatctaaata cacaacataa  127380
cttaaataca tcggttagtc ttgtagatta tagtataaaa gactttacaa atagaaaagt  127440
gtatgtaaga actaaaaaag gtttagaact tactaatatg aaaagtttaa aaagtactga  127500
gtcattagat ttattattta agtatctaga attaatttta aaaggagatg tataacatgc  127560
taacaccaga acaaagaaca caattaaaag aatatcaaaa taaaatgaca aaaaagaaaa  127620
aataaatgtt gacttactaa ataacaagtt gtataattaa cttaacaaag aaaaaggaga  127680
ttgataaata tgaaaaactt atataaaatt ttaacaggag tattctttag cactacacta  127740
ttattaggag gttgtgctta ctactcacaa gaagatacac cgacgcacaa ttataaggaa  127800
gacaagaaag aaaataagaa agatgaaact tcctcattag aagaacaaga gaataaacaa  127860
attaaagaag acaacactgt tcaaaataac caacaagata accaaacaca aggacaagat  127920
aagactcaag ctcaacaaaa tgaacaaatg caagaagcaa gtagaagtga acataatggt  127980
ttatctaatg ctgagtatgc agacaagtat aatcaatata gggaagctca acgagcacaa  128040
gcagaattag agaatagaac tgaggcggat aaagctagcg gtggtggagg cggaggagcc  128100
tcatggaact atgcaggagc taatgaaagt tttgaacaat ggttacaacg ttcacaacaa  128160
gaaagagcag aggcaggatt acaataaaat taataaaaga tacaggagaa taagtatgaa  128220
aacaataaca caggaagaac taaataaaat tctagtagaa cataagctag cgtaagtaga  128280
tacaaggatg attaaatatg aacattgtag aacaacgaaa acctataaaa agtaagcata  128340
ttaacctaac taaacacgcg tatgaacgtt ataccttaag agttagtaac gatagtaaag  128400
aacgtgcttg tcagtggttt gctagtgctt taatgcaagc tacttttgaa catacacaaa  128460
aaggcggtaa tgaagtatat gtatttaaaa attatagaat tattattgat aagcatctaa  128520
ctattattac cgttatagat actgaagatg ataattggga aggcataaag gaagcaagag  128580
aacaaataga tacgtatatt aaaggtaagc taaaaagaac tgttacacct ctatttacta  128640
agttagatag aatagatatt agtatccatg aagcacatat cagcatgatt aaaacaagaa  128700
accctaagac aaaagatata attaacaaaa atattgttga acttgaaaga aataaatctt  128760
tactattaaa tagtatagaa ggtgtaaaga aaacagcaca taagtattat gtagaattaa  128820
aagacattca taaaagatta aaggactgat aataatgtgt ttaaaagatt taattgaaga  128880
ttatataaat caagataaag aaataattat aacagttaca agtactaaag taattattga  128940
ggcagactat gatgttattt gtttacctaa aagtaaaatt gatattgacg atttaaaagc  129000
ttatgtatat ggatttaata gatttaatat agagcaaatt gtattaaagg acgtggaata  129060
atgcaagact taaaaaggat aacacaacct gaattagatt tattgataga aaagcatgaa  129120
caatggctag ctacaaatga aaaggaagga gaaaagcttt ttttacagtg tgtagattta  129180
agaaatcttg actttcattc cgctgacctt caatattcaa ctattgtaat gtctagttta  129240
agtgatgcta acctaagtta ttgtgattta agttattctg atttaagtta cagtgagtgt  129300
atatctacga gatttacaaa tgctcgaatg aaagatattg agttgcatca tactaactta  129360
gagtgggcta atttagtaaa agcaaactta gaaaatgcct gcttagctga agctaatgta  129420
agtgaggcag acgcaaggtg ggctaacatg aaaaatgcta acttaagtat ggctaattta  129480
aaaggtgcag attttggtgg tacaaaccta actaatacaa cattatatta tgctaacatg  129540
cttgacgtgt ttgggataag tatctatact ataagtaatg tacttgattt tgacgagcat  129600
gtaacttatt tacctgatta tgatagaatt attagtaatt ataatgaata taccctttgaa  129660
gagtttggta aactagaacc tacacttgag tacgaagaag atagaataaa agaagtctca  129720
aagaaaatta aattagctta cgatttcttt aaaggagtga aagaacttga taaaatttaa  129780
ttcagacgaa cataaacata tacttaatgt tatggataga ttaccatata tttgttggtt  129840
agatactgta gatggtgagt caggtgctga ctttttatgc gtatcgcata gaacacacta  129900
tgaacttact gaactaggta taatgattta tagttatggt agttggtata tgatacctta  129960
tgacaaagaa gatttaattg aatatgcaat aaaaagagat atagaggagg aaggggaatg  130020
gtaggtatgg tgattacatt tttaattgtt ttaggtatta tattgctaag tgtactaatt  130080
```

```
attgttatac cagatttaag caaagcaaaa aaacgtaaag aagactcaga tattaactat  130140
aatcaatata ctaaagacat ggcttctgag tactatgaaa agtatataac acctaccgaa  130200
cacattattc aaactaaagt agaagaggta attgaaaata taaagaaaga atataatgtc  130260
tctactgtaa ttattgactc ttctagtaat gaagacaaaa ttatcttaca tgttaacgat  130320
aagtacttaa aaaaggtagt gtataaagat acgtatgaat acatctacga ttctaataca  130380
aaataccaat acattattaa taatgtaaca tatgagtcga gtatcttatt aaaacaagat  130440
gaagtaaata aattaaaaga tatacttaat aaagtacctg tcacagctaa gcatacattt  130500
aaaaatgagt tgcttaatcg taggaatgaa tatgtgttag gttatattac aatatatatt  130560
tatggtgact taactgctaa aattacaaag aatggttatg tacaagactt tagtacacta  130620
gaagattttt gtgataagta tgaagcttac tgtagatttg ttagaattga tttatatgac  130680
tgggtaaaag aagtaagaac tattaatggg tataaattaa aggtagatat taaaccttat  130740
tttaaaatta ctgctactaa aacaagtaaa tacgaatttg tagtaagtga tgatgtatct  130800
aatgttaagg tatatagaga tgatatacta ctaacaaaca ggtatgtgca aaaagcaatt  130860
gatatacagg aaatagtaga ggaaacattg aataataata ctgtggtatt ttaaaaaaag  130920
ggtatgaata atgaaaaatt taggtaaaat tataaatatt attgaaagag aatgggatat  130980
taacatagat agagaatatt tggcagatat ttattataat gaagttgaac aaggtagaaa  131040
taaagcaatt agtacgctaa aacgtatact agaaagagat aaagagttat caaagtacta  131100
ttatgacact tttctagagg cattaaaaaa gagagacatt aaaagagttg tatcttattt  131160
taaataaatt tttataaggtg ggagaataat gataattcaa aagacatata cttgtaaaga  131220
attaatagaa aaatacttta atggttattt aaaagaaggt acttacacag gtacatccga  131280
tggcttagat acttattacc ttctgttaga aaataaccgt atgactattg gatatcaagt  131340
acctttggac gctagtttta tagtagaaga agaaattact aatgacacaa aactagaaaa  131400
ctgctgggta ttattaaata gtcatgcaaa agaactattc atggataaca caggtaatgt  131460
gagtattaat gattgtatag aaatatacgg agatgaatta ttaactgtca gtatcttaat  131520
cgatggtacc tttattaatg tatggagaaa tgatgattat tttaatagag gaggagaata  131580
atgaaaacaa taacaaaaga agaattaaat aaagttctag aagagcataa attatggata  131640
gaaagcaatg aggaagaagg taaaagagca gatttaagtt ttacagactt acgtgaccta  131700
gatttaaagg atgttgattt aagagaagct accttaatag gtgctgattt aagttatgta  131760
gatttaacag gagcagattt aagatatgct gatttagcgt gtgctaaact aatagaagtt  131820
aatttaacag aagctatctt agcatatgca gatttaagtt ctgttgattt aataaggtct  131880
aatttaaaaa atacccattt aacagaagct aacttaaaag gtgctaattt agtagatagt  131940
gatttaacaa atgctacttt aatagaggct gacttaaagc atgcctcctt atcaggtatt  132000
aatttaataa gtgcatattt acaaaatgct gatttaagat tttcttattt aagaaatact  132060
ggtttaatag gtgctaactt atctcaagca tctactcaag gtattagagg tttagaaatg  132120
tattctatag ataatattgg tagttttaaa aataaagtaa cgtacctacc taaatataat  132180
aaagtatttg taggatgttg ggaaggaaat ttagaagaat ttctaaaaaa aggattagaa  132240
atgaatgaag gagataataa agagcgtacc aacattgtac tagcttatca gttctttaaa  132300
aaccagctat aataatttaa gtatgagtat ttcttagtaa gtaataagta ggataaaata  132360
tcctacttat ttcatatata agtgttgaca tgaataagtg taaggtttat aataagtata  132420
taagttaaat aattatagag gagacattaa tcatgaaaaa aatattaagt ttagttttat  132480
ccgtattaat tgtactaaca ataatcaatg tgttgaaaaa ccaagagcaa gtagaacaaa  132540
gtaaccaaga acctaacaac caagagcaag tagaacaaag taaccaagag tctcaaaata  132600
atgatgcaga tgaccatact tcatacgtac ctgagaataa cggagagcat aaagacgtta  132660
gtgaagaacg taaaagatta tggggtacag agtatcaaga aggtgaaaca cataacccaa  132720
atgctaaagt gtttaatcaa gatacaggag aacaggttca ataaagagta agaggagcac  132780
ttattatgga gtactggaaa gaacaagaca tatattattc aaaaacaaaa caaggtgtta  132840
taagctatat agacttatct tccttaccta aaaagaagtc tcgtattgat tgggtaaatg  132900
taaaccatta tataccccttt gagtatcata gcacgaaagg taagctctat attaaatacc  132960
ttacaccaac taaaaaagaa tctagagtag aaataactta caacaataaa atccaagcta  133020
cccaagtagc taatgtctat aaggttaaat tcaactttat tacccaaggt cagaagtctt  133080
atactgttca taatataaaa caaggagata ttattaaaaa ttgcgaagta ctaaaagtag  133140
tagacactca tttaggtaca caactttatg tatataacat aaaggaagaa gtctatggta  133200
aagtagtaaa caaaatttac taaaatataa aactgataac tatataccat atggtactat  133260
tcctcaatct aagatgttat accataagaa acatattcat aagtatgcta aatataaaga  133320
cttatttaaa tataagtata caactaagaa aaagatagaa acgatttgcc ctaattgtaa  133380
aagaaaaaaa gatattagaa ttacagattt aattaaagat aactatagct gtcaatgctc  133440
taaacaatac tctagcttcg gagaaagatt aacacaaagt tatttagata ttgcaaacat  133500
agagtatatt agagaatata aatttaaaga attaggtaaa aaaagatttg atttttttctt  133560
acctaagtat aataccgtta tagaagtaca cggtgttcaa cattaccaag aagtcagtgg  133620
atacatgaac caccagaaaa caaaattatc agacatagaa aagagagaat attgtaaaga  133680
aaatagtata caatatatag agattgatgc tagaaaatct acctttaaac atatattaag  133740
taacctacaa agaacattta aatactctaa tatagatagt aaagaagtaa ttaaaagata  133800
tagacatgta tataggtaag tgtagaagag taaacaacca aacagacaaa caaataggta  133860
tagagattga tgtaggtaga agttatataa gtaagtaata ggtaaaagaa agcaatatat  133920
atatataagt agataaagaa atcagataag taacacataa agaaacaact gatattataa  133980
gtacctatat atcaaggaaa taaataatag ataaaaaaac aataattgat agcacataga  134040
taagcagtag gtagtaggta gtgtataagt aatagctaaa tagataagta aataaatact  134100
gtataacagt ttgaagatat gaataataag aagaaagaat tattaagtaa cttaagtatt  134160
aataaatatt ctaatagtaa gtaatagata ttaagtaata ggtaagtaac taaaagaaag  134220
taactaaaag aaagtagcta ccactatcac ttaggttagg taagaacagt tacctagtaa  134280
tttctttaca tcttctagat agataaataa gtagatacta agtaatagct agtaagtaat  134340
taaaagaaaa caggtacatg gtatacctat atactaagta gcaagtatca agtatcaagt  134400
atcaagtatc aagtatcaag tagcaagtat caagtatcaa gtatcaagta gtaagtagta  134460
agtagtaagt agtaagtatc aagtatcaag tagtaagtag taagtagtaa gtatcaagta  134520
tcaagtagta agtatcaagt atcaagtagt aagtaagaac agttacctag gaatttcttt  134580
gcttccccacc ttcatagtgt ataaatagtt aggtatctaa ctgttagata cctaactatt  134640
tatttttata tagttttaac tactgtgaac tatgcttatg tagtattaaa ctatgctgat  134700
tatatgctaa actattctaa tgtatagtta aactaagctg aagtagtatt tactgtgtat  134760
aaaggtatat ttagtattag atattgtgta tatggtatac tataattctg aacattactt  134820
```

-continued

```
atttaatata tatatatagt ttgtttctat ggtagtattg acttaatttt ccctagagta  134880
aaagtttaat atatttagta atttccgaac aataaagaaa ttttaactat tttacacata  134940
tgtgttgaca gtatattact tatggtttat actaagtata taaagttaaa ggagatgatt  135000
tatcatgaag attaaaagag aagtttcgtt tatagaatta atgtatatgt attataaagg  135060
tgatgtaggt aaaggtcagt actattctac taatagtcag tttattgttg ttataactgt  135120
tgatgatata tcgttttata atgcattgta ccctaataaa tctattacta ttactatacc  135180
taatgacact aagtttattg tagaagcggt tatagatgct tctactgagt taagtagtat  135240
agtagttact tataagcaag gtaacagtgt attaaactca gtatggtata ggattagtat  135300
taatgaagtt attgactact atgtcgaagg taaaaataca tggttactat ctgttagtac  135360
tgttgtagat aatgagttag ttactatatg gaaagatggt aacgtattgt gatttggtat  135420
atagtaatat tcagtatact tatatatgta catcacttgt attattatgt gtagtactag  135480
tatatagagg ggttaaataa ccgcttcaat aaagacttag taacgaggag ttgtattatg  135540
agtttatcag atatttatgt acatttaaat cagttaggat ataaaataga agttttaggg  135600
gacatgagta cattaaaagt taatgactac tacatcgaaa atagatgtat agatagtggt  135660
tttagggtta caggggataa tgtattttta tctgtatatt atggtgaaga cgtagtaaga  135720
ttctttaaac aaaggttatt aaaatagtat tttgttaagt tatacttgag aataattata  135780
aaggagggat tagtttatga gtatatttat aagtatagtt tctatatttt tagctactat  135840
tagtattgta ctaagtataa ggtttggtaa gaagtattat aagcatgtac ttgataatta  135900
tgatagtgtt agtgatttag aatcagctag tgtatttggt ttattattta tgagtatttg  135960
tattggtact atttctattg ttttgagttt aggttacata gtaagtagag tattttatta  136020
tataggaggg ttgtagatga tgagttcaac tttaatgtat attgcggtta gtattttagg  136080
tattagtatt atagttggta tgcttagtgc tttaattact gatatagtta aatctattaa  136140
gcagaaagaa gtgtttttta gtatatatct tattgtttct tttgttttaa ctgttttagt  136200
ttttgcttct ataatactac atatgttagg tatgtaatag aaagagggta ttagtatagg  136260
ttactttgta gtaagtttat cattaatgta tttagttata gatatagata tatgttatag  136320
aatatatagt aaagaaggta atagtaatag atttaagtta gcagtgtttt taactatact  136380
tatattgatt atgtttatat atggagtagg tgttttatta acacaataga aagaggctta  136440
ttatggaaga attagatata ctagatagag tgttacataa taaatcaggt ataggtgagt  136500
ttacgtatac aaattgtata agaacaagtg atgataagta tatttatagg ttctttctgg  136560
aagatactta ttttggttgt gctattatgg tatatgatga tatgagtgag tatgaagtag  136620
tagtacaagg tacaggtaag gtgtatgttt ccttattgaa agatgtagtt agtaatatgt  136680
ataagatact agtagatgag tatgataagt atttaaaaga tagtgcatat caaaaatata  136740
tgtataatat atttgaagaa caagtagaac agtataacta aagtttttct ctagggaaaa  136800
gcagtcaaag gtaaaaatag ggcttgaacc cgcattctat ggttgacatt taggtaaaat  136860
tagataggtt ttccctagaa gaaaagttta aaaggtaaaa aaggagttgg ttactatgtc  136920
aaaattagct aagttttgta ggaagtatgg agaagttact ggcataatgg agagtattac  136980
agattatgag gtgtacttag gtaggggtta taaagtaagg tgtagagtag gtaatagcct  137040
tatttatatt cttgtatata aagacaatca tatcattgct aggtttgagg aagcggataa  137100
tatagtattt cctttgagtg atacgcttga ggtgggaaca attaaagact tagaggagct  137160
agaaggtttg tatactaata tctatatatt actagggtat ttatatacag aatatgaaaa  137220
taaagttatg tatgaatatg ggaggttaga ataatggata ttatggtaag tgaattattt  137280
gagtatatat taggtcataa cactcacatt cttgggaatt ggcatactta ttacttagat  137340
aaaggttact gtattaaagt taatgatgat aaacattata ataacatgaa gtttatcaaa  137400
aatggtagag tagtaaaaga ggttattaac agtgacacct tactacctaa aggattcagt  137460
agtatctata gtcttattga ttactatgag gaagctttag atgaaaagtg cagaaaagaa  137520
aaagagcgtc tgaaagaaat tcgtacgttc ctaggtaagt aagtattata tataaccgct  137580
tctatatgaa actttatacc tatagctatt ataactatag gtattttttt atatttctta  137640
cataaatgtg ttgattttat gtgtgttaag gtttatactt aatatataat taaaggagtg  137700
aatataatat ggatatgaac aaggaagtat tagaatgatt agatagttta ggtggtaagt  137760
tagaacaagc aggtacacat agttatgaat ctttaattaa atacacaatt actcaaggta  137820
ttatagattt atgttcaata agtatattat tatctataac agctatctta tgggtggctt  137880
tgtataagtc agataaaaag tctaatgaag gtcatagtac cctattattt gagtttgttt  137940
ataagaatga aaaagagctt tctgctgcag gatgcacagt aattatattt gctgttactc  138000
tgtctattat ttcttttttta gtgctattaa taggcttgcc tattgctatt caagagattt  138060
ttaatccaga aggatatttg attaagagta cgatagataa tttaaaataa ttgtaaaaat  138120
aaggaggaaa atataatgtt agaacaagct aaaggcataa ctacagatta tattatggaa  138180
tttattgatg aacatgagca ttatttctat gaagacttac acaagttagc aggggagtta  138240
gtgttgaaag atacacatga cacaaaccct attgttatta atgatggtga tggttactca  138300
ggtactatta tatctaaatt taaatcaaag gtagagggtg ttccagatat cactgttagt  138360
gatttttacg gttcatgttc tttctgtgat actttagcta atatctatga aggtagtgat  138420
gaacttgaga taattagaga tttagctact atggtactac atacaattca atctatggaa  138480
gagaaagtag aataatgtat aagggagtga tatagtgttt agtaagagaa aagaaattaa  138540
agagtataag aaacaaggtt actctgttga ttatatgggt ggttttttag gattatttgg  138600
tcttggcgat gttttatact atgtagaaac taataagaaa tacttaaagt caattagcgt  138660
aggtaaagat gacaaccaat atgtatatga ctttaatggt tatgaatact tatcaagaca  138720
taagttaaat atcaaagaag aagaactaat gtctaaagct attgctcagt taagtatcaa  138780
aggtttaaag aattttaatg gagttaagca tatttgggat gtaggtttct tagagcaatc  138840
ttttaatata catcgtaaag atattgatac ggttaaactt aaactaagtt ttgatgaaga  138900
gggtaaccta tattatgaat tagaattagg ttggattaat atttataaag agtatacagg  138960
tgtaaaagac tttcttaata cagtagataa ctatctcaac ttcttctata aagatatagt  139020
cactagtggt cttgagttaa aacaagtact atataatact tttatgggag gagattatga  139080
gtttgtagta tctccatata atgttgtagt atatagggaa gttgagttaa ttgatataaa  139140
gaaattttac tctgatactt atggaattta ttcctatggt tatggcacta atgtacataa  139200
acctttacaa acaattaagt attatctgga ataccctatg aatgaagtat aaccacttca  139260
aatattatat aaaaggagtg cttaatatga gtaacggaaa agtagcgtta attggtagta  139320
aggtattaga agattataat atttatacaa tcatgagtga gaaacatata tacttaagag  139380
atagtgttga tgtgactttt aatgatggga aggtattacc tatatacatt gatagtgtat  139440
taaaacaatt aagtaaagat gataaaaatc tatattttc tgaagaagat atagatatta  139500
gtaaacttac taatgacgag tattatacag ttactaaaaa ataaaaggag aatagataat  139560
```

```
gagtagtaat aaaaaaatag cagaaagagt tattgagaaa tttttagatg agactaataa  139620
aggtgtagat tttactaatc aagatgaatt taaccgcttc ttagataata cagaagactt  139680
gtatgaagta tctggtactc aaagagataa gattattaag tgtttacaaa acattgtagt  139740
tactgtattt atggataagg ggaaataaca atgaaaacaa taaaaagaaa aatagtacaa  139800
gaaggtatga acaaagaaga aactatgatg gaagacgatt ctgttgtaat aaaaaaaatt  139860
caaaaaataa caggcggagc tattcttcct ttagccaatg gcaaggaata tgtagtagtg  139920
tttagtaaag tagaccctac taaattaatt gtatttaatg tggaacgtaa tcaaatctat  139980
ttaagtggtt ctggtttcga tagtgaactg tcttatgtag acagtaaaag caaccctatt  140040
accttagaaa cagttaggtt aatcactaat ttattataaa ggttattagg cttttaaaga  140100
ttaagttatt tttatagaata aatactacta gaaaatgatt actgtttaat acagaatttt  140160
aacgtaccta gcttaagggt attaaatata aaggagggta ttagaatgac taaagttgta  140220
agtagaggat atagttttga agaacaagaa gtaagtatga actataatca aggacaatgg  140280
gtgatttatg caagtagaaa accttatatt actgatatta tgaaaaagta ccctgataag  140340
gtggaagtat tagaacaatt agaaaatgaa acaccagtat tggttaaagt tgtattggat  140400
gaagatttaa ttacattgag aaagccaata agtaacgagc gtaaagaaca aatgaaaaag  140460
attgctaaag aaagatttgg taaataatag agaggctgac tttaatgaac atcagtatgt  140520
acactaacac ctgtagggac tagattaata ttacaagata tcttataggg ttatagtgtc  140580
attgagaatg agtatgcttt attaaggtta gttaaagaag ataaacagta tttataaatat  140640
catattgaag aagtagaagc ggtattaaac cgcttctttt ttatattata tttatattct  140700
gagtaattat gttgtattta atcttggcta ataattgtat atcaatttga gcatagtatg  140760
cccgtttcaa catagttaat ctaataattt gtatatttat ctgttagtta tgtataaata  140820
tttgttatta cttatttata tatttgtatt tcgtactaac cgtacgactt atctttttaa  140880
aaagataaga acaaaacagc gtataccttg ttgttttacg ctacgctaca acaaggtaac  140940
gcctgtaata agttattcgt attaaaatac taacaactaa ttacttgttg tttagattat  141000
aacatatgtt tatgagaatt agatgagaat ttagttacaa cagcattata ataatattac  141060
agttatgtta caagttgcta agtatgtttt gttactacaa tatattgaat atgaaagctt  141120
tagacctttt ctgcagacaa gtaattatta caggtatgta tgataaaaga taagtatcag  141180
ggattaaatt aaggttggat taatgaagcg gataagttag atactggtta aaataaaata  141240
ctttacatta cctaaaactt atgatacact taggatagga taaaggagga atatcaatga  141300
atattcaaga agcaaaggat aaattatacg atgaattact ttatacagta agtctttgtg  141360
agggaacaga agaagattta ctagaactta ttgagaattt attttatatt tacaatgacg  141420
agcctgcatt tttaagtaaa gacggtatgc aatatactat taaagatttt atggagagaa  141480
gaaaaacatt agaacctatc ttaactgaat taggtatagg gtacgcaatg atagaatatc  141540
acacacatac agaatacgag ttagttactt attcagtact taaagttata cagtatgatg  141600
tagataacta tactgtaatt attgatacta atagtgataa gaatattaag ttatcagatt  141660
taacattaga agctgttaag gatattttga atcaaattaa gtagctaggg ttgttttact  141720
ctagcttttt catatgcttg tgttgcctat ttaactacct tatataagca agtaagtatt  141780
ataggataaa tactacctaa aaagtattac cgttgaatat agacctataa gcttaatgct  141840
ctcttactgt tataaacatc ataagtataa atctatgatt ttcctaagta gcaggcgctg  141900
ttttcccttt atattaaccg cttcaaacaa cataaaaaaa gattaggtta atagcctaat  141960
ctataactct tttatataat tcttgtaatt ctttttctaa cttttttatt gtttctatat  142020
cattatttct tttaatagac tgacatataa atgcaatacc tttaatcaaa ttaaatggtt  142080
agttttacac tgcattgtat acaattaaat cgatcgatta taataattaa tttaatctgt  142140
actttctagt ttcttctata taatagtaag aaatcatttc ttttgaaaaa ctttcgtata  142200
acctattgac attaaatcta ggatagtgta atgtaataag cgtagtaaac aaaccgaaag  142260
gaattgataa gatatgaacg taaatcaaat tggagatata ctaatggaat tattagatat  142320
agatggttac aaaagcaata actactatag aaatgactta aaatactcaa cacattatca  142380
agttaaatat ttagcttaca ttgatggtag ttatgaaaca ttagaactat ttaaagaaac  142440
gaaagtcttt agcgtatcac attcaaatag attaccaatt aacattaatg ttaaggtagt  142500
gaacaaacac ttatttatag agctagataa tacgttatac ctagtgaatg agaatgcaga  142560
aattattaaa gaaaaaaagt taaaataata gttgacacta tcattaagat agtgtaatat  142620
aatagatgta gtaaacaaac agaaaaggaa ttgattaatt atgaaaacac taattactaa  142680
cagtaaacca tataagaact acggctatga aatggaacaa ttcgagagag aaaacaacgt  142740
aattatcaca cgagcatacc acgaaccaac aaagcaaggt tatagtcttg taatacacta  142800
tacggaggtt aaataatatg aaatatttat attacattaa aggaacttat aacagaatta  142860
aagcacaagg tacaatatca aatgactata gattatggtc aggtattgat gaatgtgatg  142920
acttatacta ccatattaat aaagcttgtc atagtcttta taataatggt gtaaaggaaa  142980
ttacagttac agacaaatgc gttaaactaa cacttaataa taataaaaca aaacttatta  143040
aaaaagttta agaaaagtgt tgacacttac taaaatacat ggtaatatat aaatataaag  143100
aaaacacaat aaacgaaaag gattgattaa ttatgaaaaa cacagtaaaa gaaatggcaa  143160
acggaaacac taaacttgaa agattattag ttttagcaat tgaggaagcg gttatgacag  143220
agcttgttga atatgatgca ttagataaat acaaccactt agaacaacag ttattaaaca  143280
atgaagcatt aacacaagca gaacgtaaac catctaacat tgattatagc acttacgagg  143340
gagctatatt agcacaagac aaagcagaac actttactaa cgttatctta aaccacatga  143400
acaaagaaca atttgaacaa atgattatgg atattgaaac actagaattt aatgcagaac  143460
aaatgctatt ctaaggagac attacacatg aacttatctg ataaagaact tatagatata  143520
atggacaacg ttaatagctt cactgatatc agtgaagcta ttaacgaaac agtaagcaaa  143580
caaacaatta aaggcagtga caaagacagc ggaacgatta aacagtacaa tagtttagat  143640
gagttaagac aagactatga cataacaaca ctagcaccag acgtaataaa agaattactg  143700
aataatcatt agtgtaaaac ttcccaaaat aattaactaa aactattgca attaactgta  143760
tatttgatat aatgtaatta aggaaataca aataaaagaa aagggattga taaactatga  143820
aattacttaa ccaaatggaa caaacagcag aacttgaagg aattgaattt gacttattac  143880
taacagctat ctatgaaaca atagaggtag atgttgctga acacgattta ctatgcaaat  143940
acattcatat tgtaaaccaa ttaaaagaga ataaagacat aacaccatta gaatatatac  144000
cgtctaacct agactttaca gacgatacaa caataagact agttgataat aaagtgtttg  144060
agttagcaga ttatatattg gaacatatgc gtgttgaaga gtttaataaa cacattaaag  144120
actatgaaca aattaaagca gaagctatag aaatgatgta aaacaaattg aaagggaata  144180
aactcccttt cttttttttt attatttatt aggattgtat acaataggtt aatataaata  144240
tattatacgg gggcaggggt aaaatgccac taaagtgggt gggtctgaca gggctatgg   144299
```

```
SEQ ID NO: 2            moltype = DNA  length = 145838
FEATURE                 Location/Qualifiers
source                  1..145838
                        mol_type = genomic DNA
                        organism = Bacteriophage ARSA0002
SEQUENCE: 2
ccttcatagt gtataaatag ttaggtgtct aactatttat ttttatatag ttttaactat  60
tgtgaactat gcttatgtag tattaaacta tgctgaacct atagtaaact gttctaatgt  120
atagttaaac taagctgaag tagtatttac tgtgtacaaa ggtatattta gtatcagata  180
ttgtgtatat ggtatagtat aattatgaac attattatta ttattcatat atattgtttg  240
tttttacagt actattgact caattttccc tagagtaaaa gtttaatata tttagcagtt  300
tccgaacatt aaagaaattg taagcacttt gtatatatgt gttgacactg tgttgcttat  360
agtgtatact taatgcataa aggtaaagga gatgatttat aatgaagatt aaaacagaag  420
tttcgtttac agagctaatg aatatgtatt acaaaggcag tatagacaaa ggtcactact  480
attctactaa tagtcagttt attgttagta taactgatgg tgaggtatcg ttctataatg  540
tgtttttccc taatactacg gttggtacac ctaatagtac tactatacct aatgatacta  600
gatttattgt agaagcggtt gtagatacca ctactgaatt atttagtcta gtaactactt  660
ttaagcaagg tagtaacgta ttaaactcag tatggtatag agttagtatt gatgagttat  720
ataatcatta taaaagtaaa aataaagagt tattatcagt tagtactgtt gtagatgatg  780
agttagttac tatatggaaa gatggtaaga tattgtgatt tggtatatag tactatttag  840
tatacttata tgtatagtta gtgttttaat tctatacgta tcttacaaag aaggttttac  900
tattaggata ctaggttact gatactacta tttatactaa cagaaattac aagatttagt  960
atcaatacaa gtaatgctat tctatgtaca gtacttgtat tgttatgtgt agtactagta  1020
tatagaggag ttaaataacc gcttctatat gaaactttat acctatatct attataacta  1080
taggtatttt tttatatttc ttacataaat gtgttgattt tatgtgtgtt aaggtttata  1140
cttaatatat aattaaagga gtgaagttaa tatggatatg aataaagaag tattagaacg  1200
tttagatagt ttaggtggta agttagagca agcaggtaca catggttatg aatccttaat  1260
taaatacaca gttactcaag gtattataga tttatgttca ataagtatat tattatctat  1320
aacagctatc ttataggtgg ctttgtataa gtcagataaa aagtctaatg aaggtcatag  1380
taccttatta tttgagtttg tttgtaagaa tgaaaaagag atttcttctg caggatgcac  1440
agtaattata tttgctgtta ctctgtctat tatttctttt ttagtgctat taataggctt  1500
gcctattgct attcaagaaa tttttaatcc agaaggatat ttgattaaga gcactataga  1560
tagtttaaag tagagtaatg tataaaggag tggtatagtg tctaaaaaaa gaaaagaaat  1620
taaagagtat aagaaacagg gttactctgt tgagtatata ggaagtattt taggtttatt  1680
tggtattggc gatgttttat actatgtaga aactaataag aaatacttaa agtcaattag  1740
cgtaggtaaa gatgacaacc aatatgtata tgactttaat ggttatgaat atctatcaaa  1800
atataagtta aatatcaaag aagaagaact aatgtctaaa gctattgctc agttaagtat  1860
caaaggctta aagaacttta acggagtgaa gcatgcttgg gatgtaggtt ttttagagca  1920
agcttttaat gtacatcgta aagctattga tatggttaag cttaaactaa gctttgatga  1980
tgagggtaac ctatattatg aattagaatt aggttggatt aatatttata aagagtatac  2040
aggtgtaaaa gactttctta atacagtaga taactatctc aacttcttct ataaagatat  2100
agtcactagt ggtcttgagt taaaacaagt actatataat acttttatgg gaggagatta  2160
tgagtttgta gtatctccat ataaggttga agtatatagg gaagttgagt taattgatat  2220
aaagaaattt tactctgata cttatggaat ttattcctat ggttatggca ctaatgtaca  2280
taaaccttta caaacaatta agtattatct ggaataccct atgaatgaag tataaccact  2340
tcaaatatta tataaaagga gtgcttaata tgagtaacgg aaaagtagcg ttaattggga  2400
gtaaggtatt ggaagactat aatatttata caattatgag tgagaaacat atatacttaa  2460
gagatagtgt tgatgtggct tttaatgatg ggaaggtatt acctatatac attgatagtg  2520
tattaaaaca attaagtaaa gatgataaaa atttatattt ttctgaacaa gatatagata  2580
ttagtaaact tactaatgac gagtattata cagttactaa aaaataaaag gagaatagat  2640
aatgagtagt aataaaaaaa aatagcagaa agagttattg agaaattttt agatgagact  2700
aataaaggtg tagattttac taatcaagat gaatttaacc gcttcttaga taatacagaa  2760
gacttgtatg aagtatctgg tactcaaaga gataagatta ttaagtgttt acaaaacatt  2820
gtagttactg tatttatgga taaggagaaa taacaatgaa aacaataaaa agaaaaatag  2880
tacaagaagg tatgaacaaa gaagaaacta tgatggaaga cgattctgtt gtaatcaaaa  2940
aaattcaaaa aataacaggc ggagctattc ttcctttagc caatggcaag gaatatgtag  3000
tagtgtttag taaagtagac cctactaaat taattgtatt taatgtggaa agtaatcaaa  3060
tctatttaag tggctctggt ttcgatagtg aactgtctta tgtagacagt aaaagcaacc  3120
ctattacctt agaaacagtt aggttaatca ctaatttatt ataacggtta ttaggctctt  3180
aaagattaag ttattttata ggataaatac tactagaaaa tgattatcgt ttaatataga  3240
aatataacgt ccctagttta agggtcttaa atataaagga gggtattaga atgactaagg  3300
ttgtaagtag agggtatagt tttgaagaac aagaagtaag tatgaactat aatcaaggac  3360
aatgggtgat ttatgcaagt agaaaacctt atattactga tattatgaaa aagtaccctg  3420
ataaggtgga agtattagaa caattagaaa atgaaacacc agtattggtt aaagttgtat  3480
tggatgaaga tttaattaca ttaagaaaac cggtaagtaa tgagcgcaaa gagcaaatga  3540
aaaagattgc taaagaaaga tttggtaaat aatagagagg ctgactttaa tgaacatcag  3600
tatgtacact aacacctgta gggactagat taatattaca agatatctta tagggttata  3660
gtgtcattga gaatgagtat gctttattaa ggttagttaa agaagataaa cagtatttat  3720
aatatcatat tgaagaagta gaagcggttt aataccactt ctttttttata ttatatttat  3780
attctgagta attatgttgt gtttaatgtt ggctaataat tgtataccaa tttgagcata  3840
gtatgtccgt ttcaacatag ttaatctatt aatttgtata tttatctgtt agttatgtat  3900
aaatatttgt tattacttat ttatatattt gtatttcgta ctaaccgtac gacttatctt  3960
tttaaaaaga taagaacaaa acagcgtata ccttgttgtt ttacgctacg ctacaacaag  4020
gtaacgcctg taataagtta ttcgtattaa aatactaaca actaattact tgttgtttag  4080
attataacat atgtttatga gaattagatg ataatttagt tacaacagca ttataataat  4140
attacagtta tgttacaagt tgctaagtat gttttgttac tacaatatat tgaatatgaa  4200
agctttagac cttttctgca gacaagtaat tattacagtt atgtatgata aaaggtaagt  4260
atcagggatt aaattaaggt tggattaatg aagcggataa gttagatact gattaaaata  4320
```

```
aaatacttta cattacctaa aacttatgat acacttagga taggataaag gaggaatatc  4380
aatgaatatt caagaagcaa aggataaatt atacgatgaa ttactttata cagtaagtct  4440
ttgtgaggga acagaagaag atttactaga acttattgag aatttatttt atatttacaa  4500
tgacgagcct gcatttttaa gtaaagacgg tatgcaatat actattaaag agtttatgga  4560
gagaagaaaa acattagaac ctatcttaac tgaattaggt atagggtacg caatgataga  4620
atatcacaca catacagaat acgagttagt tacttattca gtacttaaag ttatacagta  4680
tgatgtagat aactatactg taattattga tactaatagt gataagaata ttaagttatc  4740
agatttaaca ttagaagctg ttaaggatat tttgaatcaa attaagtagc tagggttgtt  4800
ttaccctagc tttttcatat gcttgtattg cctatttaac taccttatat aagcaagtaa  4860
gtattatagg ataaatacta cctaaaaagt attaccgttg aatatagacc tataagatta  4920
agtctctctt actgttataa acatcataag tgtaaatcta tgattttcct aagtatcagg  4980
cgctgttttc cctttatatt aaccgcttca aacaacataa aaaaagatta ggctattaac  5040
ctaatctata attcttttat ataattcttt tatataattc ttttatataa ttcttgtaat  5100
tctctttcta actttttat tgtttctata tcattatttc ttttaataga ctgacatata  5160
aatgcaatac ctttaatcaa attaaatggt tatttttaca ctgcattgta tacaattaaa  5220
tcgatcgatt ataataatta atttaatctg tactttctag tttcttctat ataatagtaa  5280
gaaatcattt ctttaaaaaa ctttcgtata acctattgac aatcaatata agatactgta  5340
atataataag cgtagtaaac aaaccgaaag gaattgatag gatatgaacg taaatcaaat  5400
tggagatata ctaatagaac ttttagacat ggacggttac aaaagcaata actactatag  5460
aaatgattta aaatattcaa cacattatca agttaaatat ttagcttaca ttgatgatag  5520
ctatgaaaca ctagaactat ttaaagaaac gaaagtcttt agcgtatcac attcaaatag  5580
attaccaatt aacattaatg ttaaggtagt gaacaaacac ttatttatag agctagataa  5640
tacgttatac ctagtgaatg agaatgcaga aattattaaa gaaaaaaagt taaaataata  5700
gttgacacta gaactaagat agtgtaatat aatagatgta gtaaacaaac agaaaaggaa  5760
ttgattaatt atgaaaacac taattactaa cagtaaacca tataagaact acggctatga  5820
aatggaacaa ttcgagagag aaaacaacgt aattatcaca cgagcatacc acgaaccaac  5880
aaaacaaggc tatgaccttg tagtacacta cacggaggtt aaataatatg aaatatctag  5940
aatacattga aggaacttat aacagaatta aagcacaagg ttctataata aatgactata  6000
gactatggtc agatatggaa gaatgtgatg atttatacta tcatattaat aaagcttgtc  6060
atgctcttta caatagcaat gtaaaagaaa ttacaacaac agacaaatgc gtgaaactaa  6120
cacttgaaaa tggaaaaaca aaacttgtta aaaaaggtta aaataatgtt tgacattaca  6180
tttaagatac tgtaatataa tagatgtaat acaaaaacaa acaaaaggga gctaataaca  6240
tgagagatat aagaatagtt ttaagagaaa ttgacgaggt acagcaagcc ttaatatatg  6300
gtaggaatag cagagagtta gcacgttttt tacgtagaca actggtaaaa ctagagaaag  6360
aaagacaaga tataaattgg tcatagccaa aagcctatta cataggctta aaaaataaaa  6420
ataagggatt gatacacaat gattaaagtt aaatataaag gcaagaaata ccgctcaaca  6480
caaaatacag atgctattgt aactattata ggtggtacag cagtaatcac attgatagac  6540
tggtttatta gattacaaga gaatattaat atatttatta gataagggct aaccacccctt  6600
attttttat gtctatataa ccgcttcaca ttagtgtaaa acttccctta tttctttgat  6660
ataatacttt acaaatacga gcttatactg taatatatta attgtagtaa ggaacacaac  6720
aaacaaaaaa agaagaggga ttgattactt atgaaaaact ataaaacttt agaagaatta  6780
aaccaagatt atacagttat tagaacacaa aacgaagctt caagcaaacg taataactta  6840
gatgttactg atatttatgt taatgattgg ggtttgttac aatatggtat ttactttaac  6900
aaattcgata acgtgtacaa tgtagtttca atgacatcag gaaacaagaa atataatatt  6960
actgcttatg aacttgatag ctttattatg gatgagttaa acaaacagtt agagttattt  7020
attaatgcag gaagactata aaggaacaca acaaagaaca gcaaacaaat aaaaaaaact  7080
taaaaaagtt ttaaaaaagt gttgacacta acatcaacat agtgtaatat aatagatgta  7140
gtaaacaaaa acaaacagaa aaggattgat taattatgaa aaacacagta aaagaaatgg  7200
caaacggaaa cactaaactt gaaagattat tagttttagc aattgaggaa gcggttatga  7260
cagagcttgt tgaatatgat gcattagata aatacaacca cttagaacaa cagttattaa  7320
acaatgaaac attaacacaa gcagaacgta aaccagctaa cattgattat agcacttacg  7380
agggagctat attagcacaa gacaaagcag aacactttac taacgttatc ttaaaccaca  7440
tgaacaaaga acaatttgaa caaatgatta tggatattga aacactagaa tttaatgcag  7500
aacaaatgct attctaagga gacattacac atgaacttat ctgagaaaga acttatagat  7560
ataatagaca acgttaatag cttcactggt attgatgaag ctattaacga aatggaaaac  7620
aaacaaacaa ctaaaggcag tgacaaagac agcggaacga ttaaacagta caatagttta  7680
gatgagttaa gacaagacta tgacataaca acattagcac cagatgtaat aaaagaatta  7740
ctgaataatc attagtgtaa aacttcccaa aataattaac taaaactatt gcaattaact  7800
gtagatttga tataatgtaa ttaaggaaaa acaaataaaa gaaaaaggat tgataaacta  7860
tgaaattact taaccaaatg aaacaaacag cagaacttga aggaattgaa tttgacttat  7920
tattaacagc tatctatgaa acaatagaga tagaagctgt tgaacaggat ttactatgta  7980
aatacattca tattgtaaac caattaaaag agaataaaga cataacacca ttagaatata  8040
taccttctaa cctagacttt acagacaata caacaataag actagttgat aataaagtgt  8100
ttgagttagc agattatata gtggaacata tgagtgttga agagtttaat aaacacatta  8160
aagactatga acaaattaaa gcagaagata tagaaatgat gtaaaacaaa ttgaaaggga  8220
gttaattccc tttcttttt ttattattaa ttaggattgt atacaatagg ttaatataaa  8280
tatattatac gggggcaggg gtaaaatgcc actaatacca cacattttat atgtatatac  8340
ccgtctaccc aggtactatg taagtactat aactatacag tatcaataca aaagtcaact  8400
aaataaataa acaaaaactt atttatttta ttataagtca acaatttttt tttatacctc  8460
ttgttagctt tacatgtatt atattatagg tagataataa aaaaatgagg tattaaaaat  8520
atggataaaa atattataaa agttaataag agtaattatg aggtatggat agacttatct  8580
aaccttcctt taaagaaaac taaatatata aaatataact ataatattat agaaaaaatg  8640
aaaaacattg aggttccttt tagttacaaa ggtttagaag acacaatgta cttaacttta  8700
aagtctagaa ctcctgaggt aacgtatgac tatgagtata aaggtgaaaa aggaacaata  8760
actatgagtt ctcttaatag agtagcatta gatagagtaa catacaatga acgtaaaaga  8820
aaaggcttaa ttaaaagatt taatggtaaa cgttctgtag acttaaataa tctaagaaaa  8880
cttgataaag aaaagtatta tggtagagta tcttatgata tagattttaa aaatagtata  8940
ggtctttctt ttacctattg ttttgaagat aagaaaggaa aacttaaaat tatagatgct  9000
ttttctaaaa aaaataacaa aggtaaagac gttgaatatg ttagattaga aaatagtaat  9060
```

-continued

```
ggagatactt tcttatataa tgctcttaat attatcatag gaaatttaca acgggttgct  9120
gaccccttatg tttatcctta tgatgtagga aatactttag gtaaatttaa tgtaaaagaa  9180
aatataacag aagaaaagat agctaaggat ggtaaagtag agacaacacg ttttagtata  9240
gtagagtgta atgaatgtgg tatgataaag aaaataaaaa caagccacat aaatagttat  9300
tctagggatt attgtgcgga ctgttcttct atgaataaat ccattaacaa ggttaataaa  9360
catagaagcc gaggggagtc tatggtggag caggtattaa aacatcaaaa tattacttat  9420
attgcggaaa aatcatttga ctggtctaat cgtaagcgtt atgacttta cttacctgag  9480
tataacaccg ttatagaggt acatggtgtt caacattacc tagaacaaaa aaagggtcaa  9540
aggtttcatt taacattaga agaaaacaag aaaaatgata aatggaagag aagtcaagca  9600
ctttcccatg gattaaagta tatagaaata gatgtaagag aacatagctt tgactatatt  9660
aaaaaaagta ttataagtag tgacttacct acagaatgcg tagactggaa agaagtatat  9720
aggtatatgg aaaatggatt tattcaagaa attatagatt tatacagtaa aggttatagt  9780
attaaaaaaa ttagtgaagc attaaatact tctacttcag taattacgga taggttaaaa  9840
aaggcatcta gtcttggtct tgtagactat acaccttttg accataatat taagcaagta  9900
gaagaaaaac tatcaagaat gaaaaaagaa agagacaagt atttaaaaaa tataaggaac  9960
ctttagttta gattccttac cttaacactt atatacctct attatgatat gaaaaaaagc  10020
acctactaaa taccataggt gcttactata catactcatt aattagacat caaggtcata  10080
tctatattca aacaattctc tatctacttg ttcgaaacct ttctttttat cttttataat  10140
atagttaccg cgtacaactt tctcaatacc tgaaggtgtt ttaataaaca ggctattgtc  10200
tccttgttta tctactgctc taaatgtttg accttctgtc cactgattaa taacatgctt  10260
attatatcct gtatattgaa tatactctac tacgtcttcc atatcgatta tgacttttag  10320
catagactct cttactttag cataatcatc tgtaggggta tctaagtcta atggttttaa  10380
ttttgctata ttgcttatat tacattctct tacaggtgtt tttgaatatt ctaccattaa  10440
atctagtaat tcttcacttg cacctagact cctaaaagaa tattgttcgt tgagaaacac  10500
ccaagcaata ggttgttggt tttcttttt aataagtatt ttttcttttc ttttggtagt  10560
atttttattt gctatggtaa caatataacc taactgtttt acattttcaa taaattcatt  10620
ggtatacata ggtggtactt cctttgttta attattatcc actatgtcta tttcatggat  10680
tgtaatcatg tcatctctat actcatctat atgcttaagg taactgacgc catcatgttt  10740
tctagacatt ccttgtaatt ctctatatcc ttcggcttta atatctttaa caagctgttc  10800
tttgttagtg tatactttat cttctctata tgagtagcta tcctcataag gctcacaata  10860
gtcatgttct acttgatata gtttcatatt atttttactc ctttttaatt ttatcttcta  10920
attctggtaa tacattttt gaaatatatt tatttaagtc atttattgtt ttaactctat  10980
aagtacgcat gtttctgtta ctaatatata aattatataa atactctacc ttactttcaa  11040
tataatagaa aggatagctt atacaactca ttaatagaga tatactatac agtatatttt  11100
caggtaattc tctagtaaat tttttaattt tatttaccct tttttctctt cttaattttt  11160
tatatagctt tcttaggttg tgctcatgtt ttttaattac aagtagttga ttttggttaa  11220
gtaagctatc gtcgttttg tttatatagt ttaatattcc tttatataaa gttagtaatt  11280
ctctatcatc catattaata ttatctcctt atgttctaca tttaaccaga ctaaagtata  11340
aatgacttga ggctctatat ctcatttatt ctatgtcctt cttttactga ttggttccat  11400
gattttagtt tttcaaagaa cttggagtct actttacctt ctaattttg gttagtataa  11460
tcatcataga aactaaatgt tccgccttta aaaaagcaat aatacgtgtc tgtcgtatag  11520
ttaatattaa tgtactctat atagtctttt gttacttctg gtttgtcata acgtaagact  11580
ggtatttctt gacgtaacaa ttttattcct tctttactta aacctgtata tctttttagc  11640
ttgaaaccga acctcaacca aaagtctatt tcattgaggt taaaaggttc atttactttt  11700
ttacctaaaa tactatgcat aaatagcata taaacaagtt ctatatactc tatacatgtt  11760
gttaaaaaat gttgtttgtc ttcaaagtga tggtaagcca acaaatacaa aaacgtaaaa  11820
gggaaaagaa caatggacat taaaaaatat aaaaatgatt ttaatcttgt gttcattact  11880
cagacacctt ctctacatca tatagtattg ggtatagatt gaagatatga actctatatc  11940
caatagtttt aactttact ttatctccta cttttaatct agcttgtatg tctgcgctat  12000
caaactttct tttgaagaat aagtctgagt tttcaatgac ttgtttgttg tctaatacaa  12060
tatagaactt gtcttcttta tcttgtcttt tgttatattt atctgtaatt gttccttggt  12120
gcgtttcttt gtgttgatag ctagccactg tatagatagg taaagtgata acaagtagca  12180
atacggttat accgaataat gacagtattc caaaaaataaa gatatcgaac caattcatat  12240
ttttaagttt tttaatcatt gttacagcaa tctcccatct tcccaaatta gtcttaactt  12300
actttgatgc ataatataga agcgctcaga tttactagat ttaacttcat ttattgacat  12360
attatgatga gtgagtatat tttcgttatc tagatactcg tatagcttag taaataccat  12420
gtcttcggta tagtcaataa ctgatagctc tttgattaaa acatggtctt ccttataatc  12480
atttatattt ttgtaatacc catatcccct tactgcatcc catacctttc gtacccttgg  12540
tctaaaagtg agtttactac ttgttcttta tccctataga cttttgtttc tgtatatgtt  12600
tcttgatatt cacgaggttt acaattatca tgttctagtt gatacagttt catagctacc  12660
ccatcctttc caataagtat ggattttcat atatatttcc tttaacttgt aactctaaag  12720
tatctgtgta tggttttatg gagaaatcac taagtaaagt aagtttacac cctgcatacc  12780
tcactatata gaaaaatccc ttacccttct taactaaacc taggtcacta taattacctt  12840
tggtatttag tatttctata atatctcctt catatatatc attaccgttt acatctttaa  12900
cttctgtgct ttgcataatt tcaaggtttt ctcctaaata accttcacaa gcaaatagat  12960
gtgaatatac tgtgtaatct gcaaaatcaa atctatcaat attaaacatt ctttgtgatt  13020
cttcatccca tgctctaaat ttcaacatca tattacctcc actttttcga tttctatgct  13080
tacagttttg aatagggggct ttttacgagt cagttttaat accgtattcg tgtcttcttc  13140
ctcattcgta ctttgcacaa aataatgctt ttttaattta taattacatt tagacgctaa  13200
gaacttgata caaagactta ctttataggt ttgcatcata ctatcaactc cccatctttc  13260
cagattaacg tcatggttag gtcatcgttt aagatgtaga atgctttggt agggaaagac  13320
gtgttctcta aacgttcttt gatactggta tttgtgtgca gcgctgacat ataggctctt  13380
tctcgaaact catatacttc aaacaaccta tcaaacttag tatcttctgt gatttcctct  13440
tcaactttga cttcgaaaag agtatcgata gaaataaaac ctcctagagt aaaacattta  13500
tttgtatctt tttgaaaaca taccgcttca taactttcac ctgttgtaca atatttttttg  13560
ccttgtgata gctctggatt ttctctagcc catttaatta actcgtctaa tggcatttct  13620
tttttagttt ttattttcat ttttatatct cctaattatt taatttttct atcattttca  13680
taatcttttt tgattctcta atgtcagcat tttcacagtt ttttaatata aagttaattt  13740
tgttttttac atcattaacg atactgtcta cttcttttttt tgttggctcg gtagggaaaa  13800
```

```
gcaaccctac aactatctga atttgatttt tatttagtga gtaaacacta atgttacatt  13860
tctcattaga gtcaatatgt ggtttacttg aattaaatac ctcatctaca attgtattta  13920
attcttggat aggtttaaaa taatgttgtt ttctttgtat cattacctgt gacattagtt  13980
tatatagttt ctgttcttta tcaagcattt cttttgtaag tcttttaact tcccctacct  14040
ttatagtatt acctcgtgca tcataattat ttttaatata ctcagcttct tctatgttag  14100
tagtatatcc tattacttct gaggtgggtt cctcatcgta gtaacagtcc tcttctacat  14160
atatagcata tatcttattc atatctatca aacctttctt taagttaaat taactataac  14220
atataagcat tagggtgtca actactaata tacacttttt acagtaaaca aaaaaaagaa  14280
ccttttttaca ggttctttac taggttatta atttttttaaa tcttgatttc cttttattag  14340
cttcttatca tcaataggat gaccattgta taaatatttt acttccatat atacatgatt  14400
atccgtagcc gtaagggcat ctaggatatc cggatttgtg ttaattgcat ttgtatcagg  14460
aaacgaaaat tttctttat cagactggat tgtatctaca tgaaattttt cttgttttgg  14520
taaagagtaa ttaaggtctt ctaaattttg taggaattta gtaagagaaa agggtttgaa  14580
ctttccttgt aaattattat ctatataatc atttaatagt cttgtcattt cctctttatt  14640
taaagtcatt gtttcataat cgttaacatc ataaaaaaca acaatattag gttgctcaat  14700
acttgtatct ccatctttgt acttagcaat gtaatagcct atttcacctt tatgagctaa  14760
ataatcttct ttcatgatat taaatacttc tctagcaata ggttttgtat atagttcttc  14820
ccattcattt gtttctgtgt tgtaaaaatg tggtaataag tttgccatta tagtttatcc  14880
tttcttattc cgatttaagc catattttgt tagtgtcttt aggtggttca ttgctgattg  14940
tgtacccgtc ggtacccata tctaatgtgt ttacaatgac aggctgagct acagcttctt  15000
tttcactctc taatgttttg aaactaggca catctgtttt attagattct tgtccatcga  15060
ctaaccaaga gactttaaag tcacctttat tataagtagt attaggtttt aaatctgtta  15120
atgttacttt tactgtgcta cctgtaactt catcagaagt taaaataagc tgttcctctt  15180
tgttgtagac ctttaatttt ttagtcataa tgttatccct ttctgttgtg taatacacta  15240
ataatatagc atataaaaaa acaggtaagg gctttcaaaa cctttacctg cttattcttt  15300
actgataatc ataccaatca agaaaatcat ctgaacagct taactctata gttatatcat  15360
ttataagttc agtagcttca tctttactta atgactctat atcaaaagta aactcatcat  15420
ataaacaatc tatatgctta taaataaaat ctttttgttt ttccgtagct ttgtttaatt  15480
cattgctttt tttacttata aattgactaa agttatcact catttaaatc ttcctcttta  15540
ataaaggtac cattaattgt tttaccttta cgtcctttaa tttcaccata agcaaactct  15600
aaacactctt gtaatgacat gtcgtgttgc tgagctaaaa taattaaagt aactacagtg  15660
tccccaatac catctttaag agcttctagg ttaccacgtg ataatgccga tgctacttca  15720
cctgcttctt cgtagaattt aagagcttgt ctatcagggt tgttattgtt caatccttta  15780
tctttactcc attcctctac ttggctaact aaaccttcta gcgtgcggtc ttctgtttca  15840
ccttcattaa agttaggttt ttcatcattt ggtacatgtt cttcttgttc tctatcctct  15900
attgtaataa ataaagtgtc tatttctttt tcgtacttat ttctctgcat ataattatac  15960
tgaccatact caggataagg tacatataca gtatcgtctg taccatcctc ataattcaaa  16020
caaacacaaa caatatcttt gccacttaat ctatcatata atgtcatgtt gtagggctca  16080
tctaagaaac catgaaactc ttcaaagtat tcatccttca taccacttac ctcaatagaa  16140
acttttttttg ctgatttact tgtatctact tcactatttc catatatcat agtttttttct  16200
tcactaatac cttctagtat caactctaca ttttctggtt ctaacattgc gctatctaag  16260
ttttcaaaaa caatttcaat atttttaatt tttttagtca ttaataatca ttcctttttt  16320
ttagtatata gtaaatataa cacataagta aatagaagtc aataaaaaaa aacacctact  16380
ttaaaaataa gtaggtgtaa gatattttga aggtagtttg taggaaaaaa tcctgagaga  16440
ggactcgaac ctcaacgact aggtagctac aactagccaa taccattact caggattgct  16500
agtaacgata aatagagtta taacgttacc gtagaccttt tctacgcttg ttagataggt  16560
agaatataat gattttacag tactcatata gttaggctgt tactctcatt ataaggttaa  16620
aaaatgctaa ctatgtttcg cattgttaag aggcgttagt taactactat aataatatag  16680
catatatttt attgtttgtc aagttcttta ttccatttac tttttttcttt tagtaatcct  16740
tttttaatta attcttcact aatactttta tactctttat tttctttata gaacacttta  16800
gctaaatatc taccaaaaga atcatctttg tatgtttgaa ttaaaacatc ttttccttct  16860
aacatagttg ttgtaaattc cttagcttct tggtaattat tttgtttctt ttctggtgtg  16920
tcgacaccta gtaatcttat tctttgctca gaatatgttc tcattccgtg gtcaatagtt  16980
acatgtatag tatctccatc cactactttg tccacgtgtg ctttaaataa atataaattg  17040
tcttctatca ttattaaatc cccttttttac taatttaaaa atatccaatc agtattgctt  17100
gatgtacctt tagctatata tacagatgag cctactacag caatttgacc tttatataaa  17160
ggtgtgttgt taatactttc tgttactcct atttgactta caacttcaaa attagctttt  17220
gtagctataa attcccaaaa tatagaacca tctgatataa caccgttatt atgagtaggt  17280
tgtgttccac cacttgtacc tgaagctact gctttatata cataattccc attataaaca  17340
atttgacctt gtgtataatc cgtgttagat gtccacttca tattagtagc aactccatcg  17400
ctaatacatc tccatttctc aggactacct gatgttaagg ttctactagt attaacaaca  17460
atatctccca atctccaact tcctgtcgtt ggtattgcag taccgttcag tactttaggt  17520
aaattataag ctatgttatc cttacttata acattaaatg cattactaga aatacttaag  17580
tttttattca tattgttatt taatacgaat aaattactac aagaaccttg aacacttaat  17640
gaatcattac ctttatctgt ttttatatca ttattagtaa ttgtactatc cataacaaaa  17700
tttaagaaca tagctttatc caaagaagta tttgtacttc ttaatgtatt atttttaaag  17760
ttaatttctg acacaggttt actagttgtt cctgaggcat aaataatact tgtttttaaa  17820
cttgttgtat cttgttttaa tacattattt tgtatatcta tgttattaac tcctggataa  17880
aggtacaact cgtaaccctc attacctgat acattattgt tactaataat tcctttacta  17940
cctcctgtaa tagcaatacc attagatggt ttattactta actctccttt attactattg  18000
ccataaatta cgttattagt aattgtatag ttagtacctg atatactcag tcctgagtac  18060
ttattgtttg tatgtatgtt attacttata ataacatttt ctgttcctga ttcaaaaccg  18120
cttgaaccat ttcctgtaga tatattatta acataatatc catttttagt accgcccata  18180
aagttaaaac cattctctaa acattgtgta gctgagcaac tgtctatagt aatgttatct  18240
gagtaaccat aaacaccatc taccgcttgc atagtgttta ctgcatttac aacgttaccc  18300
ataatattat aaccatgtac attatatgct ttacagtttc tacttccttt aaatgctatt  18360
ccaatagaac gaggtgacgc atatctaaat tcacctttac catcccattc ccctttaaat  18420
gttaatcctt ctacaagaat gttatcacag ttgataaatg agaatcctgt aaacatatct  18480
ctaccactag aagaaacatc atctatagag tctagatagt ttttagtgat tcctgacata  18540
```

```
ataaatgtag gattaccttc acctttaatg tatatattac ttcctgttac ttttacacgt  18600
gatgggtttt gtacagtagg tgttttagtt ttgaataaat agtcctctgt tcctttaggt  18660
actataagag ttccaccctt agtacttatt aaataatcta aagctctttg gaatctaggg  18720
taatcattat cttcatcatt aattcttggg taatcttcta tattaactat tactttactc  18780
ttagaattag tatctttacc tagttctttc caatcattac cttttagtac ccaaccatat  18840
gcttgtgttg taccattgtt gtatacettt tcatcatatt taaaatcttc aacactagaa  18900
ggtttaacat gagaataaaa aacatcagtt ttattcttgc tactatcgtt tgaagactta  18960
ataatattag atggattagt tgaagctaca agtaaacctt gcatagttcc agatattaaa  19020
ataacgatag acttaacatc ttcactatta acagtaaaag tatctttttg ggtgttattg  19080
aaagtgaacg ctttatattt atcgttataa taaccatcca gtaatattgt atcataatta  19140
ttagatattt tgtctaatat attaccgtct ttatcaaaac atttaataaa tataccacta  19200
gaattaccta taaatgataa cttgttaata attaactcgt caccaacact aacattatta  19260
acatataaag ccatagggta cgagcctgta aaggtaagta atcctttatt atctactaaa  19320
ctaggtgtag tactgtagtc ataagatact tcatctgtta gagaagttga ctgtaatggt  19380
tttctaaata catttttgac tgtatgatag ttacctccta atcttctata gtctttgcta  19440
aaatcattat ttttatacaa taacgttgtt ttgtattcgt ctactatttt agcaatacta  19500
cttctaggta ttttagcagt attaatattt gtaaacgtta gtttatgtcc attacctaaa  19560
acaaattcag gaataaactt aatatcttta ctatgtgtta cataagattt tgtcatatct  19620
tgagtttcta aatcaacaac cgcaaaagta gctttgttat taaattcaaa tctgtaattc  19680
ttaaatataa atcctactgc tttcttaaga taaaccataa cataattttc agatgttgtg  19740
gaagcagttt caaatttaag tgaatcgaat acattgctat ttcctccata ggtattacca  19800
tttgttagag tttgtttgat gttatagtat gtgttagggt gtttattaaa ctcagtgcca  19860
ctatatgaaa aagctgattt atagaagtaa ttactattca tccaagattg ctcaccatta  19920
gaacctatac catctgtatt taattctata tgtgtttcat tattaataaa gaaattaata  19980
atagtattat taaaccaatg acctctacca ccagtagctt tatgtttatt acctactgta  20040
aaaccaataa tttcattaat attagtatta acatttctac agttaactaa ttctagtcct  20100
atatagtttt gactcttaaa accatgatag cctccaccat aagttggata agaactatca  20160
tcataaatac ctttaattgt aacattagaa tatgataaac tatctagttt aatagctggt  20220
ttatccttac taccattata aacaatctta gcatcagata caatattaat attcttatct  20280
attatcaaag tatcatctat tttaataggt gattcactag aaggaatgtg tagggtatta  20340
ccttcacttg tatctttaat agcacgtctt aacctttgaa catccgaagt atcatctttt  20400
tgctttatat actcgttaga gtatacataa ggacttttac ctgttttaag ccaatctgta  20460
gctgaacctg taaaaccgtt atttacagct acttcataag cacttaaacc ttgcttacct  20520
tgttcccctt tctccccttt ttctccttta atagacttaa cccattcttc ttcagaaccg  20580
acaaaaccat tatctaccgc tacatcataa gcagatttag catttacaag tatatggtct  20640
ttaaaatata atgttatttc tttgaatgat gattctaggg ttgtaaaacc aggaactact  20700
actttatcgg tttcatattt ttcagcttcc catgatacat agaactcacc ttgagggtaa  20760
tgggtatgag gagctaagtt aggtatgatt acagacccta cttcttcatg taactctaca  20820
ttgtaaccta ttgccaatat attaccgtat ttatcatatg cttttaaatg aggcattgaa  20880
aatctccttt attattagtc aatgttaata tatcataaaa cacaaaaaag ggcaaattgc  20940
cctttagtta cagatatcat ttagatgaat atggtcttgt actgaatagt ctacaatgac  21000
atgtgtatgc tttttctttt ttgttaacac tttatatgtg ataaagaatg atataatagt  21060
taaacatata tttaattttt tcataaaatt tctcctttaa agaaggtatt taccgtctca  21120
gtagttaatt ctttgctttt aaagatacaa gattctgtat ttttattcaa tatttctaac  21180
atattttgca tactacttgc tttttgtaaa tccgttaagt ctataacaac tgttatttct  21240
gcgttatcta ttagaatatt acctatgtaa taatttttaa ctccgttctc cgtagcatga  21300
gaggtaacat tatgatttaa aacaactata ccttttgatg gtaagtaatc tgaaaagtat  21360
aggtaacaaa agtatttatg tatctttttt ttatcctctt ccattactat taccatattc  21420
tatgaagttt aacaaccttt cggtataggt tttaatttte tctacttctt ttctttcatc  21480
gtcttttctt cctaatcttg ttgtatattt aacaatatta aatagcatgc agtctataaa  21540
gccaataatg tagaaatatt cttctaaaaa tgatataaca tctttttac ctttataatg  21600
gttcggtgta ttagtggtag agttgacatt atagtataac tccagttgtt ctacattttt  21660
cataagcttt ttagcataat ataatgtgtc atctaaagaa tgtgtcacat ctaaagatgc  21720
ttcaacaatg tttatcttta attcttttaa ttctgttgcc tctttgttac ttccaatttg  21780
tgaatcaata aattctctag tatccatatt ggtgtccttt cgtatctaaa ataaaaaccc  21840
tatctagaat atagataggg aaaaggaaag atattatgga agtgtactat aaagtacaca  21900
tataatataa cagttccttt gccttttaat ctatatcatt tattttaact tcttgtactt  21960
taacataatc tgataaacta ttaacgacga tattatcttc tactaattcg tttctattat  22020
ttgtaacatc atatgagtct ctataaggtg tttgtactaa tgctctaact gtaatgtcta  22080
tatctacata ttctttacta tacctttcca ttactcaacg tagtttcctt tagcaagctg  22140
atacttttg tgtaattctt catataattt ctccatatct ttatattttc gtacatcttc  22200
ttcaaaatga cttaaatact ctattaatgt cttaacttct ttaggttcta aagttataac  22260
tggttttacc attacgcaac atcctcacta aattgtttat ttatattttt aatatctttt  22320
attaattcgt cttttaattc tttaggtaac tcatgacttt ttaaagattg ttgttgacct  22380
aacgtatatc catattttgt tatccttact tctacagtat accatgattt ttctaaatcg  22440
tcaactttte tagctagtaa tattaaacat ctgtcattta taatattcga agcataactg  22500
ccgacacaat gagatagctg ttcaccttct ctttttaatt tttcagtagt atccgcaggt  22560
aaaaatttaa ctttagagcc atcgtttaac ttatattctt tatttgtgat attatttaat  22620
ttattatcat atttttgttg taactttaag tcatcgactt catctttaac tgttaaatac  22680
tcatcagtaa caatatcatg ctctagtttt aaagaatatg gtgttaagtt aatactttct  22740
ttagttctat atccaagaag tactaggtct gaagcaaagt ctatataatc tctatataaa  22800
ttattaacag cgtatgaatg tatacgttgt ctgtttctga catcatagtt tatataattc  22860
accattttte taaagtcaga aaatgaaaag ttaagaactt ctttcgtagt acctttaaaa  22920
gataaagcat ttcctattga atatgaatta gtcaccatta taaagtcgtc atcgaatagt  22980
ttgtgtaagt tagactcatt atataaacta ggaaatttat ttatgataac tcgaagtata  23040
ttaaggtaat tttcttgctc ttctttacta agagtaataa acttattata tgtttgttta  23100
cttaaattta aagcttcatg taatttccat ttatttttgt ttggtattac tagaaactct  23160
ttgtgttctt taaatatatc acaatcttcg ttgttataaa ctttatcaat attagacaca  23220
actaatttta acagattgtt taaattatca gtagcatttt cacctttact aactgtgcga  23280
```

```
taaccatcag gtctatctat catagagtat acatcaaagt tttttacatt aagtctactt  23340
agatttaagt aataatcatt attctttagt gtttggatta ttatgttaaa agctaaattt  23400
tcctttccat atttacttaa aataatattt aaaaggacag gtaaagtaat gttatttttt  23460
agtttaccct tattaaaatc atcttcatac atattaaatt taaattcttt atgttgtagt  23520
gtatttgata ggtgtaggta tacatttcca tttttattat taaagtcacc gtttactata  23580
ctccaatctg ttgttactat acttatgtct tttaaataac aagtcttaat taaaaacgga  23640
gtattattat cttttatagg tgttaatttg ttaagcccta tttttatatt ttttaaaact  23700
tcattgtagt attcgtagtt attatcataa gatttaccaa atgcataagg gtcaatatta  23760
ataccaaata tactatagtc acccattaat aatacatcaa gtatatcatt agttgtagta  23820
tttatttgtc tttttaaatc tcttattttt tttgtaaggt agttattact gctcttattt  23880
tgcatactgt caaattgttt taattcattt tcatagtttg cacggcagta tatcttatta  23940
cgatagtgtc ttttgttata taaaggaaat tcagacctat cgtcactttc tatatactca  24000
ctatatacag tatttacatc tgtaactgtt ttacttaact cttgtacttt tttatatggg  24060
tctcctttaa acgtagtaag ttttttattc ccacataatg ctataaataa aagcaaattt  24120
aaagcactag aataacaaaa ggtattatta atatctctta ataattcttt agagccaata  24180
tctacaatat ttttattatt tatttttaaa tatactcttt cttcacctat aaatatacta  24240
tttctattta ctttagataa tttaagaatt tcttcttcag ttaatcctgt ttctttatat  24300
tctactgaca tgtgtcatca cctcatttat tattatataa gtatgataac atagttaaac  24360
ttaatagtca acaaaaaaga agaacttttt tacagttctt ctagataagt ttcatattta  24420
attttttag ttcttcttac gggtacaata tcgggattac tcattaagtc tttgtacttc  24480
ttagaatttt taaagttaat agtattaggc attgctaata cttcctctaa ctcatctgtg  24540
tacatagtaa ctttagatat tatatctatg tcactaatat ataaactttt agatttactt  24600
ttaaaaataa tctcatcggt actagttact tctttattat ctattaaatc catatagaag  24660
tcctttctag tctacataaa caagtataca atctttgtct gataaagaca ccgaggtcat  24720
atcattaagt tcttgtagtt gtttaataga cacatcatat ttcttactta tagtccataa  24780
ggtatcacca tttctaacct tataataaaa tttattacct ttttgtatta agtctttcat  24840
tgctatctac gcctttatat tcataataag atgcctgtag gtaacatatc ataataagaa  24900
taaagttagc tacttctgta tatattacat gtggtgtcgt atttgttatt aacatactaa  24960
taattaaaca agctaatgca atacctataa taagaaataa atatttgcta gttccatttg  25020
tacttttagt tttataaaat ttatttattt gggataaata agctacgata atactaatag  25080
tagccattat ctgtccatat tcaacactat agttagctac tgaatagcca atataaataa  25140
caattataaa cataaccatt tctaaaagac taacttctgt tgttctaaat aagtatataa  25200
taaaacaaat aatacctagt aataaattaa tacttactga tataatttga aatagaggtg  25260
catgtgttac aaataagctt gttaagctaa tacttactgt aacaacaata taaaaccaaa  25320
aatagctatc tacaccttta acattcttat ctcttatcaa acctactaaa gcaggtatat  25380
atcctacagt aactaatata gcatatagga tgcttaatat atgagctaaa ttagacatta  25440
gatgcaccta acttttctaa ttcccttaaa acttcttccc atgaaataaa acctctaccg  25500
ttggttagtg ataaaaccat tccatagaca aactggttcg ttgaaaactc cgctctgtct  25560
gggttagtgt atggcttccc gtgcccttga cgaatatcag agcaataaat taaaacaggt  25620
ttattgacga tatgatacgc ttctaatatg tcatcttgtg tgtttttatc taactcccta  25680
aaatctatat cttcatattt attgataatt tgttgagctt ggtgtttcat acctaataaa  25740
atactaagtt ctgctattgt acctagcccc tcattcagaa catcaaacac gaatatatct  25800
gactcttgca tagccttaaa gtcattattt aggatacgct cagccaaacc ctcctgtcta  25860
gcatttgctt tgtcgttaat tgagccatct tgatgaggag agtatggaga tacacctaca  25920
attccttcta cttgattgtg ttgtttttct ctatattcta tcattgcttg attaagtaga  25980
tgacctccca tatagcaaat cttatctttg atttattta ccattgtttt tatctccttt  26040
ttatttattt aaaagttact ttacccattt tcaatacttg tattctctta tttctctgat  26100
tgtagttcta tttacaccat actttttgc taattctgta tgacttaaat cactcgctct  26160
cacttctttt attttttctt catttaactt agcaacaggg tttttttcttt taccacttat  26220
ataagaatta agtttgtgcg tagaagttaa ataaagggta aaatacctttt ccatcaacat  26280
ttttaatatt tataggctct tgatttctat taacaaaacc atatttattt ttcttcttgt  26340
atgctgagta acaaccacaa cttctaatag ttttattttt atactggtct tttcttacct  26400
ctactatatt accacactta cataagcatt taacatattt acgctttcta tttttacatt  26460
gtttaaatag tgtttttatt gggattaaac atgtttcttg taattccatc atacaactcc  26520
ctcatatctt ataatttctc cttttctttt tcaaactcat cttttagtgt gatgatatct  26580
ttattcagtt cttctgagtc tttcattctt tttttactaa cacatatttc atcaaatatt  26640
ttggtcattt tttatttcc ttctcttggt ttcatttgcc ataatttatt ttactttata  26700
aaactgtttt taatttatct ttttcttctt tttttcttcc taagtattca tcgttagctt  26760
tttgctctcg ttttctatgt acattcaaat aatgttccat tgtcttgata aaaccttttta  26820
tatttaccta ggtctctagt tgttactatt actttatcag ctctgtcgta tttagtatta  26880
cggaatcctt gttcatatat ttttacgtct attgattctt tagtgtaagt tgtgctaaaa  26940
gcatcatcaa aataaacagt tacatataac ttgttgtttt ttaaactcaa atcttatatc  27000
tttatttcgt cactgttaaa agtgtcgaac attatattta tttcattttt tttaattaca  27060
tataaatcat taatagtgta gtttttgcag tacttccctg tcatcttatt ttctttgtat  27120
tttttaaaaa tatttttaaa tataattagt accttccttt attttaatta tcaagtactc  27180
ttaagtcact tttaagaaca tccatgctat tgctatgttt acctatacca tctagattcc  27240
catcttttaa cttattatct ttcatgattt ctttttttaat ttgtttttct gtctttttat  27300
ttgtcatagt gttttcaata tcaaaagaca tctcttcaat aataagtgtt ttaataaaat  27360
caataaattc cttaattgta tatctactaa aataatcttt atcctcaaag tacgtagcac  27420
aaaaactttt acgtcttgtt agtacaccta ttgacttatt ggaagtagca atataaacat  27480
gatatgtttt tccttttact tttattttaa atcttgtatt atctaacaaa tggttatagt  27540
ctttaaataa gtaattgttc aaaattagcc ctcctttgcg ttaacccaaa tttatagtat  27600
tttattgtag ttttctctcc gctgtagtaa aggtgtcatt attccaacca ccatcatgat  27660
taataaactc taaatcacct gtcacagtac ataagacatc aaaactaata ttttctcttc  27720
taccttttga aatacctgtg taaactattt taggtataca actaagggtc tgtaatccta  27780
aaccatctat atattctcta aaagatacat gaggtaataa ataagcactc aattcactac  27840
tgatacttct actaaaataa atgataatgt ctccaacagg tagttcatca ttatacacat  27900
ctacgatatc atcttcttca atagtccacg ttgtatgttc tatatctgca ggtgttacat  27960
gaacaagttg tttaactttt ccttgtataa tagactcctt ataaaaacct acagcatttg  28020
```

-continued

```
cttttctaa atactgtgca ataaaagtac catcatcact aattaaatac ggtgttctat  28080
tttgaaaatc tatagattgt tccatatcta gtttttcgta ggtatccttt aagtactcac  28140
taattttatt aacatctttt gttttaactt tatttgttcc taccttaact tttaattcta  28200
tcattatttt agtctcctta taagtacttt ctaactggtt ccgagtaatc attaatatcc  28260
tttactcttg gatactttaa aatactaaaa gcaataatac ctagagctac aataggtgct  28320
aataaaacca agccccagaa tgttaatact gtttgtaaga aaaacattac actatctact  28380
aaaaaccatg tagctactac tagtaatgtt gtaactgtaa ataaaaataa cttttcccaa  28440
aatccacctt tttgaaactt ttttgataat tttttcatca taatatttct ccttatattc  28500
caattgcttt ttttgctaat gcatctacat attcattcca tttgttatta tcatgagcct  28560
ttacttttat aaaatttata tctataaact ttgagtattc ccttagcata ttaatatatg  28620
ttttacttaa attgttttta gttttccacg aaccttcata ccattgaata agtcctatat  28680
aatctacatg aataatagcc tgcttataac ctagttttat agcctcttca ataccataac  28740
aacaagctag tatttcacct gcaacattat tatacttaat taaactacta ttttcaatag  28800
gtttactgat ttcttttaca atgttctcat ttttatctaa aataatagct cctgctccaa  28860
caagaccttt attataagat gagctaccat ctgtatatat taatgcagtc ttatgcatat  28920
ttatgccctt ctacaaagca agggaacatc tcacttgtat aaatctcttt gtagtcttgt  28980
aattttatag tagagaaatc aaaaaactta taacaatgtt cttctgcttc gatatagtca  29040
tctgcaataa cattaacttc aaaaccatca actaaaataa cgaacaattt cttaaacatt  29100
taaaaaaccc ctttataatt taataaggta cttaattaaa tcaatttcag tgtacttttc  29160
tgagtgttct agctcttcta atttttcttt tacttcttca agtctgtatg actcttctaa  29220
aagttcaaac tgctctaata atgtgatact atcaaattca ctactattaa tgatgttgtg  29280
tatatattct agatgtgtgt ctttaataat gtttgttaag tcatcaccag tataataatc  29340
ctcgatatac gataggtctc ctaataactc agccgtactt ctaataatac tatatttaga  29400
tatattaggg taagattgat ataaacaatt atctaattta ttacttaaat gctttactac  29460
tttttgcatt gtattacctt tttcttcagt actatatgaa attctaatat tagggttttt  29520
agaatcataa tcaactaaag aactcctatt agtgtttaat aacttatcta aagaagttaa  29580
aataatagct ctatcttcta tattatctaa ggttaagata gtatctataa tagtataaaa  29640
tgctttgtct cctattgctt tattaacatc ttgaagttca aaaatattaa tcatatcctc  29700
aatctcatga cgctcaacaa agttaataat agattttgta aatttattca tcaacatcaa  29760
cctctttaaa taattctaca ctattagtat ttaaagcttt ttctaatttc ataagattag  29820
cactcttagg ttttctttta ccactctccc aataagaaat aagtgagtag tgaactccaa  29880
tctcttgtgc taaacttcta actgtatgac ctttttcttc tcttactttt tttaaattta  29940
atactttagt ctcttccata ataaaccact acctatcttt cttcaatttt taaaatacta  30000
tagttatttt tattataagc atacttattt aaaacgtcaa gcgttttttc tttagcctct  30060
actttacctt tagctttcat attaacatag aaaacattac ttttatttga acgtgtgtgc  30120
ttaatatata ctttgtactg cgtaacctca ctttttaata cattacgttt aaaccatttc  30180
tttaattttt ccatttatta taaccacctt taaaacttat atatgtattg tagcatatga  30240
taaatacatt gtcaacttaa aaataaaaaa aatactaggg aaaattccct agtacattat  30300
ttccagttaa tacgacccca atacttctct tttagcatac gttcccactt gtcagtgatt  30360
ttacatactg ccatatagaa gttaccagct gacgggtttg taggatattt aaacctaatc  30420
caccagtagc cgtctgcttt aataacttgg tcaaagttta catattgacc actataaata  30480
aatgattcag cacctactat tgaacccctt aaacctggtg tgcgtcttac cttaatcgtt  30540
ctatcagcag taaatttacc tccccaattc caagttgttt gtacctcgtc tttgaaatta  30600
ggttctataa accacatagg aaagtcgtaa ccatgggctc taacggtagc tttctcccag  30660
ccaccgcctc cttgagcatc tccccaagtc caacctccac ctaaccaatt attttcaatt  30720
actataattt ggttttggtt tgcacttagt acccatgcga catgaccatg accgcatccg  30780
tatgaattat taaagataac catagtgcct ggtttaggaa tgtaggatag tgtattttct  30840
actactctag ctttatcttt taacatagct ttattatccc atggaatgtt acatgcactt  30900
gctccaccta aagaataacc tgggaagagc ttgttaaatc catagttagc taagtcgtaa  30960
cattgctgac cataccaacc atcaaagtct attgctttgc cttctagact ttttaaaaat  31020
cgaacaaatt cacttctagt catcgatgct ttcaaaagtt ttcactcctt atttccaatc  31080
tatttttcca aaatattttt ctttcttaat acgctcttgt ttatctgtta tctcacatac  31140
agcacaatag aaataatttt tactagagcc tggttttgga tatttaaatc gaatccacca  31200
atagccatct gctttaataa cttggtcaaa ctcaacccaa tcatccttat cgtatagcca  31260
tgaatctcta tttactatag tgcctttaag tcctggagat tttctaactt taatagctct  31320
atctggataa aaagtacctt tccagctcca catagtttta gtagattgtg tttttactct  31380
aggctcagca ttacctgatt tctttacatc tactgactta ataactttct tgtaatactt  31440
agctacttcc ttatctaagt tactagtgtt tctacctaat ccacatgctt ctaataagtt  31500
acccgggtct tgtttgtcgt tttggatgtc ttggtgacct ggcatatttg ttttgtaatc  31560
aacaccccag tattcagcta aataagctaa aacacgagct ccattgtcta atgatttttt  31620
agaacgttct ttatcactaa agtaacaaat ttctacacca atagcaccat cattagcgtt  31680
aattccgtac cataggtcat ccataggagc gttatacaac acatgccaag ctttttctgt  31740
agtaggaaca catatgatag cttctttatc atctacaaag atatgtgcgg atgcagtaga  31800
agcccaatca atgttatatg tatttttgta ataatctaca ttattttgag ctgtagtatt  31860
aatattccct gtatcatgag ctacaataaa aacgggtttt ttaaccgcca tagcttgacc  31920
tgtgcgtctt gttccaatag gcagtaaatc atatctaaca cttacacctt tccaaatttc  31980
tatcattact gttcacctac ttcttttggg ttatcttctt tatctaattc agacactaag  32040
tctttttcta ctttaccatg ttctaatggt tctgcatgac ttgtatctat gtcttcatta  32100
ttaactcctt caggagccat cggcatcttt gtaggaggta actctgaggt actattcatt  32160
gcttcactct tgtatgttaa agctttatct gggtcattat aatctctagg tttgttaaag  32220
tcctgtacaa tagggctatc cgctatacct ttagtgtcat gacttacaag aacacctaaa  32280
ccagtcaaga aactaataac tacacctgca attgcagtgc cttggtttac aatatcttct  32340
gcacctttga ttcctaataa actacataca ctgacaataa acgtagctaa aacaggtaca  32400
aaacctgtcc aaaatgtagc gctttttgct tttgcagtaa tattgttacc tgctattaat  32460
aatggttttt tatctttttt tgacataaaa aaataccatc ctttctgtta ttgtaaagct  32520
aataataata taacaaaaag aatggtttta gttattaaat tttaagttat tgttcgttaa  32580
tttgagaaag tgttttgatt acttctgaca tttgtttatt atctaagtct tctaacttag  32640
tgtgtggaag taaatctaat ttatcccaaa tatctttttt agttgtgaat ttttcattaa  32700
taattgctct accgattaaa ctttcagtat aataaatttg ttttgcagat gccatattag  32760
```

-continued

```
tatctaccct tctatagtat aattaaacat acatacataa accgtctcac tggtaagtaa  32820
catactagac ctattgttaa gttaatcact acgcttgact ctattaggta gctaacctaa  32880
gtccatctca cgtaacctat taaagcagta caaccgtagg gttgattctg tttaatattg  32940
taatgtgata ctaacatatt aattagtaac tttcacatgg tatgaagaat tttagcggta  33000
ttctataatt tgaccaatta ttattttgca ggtttatgct acttgtacta gtatcgtatg  33060
ttatcaaaca tttttcaatg ctccaactgc atatacttgt taaggtgtat ttgtaaagga  33120
ttccaccaag accctttaca aaaattaagc ccatcagata ctatacttta taaacctaat  33180
atgttactgc tgagtattcc gattgtaata agcattacta ttgacgaatt atctcaccga  33240
tataaaccga caagttttaa ttcgttcgac aatctcacgc cttacaggta ccacccctgtt  33300
taaatcagcc attatgtatg tatgtttaat aatactactt ttaaagtata acatatattt  33360
attcggttgt caagaaaaat ttataacttt ttatagtttt tttatactag ggtaaaaaag  33420
ttttaaaaga cctagtttcg acaaataaaa ataaggagaa ataacacctc aatttgacaa  33480
caaattaatc tctatgcaag tttaactata atataacata atattctaag tttgtcaagt  33540
tcttttttac ttttttatct tgataattct tcttgtattt tatcccaata tttttctgat  33600
tctgttctat tatcctcaat gtgagcagtg gtacatttac atctgataca atgtaaatgt  33660
tttatatgtc cttcttctct tctttgagct ctttttcttg gtactgtaaa agtattacca  33720
cattctgaac aaactaaatt actgtggaac attttctgtc ttttttttcat gattatcaat  33780
ccttttaaaa ttttttgtat agctagtata tcatataatt attttgatgt caatacaaat  33840
actgttgttt tgataaaagt ttattactag ttatatttaa ttattctgaa tatttagata  33900
ctttacctat ttggaaaata aggaggactc cttatatata taataaataa ttataaatac  33960
taaaataata atactagtta taataattaa taatatatat aggaaagtca acaaagagta  34020
ataactggtt cttgataaac tattcaatat tcttactatt atttctgagt aaaaaataag  34080
aaatcctttt atatcaaggg ttttaaagat ttttttacct atttggaaaa taaggaggac  34140
tccttatata tataataaat aattataaat actaaaataa taatactagt tataataatt  34200
aataatatat ataggaaagt caacaaagag taataaaaaa gtgacttact taaaagtcac  34260
taattttcaa atactaactt aaatgattct atgaataaag ggttaatgaa tactgtatca  34320
gaattaatat cctcagagac tttaactcta actgatgctt gtccatgtcc tctaattgtt  34380
ccatttattt ctctttgtgt atactcaata ctatcatcag agattaaata atattttttt  34440
ccactaatca ttgttacctc agcatgtttt accatatcaa aactcctaac taaatttatt  34500
gaaaatgaaa gttataatag aacctaacac tagtagtagt actttctcgg tagtatcctt  34560
ctttcttatg tccttaacaa ctgtattgtt agtgagttct tttatctttt cgtctaatct  34620
atctagctgt atgtagatag acgattgttt ctcactatta acagctactt ctttgtctaa  34680
actaactacc atttttctta gttcatcaac ttcatttttct aattccttat acgtattttt  34740
atcaatatag ctaccatctt gtattttatc ttttatctta tctacttgtc cgacaaggct  34800
ttttagttct tcattcaact aaagtcacct cttaatgtct acctttttcag attctgaatg  34860
gacgtcatag ttttcgaaaa agtcattaat aatttgcata taatcctcag taactatctc  34920
accatatgat gttttagtat ttatttcaaa cctaagctta ccaaactcat ggaggtctat  34980
ttctttaata acggtattag gattatcagt tggtatgtaa taataatcaa aatatataat  35040
agagccgttg ataagcaacc tatcaatcct ataaacgtgg aagaattttc tatctcgtct  35100
aaagtgagct aaggcatctt taaactctaa ttttaatata tctttatact tagtcaaatc  35160
aacttacccc cttataatta attttgagct acactagttt tgtgttataa tagttattgt  35220
agtagcagat atgagtatta cgtttaataa aattagcaac caccaactac ctgtacttat  35280
taaccataat gaaaaacaag ataatatata aacaaccacc aagtagccta tatatttcat  35340
aatgttttta cactctttta atactactac gtatgctagt gatttagata agctaaacag  35400
aaaataaaaa taaaaaataa aaagaggtat agctataatg cctgttagta taaccactaa  35460
ttacacctaa tttcttttag ctagataata aaatcttata taatacaact ttaatataac  35520
attgaaacct gtttataaat caacaatgtt acattaatag tgtacggtat attttaaatt  35580
aggaggactg aactaatagg gtgaataata acatagctgt atttatattt aaaactctaa  35640
taattattat ttttattttg tttattttgt ctattattaa ctcactgtca ttaatatact  35700
ctattcgacc tagtgcagtt atgacttact ttatattcgg tgggatagtt tctaatgtgg  35760
cattaacaat aactgataaa ttattattac acaaagaaga ccccttacct gattatattc  35820
taaaagaagt agagctaaat aacaatgaat tacaagtact aaagaaaatt gtagagtcac  35880
aaactaatgt ttctgctgag gaagtaagag taagagcaaa agcacaacgt cgaatactaa  35940
aagataaaaa gagagatgct gtcaatgaaa acgaagaagg acattaaaga acaacgtaaa  36000
gagctgaaag ataatgctac tgctgtttcc ttaacaaaaa aaggagataa acgtattgca  36060
agtcctagta gagtgtgttg tttatgtggt caatctcttt cagggatgaa ttatactaaa  36120
ggtaaagcta tagctaaagt taatcatttt catttacagt actctaagta cttatatttt  36180
gacatgtgcg cagatattaa taactgttac aagaatttaa agagagtagg tgaattgata  36240
gagtgagcgc tgaaagttta agagatatgt tatctaagaa aaaaattgaa gacgaagata  36300
aacgtaaata tatagctgat ggatttatgt caggtattac taaacttatg tatgacttta  36360
ataaaaagat tgatagaggg gaaatagaag taaaagaccc taatgatttg tataaagtgt  36420
ttgttatctt ccaacaaatg caaaacttaa ttacagatgg ttctgatggt ggcggtgcta  36480
taccgcaatt atcaagacca caacaagagc tctttgatga aataacaaat gagaatagta  36540
aaggtgagaa agaagtagat ttagagaagt tatctcaact atctgctgat gacattactg  36600
ctatgattat tgataaagaa aaggttatga acgaagagaa ctcaaataca ttctaaagaa  36660
aggtgtatat gaatggacgg taaagaatta ttaaaaataa cacaagaaac attcggtaca  36720
caaagtgtta cacaagaaca agttgaccat attatcaata tgttaaatcc cagtacgtat  36780
atgttaaaat atcatacgtt gagaggacac cccattacat ttagtattcc taatagggat  36840
agaagtaaag cacaagcaca tagaccttgg caggttaaaa tcgtataatc atttgcgacc  36900
ttacatagta atatgtattg aataactctg ttaaacgggc aaagctgaat aatgaataag  36960
ctggtaagag aacctaagtc caaacggata gaggcaatcc cgtgctaaat tcttaattta  37020
attgttgact acctagacta tgtagtttat aattaaatta agataaatgc ctaacgacta  37080
aatttctagg tagctatata aatggataca gtgagaacta gataagaggt ttctataagg  37140
ctaaataaaa gaaaggtagg tgtaataatg actagagtac tatcacaaaa atatgtagat  37200
aaaaacaaag ataaattcat aaaacgttta gaagatgaga aaaataatga gtaccaactt  37260
attggtgaat ataaaacaat gagaacacct acaacattta gacataaatg tggatatgaa  37320
tggactacac agccaaaaac tctaatagat gctgaagggc tattaggttg cccacattgt  37380
caatacagaa tgaaatcaaa aacaacagaa cagtttaaaa aagacataag aattaaaaca  37440
aacggagaat atatactatt agaaggacaa aaatataaaa caaatagaga aaaattaaaa  37500
```

```
tttaaacaca ttaaatgtgg tacggaattt tacatgattg caggcagtat tttaagagaa  37560
caagagagtt atccttactg tagaagctta aaaccttccc caagtaaaag aagtaccaaa  37620
tctttcaaaa aggaattatt aagagagaaa ggtaaagact acacactagt atcagaatat  37680
acacatgctt tagagaaggt aaaaattaaa catacatgtg gcaatacatg gtgggttaga  37740
ccttatcata ttctgtatga caatagttgt ccttattgtt atggctcaac aggtgaatta  37800
ttaatagctg gtttattggc aaataaaggt atagattata aaagagaata tatttttaaa  37860
gactgtaagc atattgggta tttaaggttt gattttatgt ttattattaa caataatatc  37920
attcttattg agtatgacgg agagcaacat tttaaacctg ttgaatactt tggagggcaa  37980
gaaacttttg aaaaaactaa agaaagagat aaaattaaaa ataagtattg tgatgacaaa  38040
ggatatatgt tactaagaat accttattat tatagtaatg aggaagttaa aattaaaata  38100
aataacttta tagaaaccgt aaagcagaga acccttaacc aaaactaagg aatatgatat  38160
agtctaaacc gattcttaaa tgaatgttaa agtattacga aagtaacggt agtaaatgaa  38220
atgataacca ccctaataaa gctgtaataa agtcgagaca attagggctc agtgaaatgt  38280
cagtaatgga aatggttcat tttgctgaca tgtacagtta taggaatgta aaatgtttgt  38340
atacatttcc aacacaggaa caacttaaga aatttgtaca gtcacgtctt aatcctgtat  38400
tagataaaac ttattttaga gatattgtga attgggataa agactcctta ggctataaac  38460
aaattagaaa ctcaagtttg ttttttagaa ctagtagtaa accaagttca gttgagggtg  38520
ttgacataga cttcctcgca atggacgaat ttgagagggt gaactcacta gccgaaagtt  38580
cggctttaga gtctatgtca agttcacctt ttaaagtagt aagaagattc tcaactccgt  38640
cagcacctgg ggtaggtata cacaaattat atcaacaatc tgaccaatgg tactatgctc  38700
atgtgtgtca acattgtcaa tatgaaaacg aaatgaaata tgctgattat gaccctaatg  38760
acttaaataa gagtggtaat cttttacttt taaacccaga tggtattgat gaacaagcta  38820
aaacagtaca agaaggtaca tatcaatacg tttgtcagaa atgtggaaaa cccctagacc  38880
gttggtataa tggcatttgg aaagtaaggt atccagaaag aacaaaaaat aattcaggta  38940
ttagaggtta ctacatttca cagatgaatg ctgtatggat aagtgcaagc caattagtag  39000
agaaagaaat gaatacagat tctaagcaag cattttataa ctattcttta ggtatgcctt  39060
atgaagatgt taaaatgcgt gttttaccag aagacatctt tgacaataag tcagaaattg  39120
caaaaacaca gttatttaat agagataaat acaaatttat ttcagtaggt atagactggg  39180
gtaacttcca ctgggtaact gtacatggta tgactgagga gggtaaagta gatttaatac  39240
gtttattctc tattaagaaa aacagtagac cagatatggt agaagcagat ttagaagcta  39300
taatattaga gatatctaaa tatgaccctg atattattgt tgcagataat ggtgattcgg  39360
gtaacaacgt acttaaatta attaatttct ttggtaagga taaagtattt ggttgtactt  39420
ataagtctag cccacgctca tcaggtcaat tatatgcaca atttaatgaa aacagtaata  39480
cagtaactgt agataaatta atgcataata aacgatatat acaagattta aaagctaaac  39540
gtataagaat gtaccaacag gtagatgatg aattaaaaac ttatcttaag cactggcaaa  39600
atgtcctaat catggacgaa gaagatgaaa aaacaggaga actttatcaa gttattaaac  39660
gtaaaggcga cgaccattat tctcagtctg cctgtattgg ttacatcggt cttactcgtc  39720
taaaagaatt atatgacaaa ggcaacggta cagctttcac atctactttt ataccaacgg  39780
attataatag tacacaaaac aactcgtcta atgagttcta ttttgatgac taagaaagga  39840
ctgacgactt gacaagtata ttaaattatg atacaataca agaagatgat ataagtaaag  39900
agacatttaa tttattaatt gaagagcctt taactttatc ttatgtttct aaacatagtg  39960
attctttaga tagtaaatat gactacatat ataaatcact aggctttgat aacttcatgg  40020
actgttattt atacatagca agagaaccag aacgtatata caaaggtgga gctaaagaca  40080
taggctcatt gaataaagta aaaagaactg tagtacgtaa tgggaaagaa attgaaatga  40140
cagtctatga agataataaa aatgatgata aacctaaaga gaataatagt gaagaatcaa  40200
aagaacctaa aactgctaaa ggttctaggg ttcttactca tggtgatgct gaaaaaccta  40260
atcctaaaaa gattgctagt tctctttcta cattaaagaa taaaggtgta aatactgacc  40320
atatagatgg taatgcatcg atatataaag aatttgtaga tgatagtaat aatacaatag  40380
gattagcttc ttttaaagag acagattctg acattatatt acatggatac gtatcagact  40440
ttgaaactaa tggtgtaggt gctaggtcta tattagagct tatttcttta gcaataaaga  40500
agaataagaa cgctgtagtt tatgacatag aactacctca agctgtagag ttcttaaaat  40560
ctttagggtt tatgaaaaat aaagattact atgtattaaa aaaacaagat ataaagttat  40620
ttttaggtga gtacagtgag cttacttagc actgtactca tttatacaat tatatatata  40680
agtattatta tattagtagt tgtaaatgta gtaataagag agaaaagaat gtacaatact  40740
aggaagttgc ttatacaagt aaaaaaggat attataaaca acttaaaaaa gggagatatg  40800
aatgatcaaa gataataata caaaaacatt ggaagagtta attacaccta tttctacaaa  40860
agaaaaagaa aataaagtta aagaatttag taaaacatta tgtgagatga ttaataagct  40920
atatagttct tacaatgtat taaggcaaga ccctattgat gaaacacaaa gattagacgg  40980
ttctctaatg gtgtttcaaa gtagattaga tgatacatta acaggtgagg aacaccaaaa  41040
actttttaaa ttagcttttg attataatat tgatattttt gaagctaaca agcagtttaa  41100
agaagatgta caaaatggaa aagctattag gttaggtgat gttgttgtaa ccgacacagc  41160
tttaagtaat gttttatcta gtaatgagct taatgttagt attacattta tgttaagcaa  41220
agactatgaa gaaaagaaac gtattgaaga agaagaaaag gaaaaactag ataagttata  41280
atagatatta tgagaccttt atggataggt aggaataaat aatatgaaac gtaagtttag  41340
tagtaatgag attactataa cacttataac tattgtagtt gctctattta taatattaat  41400
tacagtagca tttaacaagt accaaattgc taaagaagat aaggacagat atcaaaagct  41460
agtagaaatt tatcaaaaag cagatgatga tgacggtaaa actaaaaaaa ggtatgttga  41520
aaagttaaat agggctgaag aagaacttaa aaaggttaaa gaagaaacta attataaagg  41580
ttataatgat aaaacagaaa aagaaagaga taaagaggat aagagtgtaa gagaacgtat  41640
ttatggtaat gataaggata aagatttagt attagtaaat aataaggttg ttgtaagtaa  41700
tgaagttact agacctaaga taatagaaga taatggtgtc agtacagttg tagtacctcc  41760
tgttgtaagt cctgttgagc caccaagtga acctagtata ccttctccta ctatacctaa  41820
acctattatt cctaatccta ttaaccctaa ccctattcta cctaaaccta acatccctac  41880
ccctaaccca ctacctccta tagaacctga aaaacctata gaacctgaaa aacctataga  41940
acctgaaaaa cctatagaac ctgaaaaacc tatagaacct gaaaaaccta gctcagatac  42000
tacgatacct ttagttccat tggaacctag cacacctgta gatgaaagta atgatactaa  42060
tggggaggga taacctctcc tttttttgct atattaaaag agtaataaaa taaacattat  42120
agttggtgat tttttgatag gattaaacgt acttacagct atatccgtag tttttgcttg  42180
tgtaagtcta ctagcactaa tggtatttgc gtatattaaa actgaaaaaa gtagtaagtt  42240
```

```
ggttctatac ttgatatatg ctataatttc tataggttct tatgtagtat taacaatgtt  42300
tcaagccacg tcaatcatta taaaaaatga tgttatagac tctattgaga atacagagca  42360
gtatgtaggg tttaataacc ctttaattgt ttttggtata agtttctttg gagctgtaat  42420
aggcagtttt tggtttttag ttatgaagat tgtaaatact aggaatttaa aaaataaaaa  42480
attaaaggat tgaagcattt gctattttca aaagacgata aatgggatga agcaaaagac  42540
tttataaaag gtcaaggatt agcagataat tggatagaag tagtggatta ttatagacag  42600
ataggtggta aacatgtagc tatgtttatt gctattgata aagttaaata tatggtacta  42660
gaagctacaa aggataataa agtaatattg gtagataagg ataataatat tgtgttagag  42720
gattatgata ttgttatgga aagtaagaaa atgttttact atatagaaga accattcgaa  42780
gtaaagataa atattcctaa acatatccaa gacattacct ataataacac tgttatacta  42840
actactattc gaggaggtaa ataagatagc aataatctat aaaaccttat aaatttattt  42900
gcatttttag ataaagtatg ataacgaaaa aagttagatt aaaaccaaat cccacacaag  42960
aaaagaaact atataaatcc tctggaacag caaggtttat ttacaattgg gttttaagga  43020
aacaaaaaga aaattataaa cgtggtaata agtttatatc tgattctgta ttaagaaaag  43080
aaattaccca acttaaaaaa actgaagaat ttaattggtt aaatgaagta agtaacaata  43140
tccctaagca agcagttaaa gatgcttgta actcttacag aaggtttttt aaaggacaag  43200
ctaagtttcc taaacttaag tctaaaaaga aaacaagacc tagtttttat aatgatacac  43260
aaaaactaaa agtaaaagaa aaagtagtct tactagaaaa agtaggttgg gttaggactt  43320
ctgaacaatt acctgtagat actaagtatt ataatcctag aattactttt gatggtaagt  43380
attggtatct aagtgtttct attgaagaag aaaataaata tgaagagtta accaatgaat  43440
ctttaggaat tgacttagga ataaaggagc tagctatatg ctcagatgga attatatatg  43500
ggaatattaa taaaataata aaggttaaaa aactagaaaa acgattacgt agattgcaac  43560
gtaaggtatc tcgtaaatac caaaataata aagaagggag tacgtttgtc aaaacttgca  43620
atattataaa gcttgaaaaa acaaattaaa cacatacaac gaagattgtc taatattcgt  43680
aaaaactatt tacatcaaac aacgacttct atcgtgaaaa ccaaacctag aagaatagtt  43740
attgaagact tgaatgtaag aggtatgatg aaaaatagac atttagctaa atcagtacaa  43800
aaacaaggtt tttatgagtt tcgtagacaa ttagaatata aatgtaaaag aaaaggtatt  43860
gaacttacta ttgctgatag gttctttcct tctagtaaaa catgttctaa ttgtggtaac  43920
ataaacaaaa acttaaaact atcagataga atatttaatt gtgaatgtgg ttttagtatc  43980
gatagagact ttaacgctag tattaattta gctaactata atatttagat tatcactatc  44040
atgatactaa atatatgtac cattcgttgt atgggaattt acgcctttgg agtatcatac  44100
aaacctaagt agagtatata aaagtaatca gtaatggtga aaatactcaa aaagggatac  44160
gctgaaaaag gaataaggtt tataaagttt tataaatttt tgacaacggt aaatgataag  44220
ttgcctgatt tatttaaaag tctaaggtta ggtagtatgt ataaagaaga cactgaagac  44280
cttatggttc ctatagatga cggaatacaa gctaacatta gacaaataga acaagataca  44340
aaagagatgc aagaaattac taaatctttg tatggtaaac agcaagctta tgcagaacca  44400
tttttagaaa tgatggatac aaatcctgat tatagagata agaagagtta tatgagaaat  44460
gctcataatt tacatgaagt gttaaagaaa tttggtaata actctatact aaatgctata  44520
attattacaa gagctaatca agtatctaca tactgtaaac ctgctaggta ttcagaaaga  44580
ggagtcggtt ttgaagttaa attaaaagac ttagacgcta cacctggtat taaagaaaaa  44640
gaacagatga aacgtattga agaatttatt cttaatacag gtacagataa agatatagac  44700
agggattcat tccaagagtt ttgtaaaaaa atagtaagag atacttacac gtacgaccaa  44760
gttaacttcg aaaaagtttt tagtcctaaa aacaaaacta agatggagaa gtttattgca  44820
gtagacccta gcaccatttt ttatgctact gataaaaacg gtaagataat taaaggtggc  44880
aatcgctttg tacaggtcat agataaacaa gtagtagcta gttttacaag cagagaactt  44940
gtcatgggta ttaggaaccc tagatcagac ttaaattcta gtgggtatgg attgtcagaa  45000
gtagagattg caatgaaaga atttatagct tacaataata ccgaaagttt taatgataga  45060
ttctttagcc acggtggaac aacaagaggt atcttacaga ttagagctga ccaacagcaa  45120
tctcaacatg cgttagagaa ctttaaaaga gaatggaaat ctagtttttc aggtataaac  45180
ggtagctggc aaatttgcct ctatataaag taatttgtat agatgaaggg ttaactgcta  45240
agaacaccta aagctcaata cactacaaag taacccgaaa gggtaggctt gaatgttacg  45300
aaagtagaaa aaagatattg agatacgtta aggttaaatc ctaagacgaa gaacaatggt  45360
tgtttagcat cgaaagtcct aaagaactga aaggtctatg gaatacgttc aacgactatc  45420
ccgttacaag acgggagtaa agctccaagc tattgggaga agaaaaatcc ttaccctaca  45480
caatagggat aacaaatagt ctagtctcgt actgaaaggt agagcatgtg aaatgacaca  45540
ggtttacaaa gtagcgtttg taaataaata aaactaaggt ttataaaaaa aaattattcc  45600
tttactagtt gacaattaat cttttctatg atatacttaa accatagaaa agaggtgaaa  45660
gtcaatgaag aaactaaaat taagattatt accaactcca gaacaagaag acttaatgtg  45720
ggttcatgta aatcatacac gtaatgttaa aaatatattt ttagctaaat gttttgaact  45780
aaaagaaaca ggagaattta taagtaaaac cacatcaaat aaactaagat tagaattaac  45840
ggaaatgttg aaaacagata aatataagtt atttaaaaag tgtatcaaga gatacactag  45900
atagagctgt aaatagtgta gttcaatctt atgttgattg gtgtagaggt actcatggta  45960
aacctaaatt caaaaagaaa aataaatgta caaaatactt tgatgttagg gaaaatagat  46020
taaaaaggta tggacatact tttcatatac ccagtatagg aaaagttaaa gtatctaaaa  46080
atactttaaa gaataatttt agtattataa attctataga aagtttagat aaatttagaa  46140
aaacatctat taagtatgat ggtaagtatt ggattatgtt tattacttat gatgacacaa  46200
tagttacccc tcgaaaacca agagaattaa ctgatgaagt tataggtata gatttaggta  46260
ttaaaacgtt agccacttgt tcaaatggta aatcttataa aaatattaat aaaagttcta  46320
aagttaaaaa actagagaaa cgtttaaaac gattacaaag acaagttagt agaaagtatg  46380
aaatgaataa gcaaggtaaa aagtttatta aaaccaataa tattattaag ttagaaaaag  46440
aaataaaact cttacataga aaacttagta atattagaaa taatcatatt catactatga  46500
ctaaagaaat agtagaacaa tatcctagtg aaatagtaat agaagactta aaggtaagta  46560
acttaagaaa aaataaacat ttatctaata gtatttctaa agctaattgg tatacaatta  46620
gagaatacct tacttataaa tgtgaagata gaggaatatt acttactatt gctaaccagt  46680
actacccaag ttctcgaact tgtagtaact gtggtaatcg tttaactaaa caatataaac  46740
tatctttatc ccaaagaaca tataaatgtt cttgtggaat taatcttgat agagacttaa  46800
acgctagtat taacttaaag aactatagat actccaaatg gtatcacaat catgttttaa  46860
ctaaataaaa cagtaaacat gatatgtagg gttccgtaaa cccgaattaa cgcctttgga  46920
gtattataac aaaccttagt agagtatata aaagtaacta gtaatagtga aggtactcaa  46980
```

```
aaagggatac gttgaaaaag gaataaaatt ttttataaat tttagattac gaagtccccg  47040
tgatgatggc tgatgatgtt aagtttgtta atatgacacc aacagcaaat gatatgcaat  47100
ttgagaaatg gttaaacttt ttaatcaata ttatttctgc tttgtatggt atagaccctt  47160
ctgaaatagg attccctaat agaggaggag gagccacagg gtcaaaaggc ggttctacat  47220
tgaatgagtc agaccctgct aagaagcaac aacaatctat gaataaaggt ttacaacctc  47280
tattaagatt tatagaagaa ttaattaaca gacacattat atctgaattt ggtgataagt  47340
atactttcca attcgttgga ggagatacta agtctgagtt agataagctt agtattttac  47400
aaaaagaagt acaagtatat aaaactgtaa atgaagcaag agaagaacag ggattgaaac  47460
caatagatgg tggagatgta attcttgact cagcattttt acaaagtaca gcacaagaaa  47520
tacaaaaaga ccaataccta gatactaaac aaaaagaaag acttcaatta cttatgagtt  47580
atacacaacc acaaactgat gagcctacag atgatagtaa acaagaaact actaatcaag  47640
aagtagggac agataaccag ttaaaaggtg atgataacgt atatagaaca caaacatcaa  47700
ataaaggaca aggaagaaaa ggtgagaaat cttccgactt tatgtagata atattagcaa  47760
cctaattaat acttaggttg ttattttttta atttggagct acatttatac tatgttatac  47820
tatgtgtgta gtaatgaata atgttgatga tatacttttt gttatattat gtatgtacat  47880
ataaaataac aattaagtga ggtgtataat cactttggaa gaaatgaaat ttaatgcttt  47940
tgttcctatg gacttaaaga aatccataga tacggaagat gatacaaata aatattctat  48000
cgtatctggt tgggcttcca caccagctgt tgatttgcag aatgacatta taaatccaaa  48060
aggtattgat atagaatact ttaaaaaaaa tggatatatt aactacgaac atcaacaaga  48120
taatgtagta ggtataccta cagataactg ttatgttgat ttagaaaaag gtttatttat  48180
agaagctaag ctatggaaag atgatgaaaa tgttataaaa atgttagacc tagctgagaa  48240
actagaaaag tcaggtagtg gtagacgttt agggttttct atagaaggcg ctgttaagaa  48300
acgtaacata aatgacaata gaattgttga tgaacttatg attacagggg tagcactagt  48360
aaaaaaccca gctaatcctg aagctacatg ggagagtttt gttaaatcat tccttactgg  48420
aacggaaaca acaccagaca cacaagtaga tgcaggagcc ttacgtaaag agtcattagc  48480
aagctctatt actaatttaa cctatgtaac aaaaattaaa gatgttaaag agtataatga  48540
tatttggaat aatgtagtag aggacttaac taaatctaat aatatgggtt atgaagaatc  48600
agttattaca ttacaattag ccaaaggact atcaagaaaa gatgctgaga tagcagttat  48660
gagtattaat aaaaaaaatt tagaataggg gattatatta tatgcctacg gaattacaaa  48720
atattctaca agaatatgat aacttagaca aagaagaagt atcaaaatct gtagaagagt  48780
ctaaagaaga agtaaaagaa gaagtaaaag aagataaaac agaagacact aaaatagaag  48840
acactaaaac agaagacact aaaacagaag aaaaagaaga aattaaaaat gaagtagaag  48900
ctacagaaga gcaagtagca gaagctaaag aagaaccaca agaacctgca aaggttactg  48960
aagaagatgc taaagaagca catgaacaag aagaaaatct agaagaagaa gtatctaagt  49020
cagctaagga gtcgaaagac cctgtagata aaaaagatac taaaacagaa gacaaagaca  49080
acgagaaacg aaaaaataaa aaagacaaaa aagaagaaaa agatgaagaa gaggaagaaa  49140
aaacatctaa atctatttct gataaagata ttgtagatgg tttccgtact atcttgaaat  49200
cattccaaga cattaaaaaa gaaaatgaac aatatgtgac taaatcagat ttagaagaag  49260
taactaaatc tattcaagct ttaactgata aaattaattc taatgaagaa gtttctaaat  49320
cagttgagag caaccaagaa gataaagaag aagcagtaga aaaatccgta acgactaata  49380
acacttcgaa tgaacaagat gtagttggtt atgtagctaa atcagtacaa acagaagaac  49440
aagcagaaac tacagaagat aaagaagaac aagaagtaga agttaaagaa gaaagtagag  49500
acttatctgt agaagaccgt gaaaaattca tgagtaccta taaagaaaaa tctcaaaacc  49560
cacatacgaa tcgttcagaa gtattgaatg cttatcaagc ttacttaaat atccgcaaca  49620
atccagagca agcaagtgaa aaagacttta atattgtaaa agaatttgct aatctttaat  49680
taagaaacaa agttgtgtta tattatagtg tgtaaaataa aacaataaaa aaaagagcat  49740
atatgaaagg tgatatatat aaatgaacca aaatgaactt tcaaaaaagc aacatgcagt  49800
tgctgatgaa ttacaagaaa aattatcgaa atccttccaa actggatatg gtatcactcc  49860
tgaaacacaa gtggatgcag gtgctttacg tcgtgaaatt ttagacgacc aaatcactat  49920
gcttacatgg ggaaataatg atttagtatt ttaccgtgat gttgcacgta gaccagctga  49980
atcaacagta attaaatatg atgttttctt acgtcacggt aaagtaggtc attctcgttt  50040
tgtacgtgaa atcggagtag cgtcagtttc agaccctaat atccgtcaaa agaccgttac  50100
aatgaaatat atttctgata ctaaaaatat gtcattggca tctagtttag taaataacat  50160
tgctgaccca ggtcaaatct tgactgaaga tgctatctca gttgttgcta aaacaattga  50220
atgggcttca ttctatggtg acgcaagctt aacttctgaa gttggtggag aaggtttaga  50280
gttcgatgga ttagctaaat taattgatgc tgataacgtt atcgacgcta aaggtgctca  50340
cttagatgag aaattattaa acttagcttc agttaaaatc ggtaaaggtt ttggtacagc  50400
tacagatgct tacatgccta tcggtgtaca ttctgacttt gttactaata tcttaggtcg  50460
acaaatgcaa ttaatgcaag acaatagtgg taatgtaaat actggtttca gtgttaacgg  50520
attctattca tctcgtggat tcattagatt acatggttct actgtaatgg aaaatgaatt  50580
aatcttagat gaaactttaa tcccacaacc aaatgcacca caaccagcta cagtaaaagc  50640
tgaagtaaaa acaaaccaaa aaggtaaatt tactaaagaa gaagaccgtg caggtttatc  50700
ttataaagta gttgttcact ctgatgaagc tgaatcagca ccatcagaag cacaagttgc  50760
tacagtaaca aatgctacag atggagtaga attaaagatt actgttaact ctatgtacca  50820
acaaagccca caattcgtat ctatttaccg tcaaggtaaa gaaacaggta tgtactactt  50880
aattaaacgt gtagcactta aagatgcaca agaagatggt tctttagtat tcgttgataa  50940
aaatgaaaca ttacctgaaa cagcagacgt attcgttggt gaaatgtcac cacaagtatt  51000
acacttgttc gagttattac caatgatgaa attaccatta gctcaaatta atgctagtat  51060
tacatttgca gtattatggt atggtgcttt agcgttacgt gctcctaaaa aatgggctcg  51120
tattaaaaac gtaagttatc ttgcattaaa atagtaaata caattaaaaa ttgaatacaa  51180
tagaataagg agtataccta agggttgctc cttttttatt attacttata gtatacaaga  51240
aaggaattta aaaatcaatg ttaacttata aattaaaaaa tattaaaatg gctactgtac  51300
atggtcaagt agaagtagat gataaaggcg tagttaaagg actaactgct aaacaagaaa  51360
aagattttgc taatttacca ggttttacac atatggaaga caagaaaaca acaaagaaag  51420
aagtaaaacc taaggaagaa aaagaagaga agaaatcaat taaaaaaaca actaaaaaag  51480
aagataagta ggttgataga atggtaaaca gtatgtttgg tggtagttta gacccttacg  51540
aaagctcttt atcatatgag tatccttatc acccatctgg aaacccaaaa catatagata  51600
aaagagaatt agatagtatt actctagctg attatggttg gtcagcagat gctgtgaaag  51660
cctatatgtt tggtataaca gtacaaaacc ccgatacagg acaacctatg ggtgatgatt  51720
```

```
tttataatca tatattagaa agagctatag gtaaagcgga aagagcttta gatatatcta  51780
ttttacctga cttacaacat gaaatgagag attactacga aacagaattt aatagttata  51840
tgtttgtaca cgcatataaa aaacctatat tacaggtaga aaatttacaa ctacaattta  51900
atggtagacc tatgtatgat tatccagcta actggtggaa agtggagcat ttagcaggtc  51960
acgtacagtt attccctaca gctttaatgc agacgggtca atctatgtct tacgatgctg  52020
tattcagtgg atatcctcaa ttagcaggaa tgtacccccc aagtggagca acttttgcac  52080
ctcaaatgat tacattagat tatattagtg gtatgttacc tagacaaaga gcaggtagaa  52140
ctaaaccatg ggaagtacca ccagaattag agcaattagt tattaaatat gcactaaaag  52200
aaatttacca aatatggggt tacgatgata ttaccctgtg tgtagcgtaa gttgcacatt  52260
ttcaaaggtt aactgctaag aaatcctaaa gctaactaaa ctacaaagta atctgaaagg  52320
ataggcttga atgttgagaa atcagaaaaa attagttaga tactctaagg ttaaatccta  52380
aagagaagag caatggaagt ttagcatcga aagtcctaag tcaatagata aggaatacgt  52440
tcaacgacta ttctgtatag acgacagaag taaagctcca agtgattggg agaagaaaaa  52500
tctttaccct agtcttaggg ataacaaata gtctgcacac gtcttgaaaa ggagtgctag  52560
gaattgacct agacttattt agtagcgtaa gtaaggaaac aatgttaatt aaatgaaaac  52620
ttcctattga aattacccca agtatatgtt atattataga tatagtatat aaggtggtga  52680
aagtaaatga aaaaaacgga aaatacattt tatagaggta taacactaaa agtaaaccct  52740
acccaagaac aagaagagtt aatgtggaaa catgtaaacc attctagatt tatttataat  52800
tatatgttag aaagatattg gaaagctctc gataacggta aatatataga ccataaaaat  52860
atgatttcta tattaaaaga aataaagaat gatgataagt atagtttctt aaatgaagta  52920
tctagaaaaa ccttagttgg taaaatagat gacttaagag aaacattaat aaaatatcat  52980
aatcatgaaa ttagaaaacc taaatttaag tctaagaaaa gggaatctaa gaggtttcct  53040
attagatatg accgaatgca ctttaacaaa gaaaaacatg ttaaagttga aaaattaggt  53100
tacttaagaa tttctaatgg tacatataaa aataataaat cagtactaga gaatgaaagt  53160
attaaacctt taaaccctaa atgttactat gatggtaaat attggtatat atccttttca  53220
atagaagtag ataatcaata caagaaagaa aaggataata ctaacgaagt cataggtata  53280
gacttaggta gtggtaaaaa acacgtaatt tgttctaaca gaaaaatata tggtaatatt  53340
atttattcca agaaaatgaa aaggttagaa aaaaaattat ctgacctaca gaaaagatta  53400
agtaataaat atgatattaa tcacaccaaa acaaataatg ttttaaagct agaaaataag  53460
atagctaaag tttatagaaa aatgtcaaat atccgtaaaa atcatgtaca tgaaataaca  53520
aaagaaattg ttgaaaagta tcctaaagag attattgtag aggatataag agttcgtaat  53580
ttaataaaag acaaaggata tacaggacaa aaaagaaaac aaatacagtt ttctaatttc  53640
tatatgatta gacagcaatt acaatataaa tgtgaagata gaggtataaa atttacagta  53700
gctagtactt attatccatc atcacaaata tgcagtaatt gcggagaaag aaaaagaaat  53760
gctttaaaat tacagttagg tgataaagtc tttaaatgta atgcttgtgg atatgaagaa  53820
gatagggata taaatgcaag tattaattta aaaaattacc ataattccca atggttaaaa  53880
gaacaaaacc aataatatgt ttgcttttag tagggttcca taacccgaat gtataatgcc  53940
ttttatttta caaaggaagt taatttaatt aacatatggt aatctcatta tcggtgcagg  54000
aatagcaaat aaaactctag atgtagatgg tattacagaa acaataggta ctacacaatc  54060
tgctatgtat ggtggagcaa gtgctcaaat actacaaatt aatgaagata taaaagagct  54120
attagctggg ttgaaatctt actttggctc caatatgata ggcatatagt aggaaggaga  54180
tattaaatgc aaaaaccttt tatgataggt actaataata ataatacttc taatataatt  54240
aataagtcta ctatgtatat atctacaaca caagcagatg aacaagaaca aaagttatct  54300
acagctagac tagagtttga cactaaggat atgagaaagat ttgtcaatga tagaggtata  54360
aaggtactgt gggaaagggc ttacttttgt ccttgcctta accctgacac aggacatcct  54420
agagtagatt gtcctaggtg tcacggtaaa ggtattgcct atttacctcc taaagagaca  54480
ataatggcta tccaatctca agaaaaagga actaacaatt tagatatagg aattttagat  54540
actggtacag ctataggaac tacacaatta gaaaaacgag tatcttatag agacaggttt  54600
actgttcctg aagtattgat gccacaacaa cttatatacc atgttactaa agagcgtata  54660
caaaaaggta tacctctata ctatgatgtc aaagaagtaa cctttattac atctaacgat  54720
ggtaatgttt atgaagatga ctataaatata gagaacaata gattattcat ggacgctaag  54780
tttgaaaaca aaactatatc cttaaatatt ttaatggtac ttagatatgt agtatcagat  54840
atattaaaag aaagtcgata ccaatatact aaatttaatc aacctaatac aaagtttgaa  54900
aatttacctc agaagctatt attaaaaagg gaagacgtta ttgtactacc tgagccattt  54960
aaagttaatg atggtataga agaggactta gagatacagg tagaagaccc taaaaaagaa  55020
tctaaagata atcattcagg tggtttcttt gggggaatgc tataatgcct ataaaagcaa  55080
ctagacctaa gttatttaga gacaagagct ataaaaatgt aggtaagaga acagtagatg  55140
ctatgcgttc tgatatttta gatagattac aagctacagc attacaagta gataatgtga  55200
gtgtcaaacg tatgcctacc tacttacaaa taactgagca gaaactagag aagaaaggtg  55260
taatagacct taaaaaagct tttgcacgtt catctaagaa aaaaagagca aaagatggtg  55320
gttggtatct aacggttcca attagaataa aaacaagtaa aatgaataat aaaacatacc  55380
aagatttaag gtctttaaaa ataggcagtt caagtaattc agtatctact cttactgatt  55440
atctagaagg tagacgtaat aacataagcc atccttcttt aaaagtacct agcagtaatg  55500
gcagaataac aaaagtaaga aatggtaaaa aatctagtta ttttatgttt agaacagttt  55560
ctagtaagtc acctgcaagt tcatggatat taaatagaga caaagttaac gagaataatt  55620
tctctaaaac aacattaaaa tatgttagga atttaatgaa ttggaaaatt aaaaatttaa  55680
tgtagaaagg ttatggaagt aggatggcaa taacatcagt agactcatat ttattagagc  55740
aaataaaacc cagattacat acagtactaa gtaattgtta tattatagat gaagttttaa  55800
aagactttga ttatcaaact agggaaatgt tcaaagaggc tttttgcggt gagaacgcaa  55860
agcacgaagt aacagtaggg ttcaatttcc ctagctttaa aaacaactac gaagctcatt  55920
acctaataca actagggcaa ggtcaagagg ttaaaaactc tttaggtagt atacaggggt  55980
cttatctaga agcttcgggt aacacatata gtgaacaatc agtagctaaa agagaaggta  56040
atcgtttagt atttcatgta tctaaaccta tttctaatgt aataagagta gaagacatag  56100
cgtttgattc ttacgatgat gttaaagtat cagataacac tgtatctttt aattatacta  56160
acaatgagac ttatgaaggc tacaacgcaa atattgtata tgtagaaaaa acaaatgata  56220
gtaaagggtt agtaaaaggt attaccatag aagaacaagt aacaattgtg ggtatgtcgt  56280
ataatgtaga tgttgctaga tgtttagatg ccgtattaaa aatgatattg atatctatga  56340
gagatagtat agaagaacaa caaacattcc agctacaaaa tcttgcattt ggagatatcg  56400
cacctatatt ccaagacggt gagtcatcta tctttggtag acctactata attaaataca  56460
```

caagttcatt agatttagat tatacaataa cacaagatat taataagatt actttcaaga 56520
ataaaggagc aaaaagataa tggctaagaa aacacctaaa ggtaaaacct ttacaggtta 56580
tgtacatata gatacatttt taaaaacagc acagaccttg tttaatatga aagagtcaca 56640
ggttgcaggt tttaaagcct atatggaagg taaacattac ctattcaatg aaaaagactt 56700
tattccattt ttagaaaagt atttaggtag agaattagaa atttaatata gagataggag 56760
aattatacat ggcagttgaa ccgtttccaa gaagacctgt cactcgtcca catgcagtca 56820
ttaatgtaga tagtacaggt atcggtaaat cagctagctc cagtgaaaag attttatgtt 56880
taattggaca agctgaaggt ggtaaacctg ataccgtata tgaattaaga aactacgcac 56940
aagctaaaag actattccgc tcaggtgaat tacttgatgc aattgaatta gcttggggtt 57000
ctaatccaca atacacagca ggtaagattt ttgctatgcg tgtagaggat gctaaaccag 57060
ctacagctga agtaggcgga ttgaaagtta cttcacagat ttatggtaac gtagctaaca 57120
acattcaagt aggattagaa aaaaatacaa tcagtaattc attacgttta catttaatct 57180
tccaagatga tagatttaat gaaacatatg ataatattgg taatatcttc actatcaaat 57240
ataaaggtag tgaaagtaca gctacttttt ctgtagagca tgataaagaa acacaaaaag 57300
caaaaagatt agtattaaaa gctaatagca cagaagttaa gtcttatgac ttaacaggag 57360
gagcttacgc tactactaat gccatcatca acgatattaa ccaattacct gatttgaag 57420
ctaagttatc accttttgga gacaagaact tagagtctta cttattagac cctatgacag 57480
atgttgacat taaggataaa gctgagtatg taaaagcagt atttggtgac ttagagaaac 57540
aaacagctta taacggactt gtttcatttg aacgattagt atctgaacaa gcacctaaaa 57600
acgtagaagt agacgcacac gaagagtctg ccactgtaac agctgtatca ccaattcaag 57660
aaatcacacc ttttgaatta acaaaacttt cagggggtac aaatggtgaa cctcctgcta 57720
catgggcgga taaaatcgaa aaatttgcac atgaaggtgg atactacatg gtaccactat 57780
cttctaaaca atctgttcat gcagaagtag cttcttttgt taaagaacgt tctgatgcag 57840
gtgaacctat gcgtgctatt ctaggtggag gatttaatga aacgaaagaa cagttgtttg 57900
gtcgccaatc atcattatct agcccacgtg ttgctttagt agctaactca ggtatattca 57960
caatggacaa tggtcgtaag ttacatgtac cagcttatat ggtagcttct gctatcggag 58020
gtttggtaag tggtttagct ataggtgaat ctattacatt taagcaatta catattaata 58080
atgtagacca attatatgag tcattagact tagatgagtt aaatgaaaat ggtatcatta 58140
ccattcaata tgttcgtaat agagctaata cattctttag attaacagac gatgttacga 58200
catttaatga taaaaatgac cctgttaagt cagaaatggc tgttggggaa gcaaatgact 58260
tcttatgttc tgagttaaaa cttgagcttg aaaataactt tattggtact cgtactatca 58320
atacaagtgc ttcaattatc aaagactttg tacagtcatt cttaggacgc aagaaacgag 58380
ataacgaaat tcaagacttc ccacctgaag acgtacaagt tattgtcgag ggtaatgaag 58440
ctagaatctc aatggttgta taccctatca gaagcttcaa gaaaatttct gttagcttgg 58500
tataccaaca acaaacatta agagcctaaa ctaggacaag gagtacctag tttaggtact 58560
cctattaaat ttaataggag agtgaattaa tatggcttca gaggctaagc agtctgtcca 58620
tactggtaat accgttatgc taatggtaaa aggtaaacca gttggaagag cacaatctgc 58680
taaaggtcaa cgtgaatacg gaactactgg tgtatacgaa attggtagta ttatgccaca 58740
agagcatgtt tacttaaaat atgctggtac aattacacta gaacgtttac gtatgaaaaa 58800
agaaaacttc gcagatttag gatatgcttc acttggtgaa gaaattctta agaaagatat 58860
tattgatatc ttagtagtag ataacttaac gaaacaagtt attattagtt accatggatg 58920
cagtgccaat aactatgaat cttgtagctt ctagaagtaa ttctagtcga aaaacttttc 58980
taaacaggga accctaagtt acaatgtaat atgggaatct tgtgctaaat tcagtagata 59040
ctgataaatg ccaaacgact aaccgaaacc tacttacagt agtaagggga gtaggtgtac 59100
agccaagtgg tcagggtgtt gggtaattac catataaaac cttgctaagt ggaaaagaaa 59160
agagtcctcg attgaggatt gtgatatagt ctaaccttta tggaaacata aagcagttca 59220
taagagaacg gataaagatt aacgaccttt attgaatatg agtgaatgag acttggcaaa 59280
caaatgaaat tgtaactgaa gaaattgagt agaagaatgc tcctttaact agaaatagtt 59340
atagcaaatc cctttaattc atgggaaccc ttaacagata atgctgaagg caatcatgag 59400
ccaagcctag taaattacta ggaaggtgca acgactagtc ataatgacgt acatctaagc 59460
agatggaaat gggggacacc ttcaatatta aggtgaagat atagtctgaa ctatatagaa 59520
atatatagaa ggttcgagag tagcgttttg aatcgtaaca aatttgtttc ttatttaaca 59580
gctagtgata aagcccgtac ctaaagggtt taaagaccta acaataaaag ttaggtcttt 59640
ttttattgac atataactaa cgatatggta acattaaaat ataatattag agaggtgtta 59700
agaatggata aaaaaataat aggattaaat acaaaaacat tagaagagaa ggtttttact 59760
actataaaag aagcagaaaa agaaattgaa ttaagaggta ccgttaaaag atgtttaaat 59820
aatgaaatta agtctactaa aggatggtta ttcaggtatg aaaatgaaga ttttccggag 59880
aaggcaagaa caataacaga caaaagaatt aaggttgttg ttttaagtaa agagcaggaa 59940
caaataaagt tacctcttga gatggttaaa aatttatatg gaatacctaa acctatgatt 60000
attgaagcta ttcaatataa aaggaaaatt aatgactact ctgttagaag agctacaaaa 60060
gaagagcaaa agattacatt atctaacatt agttatatag actatataaa aacagttaat 60120
aacccaaaca atattaaaat tattaaaaat aaaggttctt ttggtgaaca gttagttaag 60180
atagtattag actataataa tatagaatat aaaagagaat attcttttaa gaatgaatta 60240
gggacagtac agagaatgga ttttttagca gtagtagata ataaaaaata ctgtattgaa 60300
tatatgggtg agcaacatta tgtagaaaaa ggtaataagt ggggctcgtt agaaaagaga 60360
caatttctag attctataaa gaaaaagtac tgttacgaaa atggaatata ttatattgat 60420
atcagttata aaaatagtga tttagagagt gtatttaatg ttattaataa acacatacca 60480
ggtattaaaa aaccaaataa atctattatt gatattggtg tgacaataaa tatagaagaa 60540
atgttagaat actataagga gcatactaaa aaagaaacag cttataagta tggagtaaag 60600
gaacataata ttgataactt attagtaaat ttaaactatg aaagcaaaag aaaacctaaa 60660
gatataatac aagtatataa gagagatgaa aaaatatttg aaggtactta taacgaaatt 60720
aaggatgaat ttaattttac tatgagtaat gttttgaaat gcttaaatgg agaactagat 60780
aaaacatcac aacattactt taaatataaa gattcagaaa aagataaagt tagacaacta 60840
aaaactaaag aaagacatgc taaaagagga acagtaagag gaagtagtaa caaagatgtc 60900
gttctaaagg acatatactc aggagaggaa actatatatt cttctattaa ggagtgtcat 60960
gaaataacag gtctaaacaa agacaaattg tacaagttat ttaatccaaa taaaagtaaa 61020
caaattgtag acaaatatat aggtaaaatc tacggtggtg agtaccctat aactgtagaa 61080
gaggctttaa acataattaa cccttgaccg atatcaaggg ttatgctatc ataataaata 61140
aggaggtatt accttgacaa acagaaaaac aattggtaag atgagtaata caagagcaac 61200

```
atggaagata aaacctgtaa ctaaaataac aaaagataaa acaaaatatt ctagaaaaaa 61260
gaaacataaa ggtattgaca cttataaata actgtagtac tatagttata taaggagatg 61320
ataaatcatg aaaacttttt attcaggtag aagaacaaca agtaaaaata ggcaagtaaa 61380
gaagcattat aaacaaatga ctaaccaaga aataactgtg tgtagaaact tattaaaaga 61440
atcttataat aaaaataatt actttaagtt aacaaatcac tttaaaggta aatgtaagaa 61500
accagtaaat tttaaagcgt ttgttcatta catacataat aagaacttag atattataga 61560
atataatgaa acattatata ataacaaaat acaacgtagg gtagttgtta gacatcctta 61620
tgtagtaaaa gtagataata aattatctta tcaatatcta gttatagaga tagaaacagg 61680
tgaagttgta actatgtatt ataacagagt tacagacaac cacagaacat taaatttaaa 61740
tgactattat gataaaaatt taaaaataaa gtattgacat aagtaaatac ataatatata 61800
ctaaggttaa attaataaag aggagaataa aaaatgacaa ataaattaag agctatccat 61860
gaagaaatga aaattgagtt acataaattc ccacagaatg tagatttaac aagtaagaca 61920
actgctattg caatcaatca aattcttgac aagtttaaaa ccttaacgga acaagcaggt 61980
aaaatcacta aaaagtattt tgagggtcaa gagattttga cgattgattt tgaatattat 62040
gactcacttc aagattacta tatttactta cttaaaaata gtgaaacaat cgaacaaaga 62100
ttacaagaaa ttgaaaaaag agtagctgaa tatgttaagt aatttggagt tataaccaca 62160
ttatgttata ctgtatgtgt ataaaaaaca taagttagct gttatattaa ttatgagaaa 62220
ataataaagg atggataaag aattggaaaa agaacaaaaa gatattaaag atatgacacc 62280
tgaagaaatt gatgagttaa aatatcagca acgaaaagat aaagagcgtg ttattaacaa 62340
agtaattaaa ggtgttaatg atgtatggga gaaagaatac aactttgaag aattagattt 62400
aaaattcaaa gtaaaaatta gattacctaa tgctagagaa caaggtaata tcatggcttt 62460
acgttctgca tacttaggtg gaatggatgc ttaccaatct gaccaagtta ttaatgctta 62520
tcagatgtta gctactttac aagaagtagg ggtagaagta cctaaagaat ttagagaccc 62580
tgaggagatt tataatctaa ctccgcttgc tattatgtgg gatgattggt tagactttat 62640
gacgtccttt cgttactagt aacgtaaagc agttaaatga agatatagaa cggttaggtg 62700
gaatttcaca tatagctaaa gagcctctat caagaaacct atgggctatt atgcgtgagt 62760
ttaatgtatt acctactgaa caacgtttta aagatttaga tgattaccaa atagagttta 62820
ttatagctaa catgaatctt gatacaaaag aaatgatgga agctagagaa ggtaaaaact 62880
atgatatgaa agcggaagac gtagacacat catggttcga agcgccgaca gatgaatttg 62940
atgttgttcc tgatttctta gacttagatg atttaaatac acaagtagat aaaagtttaa 63000
gtgagaaaga aaagatagaa agggatagac gagttgaagc tgagttagaa gatgaaactg 63060
aaggattaac aactcaacat ttggctatga tggaacacat aagacaaaaa caaaaagagc 63120
ttgatgaaag tttaggtatt gacagtaaag aaataacaca agaagatata aacaaagcaa 63180
taaaaaatgt agatgattgg tacatgtagg gtaatggtat aataccaata cccttatttt 63240
ttgattaggt ggtgaatact gtttggcaat gaatgacgat tataggttgg tcttgaccgg 63300
tgatagttct agtttagaac aaagtttaaa agctatagag atgtatatgg atgcgttaga 63360
gtctaagaac atagatgcac cattaacaaa cttcttagag aaactaaaag taatagcaaa 63420
agaagtaaaa tctgtacaaa atattatgga taagcaaagt gataaatctt taatatcacc 63480
aaaagctatg gacgaggcta ttagttctac acagaatgta actaagaaca taaatgacct 63540
aaagagagct ttaaatgaca tacaaacaga taatattaca aagggtatag ctcctgaccc 63600
tgaagtagag aaagtataca gtaaacttaa taagacacta aacaatacac aaacagaact 63660
agagaaagta gcatctcaaa agattggttc agactcagat gtaacaaaca gaataaaaga 63720
aatgaaaaca ctgaaccaag ttacagaaga gtataataaa ttagtaaaag atgccagttc 63780
agctaaggag tacacaaagc aactaagagc taatcgtaat atggttaggg gtcatatatc 63840
taggtctgaa ggctctaata gaatgtccta tgaccaaggt gctagagtac gttctgaatt 63900
aggtaaagta gacacttttg aaaagcaacg agaagctaac aatagaagaa taaaagaaaa 63960
ccaagataga tatagaggtt atagacatca acaacaagat ttagtaggta aaagagctcg 64020
tggtgaaatc agttctgaag actataaaaa acaatcagca tctattaaaa tgatgattga 64080
tgaaagtgaa aagctttctg aagtctatag aaaaacaggt gctgaattag acaagtcaat 64140
caactactat aaaaatagtg ctaaaaaaca gtttgctcag cgtgagatag aacagcaaag 64200
aggaacaatg ggtaaattgt ttcaagatag gttaccttct attggtgcac atgctactat 64260
ggcagtaact gctcttgcag gcggtatgta tatgcgtggt gcttccctat ctgaagcaaa 64320
tagacctatg gtaacatcat taggacagaa ttcagataat atggacatag atgcagtaag 64380
aaatacttat ggtgatttat ccatagataa taagcttggt tacaattcaa ctgacgtgtt 64440
aaaaatggct acatcatatg aaagttctat aggtcataaa agtgatgcag atacatacaa 64500
aggagctaaa cagttagctg taggtggacg ctcattaggt atacaagacc aagaaatgta 64560
ccaacagtct atgtcacaac ttatgcatac aggtggcgta aattcagata atatgaaagc 64620
tatgcaagat gctttcttag gtggtatacg tgaatctgat atggttggta gacaagatga 64680
acagttaaaa gctttaagta ctattgccga gcagtcagga caaggtagaa cattatctaa 64740
aggagacatg tctaatctta cttctttaca agctcaagta gcgggtacag gtagtaaagg 64800
tttacaagga gctcaagggg ctcaagcgtt aagtagtatt gatcaaggta ttaaaaatgg 64860
tatgggtaat tcttatacta ggttatccat gggttggggt actaagtacc aaggattaga 64920
aggtatgcat gacttacaag cacaaatgga taaaggtata tcagacccta ataacttagt 64980
taatatattt gaccaagcta ataatatagg aagtacaaca aaagaaaaac aagccatagc 65040
taaaaaaggc tttgaaagca tgggagctaa tttaacacaa gagcaaacag atgagttgta 65100
caatctttac gcctcaggta aactatctaa agaagagtta gctagtaaag ctaaaaagat 65160
ggagcaagaa ggttccaaag caggagataa gaatagggat aagtattccg aatctaaagc 65220
aggtaggaat gaccagaaca aagctaagac agatgataaa gccgaggata tttatgactt 65280
agctcaacct attagagatg ttcatagtgc tatggcaagc ttgccagctc ctttatacct 65340
agcttcagga gcagtacttg catttgtagc atctttagct aaatctactg ccatgatggc 65400
tggtggctct ttattaggta aaggtcaaaa aggactaaaa gattggttta ataaccgtaa 65460
aggtggttca ataggtaaga ctggtggtgg gcgttttggt ggacttaaaa acttagctga 65520
cactatacta ggagataatc ctaaaggtgg agaccgacca tttaaagacc aagtaaaagg 65580
tgcaggacaa actgctaaag gtatgggtaa aaccctattt gataccttcg gaaaaagaga 65640
ctttacattt ggtgaatata tgggaagaac caaagactta ggtaaaggtg catggaacaa 65700
aggtaaagga gcttttggta aagctaaagg taaatttagt ggtaaaggtt ccaatttagg 65760
ttttatgtca caagcaccta ctgctaacgc aggtggtctt ggtaaactag gtggtcttac 65820
aagtaagcta ggttggattg gtgtaggtct atcggcgttt gatataggta gttctttaat 65880
acaaggagat actaaagaag cttcttctaa atttggtaac actataggaa gtgtcataga 65940
```

```
cccattaaac ctaggttatg gagacggatt aagagactat gctacgaaaa cagcagaagg 66000
tgcttcgaca ggtgatggtt ggaaattatg ggctaatgga gataaagatg gtaagaataa 66060
attccaagac tcacctgtag gtaaactatg gggtggcata acagatttct tcacaccaga 66120
tgacccttct aaattagatg aaacagtgaa aaataaaaaa ggtaacataa ttagttatat 66180
actaattgcc ttgcttatag agcaatctgt aagtaccgag tgttaactgc tatgaaacta 66240
ctaaagctaa ctaaactaca aagtaagtcg aaagactaag cttgaatgtt gagaaatcag 66300
aaaaaattag ttagatactc taaggttaaa tcctaaggag aagtacaatg ggtgtatagc 66360
atcgaaactc ctttaacatg gagaacgttc aacgactatt ccgtataggt gacggaagta 66420
aagccacaag tgattggtgg aagaaaaata ctcaccctat aaactaggga taacaaatag 66480
tctgcacacg tagggaaacc tagtgtctag aaataactag agaatataca gtagcgtgta 66540
tatttaaaca ttgttaaaat atataaataa ttaaaatttg tattctactt ctgcatataa 66600
acctttctta ttttgtaagg taaacttgtt attaaataaa tatacataac taatacgata 66660
ggttatatat gaaagtatac tattgtttat atgttttaac ttatggtatt aatgataaat 66720
cacaaagtaa agacaggcaa aaagcagaag aaaaaagaga aaagaataat gattctagag 66780
aaggaaatgt aacagtatac tcacatttct tagaccattt agcagacaat ctaacaaata 66840
aaggcagtag ttccgacaat agttcatcag gaggaacact tgactatctt gatggtaaga 66900
actttacaga taaagacgta actaagcatg acttaggtaa aactgctaaa ggtgtaaatg 66960
ccgaaatgtt aaataaatgg attgagtctc aagcacctag taattctaaa atgcgtggtt 67020
taggtgagct ttatatgaaa gcaggtaaag agtcaggact tgacccaagg tacttagtgg 67080
cacatagtgc tgttgagaca ggctggggaa cctcgaacct ttccaaaggt ggagacccta 67140
acaaaggtaa ttggttcggt ataggtgctt ttgataacaa tcctaataat ggttttaact 67200
atggattagg tattgttggt ggtgctaaat ggattagaga taacttctac aacaaaggac 67260
aaaagaactt acatgatatg agacataaca atggtgttca tgagtatgca acagcaggta 67320
attgggatac tatgattgcc agtattatga aaggttcaga caagttcata ggtggtggag 67380
gtggaggcag tgatgttatg cctagacatg ctctaaaaaa tgaccatcaa ccaaagaatc 67440
ttaaatataa catagaagta cctaaaagta aaaaccctaa tgaaacaggg aaagcaatag 67500
gtagaaaatt aaaacaatta ttagaatcta atttttagaa tacaattata atatttatat 67560
actttaacaa agggtacaaa caataaaaaa cagaaaatgt ctacagaaca actaagagaa 67620
aagaataata aatcagaaac taaaaactta aaaacttaca gtaacctatt agatagggca 67680
caacaaatta tagaagatgc taaagcgcta gactcaggag gttcagacag tagttctgat 67740
tcaggaggtt cagcttccga tgtagatgga gaaggtgcgg gtaagattta caaattcctt 67800
aaaggtaaag gtttatccga taaccaagta ggtgccgtta tgggtaacct taagcaagaa 67860
tcagggcttg accctaatgc aaagaacgcc tctagcggtg cttttggtat tgcacaatgg 67920
ttaggtagta ggaaatcaga ccttgatagc tttgctaaat ctaaaggtaa gaagtctaat 67980
gacctagacg cacaattaga tttcttatgg aaagaaatga gttctggtca aaacagtgat 68040
atgcttaaaa atgcaggatg gagtaaaagt ggaagcttag aaagaaatac aaaagctttt 68100
gcacaaggtt ttgagcgtat gggtgctgga gaagctatga tgagtaccag agttaacaat 68160
gccaaaagct atgttagtaa atacggtaag tcaggtggtg gcggtggcgg agttatacca 68220
tcgtcatata cttcagtcat gagaaatcct atacttagta gtacatctgg aagtagtaaa 68280
tctcaaaaca atgtttctgt gagtgttaac atcacaggag taaacgataa agaagatgcg 68340
gaaggcataa gcaaaggtat taagtctacc tttggtgacg atttagacat cttctcaaac 68400
acgtataaac gtaattatta gggtagtatt attaagtact accctttata taaaaataaa 68460
ggaagtacat atatgtatag aattagacga cctaagatac gaatagaaat agtaacagat 68520
gataatacat ttacattaaa gtttgaagat actaaagatt acaacggcaa tcaatttgct 68580
tcaaagttac ttagttttca aactaagaat gctatggaag atgatagtgc tgtattccaa 68640
ataactatgt caggggatac gtattgggat aagctagtaa tggcaaatga tattattaag 68700
atatatatta cgcctaataa tgaccctaaa gataaagagg gaaaccaaga gaaacttata 68760
caagtgggta tggtatctca agtatctaaa gtaggtagtt atggcaatga ccaagtacaa 68820
tttagaataa caggtcaatc atttgtaaaa ccttttatga agtttggttt aggtgttata 68880
caagaagtac aagctgtatt accaactgtt ggttggttag ttgatggcga tggagagaat 68940
caggttaaat ttacaggtag ttccgctaaa gatgtaatgc aaggtattat acaacgattt 69000
attccttaca tgaagtacaa ttatacggat aaaacataca acacattaga gagttactta 69060
gattatgatg atttatctag ttgggatgag tatgaaaagt taactgaagt ttccgctttt 69120
actaactttg atggtacatt aaaacagcta atggacttag taactgctag accttttaat 69180
gagttattct ttagaaattc agataaacat aaaggtaaag cacagctagt attaagaaaa 69240
actcctttta atccaactga atggaaagca ttagaatata tagttgtacc aactgatgat 69300
tttatagagg aggatgtagg taagagtgat gtagaaacct actctatctt tacagtaaaa 69360
ccagcaggta tgttaaaaga attaacaggg gatgtattct ctaaaccaca attccaccaa 69420
gaattagtag atagatacgg gtattctaaa tatgaaacag aaaacctata tataggaact 69480
aaaagtggta gtgctacaga agatagtgaa actacaggtg gagataatgg acacgaacga 69540
gtaacttatg acagactact taaagattta aataactatg gtagagagtc tatatctaaa 69600
ggattagata aatactctag taagatatca tcaaaataca acaatattac taaacctgaa 69660
gtaaagagta ttttagaatc ttatataaaa aaaggtaatc taagtaagga agaatatgaa 69720
aaaataacaa agaacaatac ttcaagagag tcagtatctg atactagacc aaaactaaca 69780
aaagaaaaat taaagtctat attagcggaa aagtttaata agaaagaaac ttttgatgat 69840
aaagatttaa ataagaaaac aacaaaagct gtaatagatg atattacaaa gaattataag 69900
tatggtaatc ctacacatgc taagaaacta ctagagtatt acactagatt taaaggcaac 69960
ccaccgacaa gtaccacagg tgatatttat gataagtatc ttaaagccgt agaaggagta 70020
gctaatgttg ctagagatac aggttctgac gcaagtgatg actctttaat tatatttact 70080
aaaatgctat ttaattggta tcactcaaac cctaattttt atgcaggtaa tattgttgta 70140
ttaggtgacc ctaagtatga cctaggtaaa cggttattta taaaagataa acaacgaggg 70200
gatatatggg agttttacat agagtccgta gaacataagt ttgattataa acaaggatac 70260
tttactacaa taggagtaac aagaggacta aaagatgcta ttataaaaga tggtgaagga 70320
agcaaacata ggtttaaagg actatggaat cagtcatctg actttatggg tggtcttatg 70380
ggtgaagaga catctaaaga attaaaagaa aaaggtgtag ccgagaagaa aataaaagga 70440
aataaagatg gagactccga aggtggtgca caagatggag gcactttagc ttcattagaa 70500
aaatataatg gtaaattacc taaacatgac cctaactttg ttcaaccagg caataggcat 70560
tataagtacc aatgtacatg gtatgcctat aatagacgtg gtgagttagg tattcctgtt 70620
ccgttatggg gagacgcggc ggattggatt ggtggtgcta aaagtgctgg ttatagtgta 70680
```

-continued

```
ggtagaacac ctaaacaagg agcttgtgtc atatggcaga gaggcgctcc tggcggaagc  70740
ccgcagtatg gacatgttgc ttttgtagaa aaagtattag acggtggagc cagtatattt  70800
atatcagaac ataactttgc aactcctaac ggttacggta caagaacaat agatatgagt  70860
tcagcaatag gtaaaggtgc tcaatttata tatgataaag gataattgat atggcaacgg  70920
ataaacaagt taaagatgtt atagataaat ttatagataa tcttttcaat tttgaagtat  70980
taaccaaaga aaaggttgaa gaaaaagata aggaagttaa aaagataact acagaagacg  71040
tatacaataa agttgtttat attagaccat atgtaggtgt tatacaaagt gtaacaccta  71100
gacaggtaac atatgatagt tttactaata atggtacaga tatagaagct aaactcacat  71160
ttagaaaaat aagttatact actgataatc tcacagtacc tactgatgca ttatcaactt  71220
gtatggtgca tatggtagaa agaaatggtg tacttgttat agattacttt gatgagttac  71280
agaacatact gtatggtagc tacatggaga atgagcatat atttgatgaa gatgttccag  71340
ttagtacatt agtaacatta gacttgaaag agaatttaaa taattataaa catatacagt  71400
atatgtttaa agggaatacg gataaaaacc cttttgaaag taaggatata gtacctttag  71460
atacatacaa cttattatat tggatgtata aaaagagaaa tgtagagctt aaaaatccat  71520
taacagttaa ctacttcttc acaggtaaaa gcttctatac tatatttggt aagggacaca  71580
aatataaagt tgatattgac aaattcaaaa taggtgatat actattcttt ggacgtagtg  71640
atgataatat agggatatac ataggagata agaagtttat ttctcttata ggtacatttc  71700
ctaaagataa cacctctatt agtacctatg agttagacga ttattgggat gactttaatg  71760
gtagggttat gaggtttgat gaggatgata taacatggtg gtaagattac agtcttcttt  71820
aggtagaagt ttaaaaaaga tagactctga agaacttaat gttaagggtc tattattagg  71880
tacagtaagc aaaataaatt ataagtacca aactgtagaa gttaaaataa atagtttaac  71940
actaggacgt aaccctagtg atgacggtaa gttagctgtt ccttatccta aagattatgt  72000
agggagaaca cctgaaggta gtatttatgg tagtaatact ttaataacgg aaggaactac  72060
tgtactgtta ggatttatta atgatgacat taatcatcct attatactat ctatctatgg  72120
taatacagaa gtaaatcagc tcataaatac caatccttta gaaggaggta aaatgaggaa  72180
tgacgacgtg tataaataca gtagtgcttt atactctata ttacctgacc taacttatac  72240
atataaagat ggtgaaggaa catccattaa aacatttaat ggtaaatctt tcttatctat  72300
tacttcggga gataaagaaa aaccattagc gtcagacttt tatacaggca ctgaatatca  72360
agacctattc ccatcatatt atagtaacaa aaatttaata gaacctagaa tacaaaaggc  72420
acctaacatg ctatttaaac accaaggact atactttgat gatggttctg aagacaatca  72480
tgttacaact ttatttatat ccgaaaaagg tgatgtgaga gcttcagtat tagacaaaag  72540
tacacaaaaa agaacaacac aagagatgtc tcgtgatggt tcttatagag ttgtaaaaca  72600
agatgatgac ctattattag actcagcaca agtatgggta gagtttggta taaatgataa  72660
taatgtgttt tatataaaaa accctaagca tatgtttgaa tttaatgata aaggtatata  72720
tttagatgat aagccaattt tagatacgtt agatgctagt attacagagt ctatagatag  72780
acttaaggaa gtacagaaag aattagatga cattaactac ttacttgagg gtgtaggtaa  72840
agaaaactta gaggagttaa tccaagagac taaaaaatct atagaagttt ctagtaaagc  72900
aagtagcgat gttacgacta tgaaatctca aatatccaat gtaagtagta gagctgaggg  72960
cattattaca cagtttcaag agtttagaga caaaacattt aaaggcttat atgaagatgc  73020
ttctactatg ataaataaat acaaccaaga aatacctgag ttaaaaagta gattgaatac  73080
tctagataca attacattac ctaacattaa taatacctta ttagagaaat caagtaagac  73140
ctatgttaat aatagttctc aaagttttag tagtaattat ctaggttcat tactgcaact  73200
agatagtaac cttactattt atccatacac acctacacgt attacatgga ataagatagt  73260
ttttaataat tctgagtttg taaataagac taaggatgct tttgttattc cattaggtgt  73320
atctaaagtt aaagtttcta ttaatcttaa atgggatata ttacaagata aagtaaaaac  73380
tattacagtc aagaagaata gtaatacata caaaactata actaatggta atacacacga  73440
taatataatt acaaatgtta tacctgttaa acaaggagat acattcacag tagaagtaca  73500
acaagataat gatattaacc ttacattact acaagatgat acaatgttta gtatagaagt  73560
attagaaact actttagcac ctactaatac tgagttatta ggtacagtat ccgaacaaac  73620
agataagcaa ctacaaacac ttgtaaattc taatgttgat ttactaagtt taacaacaca  73680
agttactaaa gataatcagt tagtttgtct taatgattcc aaattagaca atataacaac  73740
aggtaaaggt aatgtatctg actatactct acaacaaata aagtcatttt cagctaagaa  73800
tggtgagagt attttatctt tagaagatgt attagctaaa tataaaaatt atattagata  73860
tagtattaat ttaccaacta ctgcaaacat agtagaacta ctgaaaaaat ataatttaat  73920
tggtataaga gcacctagga atcaggtgta tttgaaagtt aaagatttaa caatcacaca  73980
agaagtatta aataattttt ctaacttacc agtattatat aatacttcct atctaacaag  74040
tacagatatt aacaaaggta tatatacaaa tatatatgga gtactactac catatactaa  74100
tatcactcaa gatacagtaa atacagcaca taataataac ctatctatat atgctagtgg  74160
tgatatgaca agtgatatta taaataagct tattttatat ggtatagatg gtgtagaaac  74220
aaataaaata ttagagttta aaaaagttta aaagtcctat taatagggct tttttatata  74280
tgtcatgtta tattaaactt gagaaagtag ttgtatttaa atcctatata tgatataata  74340
cgatatagaa aggtggtaag ttatgcctca atcagatgga aagaatacaa taagacgtat  74400
tgcattacgt tttccaacag caagcggtaa atataatatg taccgtttca aagtaaaccc  74460
tgaaagttat gaaatagatg caccacaaag aacatctata actaaaacta aatcagacat  74520
tattgttgaa gattacggta aagatataga gacaataact ttttctggta ctactggatt  74580
tagacctgta aaagaagtag atggtactaa aacaggaaaa caaaaaatag aggaactaca  74640
agaacaagta gaagcatacg ctaagcaggg tggagatggt agcgtagcag gagcttatat  74700
agagttctat aactttactg atgataaata ctacaaagta catttagcac cgcaaggttt  74760
aaaaataaca aggtctaaag atgaatcctt gttatataga tacgaaataa ctttagttgt  74820
tataggtaac cttgctgaag cagacagagg ttccgtaaca tctgctgagt ttggtaatgt  74880
aaaacctaat gctaaacaaa gagttgatga gggtgttaat gatttagata gtaacgcacg  74940
aaaaacaaga aacaagaata atcaaatagt atcacaattt gaaaataaaa gtagtaaaag  75000
ctcttctaat tctagtagta gtggttcacg atatggaacg gcaggaacat taagaggagg  75060
tagtggcata agaacaggtg gttctgaagg taatagagac ggtatgagta atataggtat  75120
atataaccct agacagaata ctaacggtct tagtagtact gttgatgata tggcacttaa  75180
aataggatac ggtgatggag gtgtatctag gtaatgaata attatatacc tcaaccacaa  75240
ggactattaa ggtttttaaa tggattagag ttagacatgt cttacacaca tataaactta  75300
ttagatgagg aagtaccttt tgtttctaaa ttttatacac cacaaataca actaagtgaa  75360
cttgcaagag taaaattaaa agagattaag tctactgata tccctacttt agaaagaaca  75420
```

```
tttaacaaca atacaatagt taataaagta gaacaaacaa gtttaaagtt acaatcacct  75480
agaatgtatt taattatgca atctatcgta atggaagctt acgctattgt aaactgcttt  75540
gtagaaagtc ctgaatactt aaaatattta acagaaaaag atgtatctat agtgagaagt  75600
aatgttaact atgtagctga ctacttaagt gattatgaag aatacaatag tattgttctc  75660
gatttaagag acttagactt atgttttggc tctttggaat tacaactacc gctaattaag  75720
agtgaggtgg tataatgaga tttagaaagc atgaagtcca accagaagaa accttacaag  75780
ctatatcaca aaggtattat ggtgatgtta gttattggtt agatttaata gaacataaca  75840
acttacaata tccttatatt gtagatacag atgaagaaaa gaaaaggaac cctgaacact  75900
taataactaa gggtgatatt attattatac ctttagatgc tgagttaaca gactcggttt  75960
ctaaagaaat aacatcaaga gataaagatg tattagtaga attagcttta ggtagagacc  76020
taaatatgac ggataataaa gagtatatag acgctcatgg aacagatgat gaaatattag  76080
ccctatcttc agatggtaga ggagaccttg atatagttaa aggcatagat aacattaagc  76140
aatctttaag agctagacta ttgacaccta aaggttcttt attattacat cctgaatatg  76200
gttctaacat tcataattta tttggtttaa atatacctga acaagctacg ttaattgaag  76260
tagatgtatt aaagactcta acatcagata gtagagttaa atcagctaac ttaaaaggtt  76320
gggagataaa aggtaatgaa tactatgggt catttaatgt agaaataaag tccgtagaag  76380
aatctataga ctttgtatta ggtcaagatg attcaggtgt ctttgcttta tttgactaag  76440
aaaggaaatt tatatgagaa caagaaagtt aacacagata ttatctaggt taatagataa  76500
gacgatacaa ggtacaagca aaataacaga ctttacacct ggttcagctg tacgctctct  76560
tttagaagca gtagctttag aaatagaaca gtattatata ttaacaagag aaaacattaa  76620
ttggggcatt caagaaggga ttattgaagc ttttgatttt caaaaaagaa aagctaagcg  76680
tgcttatggt aatgtaaaca ttcaatttta ccaaccttta gacatgagaa tgtatatacc  76740
tgcaggtact acattctcat ctactaggca agaataccct caacagtttg aaacattagt  76800
tgattactat gctgaagaag gaaccactga aattacagta gaagtttatt gtaaagaagt  76860
tggtattgta ggtaatatac ctgaagatat cattaataca atagcctcag gctctagttt  76920
aattcgtaca attacaaacc cgacttcctt taatacagga acaaaagaag aatctcaaga  76980
ggattttaaa cgtaggttcc atatgtttgt agaatcgaga ggaagagcta ctaataaatc  77040
tattagatat ggtacattac aagtacctga tgttgatggt gtttatgttt atgaagaagt  77100
aggtcatgtt actgtatatg cgcatgataa aaacggaaat ttatctgcta ctctaaaaaa  77160
tgacataata acggcattag aagattacag acctagtggt ataaagttag atgttgtagg  77220
tgtagagaaa gaggaaatag atgtgtctgc agtagtaaca atatctaata aagctaggat  77280
aggtgataca ttacaaagac atattgaaag tgttatcaga gggtatctaa atagtctgac  77340
tacttctgat gatttaatta ttaacgattt aattcaagct attatgaata tagatgataa  77400
tttaatttat gatgtagcat ttaagaattt atctacaaat atagaagtat cttcgaaagg  77460
tattattaga gcaggggata ttaaggtaga attaatatag gggtaaaca atggctaatt  77520
ttttaagaaa tttacaccct ttattaagaa gaaataagaa taataaagat aaccaagacc  77580
ctaactatgc tttaataaca gcacttaatg atgagatgaa caatatagag ttagacacca  77640
ttaaaagcaa acttcaatca tcattaaaaa ctgccacagg agattactta gataagtttg  77700
gggattggtt tggtgtatac agaagaataa atgagaatga tgacagctat agaaaaagaa  77760
ttataaaata cttattatta aagagaggta ctaataatgc tatcattagt gctattaaag  77820
attacttaga taatgagaat ataaatgtta gtgtatatga acctttttaaa aatatattct  77880
ataccaataa atcaaaatta aatggtgaag attatttaat gggttattat tatagatttg  77940
ctgtgataaa tgtttctgtt gatggttact ttcctttaga gattatagat gtaataaatg  78000
aatttaaacc cgcaggtgtt aagttatatt taacttatga tggtgctact accataaagg  78060
gtgatggtgt tgttaaatgg cttaaaaatc tacctaaaat tgaaacatat acggatttag  78120
atagattatt aggttatgat gaaactttct atgggcattt aaacatgagt gaagcaacag  78180
ctgaacaatt tgataaaaca aggttcagaa caaataagag tatattaaat agtgaagata  78240
ttctatcagg ctcttctaat attggacgta gatttataaa ttatgcttat gttacgacat  78300
atgcatatga acctactagt acatcagccg tcacacatat agcttcttta aatgataaag  78360
gaaaagaagc acctttagat tattacttat acacatcctt aaagaatact aatggtataa  78420
atatatcaat ggaaactgct tatggtgtat cttatttata caataacttt aatgtaagtg  78480
agtttatcag cagatacaaa ccgaatatag atataactag agataatgct aaaaaacaaa  78540
tatccgattt tataggagaa ctaacaattg atttctttgc aaaagcttta gtttcacctg  78600
atgaatcatt acctattaag ttacaaatat ttgattttcg tactaatgaa tggttaactg  78660
tatcagaaac agaactatct ttttacgaga aaaacatagg tgtaaacata ggttatataa  78720
gagattactt aaatgatgac cttaatttat ttacaagatt agaggttaat ataggtaaag  78780
atgagcaaaa agatataagt attaactaca tggatttaca tttttataat tataaaaaag  78840
atgtgtatac tatcaaacct tttaaggcac tagttgaaaa ctacatagat ttgactaaag  78900
atacttatat tgaaggcttt aaagtagcct cattattaaa tggagacata attaataaaa  78960
atggatatca acccataaaa tatttaaggt tacatgctac ttatgattca actaaaccta  79020
ttgtaagtat tacaggtaaa aacagcaata atgaggtaca aaataataca cctatagatt  79080
tatataaaaa tacaactaat agaaacttat tgcaatcata taaaggtgat agtaatatat  79140
tcaagggtgt tgtaagcaca aaagagtttt atatctcatc atgggctgac accttatata  79200
attcaacgta tttatctaaa gtactagaac cacaaaaatt atatactttg tcattcgaga  79260
tggaaatcac agatgctaat atggacttaa aaacatattc tgacaatcat ggtatatatt  79320
tatatagtag tactaaaggt attgttgcta atggtgttaa aagcatgcaa agaaaaatag  79380
gtaataagat tgaggtatct atcacattta cagcacctac aattacagac catagacttg  79440
ttgtttacac aggtagatat acagcagacg gtactgcttc taaaacacct attgcttata  79500
atacggtaaa agtaacaaac cttcaattaa aagaaggagc tactaagaag gactacacgg  79560
tagcacctga agatgtaact aatgttatag acaaagctat tgtgtttgat aacatattaa  79620
cagatataca aacaatagga ataaatacaa caacacctct taaaaatatt gagctaagtt  79680
attcttacta tggggataat tggacaagcc taaaaacaat aagtaattta agtcaaggtg  79740
aaacaataac acctaataac ttagtagatt tatatgtctt agaaacaata gattattcaa  79800
gtattacacc tttctctagg gttatactta aaactatatg gaatgctaac ctgaataatt  79860
taacaaataa aaaaggtagt atttctaaca tgagtaataa ctatttcaat gctgtgtggc  79920
aagaggtaga tatgatatat aacactacat taagtagcat gagcatactt actgatagtg  79980
aaggtaatgt atttgatagt tcaacaggac aggtaataaa attagcacct aagatatacc  80040
aaggatatac tgatgtagat agattgctaa cgtctactac tctatataac gagaatatta  80100
cattaggttc aaatagattt atttatgact tacgggatat gttactatca agtgatacat  80160
```

```
tcacagtaga taatagaatt aaagtaatag atacgtacac agaagtacag taaagatatt  80220
gacaataaag tattaatatg atatagtaag gtatgcgtat tatagtatac cttgttatat  80280
taatacagaa tactagacat gaaaggaata aaaaatatgg ctatagcaac aaatgcttca  80340
catgtagaat tagctaaata cattgtaagt aaggctgatt ctatttattt aacaattggt  80400
aaaagtacag cgtgggctaa tgaaacaaga ccacctcaac ctgaagaaac agcaacatca  80460
ttacaagaag ttatcggata taaaaaagca actaaggtag cattagttag acctgcaaaa  80520
acaacgggtg atgaaagtaa aaaagaaatt acatatggta ataaacgatg ggtagaaatt  80580
gactcagcta atgcagttgc tgaaggtgct aagtgggtgt acttagaaag tagtattgtt  80640
ggggatgagt taccccttagg tacatataga caagtaggat ttgttatgga tttgttagct  80700
aaagatagta tttctaaatt taacttacta cctagtgaag tgcaatctac aggaacttta  80760
ttattttatg ataataaaca gttccaaaat agaagtgaac aaacaactgt aaaagagcgc  80820
tttatcattg aagtttaaaa aggagaattg aatatatatg gcaattaatt ttaaaagttc  80880
tccatactta gatagatttg accctacaaa agatagaaca agagtactat ttaatccaga  80940
tagaccacta caacaatcag aactaaatga aatgcagtct attgaacaat attacttaaa  81000
aaatttaggg gattctattt ttaaagatgg ggataaacaa tcaggattag gttttacatt  81060
aactaaagat aatgtactac aagttaaccc aggttatgtg tatataaatg gtaagatacg  81120
ttactatagt agtgaagaca ctgttaaaat tacgggtgta ggtaaagaaa cagtaggtat  81180
taaactaaca gaaagaatta ttacacctga tgaagataat agcttattag accaaacaag  81240
cggagttcct agttattttt ctaagggtgc agaccgtcta gaagagaagt tatctttaac  81300
agtcaatgac cctacttctg ctactattta tacttttatg gatggagacc tctatatcca  81360
atctactaat gctgagatgg ataaaatcaa caaagtatta gcagagcgta cttatgatga  81420
gtcgggttca tataaagtta gtggatttga gctattttca gaaggaaacg ccgaagatga  81480
taatcatgta tctgttgttg tagatgctgg taaggcatat gtaaaaggtt ataaagtaga  81540
taaaccagtt tctaccagaa ttagtgtaga gaagtcaagg gaattaggta aagcagagaa  81600
tgaaagtact gtatttaata aatcatcaaa taatattact ttagctaata cccctgtaaa  81660
agatgttcaa cgtgtaacag cgcaagtatt agtagataaa gagcgtgtta caagaagttc  81720
aacaggagat tctcaagact atttatctaa taaaacagct tttgaagtag ttagagtatg  81780
gacagaaaca agtccaggtc agacaacaaa agaatataaa caaggagaag actatagact  81840
tactgatggt caaacaatag attggtctcc ttcaggtcaa gaacctaatg gaggtacatc  81900
ttattatgtt tcgtataaat acaacagaaa gatggaagta ggaaaagact atgaagtaac  81960
tactactggt gaaggtgtag gtaaacgctg gtctattaac tttacgcccg ttaatggtac  82020
taaacctatt gaccaaagtg ttgttcttgt agactatact tattacttag cacgaaaaga  82080
tgctgtattt attaataagt ttggtgatat agctatcctt aaaggtgaac ctaatattat  82140
gagattagta acaccacctc taaacacaga ccctgagaat ttgcagttag gtacagtaac  82200
agtattgcct gattctaacg aagcagtatg tatttcatat gctattacta gattatctat  82260
ggaagaccta caaaaagtaa aaactagggt agataactta gagtataacc aagctgttaa  82320
tgctttggat gatggtgcaa tggagaaaca aaacccatta acattacgtt ctgtatttag  82380
tgaaggtttt atatctttag ataaagccga cattacacac cctgactttg gtattgtatt  82440
tagttttgat gatgcagagg ctactttagc gtataaagaa gctgtaaatc aacctaagat  82500
tatccaagga gacactacag ctcatatatg gggtcgatta atttctgctc catttacaga  82560
agaacgtaca atttaccaag ggcaagcatc agaaaacctta aatgtaaacc catacaacat  82620
accaaataaa caaggtgtat taaaattaac tcctagtgaa gataactgga tagatactca  82680
gaatgtaaca atcacagaac agaaaactaa aaaagtaaca atgaaaagat tctggagaca  82740
taatgaaagt tattatggag aaacagaaca ttacttatat tctaacttac agctagataa  82800
aggacaagag tggaaaggta agtcatacgc atatgataga gaacatggta gaacaggtac  82860
tctattagag gctggaggac agcgtacact tgaagaaatg attgaattta ttcgtgttcg  82920
tgacgtatct ttcgaagtta atggtttaaa tcctaatgat aataatttgt atattttatt  82980
tgatggtgtt cgttgtgcta ttacaccaga aacaggctat agaaaaggtt ctgaagatgg  83040
tacaattatg tctgatgcta aaggcacagc taaaggtaaa tttacaattc cagcaggtat  83100
tcgttgtggt aatagagaag taacattgaa aaatgctaac tctacaagtg ctacaacata  83160
tacagctcaa ggacgtaaga agactgtaca agatgttatt atcaaaacac gtgttacagt  83220
aaacttagta gacccattag cacaatcatt ccaatatgat gaaagtagaa ctattagttc  83280
tttaggttta tactttgcta gtaaaggaga taagtctagt aatgttacaa ttcaaattag  83340
aggaatgggg gacacaggat accctaacaa aacagtttat gctgagacag taatcaatgc  83400
agatgatatt aaagtatcta ataatgcaag tgctgagaca cgtgtttact ttgatgaccc  83460
tatgatggct gaagctggta aagaatatgc tattgttatt attactgaaa atagtgatta  83520
tactatgtgg gtaggaacaa gaacaaagcc taaaatagat aaaccaaatg aagttattag  83580
tggtaatcca tatgtacagg gtgtattatt tagttcttca aacgctagta catggacacc  83640
acaccaaaat tcagatttga aatttggtat atacacatct aagtttaatg aaacagctac  83700
aattgagttt gaacctatta aaaatgtatc agcagacaga ttagttttaa tgtctacata  83760
tttaacacct gaaagaacag gttgtacttg ggaaattaag atgattttag atgatatggc  83820
aacatctact acatttgacc agttaaaatg ggagcctatt ggtaactatc aagacttaga  83880
agtattagga gtagctaagc aagttaaact aaaagctaca tttgagtcta ataagtatat  83940
ttcaccttta ttaagttcta atgacttgac ttttactaca ttcttaactg agttaaaagg  84000
ttcatacatc ggtagagcta ttgatatgac ggaagcacca tataatacaa ttagatttag  84060
ttatgaagca tttttaccta aaggtacaaa tgttattcct aaatactcag atgatgatgg  84120
tagaacttgg aaaacattta ctacatctgc tcaagtagtt aaggctaata gagactttaa  84180
cagatatgtt attgatgaga aagtaaataa atctactaag aatagtaaat tacaagtaag  84240
attagactta tcaactgaaa acagcttctt aagacctcga gtacgtagac ttatggttac  84300
aacaagagat gagtaagttt aaagagggtt taatacctc tttttattta attaaggaag  84360
tgatatcatg cctacagaat acagagaccc ttattcacaa gcaaaactct ttattcctac  84420
tgtagaagag aaggctataa aagaaatgga acaaacatat aaaaataaat tacaagaagt  84480
tgatgagctt atcaatgaac ttaaaaaatt gaaaggtgat tatacacatg gcgtttaact  84540
acacaccctt aacagaatca caaagattaa aagatatgta ccctaaagta aatgagatgg  84600
gtagatattt acaagaagaa gttaatctag cggatgtaaa aacaataagc taccctgact  84660
taagtaatat tctaacttac atacaagagt caggagatta ctttgttaca caagcaagaa  84720
acacaccagg aggagtaagt aacacaggtt ttttacactt agataaaaaa ggagatactt  84780
attataagtt atattatgct ccttctaata caaataaatt atttgtaaag acatactata  84840
atggtacggt atatgattgg gttaacttta aattagatga aggtaaccta tatgatgcag  84900
```

```
gtaatacaat taatgtaaaa tacttaaatg aatctactac gcagtttgct actttagtaa  84960
atccacctaa aagcaacttg aatacagggt ggataaatta caaagagagt aagaatggta  85020
tgtctgcttt agctgaattt aaccctatta actctacttc tacttttaaa atgattagaa  85080
agttacctaa ccaagaccaa caacctaact tactgagaga tagtttgttt accttaccta  85140
tggctgatat atctaatgta agaacggatt acatagataa tacatctttt tggggtttta  85200
ccgataatgc ttctatatca acagttaagt atatgggtga aaatacggta cagttagatg  85260
atggtaagga gacgtatcct acagttatgt caaaacgatt cagaatagga aacgaactat  85320
atgtaggaga tactgttaca atgtctgtgt atcttaaagt aaatgaccct aatttgttaa  85380
atggtaattt cccttacttt gagattgctg ggtatgatta tgtttatcaa gacaataatc  85440
catatacagg aggtaggaga gaggttaact attatgattt atctacggag tggaaaaagt  85500
tctcttttac ctttactata cagtcctata atcaagagta cggcaatgga agagttaatt  85560
atatatcagc tttattaaga tttaactgtt ctaactctac taataatggt gcaattgtgt  85620
attatgcact accgaaatta gaaaaatcat actcagtaac tccttttatt acaaatactt  85680
atgataatag aaagtatgat gagatatgga gtaattggat tgaaacaaca agtaaagatg  85740
agcttcaatc acatagtatt gtagacacat ctaataatga ttattacaag tatatgtgga  85800
attaccaaaa cgcaaacggt aaaaatttac aacagttagc aatgtctgta cctcaaggtt  85860
tttatacctt ttactgcgat ggttctataa gtggaactcc tagtaataaa acaatacaag  85920
gtacaataca agtagcatat aaaaataata atataaacac tacaaataaa gtaatacaaa  85980
tggattttaa tgacactaaa ggcaagaaat attctctaac ttataataaa gatgataatg  86040
gttggcaaga catgaaagtt caaatggcta gtaacagtct ttgggaagga acgctcgacc  86100
tatcttcagg aaatatagta aacttatcag attcgttaga taattatgat tttattgacg  86160
tagtatattg gactagaagt tctggacata atgcaactag aagattccct gctactacat  86220
ctagtattgt aattagagac tttaacctag taaatgatgg ctctaactct agtgtagatt  86280
tctttgaagg gtattgtgat attactgata gggtaaacgt cactgctaaa atgtcaaaaa  86340
cagttaacct agacggaaat agaaatacta catcagtagc acaattcaat caaacaggtc  86400
acattgaagt actaagagta atagggttaa catatattta ataaaagggg ttttatagat  86460
gataaagtat gatattggta aagatgaaat tgtattacat ttaaaagata ataaatatat  86520
tatggggtac actattgtag gaggttataa tgagagcaat ggtgatgtaa aaatatcaag  86580
gtctatttta cccgatggat tctttgctga ctttgttagt aataagtatg tgtactataa  86640
gaacaccaac gaagtaatat ataataaaaa ctttgaagat aatacaaaga gtgtagaaaa  86700
cacagaatac caaccgccag cagagtttgt acctaaagaa gattacaaaa aactagagag  86760
tgaagtagaa gaactaaaaa gaatgttaca agaattgtta tctaagaaag gataaatagt  86820
atggcactaa attttacacc tattacggaa aatagtacaa tagcagacct aacaaaacaa  86880
gttaataata taggtggtgt attaactgag gatagaaata tcttcgaagt aactgcagac  86940
ttacaattag atgtaagtag aacacagaaa gttaagttaa caacagataa agggttagct  87000
aaagatatag actataccaa ttacttaaga gatattaaaa aagtaggttt atattacata  87060
ggggcacgta cattagctac tatgtatgat aaaccagata tggaaaatat agatgtatta  87120
ctgcaagtat taacactaga tactgaggat agagtaatac aaatattgta tacattatca  87180
acggcggata gtaaatcaaa aatgatgcat cgattcgtta ctaactatca aacatcacaa  87240
tggcaagtag tacaaagttt acctaataat aaatatacat ctcatatagg tggaagtcct  87300
tttgatatta atacacaagg tacatattac gtgtctaata tgtcggatat gcctagtggt  87360
gtttatgagg gattcttaca agtttctata gataataatg ataatagaat gttgagatta  87420
acagatagta gtacaggaaa agaatatctt aatgttaaga aagagtatgg caattggggt  87480
tcttggagaa ctgatttaga tgtacaaaag ataagcaaat atcttgtatc taatgtaaat  87540
ggagatgcgg aaaacaataa ttactcatta tccgtatata cagcagataa tataacattc  87600
caacaagcta tagctaaaca tatcgaagaa acaagtaaaa ctgtttttac tttttatgta  87660
caaggaggtg ttgtagggtc tccatcttca gttagttgta gaggcgtatt catatcagat  87720
tcaactaact ttactaatct atatggtgtt tatactgcta taggtactga tggcagaacg  87780
attaatggtt ctgtaaatgg taacacatgg aatgtagcaa aaacattacc tggatttaaa  87840
gagctgtgga atggtgcaca taactttaaa gatacaaata aaaaagaaac catgtctgat  87900
tctatatcta actaccagta tgtagaagta tacacaagat acagagcctt acaaaacaca  87960
aaaggtacgg ataaaacagg tactttatgt cataagtttt atgtagatgg agatggtatt  88020
tacacatgtt caggttcata tgtatcaggt gactctaata ttggagtaga gtactatcga  88080
gtaactttat ctattactgg tgatacatgg acagttaaag atagtgcagt aaataataat  88140
aaagaccaat atgttacacg tgttgtaggt atctctttac catagactag gataattcct  88200
agtctttttt ttttcttgac taactttaat aaatatggta agataataaa ggactaaaaa  88260
gaaaggagaa tatatgcagt taagacaaca gaatatatat acatatgtag attttgatga  88320
aagtgacggg tatattaaag atatcatact taagcgtgtt cataaaacgt taggagctaa  88380
gaaagatggc tatcaacata gcttagcttt taaacgaggt gtgtgggatg gttatgtaga  88440
tttctatgat tatgctgaga acaaattccc tagtgggtta ttacctaaga tgataacatt  88500
actaggtgag ttacaatcaa gacataactt tcaatacgaa attattgatg aaaaatctga  88560
aagcttttta gctgaagaag atattgatga tgaaatacag ctactagata ataacgtagg  88620
taagattaca ttacgtgact accagtatga agcggtgttt aatagtttag tcaattataa  88680
tggtatatgt aagcaagcta ccaatgcagg taaattttgc cccttatagt agaaatatta  88740
taagtgtaac tcctttaatt cacggaaact ctctcatttg agacaatcat gagccaagct  88800
tagtaaatat caggaaggtg caacgactat tatgtacatc caagtggatg gaaacaggga  88860
gaacctaagt ctcattagat atggttaaga tatagtctga actttgtagg tgactacaag  88920
aaggttagga ataacgaacc taatcgtaac ataattgaaa acagaggttg ctagcggtat  88980
catagaccaa ctattaccac aactagaaaa aggagagcgt gtggctttct ttacaagctc  89040
taccgagatt tttaatcaat ctgctgaccg tttaagtgaa cgattgaata taccagtagg  89100
taaagtaggt tctggtaagt ttgatgttaa acaagtaact gtagttatga ttcctactgt  89160
taactctaac ttaaaagacc ctacagaagg agtgaaagta tctgctaaag taaacttaag  89220
taaaaagata gctaaagaga tactccctaa atttgaaggt ggtaaaaatc aaaaaaggtt  89280
acttaagtta ttattagaaa gtacgacacc taaaactaaa gtagagcaga atgtgcttga  89340
tatactgcaa gatatttatc ataattcaaa gacggatgct gaagtattaa tggcattaaa  89400
caatcataat gttattttcc aaaaagaagt aagaaagaaa aatcaaaaga gttatgacaa  89460
gtatcataaa atgcgtgaat ttctagactc tatagctgta atgatagttg atgaagctca  89520
ccactctaaa tctgattcgt ggtatacaag tttaatgtcc tgtgagaatg cactatatag  89580
aatagcacta acaggctcca tagacatgaa agatgagcta ctatggatgc gtatgcaagc  89640
```

```
attattcgga gatattattg taagaacatc taatgagttt ttaatcgaga atggctattc  89700
agctagacct acaataaata ttattcctgt tgctaatcct gatgatatag ataatattaa  89760
agattataga gatgcatata ataaaggtat tgtacagaat gagtttagaa ataaacttat  89820
tgcaaaacta acagctaagt ggtatagtca agataaagct acgcttatta ttattaattt  89880
tgtcgagcat ggtgaaatat tatccaatat gttgaatgat atgggcgtag agaatttctt  89940
tttacatggt gaaatagagt cagatatgcg taaacagaag ttagatgaaa tgcgtaatgg  90000
taaacttaaa gttatgattg ctacaagcct tattgatgaa ggtgttgata tcagtggtat  90060
tcgttcatta atcctaggtg cgggtggtaa atctttacga caaacactac aacgtgtagg  90120
tcgtgcgtta cgtaaaaaga aagaagataa tacaacacag atatttgatt ttaatgatat  90180
gacacataag tttttatata aacattctaa tgagcgtaga aaaatatatg aagaagaaaa  90240
atttgaaatt aaagaattag gaaagtaggt atgagtagtg actaagacag aaagaagatt  90300
atatgattac attgaaaaaa aatcaaaaaa taatacttat caattagcta ctaaaaaaga  90360
gttagcagaa gagctaggtg tctcagtctc tactttatct aaaaacctta aaagattaga  90420
gcaagataat aaaatcaatg ttgtttctaa aagaggaaat aaaggcggta ttattatatc  90480
actagtaaga gattatgata cagatagtct cttacatttt aatgacacag atgataatgt  90540
tattacttct aatctagaat acgctactga attacgaaat agattttttc ctagctacgt  90600
atatgaaaga aaagaaaata aacgtagaac aaaactagaa atggttcaat ataatgctat  90660
taaagataaa aacaggaaaa taatagcaga tatgaatttt tataataata gtttacctta  90720
tcctactaaa gatattttta atatgtctta tgaccctgag ggtttttata aagcatatat  90780
cttatgtaag ttatatgacc aatacgctat agcacatatg aatgctaagt acatacaaca  90840
tttaacatta gcaaatggta atgaagatgc agatagacat aagcatttat ctgagtacta  90900
cagaaagaaa atgttacaga atttatcacg agatagtatt tgtaaagact tctttggtag  90960
taagacattt aatacattct acaactttta ccttaagata aaggataaaa atattaatgt  91020
atttaagtat atgcaaaatg tttttaaaaa tacaacattt ggttttgaga ataaaacaca  91080
accttaccct atacctgcac caaatttttt tagttccgat aaatacctaa ctaattatga  91140
aaattatgta aaaggtatta aacgtggagt aaataaaaca aatagacaag taggagaagt  91200
agagtcttta attaagtcat ctgattacct attaaatcct gctgtagcac aattacatca  91260
attatataca acacctttaa atgaagagat acatgatatt gatacaatgt ttaaaacagc  91320
tttagatata gaagatacta tttatggtat atttaatggc atgaaacata ttatactttt  91380
atcatataat aaatatatag aacatctaat agaaaaatta cctagtaaac ataaaaactt  91440
attaaataaa tttattaaac aatgtattgt aaatgagtat tcacctacta caatacctaa  91500
caatgctaga ctatctatgt ttttaatgca aaaagagtat aaagcaaata ccgcagaatt  91560
aaatggtggt atagatagaa gagacttaat agatataagt ttagtaaaca ctacagactt  91620
aagtaaacaa gatattgtaa atatagaaca aacaacaatg aattatctac atatgagaag  91680
atttacttca acatcatata ttctacaaat gtatagtaac tacttaggat atgaggttaa  91740
tttaacagaa gttaagacta ttattgaaaa gtataattta tttgatgaaa taccattgac  91800
aaaagaaggt atgatagaat acaataaggt tattgatata gtaaaggatg acacatatga  91860
gtaaacgaat taaggagatt atcctacata aatctatgaa ggatatacat tttgcaagag  91920
aagtactaga taagttacct aaaagtctat ttgctacaga atcggaagac atgggttact  91980
tattcacagc tataaaaaga acagcacaca ttgctgataa aatgtcaaat gaatctttag  92040
ctattaaagt agaacagtta atgggtaatg ataaacaaga tgacgagaaa gtaacacaaa  92100
cattaaaata tttagatagt ttatatacag tagacatgaa taataaagac gattctgtaa  92160
actatgaagt agaaaagtat attaaaacag aaatgtctaa agaagtatta gttaagttca  92220
tagctgagaa taagcaagag gactcagata acttacccga attagtagag aaactaaaac  92280
aaatagaagt tagtgacatt aatggtactg atggtgaatt tattgacttc tttgaagacg  92340
tagataagaa gagggaacta ttaagtaact taagtattaa taaatattct acaggtttcc  92400
attctataga ccaacaaatt gaaggtggta taggtagagg ggaagtagga ttagttattg  92460
cacctacagg tagaggtaag tccttaatgg ctagtaattt aggtaaaaat tatgttaaac  92520
aaggcttaaa tgttttatat attgcactag aggaaaagat ggacagaatg gtattaagag  92580
cggaacaaca aatgataggt gtacaaaaga atcaattact taatggtgac ttatctttaa  92640
acacagatgc ttataataag atacaagaac actataaaaa gaacagacag ctactaggta  92700
atttttatat agttaagcat atgcctggtg aggtaacacc taaccagcta gaacaaatta  92760
tagttaatac aacaattaag aaagataaac atatagatgt tgttattatt gactatccta  92820
agcttatgcg taatccttac ctcaagtatc aaagtgaatc agatgcaggt ggtcgtattt  92880
ttgaagatat tcgaaaatta tcacaagaat ataattttgt ttgttggact ttagcacaaa  92940
caaacagaac agcttatggt tcagaaatta ttacaagtga acatgttgaa gggagtagaa  93000
agattgtcaa tgctgtagag gttgcttttg ccgttaacca aaaagatgaa gaatttaaaa  93060
atggtttctt aagattgtac ttagacaaag taagaaatag ttcaaacaca ggtgagagat  93120
ttgttaatct taaagtagaa cctactaaaa tggttgttag agatgaaaca ccagaagagg  93180
cagaagaaca taaacaaata ctagcagaac ttaacggtga agataaaagt agatttaaag  93240
aaaaacctaa taaagctgaa gctattaata attcttttgg aggtattagt ttctaatgga  93300
cgattttact aagctttata aaaaagtacg tagaacattt acacgtaata aagcagaatg  93360
ggattataca aatacagggt taagaacttt ccaattaaaa ggaactaatg tatgtgttac  93420
attactagat tctatagcaa ggaacaatac aacaggatat aagtataacg ttatgtcgaa  93480
taaagtacct gctatacctt gcaatacaca tcaagaagta atcaaagcaa ttgaatataa  93540
attaaaaaat tgagaaaaag ccttgacaat atgtttgtca gggcttatac ttttattata  93600
aacaataaag aggtggtata ctttgaactt aaatgaagca aaagtaaaat tagaaaactt  93660
taaagttatt aataaaaatg gatttataga aactgcgagc acaagatata ctgaaaaaaa  93720
attagaagat gtttcaacta acatatttaa tacattaaat aattacgtaa cagataaata  93780
tggttgtaaa ttgtttaata ttaaacctaa aaggagtatt atagagttag aattaacaaa  93840
caataaaatt aaacacttaa gaaagtagga tattaatatg gaattagaat taaataaaat  93900
atataacgaa gattgtttag aaggtatgaa aaagatacct gacaatagtg tagacttaat  93960
tgttacagac cctccatatt taattaatta tagaaccaag cggagaaaaa ataaagaaca  94020
tagatttgga aaagttattt taaacgataa taacgaacaa cttattatag attatataaa  94080
tgagtgctac aggttactaa aaaacaatag tgccatgtat atgttttgct catcagacaa  94140
agtagatttt tttaaacaac aattagagaa gaaatttaaa ataaaaaata tgattatata  94200
ggtaaaaaac aatcatatag caggagattt aaaaggttct tttggtagaa aatacgaaat  94260
cttattttta gtagtaaagg gcaaaaaaca ttttaatggg agaagattaa ctgatgtatg  94320
ggaatttgat agggtaagtg gtaaaaaaca attacaccaa aatgaaaaac cattagattt  94380
```

aataaaacaa tgtattatga agcatagtaa taaaggagat gtggttttag atgggtttat 94440
tggtagtggc actactgcta ttgcttgcat gagtactaac cgcaattaca ttggttttga 94500
attagacgaa gaatactata atttagccag tgaaagaata gaaaaacata aggagatact 94560
aaacaatgaa aatgacaata caggaactac aagataagac tgaattttta agacatgtaa 94620
aggtagatac ggaagaagca atggatatcc ttgaagatat attaagagga gagccttaca 94680
cagatgaggt atgtgaattg atacattttt attcaagtaa gctactaaat gagattaatg 94740
acaatcatat gtttaaatta caggagtttg ctaatcatga tgttatagaa attagtgaag 94800
agggagtaaa ataatgataa aattattaca gggggattgc ttagagttat tagatacaat 94860
tgaagatagt agtatcgatg ctattatcac agaccttcca tacaatattg caaaagaaaa 94920
taggttcaca actatgggca gagctggtat tgattttggg gattgggata aaaattttga 94980
aactacctta tggattaata aagctatacc aaaagttaaa aaagggggta atatcgttgt 95040
gttttgtgac atgagacaat ttacacctat tattgatact atggaagcat taggctgtga 95100
atttaaagat gttatacgta tggaaaaatc taatcctatg cctcgtaata gagatagacg 95160
atttattttt gatactgaat ttgctcttta ttttgttaaa aaaggagcta aatggacttt 95220
taaccgttta gatggaaaat atgaaagacc ttgcattaaa acaagtgtta cccctagaag 95280
tgaaaaatta ggtaaaggac acccgacaca gaagccttta tatgctatgg agtggttgtt 95340
agagcgttta actaatgaag gagatattat tctagactgc ttcatgggaa gtggaacaac 95400
aggtgtcgca tgtaaaaatt taaataggga ttttattggt tgtgaactat caaaagaata 95460
tttcagtatg gcacaagaca gattattaag tactacaaat taaaacaaaa cccttgacaa 95520
catgtttgtt aggggttata attttgttat aacgtactaa aggagggtac taatgaaatt 95580
tatatttttt acagatagtc attttcatat gtttacaaat tatagtaaac ctgatgaaga 95640
atatggtaat gatagattta aagaacaaat tgagacatta caaaaagtat ttgatttagc 95700
tagagaaaac aaagctaaag ttatctttgg aggagactta ttccataaaa gaaacgcagt 95760
agacacaaga gtatataata aggtatttga aacctttgct aagaatcaag atgttaaagt 95820
atatatggtt agaggaaatc acgatgctgt gtctaattct ttatatacgg aatccagtat 95880
tgatatattt gaaacattac ctaatgtgga agtaactaaa gatttacgta gtgactcact 95940
ttctagtaaa gtacaattaa ctatgtgtgc ttacggagat gaaacagaag aaatcaaaga 96000
gtatattaaa aaatcttatc aaaaagataa agtaaatata ttagtagcac atttaggcgt 96060
agagaatagt ttaacaggta aaggctctca cagattagaa ggtgcgtttg gctatcaaga 96120
cctattacca gaacaatatg attttattct tcttggacat taccatagac gccaatactt 96180
aaacaataat cctaaacata tgtatggtgg ttctctaatg caacaatcct tttcagatga 96240
acaagaagct aacggtgtgc atttaataga tatagataag ctaacatcaa cgttcattcc 96300
attagatact agaaagttta ttacagtaca aggtgacaat gtaccagata acatgaatga 96360
tttagtaaac aagggtcact ttattaggtt tattggtact ccagaacaag ctaaagtaat 96420
tgaattagat aaaacagaag atgaatctaa tgtacaagta caaatgaaga aagaatacac 96480
ggtagaaaag agagtcgacg ctgacgtgtc tgacagccct ataacgatta cttctagtta 96540
tgcagacaaa tattatccag aagcaaaaga tgagcttcta gagtgtttaa aggcggtgct 96600
gtagtatgat agatattatt ataaagaata ttaaaccaag tatagataaa tctaaaccta 96660
ttttacagtt cttacataat aaaagaacat atgatgtatg taatgttaaa aatattgatg 96720
atgcgatgta ccttattaac aaagtattag aggaagctaa ctacgctcat tattatacga 96780
gggttattga acaagaagat tgttatattc tagattatgg ttcacatcaa tgtttcttta 96840
aattgttaaa agaaggtggt acaaatggtt aagtttaatt atgtagagat gaataacttt 96900
ttagctattg agcatatcaa gctaaatctg gataagcaag gtcttgtact tattgaaggt 96960
attaataaaa caaatgatag ttttgaaagt aatggaacaa gtaaaacaag catgatatcc 97020
tctataacat atgcactgtt cggaaagact gagaaaggtt taaaggcaga tgatgttgtt 97080
aataagtata agaagaaaga cacctacgtt aagctttctt tcaacatagg taaagacgag 97140
tatttaatcg aaagataccg taaacataaa gaaaacaaga ataaggttaa gctgttctgt 97200
aataacaaag agataacagg ctctacaaat gatgttacgg atactcaaat acaagagtta 97260
tttggtattc cttttaatac atatgtaaat gctattatat atggtcaagg agacattcca 97320
atgttttcac aagctaccga caaaggtaaa aaagaaatat tagaatctat tactaagact 97380
gatatttata aacaagccca agaagtagct aaagaaaaag ttaaagaagt agaagagaaa 97440
caaagtaaag aacaacaaga aatagaaaaa ctagaatata aaagaaacct aaaacaagaa 97500
caatataata atgaagtaaa taaatataat aacttattag agcgtaagaa gcaagaagag 97560
gaacagttta atcaaaagaa gcaagaatat gaggataaat taaaagattt agataatcaa 97620
atcagtgaat ataagaatga tattcctagt attgaatctt ctgaatttgt atttagtgaa 97680
agctatacaa aagccaagca aggtatcgaa aagattaata caaatatcaa tgataaactg 97740
ttacctttac ttaaccaaga aacaacaaat aagaatacaa ctctaaatat gattaatcaa 97800
ctaaaacaat ctattaataa attagataca aatgaccatt gtcctgtttg tggttcccct 97860
atagataata cacacaaaat caaagaaaaa gaaaatttag agttacaaat tcaagatgag 97920
caagctaaaa tagcacaata tgaacataat gagcaggcta tagttaacaa gaaagaagag 97980
ttactagcta aatctaaaga attacaacaa tttatacaac aagaagatat agaaaagaaa 98040
aaacatgatg atgacattca atggcaatat agagaacaac aagaggtgta taataagatt 98100
agtcaattag aaaatactag agctaactta aaagaaccaa cattaaatga ttattcttat 98160
atagaagaac ctaatgaaga attacacaat aaagaactaa aagatattga caatactatt 98220
gacaaacata aggaaaatat agtacaatta gagagtaaga aaacaaaata taaacaagct 98280
gtagatgcat ttagtaataa aggattacgt tctgtaatat tagactttat tacaccgttc 98340
ttaaatgaga aagctaatga gtatttacaa atattagcgg gttcggatat cgaaattgaa 98400
tttcaaacac aaatagaaaa tgctaaagga gaacttaaag ataagttcga tgttattgtt 98460
aagaataaca atggagggga gtcttacaaa tctaattcag ctggggtaat gaaacagcta 98520
ggaaataatt acaaaaatat ataaactgtt tgccctgctt atagagtaat ctgtaagtac 98580
cagaggttaa atgctatgaa atcctaaagc tagttaaact gaaacataat ctgaaaagat 98640
aaatggaaga gttacgaaag tagaaaaaat taactagatg tactaaggtt aaatcctaag 98700
gtatagaaca atggaagtat agcagggaaa gtcctaaatg agcttatagc tcacatggaa 98760
gaccctcaac gactattccg tataggtgac ggaagtaaag ccacaagtga ttggtggaag 98820
aaaaatctct atcctagtaa aactaggaat aacaaatagt ctgcgcacgt aggaaaacct 98880
agtgtctaga attaactaga gaatatacag tagcgtgtat atttaaacat tgttaaaatt 98940
tataaataat taaattaaat tttatcctaa attcctgttg acatattcat ttctttatag 99000
tatattagta ctataaggag gtgaaatgaa tgtcaaagga aaaagaaacg tacaaatatt 99060
taaaattaag attagtacca acgaaagaac aagaatctaa aatattattg catataaacc 99120

```
attcaagagg attaagaaat attttagttg aagaaggaaa tagaatatta gatactgata  99180
acgagtatat ttatagagat acatttagaa agtatcttaa atatctactt aatttagaag  99240
aataccaatg gttgagagag gtatctaaag gctctatatc ttatttatgt gataagttat  99300
accaacagta taaaaggtat tttaataaag tttctaacaa acctaagttt aaatctaaaa  99360
gaaatgctaa aatgtattat tatccaagaa gtgatagtaa agataaattt tacttagata  99420
aaaataataa attgcaaatt gaaaaattag gtcgagttaa aatatctaaa ggtactttaa  99480
aatctaattt aactaaatta aaacttatag agaaaaatga tagattaaga caatctatta  99540
ttacttttga tggaaaatac tggtatatat ctatttcata taaagttagt gctttaagtg  99600
agaaccaagc taaaaaagaa ttaactaatg aagttatagg tatagactta ggtattaaga  99660
cattagcaac ttgttcaaat ggtaaatctt ataaaaatat taataaaaca aaaagagtta  99720
agacacttga aagaagatta aaaagaaagc aaagacaact tttacgtaag tatgaaataa  99780
ataaggatta ctttactatt tgtttacttg atgagaaggg taaacctaaa cgtaataaaa  99840
gtaatggaga agttattcaa aagaacataa gaaaaacaca aaatattatt aagttagaac  99900
aagaaattaa actcttacac agaaaactta ctaatatacg taaaacttat gtacatactg  99960
taacaaaaga acttgttgaa gaattaccac aagaaataat catagaagat ttgaaagtaa  100020
gtaacttgat gaagaataaa tatttggcac caagtattgc taaagtaact tggtatcgat  100080
ttagagaata tcttacctat aaatgtaaag atagaggtat attacttaca gtagcaaata  100140
ctttctaccc ttcaagtcaa ttatgttcag tgtgtggtaa tcgtaaaaat aagcaaaaca  100200
aacttaatct taaacagaga atttataatt gtgagtgtgg taatacactt gatagggatt  100260
ataatgcaag tcttaacttg aaaaactata gatactccaa ttggtatcat gaaaatgtta  100320
atctcaagct aactaaaaca gattaacctt atgtacctgt ccgtaacagg gaattgaaag  100380
cctttggagt gctatagcaa ctttagtaga agtcataaaa agtaattcta tttatagaac  100440
gaaagatttc gaggaagagt acgtagaaga aggaataaaa tttatagtaa ttaagttaat  100500
tatttataag ttttaactta cggaacaaaa acgtattgat ttagctatta gttttgctat  100560
ccaagactta attatgagta aagaagatat atctacaaat atagcccttt acgatgaatg  100620
ctttgacgga ctagacacta ttggttgtga gaacgtagtt aaactactaa aagatagact  100680
aaaaacagta ggtactattt ttgttattac tcataataag agtctagcac ctttatttga  100740
gaatacaatt acggtagtaa aagaaaatgg tgtagctaca ctaagaaagg aattaaataa  100800
tgaaattaaa gattaaagat aaccagtttg catctttaac agtaaattat acaaacaatg  100860
caaagttaca tatagataat attcctgttt ctactttagt agactggtac cctttaagta  100920
atgcatacga gtataaagct agtaatgact ttggatatat tgaactaaag agattacgct  100980
ctagcttacc tgtgtcttat gggttaactc accaaacctt atataaatgt gaaactgtta  101040
aatgtaaatt aggattatgg tataatgaaa aaataaaaga agataatgag aaaattattg  101100
agaaagctaa gttgtacggt ttacctacta tagatgaacc cttcacaagt aaagatgtaa  101160
agcaaggatt tagtgactta ggtgttattt tccaaacgct aaaaacaatc agtacaaacg  101220
agtacttaaa agataaaaca attgaagaga ttaacacctt tagtaagaaa tcagaggatt  101280
atcaattaaa tgaagtactc aagtacagta caacactggt agatgatact tatagtgact  101340
taagtcaaat ctataatatg ttactattaa tgaagaaaat tgtttctata taggaagtga  101400
ctgaaaatga ggtttgaaga ctttttaagt caagagattg gaacacctaa agagaatact  101460
gtaggagaat tacgatattg ttgtcctttt tgtagggaac agaaatacaa gttttatgtt  101520
aagcagtctt tagactctac taatggtatg tatcattgta agaagtgtgg agaacatggt  101580
aaccctatta cttttatgaa gtcttattat agtattacag gtagacaagc ttttgagtta  101640
ctagaaacaa agaatattga tatacaattc tcaccaacat tagaaatata taacacagat  101700
ttaactgaaa gtgagaaatt attactaagg cttaatggat atacaaaaga taatagtagt  101760
ataaaatcaa aagcacctga actacctata gggtttaaat cgattaaaga taacttaaat  101820
aataaagaag tagtaccgta cttaagatat ctcaagaata gaggtattac actacagcaa  101880
atcctagatt acaacatagg ttatattaca gatggttatt gttattctta tggtattaat  101940
aatgagaaaa agaaaatagt acttagaaat agtgttatat tttttactta tgataatgaa  102000
ggtaagtata tatattggaa cacaagaagt attgaaacta atccatatat taaatctata  102060
aatgcacctt ctaaacctaa tgaatatggt aagagtgatg ttatatttaa tttaaatata  102120
gctagtaaac aaaagtttgt cgttataact gaaggtgttt ttgatgcgct tacctttgac  102180
agatacggta tagccacttt tggcaaacaa gtttcaaaga cacaagttaa caacctcatt  102240
tcaagtattc ctaaagaaac acctatatat attatgttag acacagacgc tacagacttt  102300
agtattaatt tagctagtaa acttatcatg catttaatg tagtgtactt agtacctcat  102360
ggtaatgaag acgctaatga tatgggtatg gaaaaagctt ttagtacttt gaaacacaat  102420
agatttttag ttacacctga aagtactcaa agttacaaac tacaacaaaa gttaaaactt  102480
taatcctgta ctataatgta taatgtgtta taatacatat ataaaaataa aggaagtgtt  102540
agtgtggaag agaaagagaa agatattcta caatttgtag atgaatatgt tacagcatta  102600
cgtgtaggta atgaacagcg tatgcaccaa ttagaagagt taggcaaaga acaaacagca  102660
actttaacag atgttatgaa agctattact aacttattgt taggtgttaa taaacaaatg  102720
gttgacctag agcaaaatac agagttaaac ttaaacattc taattgatgc tttatacaaa  102780
gctgagttag ttaacgatga cgtattaaaa tatattgagg aagcaattga agaatcaaaa  102840
gaaaaggatg aagaataatg gaaaaaaata ttagtacaca tacaaaaggt atttcacaaa  102900
aagatatgga catgtggtta gaagctatta cacaaggaac agtagaaggc aaggaattaa  102960
ctgaggacac tgctaagcaa ttacaccgta ttggagcacg tagtgtatca ttagatgaag  103020
ctactagaat tgcacgagca attaatacca ttacagttca agagtatgca tctgctttta  103080
atgatgcttt taatgctatt gatttgttaa tgattgttat ggaagataac ctagatgtaa  103140
ctactgagca agtagagaag gcgcaactta aattaaaaga aaaacgtgaa aagtatttag  103200
aagaaaaaca agaagaagta agaaaaaaac aagaagagca taaagcaaaa gaagataatg  103260
aaaaagtagt gcagttgaag aaacatgaca aatagtaaaa aaaaaggtga tgtattcgaa  103320
agaaagattg ccaaagaact ttctgattgg tggggttatc cttttagtag gtctccacaa  103380
tcaggaggtg catcatgggg agctaacaat aatgctgtcg gtgacattgt agcaccttta  103440
gagtctaatt ttccattagt tgtagagtgc aaacatagag aaaattggat tatggacaat  103500
gttttactta ataataaaga acctcataca tggtgggaac aagttatagg agatagctta  103560
caagttaata aaactccttg tttaatattt acaagaaata gagcacagtc atatgtagca  103620
ttaccttata tagaagatgt atatgtaaag ttaagagatg gagagtaccc tattatgaga  103680
acggatttta ttgtagaaaa tgttagaaaa gataaacatt tttatgatgt tcttataact  103740
acgatagatg ggttgactaa cttaacacct tcttatatta tatcttgcta caacaaaata  103800
gagattaaac catatagagt tgtcaagtct aaaatatcta aagttagtaa aaaagaagat  103860
```

-continued

```
aagttgattg atgatttact tgatggtata taaggaaggg atactagttg attacacaaa  103920
taaaaaaacg tgatggttcc gttgtagatt atgatttaag taaagttact aatgctattt  103980
taagagccaa ctcagaaaca gaagaatata ttgaagatgt tattgattct cttgtagatg  104040
acgtagactc tttactagaa gaacaagaca ctatcattac tgtagaatta atacaagata  104100
tagtggagga agttttattt agtagtatgt ataaagatac tgctaaagct tttattttat  104160
atagggataa aaagaaaaga gagcgtaaaa gagacctatt caaaccaaga aaagaattaa  104220
aaccctatga ataccctgaa ttattagaat ataaagatgc tatacgccaa agttactggg  104280
tacacaccga gtttaactat acatcagata ttcaagatta taagaataac gttaaataca  104340
atgagcaaat gaccattaaa aaagctatgc tagcaattgc tcaagtagaa gtagcagtaa  104400
agactttctg ggtgacctta tatcatagaa tgcctaaatg ggaaacagga gctgtaggtg  104460
caacttttag tgagagtgaa gcacgtcatg cagacgctta ttcacattta ttagagattt  104520
taggtttaaa tgaagagttt aaaacaatcg ataatatacc tgctcttaaa gaacgtgttg  104580
atgagttagc aatgcatgta aaactaagta agagtgagga tgatagagac tacgtattat  104640
ctgttttatt attttctata tttattgaac atgtatcttt atttagtcaa tttttaatta  104700
tgatgagttt taataaatat aaaaacttat ttagaggttt atcaaatgct attgaagcta  104760
catctaaaga agagcaaatt catggtttat ttggaacaga aatcattaat attcttagag  104820
aagaaagacc tgagtggttc aacaaagaaa tggaagatgc agtttacaca gcgtgtaaaa  104880
aatcttatga atcggaaaca cgtttacttg attggatgta tgaagatggg gaactagagt  104940
tcttacctaa gaaagtagta caagaattta ttaaaaatag acttaataac tctctagtag  105000
ctgttggata taataaactt tttgatgttg atgaagagtt actaagtgaa gtgtcatggt  105060
ttgatgatga agttattagt actaagttaa cggacttttt atctaaacgt tctgtaaact  105120
atacaaaatt tagtaattct gtaacggaag atactatttt ttcaacggaa tctgattttg  105180
aaaatactgg taaacgagtt actaaagata aagtaaacgc tattttaaga ctaaaaatga  105240
tataaaggca gtgtatatag atgagtaatt ttgaatggtt gaataatgat tctagagttt  105300
ttctagaacg tggttattta agtgatggtg aaacaccaga acaaagaatt aaagatattg  105360
cagattatgc tgaagatatc ttagatattg atggtttttc tgacaagttt tatgattata  105420
tgagtaaagg ttattattcc ttatctagtc ctatatggtc taatttcggg aaagatagag  105480
gatttagtat tagttgtttt ggtagttggg tagatgatac tataccatcg atacttaata  105540
ctgctagtga agtaggtatg atgagtaaat acggtggtgg tacaagtggt tacttcggta  105600
acatcagacc tagaggctca gaaatcactg ataatggact gacaagtggt tccgttcatt  105660
ttatgaagct atttgagcaa atgacagata cgataagtca gggtagccaa agaagaggaa  105720
gatttagccc ttatctacct atagaacaca aagatattga cgagttttta gagattggta  105780
ccgaaggtaa tccaattcaa aacttaacac atgcggtaac agttactgat gattggttat  105840
tagacatgat taatggggac aaagaaaaaa gaaaaacatg ggctaaagta ttaacaagaa  105900
gaacacaaat aggataccccc tatatcttct ttcatgataa tgcaaatagt aatacagtag  105960
atgtatataa agacaaaggg ttaactatta ataattctaa cctttgtgtt gcaccataca  106020
ctaaaatact gactgacgag ggatacaaag aaatagataa acttaaagac caaaaagtta  106080
atgtatggaa tggtgaagaa tggtctgaag taacagttaa acaaactgga gaaaaccaag  106140
aaatgttaaa agtaaaaact aatagtggtt ttgagttaga ctctacacct tatcataaat  106200
attacgtatt agaaacaact aaatcaggta aaagagcaag aaaaaataaa tataaagaag  106260
ttagagctaa agaccttaaa gtaggagata aattaattaa atttgattta cctgttattg  106320
aaggtcaaaa agaactaaat tttgcttatg ataatggttt ctttactggt gatggaacac  106380
taaatggtaa aaatcaagtt atctatttgt acggtgaaaa gcaaaaactt attgattatt  106440
ttaaatctat agacaaatgg tcagaaagta aagaacagga tagacatgta ggtcttacta  106500
aaaaattaga agataaatat tttgttccaa tgaacgagta cactattgat agtagattaa  106560
aatggttagc aggtttctta gatgcagatg gtacagtaac aaataataat ggttctcagt  106620
ctattcaagc aggttcaatt aacaaagagt ttttaaaaga tgtacaatta atgttgcaaa  106680
cattaggagt agatagtaaa gtaactctag gtaaaaaaga gggaacttct atgatgccag  106740
ctaatgatgg tactggagaa tataaagaat ttaagacaaa agagctatat agaatattaa  106800
taaatggtaa ttctttatat aaattaaatc aattaggtct tgaatgtaat agacttacat  106860
gggaaacaaa agaacctaac agagaatgtt ctcaattcat aaaagtaaca ggaattgaag  106920
aaattgaaaa aacaatggat actttctgtt tcacagaacc taagagacat atgggaatgt  106980
ttaatggtat tttaacaggt caatgttctg aaattatgtt acctaataaa gaagattggt  107040
catttgtatg tgacctatct agtatgaacc ttgttaagta tgatgagtgg aaacacacgg  107100
atgctgtaga gacacttgtt tacttttag atgctgttat gtctgagttt attagagact  107160
tagaatatct aagagactca gatgaaaaag ataagcaaga agcatttaaa tttatggaga  107220
gagcttataa cttttctgtt gagaacagag ccctaggaat aggcgtgctt ggatatcatt  107280
catacctaca atcaaaactc atacctttttg aaagtattag agctagccaa attaatgaag  107340
agatatttaa attattaaaa gaaaaaactt ataaagctag tgagcagtta gctaaacttt  107400
atggagagcc ttctatttta aaaggttatg gtagaaggaa ttcgtgtttg atggcggtag  107460
caccttaatt tatagggcgt atatggatta acatatatga taacactctt gaatttctga  107520
aaagcctaag tgtgtaaaca taaggtaatc agaagctaag atttatttat agttaacttg  107580
acaaaaacaa atatatacat tatactagtt actaagaggt gataataaat gtggaaaaat  107640
agtattagtt ttcctaggct cgaagtaact aaggatggaa gagtaagaat gtggaataaa  107700
tcatggaaaa gatatgtaga aaaaagacat aggtatgata aagatggtta ctcaataatt  107760
tctacaagaa aagaagatgg tacatccaca tcagcaagag ttcatagatt agtagcagaa  107820
gcgtatatac caaacccata caataaacct gttgtaaatc ataagaatgg gattaaagat  107880
gataataggg ttgaaaattt agaatggact actatatcag aaaatactaa acatggttat  107940
gatgttttag gtgttaaaca cgctaacgct caactaattt tagtctactt agatggcaaa  108000
cctttttcta gttatgactc cttaacttta atgggtaaaa cattaggtat aaatagaaat  108060
cttatacgta gagtagaaaa agaaactgat gggtacatct catttaaatg gatagaaaaa  108120
ccatataaag tacacaataa agatttttgg aaaacatcaa gaaaattaaa tacgagaggc  108180
tcttgttatg ttgtaaataa tgtatactat aatagtgcaa aaaaagctat ggaggctctt  108240
aaagtaagac aagatgtttt ctataataga cttaaaaaag ataaaaatgt atatagtgta  108300
agtattaaag agtacttaaa aaattgtcaa gatataaata gataaagttc aacgactatc  108360
ctgttgcggg gagtacactc aagtgagtgg aagtgggagt ggtcttacat ttagtaagat  108420
gtgatatagt ctgctctcta tggaaacata gagctgttat taaattaacg catgtaaagt  108480
aacgaactac atggaacata aaggacaaca agttcatcat ttatcctagg tcaagtttct  108540
aaatcaattg agccttttat gagtaattac tacgttgtag acactgctaa agtaaagaaa  108600
```

```
actatgatta atccttacct taaaaaatta ttaaaagaaa aaggaaaaga caataaaaaa  108660
gttattgaga gtatcaggga taatgatggt tccgtacaac acctaacctt cttaagtgat  108720
tatgaaaaag aagtatttaa aacatatggt gaaattaatc aatataatat attagaccaa  108780
gcttctacaa gacaaaaata tattgaccaa gggcaatcta taaacattat gattaatcct  108840
aagcatgtta cagcagagga gttaaatgaa ctttatctct ttgcatggtc taatggtatt  108900
aagtcattgt attatcagca tggtacaaat gcatcacagc aattcaattt atctaaaatt  108960
tgtattaatt gtgaagccta aagaggtgac taaatgaata aaaaagaagc attagaacta  109020
ctaaataaag tagaagttat atttaaatca aatgatattt tctcacaagt aagtaatgta  109080
caagacccta ttaagatgtt taatagggag gacgatacta aagcagatag taaatcaagt  109140
aaatttcagc tagagtttat ttataataca tatgtgtata ttcttatata cgaaggtaca  109200
ttgaagctat ttaaagctga tggtacggag cagttaacac atgtagctga tattgaaaca  109260
tttaaagata ttattgacac actagaaaag gatgatacag aaaatggaaa aagtgaatag  109320
tttattagaa ttaaatacaa caattagaca aaaacaggat gttattgtca tggttacaca  109380
agatgagtgt gctaaatgtg aaattttaaa aagtgtgatt cctctttttg aagcagaagg  109440
ggatattact aaaccggttt atgttattaa cttagatgat aaagatgtag acagagaaaa  109500
agcggtcaag ttatttgata tcatgagtac acctgtactt attggttata aagatgggga  109560
acttgctaag aagttcgaag accaagtaac acctaaaaac ttaatggaat tagatttact  109620
ttaatttgta attacctact acttatgcta tacttatatt agtaaaaggt agtaggtttt  109680
ttcatgaaag gatgaatagt tatcgcaaaa aataaaacat taactatata taatagtgat  109740
agatatttta atatacatgt aaaaaacaaa gatgaattat ctaaagctat taaagttaca  109800
actttaaatg aggatgatat agaaaaagat atggatatct tagctaataa atcaactagg  109860
tatatactaa gagacgataa acattacatg ctatttaatg agaagtataa caatgataag  109920
ttgattgaaa aaatatgtaa gcatggtgga caagtaacat actataccga ttcagtagtt  109980
ccttactatg tgcttaaaga cttatcagcc caccctaaat cctcagttgt atacagaatg  110040
cgtagtaaat tcagtaacaa agagatggat aatatagctt tgagtttcat gggaacaaaa  110100
gtcattattg atatttcagt tgtatttcct tacgtcaatc cttacgatat tattagaagt  110160
ttatacgatg ttaaaacgaa tgtagacgag gttcatctat cattccctcg tattagttct  110220
gtagacgcta aacaaggtaa gtactatacg tatgataaag aagcttataa actaaatcct  110280
gagtatatac ttgattttgc agataaatta agagtttctt tgtccgtgtg gaaaatgtat  110340
atctatattc ttgctagtaa agaaaataaa gattatgaaa taatagaaga cctacttact  110400
gaattaaaaa gacaaagaaa gattaagatt taggtgattt tgtgagtaca gcaaatagaa  110460
gagatatagc aagaaagata tctgagagta cagggtacta tatccaagac gtagaagaga  110520
tactagaggc agaaacaaaa gctatttctg aattgttact tgaagattat gataaggtaa  110580
agaatcataa gtactttcaa atagaagtag tagagcgtaa aggtaaaaaa gcatgggatg  110640
gattaaataa aacatacttt acattaccta atagaaaagc actaaagttt aaacctttgt  110700
ctgaactaga taaagttata gacgtactaa acaaagagga ttaaattcct ctttttttat  110760
tgactattat taatagtcat gttatactgt atttaagtta aagaagggat tggtaatgat  110820
atgaaagttt taattttata cgactatatc agggaggaac acttttcagt tggtagtgat  110880
ggtagtgtta agaatgtatt actaaataca cctaatggta gagtattaaa acaactatta  110940
tctaatattt ctggtattaa tcgagataga agtacaaaag attatgatat tgagttttta  111000
tatcctatgg tgcctacacc tattaagaat aattatggta aaacaattaa gtaccaagac  111060
gttaagttat ctgaagttaa accttactat gaaagaatga atcaaataat cataaacaat  111120
aagtacgata ttattattcc tttaggtaag ctaggggtta aatatttatt aaatgtatca  111180
gctattagta aagttagagg tgtacctaat aaagtaacta ttactagtga agataaaaaa  111240
catgatgttt gggtattacc tacttatagc atagagtaca caaacgttaa taagaatagt  111300
gagcgtcatg tagtagtaga ccttaagtta ttaggtaagt ttgtagaaca aggtgaagac  111360
gtatttaaac ctaaagaagt taagtatgaa cttgttacaa gtattgagcg tgtaagagaa  111420
atatttaata aagaagtaaa gaatgataat catgacggtg tagacattac cgcatgggat  111480
ttagaaacta actcacttag tcctgataga gaaggaagta aacccttagt actatcaatg  111540
agttgggaga atggtcaagg tgttacaata cctttatata aatcagactt tacttgggag  111600
aatggacagc aagatattga tgaaattctt tccttactaa aagaatgggt agctagcaaa  111660
gaagacatta aggtactaca taatgctact tatgatataa atttccttat ggcaacgcaa  111720
ggtttcacaa actttgaaaa taatcaagac actaaggtag gttggtattt agctgtaaca  111780
caagaacaag cagagtctct aagattatca gaccttgctt acgaagtaac agatgtagga  111840
ggatatgaca aacccccttga agattttaaa gagtggtatg tattgaagct actacgattt  111900
ttatcagata aactaaaaga aattaaaaaa gaaaataaaa aagttactaa gaaagaatat  111960
aacataaaag caaatgagta tgatacttgg ttgaaaaata aactcgataa catcgatgta  112020
gaactaacag atgaagatag gtattatggt atcacagaag agcaaaaaag atatttagag  112080
ttaaaactaa cacctgaggt tattacaaag aatatgctta tggattctga atttaaagaa  112140
gtagccgaat catcacctga gtatatgagt ttatctaaca aagctaaaga ttatgtatta  112200
ggtacatcta ttaatttaat taacacgtat aaagacaata ctaaagttat taatgaggta  112260
gatggaggtg actttaatta tgattggatt ccattagagc ttatgcatcc ttatgccagt  112320
ggtgataccg atgtctgtag aagaatatac tgtgatgtta ttgaaaagtt aaaagaacaa  112380
aatagaccta aagcattgga cttaatgtca ataagttacc ctagattaat tagaacatta  112440
gctagaatac aatcaaatgg tttacattgt gacctagaat acatgcataa aaatgatgaa  112500
ttttatatta atgagatgga aaaaacccac caagaaatta gagaacattg ggctatccaa  112560
gaatttgagg agactaggta taatttatac caattagcct tagcagaaca tgagaagaaa  112620
ccatctgata gaaataaaga aatacatgag tatagagcta aatttaaaga tgaaggttgg  112680
aagtttaaac caagctcagg tgaccataaa ggtgaagtat tgtatagcat tttaggtata  112740
cagttacctt atagtaaaga gacagttaag gataaacctt tcagtaatgg tactaaagaa  112800
gatgagttat catggaaaga ttacaaaaca gatactaagt ctataaagat ggcattatct  112860
ttggttgaga atgaagataa taaaaagcta ctagacttac ttatttatta tgcctctttg  112920
caaactaaaa gaaattcttt tactaagaaa ttacctaaaa gagtaaataa gaatacacat  112980
aatttacatg gtaactataa tagtacagga actgcatgta ttacaggtga ttctttagtt  113040
attactgata aaggtataaa aaaaatagaa gacttatcaa ataatagaaa agaaaaagta  113100
tttagtagta ttgatgtagg tattgttaat agacagggaa atttagaaaa agcttcacac  113160
ttttattata gtggtgtaag aaatggatta aagattactt tagaagatgg tactacatta  113220
actactactt taaaccaccc cttattacga aataattatt atagtaatac tggtagggtt  113280
ctaaataaaa caaaacaaac aactaagcat ttactagata atgattgggt tgtagctgaa  113340
```

```
gatttaaaaa taggtgatta tataaaaatg tcttataatt ctaatcttta taataatagt  113400
tatattgatt tagatactaa agattttata tatagtaaag aaaaaagtat tacaaacaca  113460
aaaagctata cactacctaa ttatgtatct gaagattttg ctgaatggta cggtatgtat  113520
acagctgatg ggtctttttc tacaaataac ggttcattca gtataagatt aactaatagt  113580
aatcttgaag ttaggaatag attctttaac ctaactaaag atttatttga tattacacca  113640
tactacatta gtaataaaga tagaagtgat tctattgaat tttcttcaat tggtttaggt  113700
agatggttag aacatatttt taatatgcaa agtaaagcat taaataaaga aatcccacaa  113760
caaatattag atagccctaa aagtgtacaa caagcatttc ttaagggttt aagtttagat  113820
actgcaacag aaaagaaaaa gtatcctagt ttgtactata atactgtatc taataaaatg  113880
gctttacaaa taagaacaat gctaatgaat atgggtatct attgtaggta ttctataggt  113940
aaagtttata aaaatattaa tagaaaagta caaaatgaat gctattctat acaaataact  114000
tatgatgcat tagataaatt ttacgatgaa atagggttta ttgaaagtat taagcgtgat  114060
agagtaaagt ataaatcaga aaatctaaag gcattaggca gaagaaacgg tattcttta  114120
tatgataatg ttttattagg tagaataaag aaaattgaaa aaataaaaga tatggaattt  114180
tttgatttac atgttcctag tagccattca tttgtagtta ataatattgt aaaccataat  114240
actagcaggc tttctagtaa caaccctaac cttcagaatc ttcctgctca tacatctgat  114300
gtaaataagt ttgattatca ccaccctatt aaacgttctt ttatctctag atttaaagat  114360
ggtgtaattt tacaagccga ttacagtgcc ttagagatgc gtattacggc actatataca  114420
gatgataaag aaatgttaga gatgttttta acaggacaag atattcataa aaatacggca  114480
agtattatgt atggtaaaag tatgaaggac gtaacagcag aagaaagaca agccagtaaa  114540
gctgtagcct ttggtttaat ttacggttaa caaaatatag ccgtagtaaa actaggtaaa  114600
cctattgagt atagggtgta tagttcacgt taggagctac aggaaatggt agttaagaac  114660
tatgctaaca gggaaggctt taaaatgcta atcctgtgta gaataattta agtgtaattt  114720
aataagtaag gatgatttaa atagaattta aaataggaga aagatataat cacaataagc  114780
tatattctaa attagctcat gtatggtctc atatgataga tagatgttat aatcctaaat  114840
gtaaggaata taaatattat ggattactag gaataacagt agacgataga tggcataatt  114900
ttaataactt tcttaaggat gtagagttaa ttgatggttg gagtttagag aagtataaaa  114960
atggtgagtt agtgttagat aaggatatta aagaactagg taataaagta tatagcttag  115020
ataaatgtaa atgggctact agagaagaga acttaggatt tgtaccttca agaagtaaaa  115080
agatattagg tatagaccct acaggtaaag aatatacatt cttcaatcag tctaaatttg  115140
ctaaggaaca taacttaatt caaagccata tttctgcagt tcttagaggg gaaagaaaac  115200
atcataagaa ctgggttttt aaaacactac aagaatataa ttatcaacct gtagaaaacc  115260
cttctaaact ttatgcacct cactatgttg cttataagaa tcatgtggaa attgattatg  115320
atagagtaaa aactaagcta ctaaagagac taaatatacc tacgtcaggc actaacttta  115380
gaaaaatgga aaccggtgaa gattgttatg ggattacatt caaaatagag aaaagagaac  115440
gatttgatta cacttaaaca cttaaattat tttatcgaac gactatcaaa aggtgagctt  115500
tacgccgaga gggcttattg caatataacc gagtagagta catgtagctc atacctacat  115560
ggaatagcct agaagtagat agtaacgtat ttacttaaga tatagtctag tcccctaata  115620
aatatcggga aaccgagggt ataaacggag tcagagtttt cgtttgcagg taaaaataat  115680
atgacagttg atgaagctac tgaaatattt gataagtttt attctaataa acctgctatt  115740
aagaagtcta tagatgaaac tcatgagttt gttcaaaaac atggatatgt agaaacaatg  115800
aatggacaca gaagatatat acactcagca caatctagag ataaaaagat taaaaatgag  115860
ggtcttagac agtcctttaa cacgattatt caaggtacag gtggttacct tactaacatg  115920
gctattactt atattgacga ctttattcaa aataagaata tgaaatcgaa gttagtagct  115980
actgttcatg atagtattgt agtagactca cctcctgaag aagttaatat tatggctaaa  116040
gttattgtcc atgtaatgga gaaccttcct tatgatttct taaaaataaa aattaatggt  116100
gagttaagac agtaccctat agatgcagat atagagatag gattaacata taatgatatg  116160
gtagaataca acgaagagtt aataaagcaa tttaattcgt ataaaggata tattaagtat  116220
aaattagcct tacaacaaat caaagactac tatgaatcag ataaactaac tgaggagcaa  116280
tacaaacaaa aaacggaata tattaaaaat aatattgaca gttttaaagt tatatagtac  116340
agtaaaatag aggagggtat tatggagata catttagata cattagattt caatgagtta  116400
accttaaaag ataacaatgg aaacactcag acttttaata tccatgatga actaaaactt  116460
agtgagtata caattcaaga cgaaatgtac caacagtcgt ctaaatttgc atggtgggct  116520
tcattaaaag agcgtgtgag taattatgcc gaagcagagc aacgtaagct agaaaaaata  116580
ggagctcaac ttaatctaca aattagagct caatatgaac aacagggaaa gaaacctaca  116640
aaagaccaag tagagtctgc tgtatttctt tctgatgaat accaacagca agcacaggtt  116700
gtagaagcat ggaactatag agaaaaacaa ttgcattaca ttgtaaaagc ttttgaaaca  116760
cgtacaacta tgttagtaca gattagtgcg gaactaagac aaacaaataa aaatggtggt  116820
attacaaatc catttacaca ttaaaaaagg agaagtatgc taaatatggc aagtgaagtt  116880
aagaaatatt ttttagaatt agctgataaa aaaagactag catacatgga agagcacggt  116940
atagacttta tcgttaatag agaaaggtat tcttggaaaa caaataaaaa aatgtttacc  117000
atcttatgaa gaattgataa aagaaaaata aagtaaatgg tacggttgac agcaaaggaa  117060
aaatatgtta tactaattaa gtaattttta aaataaaagg agaaaagata ttatggattt  117120
taatcaattt attaatcagc aatcagaaaa gctacaatca agtggttttg acaatgaggt  117180
agaagtatac aagccaaaac aacccgtttt gcgcttaggt aaagtaaaag atgctaacgg  117240
taatcaaatc aataaagagt ctgcacttgt acgtgtacta ccgcctgtag aaggttctaa  117300
tgagttcttt aaggaattta gaacattagg tattaactat gttaaaaaag acggggcaca  117360
aaagttctct atgcttactt tacccgagaa agttaactca tctgttgtag acctttatgt  117420
aaatacatgg ttaaagcaag gtgtacaatt tagtaacttc cctaataaac ctgcacgacg  117480
agcatatatt catgtgattg aatactttaa tcaaaatggt caattagttc ctaacacaga  117540
tgaacaaggt aatgttatta ttcaacctat ggagctatct aatacgggtc tgtctcaatt  117600
gattgaccga ttaaaagata aaatgttatc accatcacct actgctacac atagttttat  117660
ttcagcagat gatgcattcc ctattaatat tgctaaagct aaaaaaggtg aaaaatcatg  117720
gaatgtaact gtttatccta cagtaaaatt aggtgcttta cctcaaggtt gggaacagca  117780
gttatctgat ttagataagt tagctacacc aacagaggaa aataacccta actttgtaaa  117840
ctggttgatt aacaatgtta ataacacaga agtttctcat gataatttta aattcaatag  117900
agaaacaaac acattaggtg aagaaccatc aacgcaagca cctacgcaac aaagcataga  117960
acagcagttg ccagataatt taggagggca aaataacaca caaccaaact ttaataatgt  118020
acaacaacct gtaccacagg taccaccaca acaaaacaca caatttggtc aaggaacacc  118080
```

```
tgtacaacaa gaaccacaaa cacaaagtaa tccatttgag aactttgatg caaacaatat  118140
cgatgattct caaattccat tcaacacaaa tgaatcaaca ccagaacccc ctaaacaaaa  118200
tcaacctaaa agtgtagatg atgtattagc aggtttagat ttataataat tttatagagt  118260
gctaggatag cactctttta tttaaatttc acataaaagg atgatataat ggttagagca  118320
aaaaaaggta aagaagtaga cattacaaat ttaaatacta ttgacttagg taaagagtta  118380
ggtttaactt tactatcaga tagtaataga gcagatatta agaatatcat tcctactatg  118440
attccacaat atgataggat tttaggtgga ggtattcctc ttggtagatt aaccgaggtc  118500
tacggattac aagcctcagg taaatcgacc tttgcagtgc acttgtctaa aatatcaaca  118560
caactaggag ttattacagt atggattgat gttgaaggta ccgctgataa tcagcgtatg  118620
gaacaactag gtgtagatgt atctaaattg ttctcagtac aagctggtga aggtagactt  118680
aaaaatatta ctgaactatc agtagaaact gtaggtaaag agttagaata ctggattgat  118740
acatttaatg agaaagcacc aggtgttcct attttattta tttgggactc attaggagct  118800
acacgtacgc aacgtgaaat tgaaggcggt attgacgaaa aacagcttgg ctcgaaagcg  118860
acagctactc aaaaagtagt aaatgctatc tcacctaaac ttaatgatac aaacacaggt  118920
ttaattatca ttaatcaagc acgtgataac ttaaatatga gtaaccctta tgatgaccct  118980
attaaatcta caggaggaag ggcttttcaa catggtgcta gtttacgtat taaagtaact  119040
aggggtaaag agtcggagtt aaaacagaat gatgttatga caggtaaacc tacgtataaa  119100
ggtcatgtta tgcgtattga aactaagaag tctaagctta ctagacctgg tcaaaaagcg  119160
gaagctgatt tattatcaga gtatgaagta ggttctgatg aagatactat ccaattaaat  119220
ggtattgacc cttaccatat tatctataaa gaggctgttg agcgtggttt aattactaaa  119280
ggaacatggc gtaattatgt tacgttaaat ggtgaagaaa ttaaaaagta tgataaagat  119340
tgggtaccga cattaatgga caaccatgag ttatacttag aattatttaa tagagtttat  119400
catgaaaact tccctaataa gtatgcacct ttaagcaata caaaagtaga cattacccaa  119460
ctagaagagt ttaaagcatt acaagattac tacgaagagc ttagctctac taataaagag  119520
actaaggaag atgtaaatga ataatctaat agatagaaat attaatagtg ttaaagaagc  119580
attaggcagg gctaatacaa atgacgtatt gcccttacct tatattgaaa tagcagaacg  119640
ttttaaaaaa gctagagata ctaaggaagc tattattgta gaagaagcag gctttcctta  119700
cactgattct acagttatgt atattgagca tgtagagtca aggtgggcag gggttattc  119760
tttagtacgt tataatggtt ctatggttaa agtacctaaa acaatacatt attccgatat  119820
ctatgtatca aatgatgtac acaggattaa gattatattt gagggagcac atccttatga  119880
agaaagttaa taatgggaat agatatatta tagacttaga tggtattcct actgactttg  119940
gtagagactt agacatgctt ttaaagagat ataaaaacct tagatggtca ttatttcata  120000
ggtactctag aggtatgagt catgactttg aaaaacaaga gttacgggaa tacatagatg  120060
agcagtttat taagttagtt aaggagtatg atatacaaag taaagtagat tttccaggat  120120
atattaaaac gaaactaaca ctacgagtac agaacagtta tgttaagaag aacaataaat  120180
ataaacgtac tgaacttgta ggtaaaacag attatacagt agagtcctta acacaggagt  120240
taaatgtggg attagaagaa aatgaattac ttaattatgt ctttgatgac acacaattta  120300
ctgaagtaca aagtgaactg ctaaaagaac tccttattaa tacagataaa gaagacaacg  120360
catttattgt ttcaactgta gctaataggt tagaggtaga gcgtccagaa gtatctagag  120420
agcttacaga acttaaagaa tatgttaaat ttaaaataaa tgcttaccac gaacaaaaca  120480
gtagaagata cattagggac aacaaaatag atacacaaaa tcatgtatgg gaataacaca  120540
aacaagcctt ccttttgtta tattattaat gaaaataata acatagggag gtttttttcta  120600
tgttataatg taaaaaataa tgattggagc ttaattatta tggctaagaa aaatattaat  120660
gaagtattaa aacaagctac cgctactgta gcagataagt atttacaagt tcaagtagag  120720
caagatggtt atacacgtac acaccgtggt cagtataact acaaagtagt agataataag  120780
ggagaattat tcttataccc gattgaaaca gatggtagag gaaatattaa aattatgaaa  120840
aaggctccta ttgtctatac agatggtgac caaattcatt ttgtagttaa tactgttaaa  120900
gacccttaca accatgcttt tattagaact gaaaatatta aaggtaaaga taaaggtaaa  120960
caattaattc aagcgttttt agcattcgtt gaagaccgtt tcagctttgg agtatacaat  121020
gtattccttg ctaataacaa gaaggatgtt tttgctttag ttgatgctga aagtaaagat  121080
gctaaaaaag tagtagatag taatgagaaa cctcatgaag acgtgagtgc tgagtttcct  121140
gctagcccat tacgtaaaga cgttaagggt gtagattcag gagaaggtca aggagacact  121200
tcagagcctt cagtacctaa aaatgtaaca gtaaccgcta aagaaacaac agctgatatt  121260
acagctgaat aaacatacaa aggatgactt agtttggata aattaaattt atacaaaggt  121320
gaccagctat taaaaagtga agagaaacaa gcaggtaaaa catcaattac aattgataac  121380
ttaactgcta acacagacta ccccacaaggt acatataaag tatctttctc taatgaatca  121440
ggagaatcag aaaaagtaga tgttcctgcg tttaagacta aagatattaa agtagtatct  121500
gttactttag atgttgaaag tttagattta aaagtaggag aaacacataa tttagtagct  121560
acgattgaac ctagtaacgc aacaaaagct acttatacat ttacttcaga acatgatgat  121620
attgctagtg tatcaagtaa aggtttaata gaagctaaag caaaaggtca aactacaatc  121680
actgttacta ctgatgatgg taatcataca gatactgtaa ctgtagttgt taaagataaa  121740
gtacctgaag ctcctacaaa tgtaactgta gaccctaaag aaacaacagc tgatattaca  121800
gcataatcgg aggtaaaaat aaatggaaaa aacattaaaa gtatataaag atggtgaagt  121860
agtaggtact aagactgctg aacaaacagg taaaacaact atttctatta gtggtttaac  121920
agcagatact acgtatccta aaggaactta taaagtagca tactctaatg agtctggtga  121980
atcagaaaag gtagatgtac ctgaatttaa gacagcacca catagtgagc tataataaat  122040
taaagtccaa cttaattgtt gggctttttt ttattgactt atatttattt atatgctata  122100
gttaaacaag aattaataaa ggaggtacta tatggatatt aaaacagtat acttaacttc  122160
agataacgac catttgaaag ttaaaaaatt aatggaaagt aaggaaaagt atattgcagt  122220
tacgtatgat aataaatcag taagtaaggt caatgtcgtt atggttatta atgttattaa  122280
agacctagtg catatgtata ggtataaaat tgttgagtat gggttatcta ataatgataa  122340
ggataaggaa atggtagggt atttattaga aaggattgag gattgatgtt atttatttta  122400
aatgaagtag cttcacacac agaacattta tccgaaggta tagatatatt cgacgttgaa  122460
agtgtagtat cttttgactc ggcattacat ttagctagtg ataatacata tgattctgtt  122520
atttttttag gtttatata caataatgag gattacttaa agtataaaga attattaaag  122580
gatacaaaat tatactttgt ttctaatata aacttacctg acaataagga gtttattaca  122640
gtaggtgatg atttaaaata tttatcctta ttagagcaac ttgtagtatt agaagataaa  122700
gacctagaca ttaactttag tcagtatact aaagacacgg cttctaagta cactgagttg  122760
tttagcttta aatctactta tgaggaggca aaagaaatgg gtctagtagg ttaccccgca  122820
```

```
gatatagtat tacctattat gactgacaag ttttacaacg taaatgattt gtatgtacta  122880
tacgaagtag cacctgagta taaattacct ttagcatatg aatgccttaa ggataaagaa  122940
aaaggtattg ttgttatagg ttcacaaaca agaggtacta gtgatatcct tactttctat  123000
gtaaaaggtt atgatgttaa tagtgttgct aaaacattcg gagcatctta taatgaaaat  123060
tctaatatat tcagtatatt tattgatagt catatccatg tgttaggtga gaatatgaat  123120
aagtatttaa taacggaagg aagtatttat gagtaattat aaaacagtag aagagttaca  123180
agcagttatt gtaggtgtgt ttcttaaaga tgaaggtaaa gtagttacct ctaaatttaa  123240
taaagtatta gcaagttttg gtattgatag agtaaatcgc aatgaattaa aagatattgt  123300
agataatatt aggaaagaca catacttaaa tgacttgaaa aataaagcag ttaaaggtga  123360
agtgttatta gaggacttaa gagatgtaga agataaacaa gtatttgagg gtaatgatta  123420
tcatgaagaa gtatcatctt atgtagtagc acatgaaaaa gaactatcta gactaagaga  123480
attacgaaag attaatagac aaactgcata ccctactatt ttgtttgatg aattaaagcg  123540
tactatggtt aatgagctca aaggtaataa gttactagac catagagtaa gtaagtatac  123600
ttctactgag gaagaagaag agctggttat cttactgtcg gacttccatg taggttgtgc  123660
ttttcaagat ttaactaatg agtataactt tgaggtacta aaaagaagat taaatcagct  123720
actacaggaa actattaagg atattagtaa acgtggtatt agtaatgtta cagtatactt  123780
tgtaggtgat ttaatagagc atattaatat gagagatgtt aaccaagctt ttgatactga  123840
gttcactatg gcagagcagg tagcaaaagg aactagacta ttaatcgact tcttaacaga  123900
attatctcca tatgtagagg gtaatttacg tttcggtatg atagcaggta accacgaccg  123960
tgtacagggt aataagaacc aaaaagtata caatgatagt gtagcttata ttgtattgga  124020
ttctttactg ctgttaaaag aaaacggtgt attagaaggt attgagatta tcgacaatag  124080
aaaagatgta tatactatta aagacacagt atgtaactta aatattatta taaaccatgg  124140
agatggactt aaaggtaaag gtaagcatat tcctaaattt attgagaaca ctcacattga  124200
tttgttaatt acaggtcatg tacaccactt ctcagtaaca caagaagatt acaatagaat  124260
gcatattgta gcaagtagtc ctatgggata taataattat gctaaagaac tacatctatc  124320
tagaacaaaa ccatcacaac aactactatt tttaaacaaa aaaaataaag acattgatat  124380
taaaactgta ttcttagatt agggagagat aatatggaca ttctatcaat tatagcctta  124440
acattgctta tcattattat tgttaatacc acaatgaact ttgtaggtat gttacgtggt  124500
gagcgtgaat tagtaaaaaa aggaggtaac cctctaccca attggcagta ctataatgtg  124560
ttattaccta atttatgtgg tattatcctc ttaggtattg ttgtttattt tggagattca  124620
atttataaaa ttacaacaag gttagaagtt ctttttgcta ttattgcgct tattgtaata  124680
gatgtattgt taacagcgtt agtattatta gtattgagtt tcgtaacaaa aaataaagaa  124740
tagtaaagaa gggagtctgg tttatacttg actctctttg ttatttatgg tatattagat  124800
atgaggtgat ttttgttgca attaaatttt ggtaaatttg ataatgaaat tattaagaca  124860
aaagtaagtg aaggtgtcta ctcttttaga ggtgttcctt attactacat agaacatgtc  124920
caagatgaaa cttctgagta tgtattagta tataacatac atagtgttga tgatgaagta  124980
ccacaaaaga aatataaaat agaaacagta agtaaaacta ttagaggtgg tacgatatta  125040
agtaatacaa ttaagtcaat gctacctaat aataagaagt ataaaaaggt atatgaacct  125100
cctatctttt tagctaatat tataccttta ggtacagata caactacagg ttctgtaggt  125160
aaagggtttt tcgaaagaga aaaagataga gtaactatta cacaaaaaga aggcactaaa  125220
gttatacatg gtgaatatac aggagtattt atatgtttat ctaatattaa atggattaag  125280
tcctatactc ctttagacag tatattacaa tattatcaac gtattaaagg ggatagaata  125340
aatgtctgag ataactaaat tctatgagca ggacattaaa gatttaatta gaacgaagag  125400
acatatgttt aaagatgatg agataacaag taatatacaa gatattagaa tatttaatga  125460
aaaagctatt tgtcaaggta aatgtagaac tgactgttta attcttgata gaaacggtac  125520
tgttatgggt atagagataa aaacagaacg agactctaca caaagactta ataaacagtt  125580
atactattat agtctagtat gtaagtatgt ttatgtgatg tgtcatgata agcatgtacc  125640
taaagtagag caaatactaa aaaggtataa acaccatcat gtaggtatta tgagctatat  125700
taactttaaa agcagtccag tagtaggtaa gtataaggaa gctacgcctt caccactaag  125760
aagtccttat catacactaa atattttatg gaagcaacat ttaatgacta tacttaaaca  125820
gttaagagat tataatacat atctaactgg atataactat agggagcacg gtaaaaatac  125880
taacaatgaa ggcagttata tagaaggaac acaacgtatg agaatgaaaa agtcagctat  125940
tattaaccaa gttattcatt atttaggtgt agagaactct tataagatat ttactagagg  126000
tgttatctat ggttatagta ataggtggca gatattagaa gatgatttct ttaaagttat  126060
acagaacgga gtgagggtat tatatggcaa agaggaaacc tgatacatta aaacctaaat  126120
ctaacggata taaacatcaa cctgttaact ttgctcctac aggtaactta tcaggtagaa  126180
gtacttcttt ttttaataaa aaaagaaaag atatatcaga tgaaagtatt gttgttaaat  126240
acaaaccttt gtttgttaaa aggtttgata atattactgc tacagacatt aaaatacaaa  126300
agaagtatgc gttagactta atcagtgaag ctgtgaatat aaagaagaaa tatcttgtaa  126360
tgaagcaaaa aggtaaatta acacaaacta ttttacatac agatagagtt tattatgttt  126420
atagaggtaa gaaattaata ggtaaatgta gcattcgtga acaacgtaca tttagaggta  126480
cacatttaat ctacattttt agtactagac atagaatatc tatacgcaaa aatagtagat  126540
tagataagaa aagaacacca aagaaaatga tatataaagg tggtaaataa tggttaaata  126600
tttaagaaca aaagctaaaa aaacaaatat aagtacttta tttaagaaac tacaaagtaa  126660
agatattaca ctattaggag tgtcctatga tagtgattat ttccctagcg gtgtaacaat  126720
aataccttat ttagaggata tatcacaagt agaagatggt atagaattta cgaataaagt  126780
aatagttact gagaacttaa aacctgctat tgtaggtatg aataatatga taagtgattc  126840
aggactaggt tatgttaaaa cagagcagtt aaataaaaga ttagaaaata ctggattaat  126900
gacagattta ttatctaaag gaacagaatt aacttcaaca aagaaagtag acattgtatc  126960
aacttttatt gaacctacta ttatgtacca agatactact attaataaag aattaaaact  127020
tagattatac actatcgaag atgtatcccc tttaaatgac tacacacatg ttgtatactt  127080
actagtaact gataaacaat atgacggtca atcattcata ggtacattat gtaaccaagg  127140
tacattaaac aaattagata ccctaaaagt tcttacatta ttcaaaggta ataatttaat  127200
caatagaagt gtgttttctg ttaagttaga tacgaataaa tatcattata gtttatataa  127260
tacacatgag accggtattt tctttttaga tgatgataaa gacttaatta ttgcttgtgg  127320
tcaatcctat gtaaaagtta gatataaaga tattgttagt agtaaagtag agaaagttag  127380
tgataataac tataaaatga ttgttaatct tgttggtaat gatgagctaa caattctctt  127440
atagtataat actcccttaa atatgtatac taaggtataa gtatacgtat ataagggatt  127500
ttttatatat attttttca agtagttagt taatttttaa aaggtattat tcttatttta  127560
```

```
aaattatatt tataaaacat taaaatacct tttaggtata gggttttaga aaaaagattt  127620
atattgctta aaatagttac actatagtgt aaaaaattag aatatccttt atgaaaataa  127680
aatagatgca gaaattgtga tatattatat agtgtaaagt ataaaacagt tgatttgata  127740
aggttatgtg aatacacata ctccttattt tagttcacac atatgtaaag acacttgaga  127800
caagaaggga atatataatg gctagaaaaa agaatttaag aaataaaaaa tctgatataa  127860
aggtagttcc agataaggaa agtattctat ctaaactata taataataaa ctattaaggt  127920
ctaaagtgga taatgctata gatgaagatg ttagttatga tgatattata gacctatgta  127980
aagagtatga cttagagtta tccaaatctg ccattacaag atataagagt aaacgtaaag  128040
aagctattga aaatggatgg gatttagggg aacttattga taaaagaaag aaagttagcg  128100
ctactcaaat acagaaaaaa gaaaacccta tgaaagaatt agatagtgaa aattatacac  128160
cttttgaact ggctacacag aatgtacaaa caatatatga tgacattcaa atactagata  128220
tgattattca aaaaggtgct aaaggtttaa actttgtaga aacattagac cctgctttaa  128280
tgattaaagc tatggaaaca aaagatagaa ttacgggtaa ccaactaaaa ggtatgtcat  128340
tcataggact aagagaacta atgattaaac aacaagcaca agatactgct atgacagaag  128400
ttatgcttga gtttattcct gaagataaac atgaagaagt tcttcaaaga atggagcaat  128460
tacaagaaga gttctataaa aacttagatt tagatgaaga aggaagaaag ttaaaagata  128520
cattagatag agtaggctat acaatataga taatgaggta atacatatga cagaagaaat  128580
tagtttaatt ccaataaaag atgttaaacc acttacagat atagtagata ttataacaca  128640
cctacataaa ggtgatgtac ttagagttaa acaagagaac caaggagata tattactcag  128700
actaagtact ggaaaacata agtttactga agtgtcaaga gacttagata aagaaaccat  128760
gttctataaa aggtattggg tactatacaa tgtatctatt aattctttac taacttttga  128820
tgtttattta gaaaacgatt atgtagagtc tacaaaagtt aagttcccta agaacacaat  128880
tgtagaatat gtaagagata atcaagaatc agatgtagct aaggttaaag atattttagt  128940
agatagtaac ggtaattatt tctatgcact ttcaggagaa acatctttat ataatgaaga  129000
taaacttaat aaaattaaaa attaatgatt gacacactca tatgggtgtg ttattctttt  129060
attacaaaca ataaaaggag caattgatta tgattattac attaaatgaa gaagagaaag  129120
cattattaga aaataaaagc aactatacgc cattaagtaa gaataaagag ttcaatacac  129180
caaaagaaga atatattgtt acaagttata ataaaggtgt acctgtgact gatattgcta  129240
aggaagctaa agtaagtatg ggtttgattt atacagtgtt aaacttctat aaagtaccta  129300
agaaacataa gaaatctaga gtagcaaaac gtgtaaaaca tattactaat gataagaata  129360
aagtacaagc cttaattaaa gattatcaat atatggactt acaaagtatc tataaaaagt  129420
ataacattca taagaatggt ttatattata ttttagattt gtataatatt gaaagaaaat  129480
cagatttaaa agagaaagcc ttagaagata ctatcgaggt agaataagag gtgtcatatg  129540
cgcaaagaac gaattgtaga ttacttgtat aatgtaaaga acattgataa taatttaact  129600
atacaaggaa tagaaaatag tttatttaac aaagaatctt tacaagactt agtacctgat  129660
tttgatactt ctagtaaaga tattaatgaa agtaatttat acctatgtac aataccagaa  129720
gattataact ccgaccatgt agaaagtggt cagtatatag gtatagatgt tggatatgta  129780
tctgaagacc ctgcttttga ccatttaata ggtcaagttc ctagaagtgt atatgagaaa  129840
gcgcatgtta tgcaaccact aattaagata gaaaatactg atatagatta tactcaggct  129900
gatatgatta atgatattaa agtaggtaca agtattagtg atgtaaagat taaagataaa  129960
ttaagtttaa tgtcaaataa tcttattaca catttagaaa ttgttgataa gtattacttt  130020
gatagtagta tagaagaaac attattaaag tattatgagt taaagaatcc tgactattat  130080
ttaaaacatt ttcttaaact aaaagaactt gtcggagaca atagaataat atattgtcct  130140
ttactgttaa aatgtattaa agttatagac taagttatta tattataagt agtaaaggat  130200
ggtgcgctat gagtaaaaaa gcaataattg cttatgtaat tatcttagtt atgttagcct  130260
tatctatatc tacttattac gtatcctcat acttatatca tgaaaaaacc aaatcacaag  130320
ttacagacca attaacacat cacggtaaac taaaaaaaga taagaatgta gagtatgtag  130380
gggactatac acttaagaaa gtaatagaca acaaagcata ctttatggaa aaactaccta  130440
cctatttacc aggaagaaca agtgataaaa gtattgatat gagatattat aggactagta  130500
aatttagaga aggtgtaaac tttaaactta ttcgtatata cacagaggat aatgacaata  130560
atccagtaca taaatatagg tttgaagcag tattaaataa aaagtaaagg tatgatagtc  130620
tatgacagta gtaattatac tagtatgttt tgctattata tactacttat ttaacaaaga  130680
ttgagtcaag tttatgcttg actctttttt tgcgttatgt tatagtttat ttataaggag  130740
atgataaatg atgaaaaaaa gtgatttaga taatttgtat attgtggtcg taagtattaa  130800
gaacggtgtt ttacctgatg agcgtataat tccaattggt ttagatgtac taagtaaagt  130860
attagaaggt aaaactacat ggacagttaa gaaagaaatt aaacatacat ttggtaaaga  130920
tgaattaaaa agatttaaag ataattacaa gttcttgcaa cataaaattg tagaccttgc  130980
tacaaaagga tataggtagg tggtataaat ggatatagta aataaactca tgttaggttt  131040
tattttattg ttttatgtag gtgtatttat ttggtactta tgggaagtct ggaaattaac  131100
ttctttaata tctgatatag ttattaagta ttatgttcgt aaggagtggg ttaaaggttt  131160
attaccttat ttgattcatc aagttattat tacgttagtt tgggctactc tagtattagt  131220
accttttata cttagttata taatgataaa atatttgata ggaggttact aaatggaagt  131280
agtatatgag aatgaatgta gagggtatta tatttgtgtt atagataatg aaggtaagta  131340
tgaagtatca tcttttaaaa aatcagtaaa caaatatacc cctgaaatta tagggtatac  131400
tacagaaaag ttaatcttgg aattaaaaat accatgtaca tatgtaaatg ctagtgaagt  131460
agaaagtttt atgcaagaat taaaagtagc acgtattgcg cttgacaagt ttactaaaga  131520
tttatataat aaaggcataa caaatattat attctaaagg gtggttagta tgtatacaga  131580
aaaatataga aatttaatcc atattacaca tagtatcttg gttagtattc aagaattagc  131640
aagtaattta ttaaataaag aagtaaaact agttacaaaa gaaaataagt atttatgtgt  131700
tgtagatggt attattatgt taattgttga ggaaggatta gtatacacct attttgataa  131760
ggtaggttta aaagtacctg aacgtattgc acttggtcat ttagcaaaga gtttacagtt  131820
tacaatatcg gaatcaaata aagatttaga aaatcaaaaa taagtgttga cacctttaac  131880
atgttgcttt atactaagag taacaaaacg ttagaggtga ttttttatgt gtaaagaaaa  131940
agttcataga cagctatcta atgctataga aatattagca acttacaaag agtggtggtc  132000
ttttccaaaa gaattaagta ccacagaaac atttaagatt attaactgga aagaagatac  132060
attagtattt gaagttagag aatatggtaa gtatataggt aggtttagtg tagcaactcc  132120
tattattgat tttcattatg atagaattaa aaatacaaca acacaatata tgataaatta  132180
ttttgctaaa atagtatgta aagatatgta tgcgtattat aaattacaga gaggacagta  132240
aaaaatgaaa aatttaaata aacaaaaacg cttgacgttg gaattgatta gtgataatct  132300
```

```
aaatacacaa cataacttag atacatcggt tagtcttgta gattatagta taaaagactt  132360
tacaaataga aaagtctatg taagaactaa aaaaggttta gaacttacta atatgaaagg  132420
attaaaaaat actgattcac tggatttact atttaagtac ttagaattaa ttttaaaagg  132480
ggatatgtag tatgctaaca ccagaacaaa gaacacaatt aaaagagtat caaaataaaa  132540
tgacaaaaaa gaaaaaataa atgttgactt actaaataac aagttgtata attaacttaa  132600
caaagaaaaa ggagattgat aaatatgaaa aacttatata aaattttaac aggagtattc  132660
tttagcacta cactattatt aggaggttgt gcttactact cacaagaaga tacaccaaca  132720
catgattata aagaagataa gaaagaaaat aagaaaaatg attcatctaa agtagaagaa  132780
caagaaaata aacaaattca agaagacaac actgttcaaa ataaccaaca agataaccaa  132840
gtacaaggta accaagcaca gcagaacgaa caaatgcaaa aagcaagcag aagtgaacat  132900
aatggactat ctaatgctga gtatgcggac aaatacaatc agtatagaga agctcaacaa  132960
gcacaagcag aattagaaaa cagaactgaa gcagataaag ctagtggtgg tggaggcgga  133020
ggagcctcat ggaattatgc aggtgctaat gagagctttg agcaatggtt acaacgctcg  133080
caacaagaaa agactgaggc tggagtacaa gcaaattaat aaaaggtata ggagaataac  133140
aatgaaaaca ataacaaaag aagaactaca taaagtttta gaagagcata aattatggtt  133200
agatagtaat agtgaagaag gagctaaagc agatttaagt tatactatct taagaaatgc  133260
taatttagta gatgctgact taaggagtgc taatttaaga ggtgctgtct taaggtatgc  133320
tgatttagag gatactaatt taagaggtgc tatcttaaaa ggtgcagatt taacaagagc  133380
taacttaaca tgtgctaact taagctgtgt tgatttaggt gatgctaact tagaaggttc  133440
tgttttatat ggaactgatt tatattatgc tgatttaaga aaagctaatt taacagattc  133500
cagattaaat gaggctaatt tagaatatgc agacttaaca aataccaatt taacagatgc  133560
taaattatcc caagcaagta ctcaaaatat caaaggacta aaagtatact ctatagataa  133620
tattggaact tttaatggta aagtgactta tattcctagc ttagatagag tatacgcagg  133680
gtgttggata ggtagtttag aagcgttttt agaaaagggg ttagagatga atgaaggaaa  133740
taatagtaaa cttgaggaaa taagagatgc ttactgcttt tttagtaaac gtaaatagat  133800
ataaggatga ttaattatga acattgtaga acaacgaaaa cccataaaga gtaagcatat  133860
taacttaact aaacacgcat atgaacgtta tactttaaga gttaataaag atagtaaaga  133920
acgtgcttgt cagtggtttg ctagtgcttt aatgcaagct acttttgagc atgcacaaga  133980
agacggtaat gaagtatatg tatttaagaa ttacagaatt attattgata gacatctaac  134040
tattattaca gttatagata ctgaagatga taattgggaa ggtataaagg aagcaagaga  134100
acaaatagat acgtatatta aaggtaagct aaaaaaaact gttacacctc tatttactaa  134160
gttagataga atagatatta gtatccatga agcgcatatc agcaggatta aaacaagaaa  134220
ccctaagaca aaagatataa ttaacaaaaa tattattgaa cttgaaagaa ataaatctct  134280
actactaaat agtatagaag gtgtaaagaa aacagcacat aagtattaca tagaattaaa  134340
ggacatccat aaaagattaa aggactgata atagtgtatt taaaagattt aattgaagat  134400
tatgtgaatc aagataaaga agtaattata acaattacaa gtaataaagt aattattgaa  134460
gcagactatg atgttatttg tttgcctaag agcaaggttg atattaatga tttaaaagct  134520
tatgtatatg gatttaatag atttaatact gagcaaatta tgttaaagga tgtggaataa  134580
tacaagactt aaaaagaata acacagcctg aattagattc attgataggg aagcatgaac  134640
aatggctagc tacaaatgaa aaagaaggag aaaagctctt tttacagtgt gtagatttaa  134700
gaaatcttga ttttcattcc gctaaccttc aatattcaac tattgtaatg tctagtttat  134760
gtggtgctaa cctaagttat tgtgatttaa gttatggtga tttaagttac aatgagtgta  134820
tatctacgag atttacacat gctcgaatga aggatattga gttgcctcat actaacttag  134880
agtgggctaa tttaataaaa gcaaacttag aaaatgcttg tttagctgaa gctaatataa  134940
gtgaggtaga cgctaggtgg gctaatatga aaaatgctaa cttaaatatg gctaatttaa  135000
aaggtgcaga ttttggtggt acaaacctaa ctaatacatc attatattat gctaacacgc  135060
ttgacgtgtt tgggataagt atttatacta taagtaatgt gcttgatttt gacgagcacg  135120
taacttattt acctgattat gatagaatta ttagtaatta taatgaatat acccttgaag  135180
agtttggtaa actagaacct acgcttgagt ataaagaaga tagaataaaa gaagtataaa  135240
agaaaattaa attagcttac aatttcttta aaggagtgaa agaacttgat aaaatttaat  135300
tcagacgaac ataaacatat acttaatgtt atggataaat taccatatac ttgttggtta  135360
gacactgtag atggtgagtc aggtgctgac ttcttatgtg tattgcatag aacacactat  135420
gaacttactg aactaggtat aatgatttat agttatggta gttggtacat gataccttat  135480
gacaaagaag atttaattga atatgcaata aaaagagata tagaggagga ggaagaggaa  135540
tggtaagtac ggttattata tttttaattg ttttaggtat tatattgcta agtgtactaa  135600
ttattgttat accagattta agcaaagcaa aaaaacgtaa aaaagatgca gatattaact  135660
atagtcaata tattaataaa gacatggctt ctgagtacta tgaaaagtat atagtaccta  135720
ctgaacacat tgttcaaacc aaagtaacag agataattga aaatataaag aaagagtata  135780
ttgtctctac tgtaattatt gactcttcta gtaatgaaga caaaattatc ttacatgttg  135840
atgataagta tttaaaaaag gtagtgtatg aagataggta tgaatgcatc tacgattcta  135900
atacaaaata tcaatatgtt gttaatcact taacatatga atcaagtact ttattaaaac  135960
aagatgaagt aaataaatta aaagatatac ttaataaagt acctgtcaca gctaagcata  136020
catttaaaaa tgagatgctt aatcatagga atgaatatgt gttagattat attacaatat  136080
atatttgtgg tgatttaact gctaaaatta caaagaatgg ttatgtacaa aaatttagta  136140
cactagaaga tttttgtgac aagtatgaag cttactgtag atttgttaga attgatttat  136200
atgactgggt aaaagaagta agaactatta atggatatag attagaggta gatattaaac  136260
cttattttaa aattactgct actaaaacaa gtaagtatga atttgtagta agtgatgatg  136320
tatctaaaat taaaatatat agggatgata tgttactaac tagtaggtat atacgaaaag  136380
caattgatgt acaggaaata atagaggaaa cattgaacaa taatactatt gtattttaaa  136440
aagtagaaag taggtaaatt ccttactttt ttcatatata agtgttgaca ttaataagcg  136500
taaggtttat aatatgtata taagttaaat aattatagag gagataataa tcatgaaaaa  136560
aatattaagt ttagttttac tcgtactaat tgtactaaca ataatcaatg tagtgaaaaa  136620
ccaagagcaa gtagaacaaa gtaaccaaga atctcaaaat aatgaagatg tagatgacca  136680
tacttcatac gtacctgata atgatggaga gcataaagac gttagtgaag aacgtaaaag  136740
attatggggt acagagtatc aagaaggtga aacacataac ccaaatgcta aagtgtttaa  136800
tcaagataca ggagaacagg ttcaataaga gtagaaggag cacttaatat agagattgat  136860
gctaggaaat atatattaag taacctacaa aaaacattta aatactctaa tatagatagt  136920
aaagaggtaa ttaaaagata tagacatgta tataggtaaa tggatagttt ataagtagta  136980
ggtaagtaat taaaagaaag tcatatataa gtaataagta acacataaag aaacaacgtt  137040
```

```
tgatagtata cagataagta ataggtaagt aaataattaa aagaaaacat ctactactac  137100
tatcacttat attgtaagta cctatatata tatataccaa gtaataggta ataggtaagt  137160
agtaacaaca gctaccgata ttacagatac cttgtatata gatgcatagt aagtagtaaa  137220
taattaaaag aaaatagcta tatggtatac ctatatatat taagtagtag ataagtatta  137280
agtagtagat acgtattaag tattaacaac agctacctgg gaattttata tataataagg  137340
aatagataat aggtaagtag taagtaacaa gtagtaagta acaagtagta agtaacaagt  137400
agtaagtaac aagtagtaag taacaagtag taagtaacaa gtagtaagta acaagtagta  137460
agtaacaaca actacctggg aatttcttta catcccacct tcatagtgta taaatagtta  137520
ggtgtctaac tatttatttt tatatagttt taactattgt gaactatgct tatgtagtat  137580
taaactatgc tgaacctata gtaaactgtt ctaatgtata gttaaactaa gctgaagtag  137640
tatttactgt gtacaaaggt atatttagta tcagatattg tgtatatggt atagtataat  137700
tatgaacatt attattatta ttcatatata ttgtttgttt ttacagtact attgactcaa  137760
ttttccctag agtaaaagtt taatatattt agcagtttcc gaacattaaa gaaattgtaa  137820
gcactttgta tatatgtgtt gacactgtgt tgcttatagt gtatacttaa tgcataaagg  137880
taaaggagat gatttataat gaagattaaa acagaagttt cgtttacaga gctaatgaat  137940
atgtattaca aaggcagtat agacaaaggt cactactatt ctactaatag tcagtttatt  138000
gttagtataa ctgatggtga ggtatcgttc tataatgtgt ttttccctaa tactacggtt  138060
ggtacaccta atagtactac tatacctaat gatactagat ttattgtaga agcggttgta  138120
gataccacta ctgaattatt tagtctagta actactttta agcaaggtag taacgtatta  138180
aactcagtat ggtatagagt tagtattgat gagttatata atcattataa aagtaaaaat  138240
aaagagttat tatcagttag tactgttgta gatgatgagt tagttactat atggaaagat  138300
ggtaagatat tgtgatttgg tatatagtac tatttagtat acttatatgt atagttagtg  138360
ttttaattct atacgtatct tacaaagaag gttttactat taggatacta ggttactgat  138420
actactattt atactaacag aaattacaag atttagtatc aatacaagta atgctattct  138480
atgtacagta cttgtattgt tatgtgtagt actagtatat agaggagtta aataaccgct  138540
tctatatgaa actttatacc tatatctatt ataactatag gtatttttt atatttctta  138600
cataaatgtg ttgattttat gtgtgttaag gtttatactt aatatataat taaaggagtg  138660
aagttaatat ggatatgaat aaagaagtat tagaacgttt agatagttta ggtggtaagt  138720
tagagcaagc aggtacacat ggttatgaat ccttaattaa atacacagtt actcaaggta  138780
ttatagattt atgttcaata agtatattat tatctataac agctatctta taggtggctt  138840
tgtataagtc agataaaaag tctaatgaag gtcatagtac cttattattt gagtttgttt  138900
gtaagaatga aaaagagatt tcttctgcag gatgcacagt aattatattt gctgttactc  138960
tgtctattat ttctttttta gtgctattaa taggcttgcc tattgctatt caagaaattt  139020
ttaatccaga aggatatttg attaagagca ctatagatag tttaaagtag agtaatgtat  139080
aaaggagtgg tatagtgtct aaaaaaagaa aagaaattaa agagtataag aaacagggtt  139140
actctgttga gtatatagga agtattttag gtttatttgg tattggcgat gttttatact  139200
atgtagaaac taataagaaa tacttaaagt caattagcgt aggtaaagat gacaaccaat  139260
atgtatatga ctttaatggt tatgaatatc tatcaaaata taagttaaat atcaaagaag  139320
aagaactaat gtctaaagct attgctcagt taagtatcaa aggcttaaag aactttaacg  139380
gagtgaagca tgcttgggat gtaggttttt tagagcaagc ttttaatgta catcgtaaag  139440
ctattgatat ggttaagctt aaactaagct ttgatgatga gggtaaccta tattatgaat  139500
tagaattagg ttggattaat atttataaag agtatacagg tgtaaaagac tttcttaata  139560
cagtagataa ctatctcaac ttcttctata aagatatagt cactagtggt cttgagttaa  139620
aacaagtact atataatact tttatgggag gagattatga gtttgtagta tctccatata  139680
aggttgaagt atatagggaa gttgagttaa ttgatataaa gaaattttac tctgatactt  139740
atggaattta ttcctatggt tatggcacta atgtacataa acctttacaa acaattaagt  139800
attatctgga ataccctatg aatgaagtat aaccacttca aatattatat aaaaggagtg  139860
cttaatatga gtaacggaaa agtagcgtta attgggagta aggtattgga agactataat  139920
atttatacaa ttatgagtga gaaacatata tacttaagag atagtgttga tgtggctttt  139980
aatgatggga aggtattacc tatatacatt gatagtgtat taaaacaatt aagtaaagat  140040
gataaaaatt tatatttttc tgaacaagat atagatatta gtaaacttac taatgacgag  140100
tattatacag ttactaaaaa ataaaaggag aatagataat gagtagtaat aaaaaaaaat  140160
agcagaaaga gttattgaga aatttttaga tgagactaat aaaggtgtag attttactaa  140220
tcaagatgaa tttaaccgct tcttagataa tacagaagac ttgtatgaag tatctggtac  140280
tcaaagagat aagattatta agtgtttaca aaacattgta gttactgtat ttatggataa  140340
ggagaaataa caatgaaaac aataaaaaga aaaatagtac aagaaggtat gaacaaagaa  140400
gaaactatga tggaagacga ttctgttgta atcaaaaaaa ttcaaaaaat aacaggcgga  140460
gctattcttc ctttagccaa tggcaaggaa tatgtagtag tgtttagtaa agtagaccct  140520
actaaattaa ttgtatttaa tgtggaaagt aatcaaatct atttaagtgg ctctggtttc  140580
gatagtgaac tgtcttatgt agacagtaaa agcaacccta ttaccttaga aacagttagg  140640
ttaatcacta atttattata acggttatta ggctcttaaa gattaagtta ttttatagga  140700
taaatactac tagaaaatga ttatcgttta atatagaaat ataacgtccc tagtttaagg  140760
gtcttaaata taaaggaggg tattagaatg actaaggttg taagtagagg gtatagtttt  140820
gaagaacaag aagtaagtat gaactataat caaggacaat gggtgattta tgcaagtaga  140880
aaaccttata ttactgatat tatgaaaaag taccctgata aggtggaagt attagaacaa  140940
ttagaaaatg aaacaccagt attggttaaa gttgtattgg atgaagattt aattacatta  141000
agaaaaccgg taagtaatga gcgcaaagag caaatgaaaa agattgctaa agaaaagattt  141060
ggtaaataat agagaggctg actttaatga acatcagtat gtacactaac acctgtaggg  141120
actagattaa tattacaaga tatcttatag ggttatagtg tcattgagaa tgagtatgct  141180
ttattaaggt tagttaaaga agataaacag tatttataat atcatattga agaagtagaa  141240
gcggtttaat accacttctt ttttatatta tatttatatt ctgagtaatt atgttgtgtt  141300
taatgttggc taataattgt ataccaattt gagcatagta tgtccgtttc aacatagtta  141360
atctattaat ttgtatattt atctgttagt tatgtataaa tatttgttat tacttattta  141420
tatatttgta tttcgtacta accgtacgac ttatcttttt aaaaagataa gaacaaaaca  141480
gcgtatacct tgttgtttta cgctacgcta caacaaggta acgcctgtaa taagttattc  141540
gtattaaaat actaacaact aattacttgt tgtttagatt ataacatatg tttatgagaa  141600
ttagatgata atttagttac aacagcatta taataatatt acagttatgt tacaagttgc  141660
taagtatgtt ttgttactac aatatattga atatgaaagc tttagacctt ttctgcagac  141720
aagtaattat tacagttatg tatgataaaa ggtaagtatc agggattaaa ttaaggttgg  141780
```

```
attaatgaag cggataagtt agatactgat taaaataaaa tactttacat tacctaaaac  141840
ttatgataca cttaggatag gataaaggag gaatatcaat gaatattcaa gaagcaaagg  141900
ataaattata cgatgaatta ctttatacag taagtctttg tgagggaaca gaagaagatt  141960
tactagaact tattgagaat ttattttata tttacaatga cgagcctgca tttttaagta  142020
aagacggtat gcaatatact attaaagagt ttatggagag aagaaaaaca ttagaaccta  142080
tcttaactga attaggtata gggtacgcaa tgatagaata tcacacacat acagaatacg  142140
agttagttac ttattcagta cttaaagtta tacagtatga tgtagataac tatactgtaa  142200
ttattgatac taatagtgat aagaatatta agttatcaga tttaacatta gaagctgtta  142260
aggatatttt gaatcaaatt aagtagctag ggttgtttta ccctagcttt ttcatatgct  142320
tgtattgcct atttaactac cttatataag caagtaagta ttataggata aatactacct  142380
aaaaagtatt accgttgaat atagacctat aagattaagt ctctcttact gttataaaca  142440
tcataagtgt aaatctatga ttttcctaag tatcaggcgc tgttttccct ttatattaac  142500
cgcttcaaac aacataaaaa aagattaggc tattaaccta atctataatt cttttatata  142560
attcttttat ataattcttt tatataattc ttgtaattct ctttctaact tttttattgt  142620
ttctatatca ttatttcttt taatagactg acatataaat gcaatacctt taatcaaatt  142680
aaatggttat ttttacactg cattgtatac aattaaatcg atcgattata ataattaatt  142740
taatctgtac tttctagttt cttctatata atagtaagaa atcatttctt taaaaaactt  142800
tcgtataacc tattgacaat caatataaga tactgtaata taataagcgt agtaaacaaa  142860
ccgaaaggaa ttgataggat atgaacgtaa atcaaattgg agatatacta atagaacttt  142920
tagacatgga cggttacaaa agcaataact actatagaaa tgatttaaaa tattcaacac  142980
attatcaagt taaatattta gcttacattg atgatagcta tgaaacacta gaactattta  143040
aagaaacgaa agtctttagc gtatcacatt caaatagatt accaattaac attaatgtta  143100
aggtagtgaa caaacactta tttatagagc tagataatac gttatacctta gtgaatgaga  143160
atgcagaaat tattaaagaa aaaaagttaa aataatagtt gacactagaa ctaagatagt  143220
gtaatataat agatgtagta aacaaacaga aaaggaattg attaattatg aaaacactaa  143280
ttactaacag taaaccatat aagaactacg gctatgaaat ggaacaattc gagagagaaa  143340
acaacgtaat tatcacacga gcataccacg aaccaacaaa acaaggctat gaccttgtag  143400
tacactacac ggaggttaaa taatatgaaa tatctagaat acattgaagg aacttataac  143460
agaattaaag cacaaggttc tataataaat gactatagac tatggtcaga tatggaagaa  143520
tgtgatgatt tatactatca tattaataaa gcttgtcatg ctctttacaa tagcaatgta  143580
aaagaaatta caacaacaga caaatgcgtg aaactaacac ttgaaaatgg aaaaacaaaa  143640
cttgttaaaa aaggttaaaa taatgtttga cattacattt aagatactgt aatataatag  143700
atgtaataca aaaacaaaca aaagggagct aataacatga gagatataag aatagtttta  143760
agagaaattg acgaggtaca gcaagcctta atatatggta ggaatagcag agagttagca  143820
cgttttttac gtagacaact ggtaaaacta gagaaagaaa gacaagatat aaattggtca  143880
tagccaaaag cctattacat aggcttaaaa aataaaaata agggattgat acacaatgat  143940
taaagttaaa tataaaggca agaaataccg ctcaacacaa aatacagatg ctattgtaac  144000
tattataggt ggtacagcag taatcacatt gatagactgg tttattagat tacaagagaa  144060
tattaatata tttattagat aagggctaac caccccttatt tttttatgtc tatataaccg  144120
cttcacatta gtgtaaaact tcccttattt ctttgatata atactttaca aatacgagct  144180
tatactgtaa tatattaatt gtagtaagga acacaacaaa caaaaaaaga agagggattg  144240
attacttatg aaaaactata aaactttaga agaattaaac caagattata cagttattag  144300
aacacaaaac gaagcttcaa gcaaacgtaa taacttagat gttactgata tttatgttaa  144360
tgattggggt ttgttacaat atggtattta ctttaacaaa ttcgataacg tgtacaatgt  144420
agtttcaatg acatcaggaa acaagaaata taatattact gcttatgaac ttgatagctt  144480
tattatggat gagttaaaca aacagttaga gttatttatt aatgcaggaa gactataaag  144540
gaacacaaca aagaacagca aacaaataaa aaaaacttaa aaaagtttta aaaaagtgtt  144600
gacactaaca tcaacatagt gtaatataat agatgtagta aacaaaaaca aacagaaaag  144660
gattgattaa ttatgaaaaa cacagtaaaa gaaatggcaa acggaaacac taaacttgaa  144720
agattattag ttttagcaat tgaggaagcg gttatgacag agcttgttga atatgatgca  144780
ttagataaat acaaccactt agaacaacag ttattaaaca atgaaacatt aacacaagca  144840
gaacgtaaac cagctaacat tgattatagc acttacgagg gagctatatt agcacaagac  144900
aaagcagaac actttactaa cgttatctta aaccacatga acaaagaaca atttgaacaa  144960
atgattatgg atattgaaac actagaattt aatgcagaac aaatgctatt ctaaggagac  145020
attacacatg aacttatctg agaaagaact tatagatata atagacaacg ttaatagctt  145080
cactggtatt gatgaagcta ttaacgaaat ggaaaacaaa caaacaacta aaggcagtga  145140
caaagacagc ggaacgatta aacagtacaa tagtttagat gagttaagac aagactatga  145200
cataacaaca ttagcaccag atgtaataaa agaattactg aataatcatt agtgtaaaac  145260
ttcccaaaat aattaactaa aactattgca attaactgta gatttgatat aatgtaatta  145320
aggaaaaaca aataaaagaa aaaggattga taaactatga aattacttaa ccaaatgaaa  145380
caaacagcag aacttgaagg aattgaattt gacttattat taacagctat ctatgaaaca  145440
atagagatag aagctgttga acaggattta ctatgtaaat acattcatat tgtaaaccaa  145500
ttaaaagaga ataaagacat aacaccatta gaatatatac cttctaacct agactttaca  145560
gacaatacaa caataagact agttgataat aaagtgtttg agttagcaga ttatatagtg  145620
gaacatatga gtgttgaaga gtttaataaa cacattaaag actatgaaca aattaaagca  145680
gaagatatag aaatgatgta aaacaaattg aaagggagtt aattcccttt cttttttta  145740
ttattaatta ggattgtata caataggtta atataaatat attatacggg ggcaggggta  145800
aaatgccact aataccacac attttatatg tatatacc                        145838
```